US010870888B2

(12) United States Patent
Salomon et al.

(10) Patent No.: US 10,870,888 B2
(45) Date of Patent: Dec. 22, 2020

(54) METHODS AND SYSTEMS FOR ANALYSIS OF ORGAN TRANSPLANTATION

(71) Applicants: The Scripps Research Institute, La Jolla, CA (US); Northwestern University, Evanston, IL (US)

(72) Inventors: Daniel Salomon, San Diego, CA (US); Sunil M. Kurian, San Diego, CA (US); Steven Head, Lakeside, CA (US); Michael M. Abecassis, Highland Park, IL (US); John J. Friedewald, Chicago, IL (US); Josh Levitsky, Evanston, IL (US)

(73) Assignees: The Scripps Research Institute, La Jolla, CA (US); Northwestern University, Evanston, IL (US)

( * ) Notice: Subject to any disclaimer, the term of this patent is extended or adjusted under 35 U.S.C. 154(b) by 0 days.

(21) Appl. No.: 15/898,513

(22) Filed: Feb. 17, 2018

(65) Prior Publication Data

US 2018/0371546 A1 Dec. 27, 2018

Related U.S. Application Data

(63) Continuation of application No. 14/481,167, filed on Sep. 9, 2014, now abandoned.

(60) Provisional application No. 62/029,038, filed on Jul. 25, 2014, provisional application No. 62/001,889, filed on May 22, 2014, provisional application No. 62/001,909, filed on May 22, 2014, provisional application No. 62/001,902, filed on May 22, 2014, provisional application No. 61/965,040, filed on Jan. 16, 2014, provisional application No. 61/875,276, filed on Sep. 9, 2013.

(51) Int. Cl.
| | | |
|---|---|---|
| *C12Q 1/6883* | (2018.01) | |
| *G16H 50/30* | (2018.01) | |
| *G16B 25/00* | (2019.01) | |
| *G16B 40/00* | (2019.01) | |
| *G01N 33/68* | (2006.01) | |
| *G06F 19/00* | (2018.01) | |
| *C12Q 1/6881* | (2018.01) | |
| *G16H 20/40* | (2018.01) | |

(52) U.S. Cl.
CPC ......... *C12Q 1/6883* (2013.01); *C12Q 1/6881* (2013.01); *G01N 33/6893* (2013.01); *G06F 19/3481* (2013.01); *G16B 25/00* (2019.02); *G16B 40/00* (2019.02); *G16H 20/40* (2018.01); *G16H 50/30* (2018.01); *C12Q 2537/165* (2013.01); *C12Q 2600/112* (2013.01); *C12Q 2600/118* (2013.01); *C12Q 2600/136* (2013.01); *C12Q 2600/158* (2013.01); *C12Q 2600/16* (2013.01); *G01N 2800/245* (2013.01); *Y02A 90/26* (2018.01)

(58) Field of Classification Search
None
See application file for complete search history.

(56) References Cited

U.S. PATENT DOCUMENTS

| | | | | |
|---|---|---|---|---|
| 2010/0233716 A1* | 9/2010 | Saint-Mezard | ...... | C12Q 1/6883 435/6.17 |
| 2016/0348174 A1* | 12/2016 | Sarwal | ................ | C12Q 1/6883 |

* cited by examiner

*Primary Examiner* — Channing S Mahatan
(74) *Attorney, Agent, or Firm* — Hugh Wang; Thomas Fitting

(57) ABSTRACT

Disclosed herein are methods of detecting, predicting or monitoring a status or outcome of a transplant in a transplant recipient.

31 Claims, 7 Drawing Sheets

METHODS AND SYSTEMS FOR ANALYSIS OF ORGAN TRANSPLANTATION

CROSS REFERENCE TO RELATED APPLICATIONS

This application is a continuation of U.S. application Ser. No. 14/481,167, filed Sep. 9, 2014, which claims the benefit of U.S. Provisional Application No. 61/875,276 filed on Sep. 9, 2013, U.S. Provisional Application No. 61/965,040 filed on Jan. 16, 2014, U.S. Provisional Application No. 62/001,889 filed on May 22, 2014, U.S. Provisional Application No. 62/029,038 filed on Jul. 25, 2014, U.S. Provisional Application No. 62/001,909 filed on May 22, 2014, and U.S. Provisional Application No. 62/001,902 filed on May 22, 2014, all of which are incorporated herein by reference in their entireties.

STATEMENT OF GOVERNMENT SUPPORT

This invention was made with government support under grant Numbers AI052349, AI063603, and AI084146 awarded by the National Institutes of Health. The government has certain rights in the invention.

BACKGROUND

The current method for detecting organ rejection in a patient is a biopsy of the transplanted organ. However, organ biopsy results can be inaccurate, particularly if the area biopsied is not representative of the health of the organ as a whole (e.g., as a result of sampling error). There can be significant differences between individual observers when they read the same biopsies independently and these discrepancies are particularly an issue for complex histologies that can be challenging for clinicians. Biopsies, especially surgical biopsies, can also be costly and pose significant risks to a patient. In addition, the early detection of rejection of a transplant organ may require serial monitoring by obtaining multiple biopsies, thereby multiplying the risks to the patients, as well as the associated costs.

Transplant rejection is a marker of ineffective immunosuppression and ultimately if it cannot be resolved, a failure of the chosen therapy. The fact that 50% of kidney transplant patients will lose their grafts by ten years post transplant reveals the difficulty of maintaining adequate and effective longterm immunosuppression. There is a need to develop a minimally invasive, objective metric for detecting, identifying and tracking transplant rejection. In particular, there is a need to develop a minimally invasive metric for detecting, identifying and tracking transplant rejection in the setting of a confounding diagnosis, such as acute dysfunction with no rejection. This is especially true for identifying the rejection of a transplanted kidney. For example, elevated creatinine levels in a kidney transplant recipient may indicate either that the patient is undergoing an acute rejection or acute dysfunction without rejection. A minimally-invasive test that is capable of distinguishing between these two conditions would therefore be extremely valuable and would diminish or eliminate the need for costly, invasive biopsies.

SUMMARY

The methods and systems disclosed herein may be used for detecting or predicting a condition of a transplant recipient (e.g., acute transplant rejection, acute dysfunction without rejection, subclinical acute rejection, hepatitis C virus recurrence, etc.). In some aspects, a method for detecting or predicting a condition of a transplant recipient comprises a) obtaining a sample, wherein the sample comprises one or more gene expression products from the transplant recipient; b) performing an assay to determine an expression level of the one or more gene expression products from the transplant recipient; and c) detecting or predicting the condition of the transplant recipient by applying an algorithm to the expression level determined in step (b), wherein the algorithm is a classifier capable of distinguishing between at least two conditions that are not normal conditions, and wherein one of the at least two conditions is transplant rejection or transplant dysfunction. In another embodiment, a method for detecting or predicting a condition of a transplant recipient comprises a) obtaining a sample, wherein the sample comprises one or more gene expression products from the transplant recipient; b) performing an assay to determine an expression level of the one or more gene expression products from the transplant recipient; and c) detecting or predicting the condition of the transplant recipient by applying an algorithm to the expression level determined in step (b), wherein the algorithm is a classifier capable of distinguishing between at least two conditions that are not normal conditions, and wherein one of the at least two conditions is transplant rejection. In another embodiment, a method for detecting or predicting a condition of a transplant recipient comprises a) obtaining a sample, wherein the sample comprises one or more gene expression products from the transplant recipient; b) performing an assay to determine an expression level of the one or more gene expression products from the transplant recipient; and c) detecting or predicting the condition of the transplant recipient by applying an algorithm to the expression level determined in step (b), wherein the algorithm is a classifier capable of distinguishing between at least two conditions that are not normal conditions, and wherein one of the at least two conditions is transplant dysfunction. In some cases, the transplant recipient is a kidney transplant recipient. In some cases, the transplant recipient is a liver transplant recipient.

In some embodiments, a method of detecting or predicting a condition of a transplant recipient comprises: a) obtaining a sample, wherein the sample comprises one or more gene expression products from the transplant recipient; b) performing an assay to determine an expression level of the one or more gene expression products from the transplant recipient; and c) detecting or predicting the condition of the transplant recipient by applying an algorithm to the expression level determined in step (b), wherein the algorithm is capable of distinguishing between acute rejection and transplant dysfunction with no rejection. In some cases, the transplant dysfunction with no rejection is acute transplant dysfunction with no rejection. In some cases, the transplant recipient is a kidney transplant recipient. In some cases, the transplant recipient is a liver transplant recipient.

In an embodiment, a method of detecting or predicting a condition of a transplant recipient comprises: a) obtaining a sample, wherein the sample comprises five or more gene expression products from the transplant recipient; b) an assay to determine an expression level of the five or more gene expression products from the transplant recipient, wherein the five or more gene expression products correspond to five or more genes listed in Table 1a, 1b, 1c, or 1d, or any combination thereof; and c) detecting or predicting the condition of the transplant recipient based on the expression level determined in step (b). In another embodiment, a method of detecting or predicting a condition of a transplant recipient comprises: a) obtaining a sample, wherein the sample comprises five or more gene expression products from the transplant recipient; b) an assay to determine an expression level of the five or more gene expression products from the transplant recipient, wherein the five or more gene expression products correspond to five or more genes listed in Table 1a; and c) detecting or predicting the condition of the transplant recipient based on the expression level determined in step (b). In another embodiment, a method of detecting or predicting a condition of a transplant recipient comprises: a) obtaining a sample, wherein the sample comprises five or more gene expression products from the transplant recipient; b) an assay to determine an expression level of the five or more gene expression products from the transplant recipient, wherein the five or more gene expression products correspond to five or more genes listed in Table 1a, 1b, 1c, or 1d, in any combination; and c) detecting or predicting the condition of the transplant recipient based on the expression level determined in step (b). In another embodiment, a method of detecting or predicting a condition of a transplant recipient comprises: a) obtaining a sample, wherein the sample comprises five or more gene expression products from the transplant recipient; b) an assay to determine an expression level of the five or more gene expression products from the transplant recipient, wherein the five or more gene expression products correspond to five or more genes listed in Table 1a, 1b, 1c, 1d, 8, 9, 10b, 12b, 14b, 16b, 17b, or 18b, in any combination; and c) detecting or predicting the condition of the transplant recipient based on the expression level determined in step (b). In some cases, the transplant recipient is a kidney transplant recipient.

In an embodiment, a method of detecting or predicting a condition of a transplant recipient comprises: a) obtaining a sample, wherein the sample comprises one or more gene expression products from the transplant recipient; b) performing an assay to determine an expression level of the one or more gene expression products from the transplant recipient; and c) detecting or predicting the condition of the transplant recipient by applying an algorithm to the expression level determined in step (b), wherein the algorithm is a three-way classifier capable of distinguishing between at least three conditions, and wherein one of the at least three conditions is transplant rejection. In some embodiments, one of the at least three conditions is normal transplant function. In some embodiments, one of the at least three conditions is transplant dysfunction. In some embodiments, the transplant dysfunction is transplant dysfunction with no rejection. In some cases, the transplant dysfunction with no rejection is acute transplant dysfunction with no rejection. In another embodiment, the method disclosed herein further comprises providing or terminating a treatment for the transplant recipient based on the detected or predicted condition of the transplant recipient.

In another aspect, a method of diagnosing, predicting or monitoring a status or outcome of a transplant in a transplant recipient comprises: a) determining a level of expression of one or more genes in a sample from a transplant recipient, wherein the level of expression is determined by RNA sequencing; and b) diagnosing, predicting or monitoring a status or outcome of a transplant in the transplant recipient.

In another aspect, a method disclosed herein comprises the steps of: a) determining a level of expression of one or more genes in a sample from a transplant recipient; b) normalizing the expression level data from step (a) using a frozen robust multichip average (fRMA) algorithm to produce normalized expression level data; c) producing one or more classifiers based on the normalized expression level data from step (b); and d) diagnosing, predicting or monitoring a status or outcome of a transplant in the transplant recipient based on the one or more classifiers from step (c). In another aspect, a method disclosed herein comprises the steps of: a) determining a level of expression of a plurality of genes in a sample from a transplant recipient; and b) classifying the sample by applying an algorithm to the expression level data from step (a), wherein the algorithm is validated by a combined analysis of a sample with an unknown phenotype and a subset of a cohort with known phenotypes.

In another aspect, the methods disclosed herein have an error rate of less than about 40%. In some embodiments, the method has an error rate of less than about 40%, 35%, 30%, 25%, 20%, 15%, 10%, 5%, 3%, 2%, or 1%. For example, the method has an error rate of less than about 10%. In some embodiments, the methods disclosed herein have an accuracy of at least about 60%, 65%, 70%, 75%, 80%, 85%, 90%, 95%, or 99%. For example, the method has an accuracy of at least about 70%. In some embodiments, the methods disclosed herein have a sensitivity of at least about 60%, 65%, 70%, 75%, 80%, 85%, 90%, 95%, or 99%. For example, the method has a sensitivity of at least about 80%. In some embodiments, the methods disclosed herein have a positive predictive value of at least about 60%, 65%, 70%, 75%, 80%, 85%, 90%, 95%, or 99%. In some embodiments, the methods disclosed herein have a negative predictive value of at least about 60%, 65%, 70%, 75%, 80%, 85%, 90%, 95%, or 99%.

In some embodiments, the gene expression products described herein are RNA (e.g., mRNA). In some embodiments, the gene expression products are polypeptides. In some embodiments, the gene expression products are DNA complements of RNA expression products from the transplant recipient.

In an embodiment, the algorithm described herein is a trained algorithm. In another embodiment, the trained algorithm is trained with gene expression data from biological samples from at least three different cohorts. In another embodiment, the trained algorithm comprises a linear classifier. In another embodiment, the linear classifier comprises one or more linear discriminant analysis, Fisher's linear discriminant, Naïve Bayes classifier, Logistic regression, Perceptron, Support vector machine (SVM) or a combination thereof. In another embodiment, the algorithm comprises a Diagonal Linear Discriminant Analysis (DLDA) algorithm. In another embodiment, the algorithm comprises a Nearest Centroid algorithm. In another embodiment, the algorithm comprises a Random Forest algorithm or statistical bootstrapping. In another embodiment, the algorithm comprises a Prediction Analysis of Microarrays (PAM) algorithm. In another embodiment, the algorithm is not validated by a cohort-based analysis of an entire cohort. In another embodiment, the algorithm is validated by a combined analysis with an unknown phenotype and a subset of a cohort with known phenotypes.

In another aspect, the one or more gene expression products comprises five or more gene expression products with different sequences. In another embodiment, the five or more gene expression products correspond to 200 genes or less. In another embodiment, the five or more gene expression products correspond to less than (or at most) 200 genes listed in Table 1c. In another embodiment, the five or more gene expression products correspond to less than (or at most) 200 genes listed in Table 1a. In another embodiment, the five or more gene expression products correspond to less than (or at most) 200 genes listed in Table 1a, 1b, 1c, or 1d, in any combination. In another embodiment, the five or more gene expression products correspond to less than about 200 genes listed in Table 1a, 1b, 1c, 1d, 8, 9, 10b, 12b, 14b, 16b, 17b, or 18b, in any combination. In another embodiment, the five or more gene expression products correspond to less than or equal to 500 genes, to less than or equal to 400 genes, to less than or equal to 300 genes, to less than or equal to 250 genes, to less than or equal to 200 genes, to less than or equal to 150 genes, to less than or equal to 100 genes, to less than or equal to genes, to less than or equal to 80 genes, to less than or equal to 50 genes, to less than or equal to 40 genes, to less than or equal to genes, to less than or equal to 25 genes, to less than or equal to 20 genes, at most 15 genes, or to less than or equal to 10 genes listed in Table 1a, 1b, 1c, 1d, 8, 9, 10b, 12b, 14b, 16b, 17b, or 18b, in any combination.

In one aspect, the biological samples are differentially classified based on one or more clinical features. For example, the one or more clinical features comprise status or outcome of a transplanted organ.

In another aspect, a three-way classifier is generated, in part, by comparing two or more gene expression profiles from two or more control samples. In another embodiment, the two or more control samples are differentially classified as acute rejection, acute dysfunction no rejection, or normal transplant function. In another embodiment, the two or more gene expression profiles from the two or more control samples are normalized. In another embodiment, the two or more gene expression profiles are not normalized by quantile normalization. In another embodiment, the two or more gene expression profiles from the two or more control samples are normalized by frozen multichip average (fRMA). In another embodiment, the three-way classifier is generated by creating multiple computational permutations and cross validations using a control sample set. In some cases, a four-way classifier is used instead or in addition to a three-way classifier.

In another aspect, the sample is a blood sample or is derived from a blood sample. In another embodiment, the blood sample is a peripheral blood sample. In another embodiment, the blood sample is a whole blood sample. In another embodiment, the sample does not comprise tissue from a biopsy of a transplanted organ of the transplant recipient. In another embodiment, the sample is not derived from tissue from a biopsy of a transplanted organ of the transplant recipient.

In another aspect, the assay is a microarray, SAGE, blotting, RT-PCR, sequencing and/or quantitative PCR assay. In another embodiment, the assay is a microarray assay. In another embodiment, the microarray assay comprises the use of an Affymetrix Human Genome U133 Plus 2.0 GeneChip. In another embodiment, the mircroarray uses the Hu133 Plus 2.0 cartridge arrays plates. In another embodiment, the microarray uses the HT HG-U133+ PM array plates. In another embodiment, determining the assay is a sequencing assay. In another embodiment, the assay is a RNA sequencing assay. In another embodiment, the gene expression products correspond to five or more genes listed in Table 1c. In another embodiment, the gene expression products correspond to five or more genes listed in Table 1a. In another embodiment, the gene expression products correspond to five or more genes listed in Table 1a, 1b, 1c, or 1d, in any combination. In another embodiment, the gene expression products correspond to five or more genes listed in Table 1a, 1b, 1c, 1d, 8, 9, 10b, 12b, 14b, 16b, 17b, or 18b, in any combination.

In some embodiments, the transplant recipient has a serum creatinine level of at least 0.4 mg/dL, 0.6 mg/dL, 0.8 mg/dL, 1.0 mg/dL, 1.2 mg/dL, 1.4 mg/dL, 1.6 mg/dL, 1.8 mg/dL, 2.0 mg/dL, 2.2 mg/dL, 2.4 mg/dL, 2.6 mg/dL, 2.8 mg/dL, 3.0 mg/dL, 3.2 mg/dL, 3.4 mg/dL, 3.6 mg/dL, 3.8 mg/dL, or 4.0 mg/dL. For example, the transplant recipient has a serum creatinine level of at least 1.5 mg/dL. In another example, the transplant recipient has a serum creatinine level of at least 3 mg/dL.

In another aspect, the transplant recipient is a recipient of an organ or tissue. In some embodiments, the organ is an eye, lung, kidney, heart, liver, pancreas, intestines, or a combination thereof. In some embodiments, the transplant recipient is a recipient of tissue or cells comprising: stem cells, induced pluripotent stem cells, embryonic stem cells, amnion, skin, bone, blood, marrow, blood stem cells, platelets, umbilical cord blood, cornea, middle ear, heart valve, vein, cartilage, tendon, ligament, or a combination thereof. In preferred embodiments of any method described herein, the transplant recipient is a kidney transplant recipient. In other embodiments, the transplant recipient is a liver recipient.

In another aspect, this disclosure provides classifier probe sets for use in classifying a sample from a transplant recipient, wherein the classifier probe sets are specifically selected based on a classification system comprising two or more classes. In another embodiment, a classifier probe set for use in classifying a sample from a transplant recipient, wherein the classifier probe set is specifically selected based on a classification system comprising three or more classes. In another embodiment, at least two of the classes are selected from transplant rejection, transplant dysfunction with no rejection and normal transplant function. In another embodiment, three of the three or more classes are transplant rejection, transplant dysfunction with no rejection and normal transplant function. In some cases, the transplant dysfunction with no rejection is acute transplant dysfunction with no rejection.

In another aspect, a non-transitory computer-readable storage media disclosed herein comprises: a) a database, in a computer memory, of one or more clinical features of two or more control samples, wherein i) the two or more control samples are from two or more transplant recipients; and ii) the two or more control samples are differentially classified based on a classification system comprising three or more classes; b) a first software module configured to compare the one or more clinical features of the two or more control samples; and c) a second software module configured to produce a classifier set based on the comparison of the one or more clinical features. In another embodiment, at least two of the classes are selected from transplant rejection, transplant dysfunction with no rejection and normal transplant function. In another embodiment, all three classes are selected from transplant rejection, transplant dysfunction with no rejection and normal transplant function.

In another aspect, the storage media further comprising one or more additional software modules configured to classify a sample from a transplant recipient. In another embodiment, classifying the sample from the transplant recipient comprises a classification system comprising three or more classes. In another embodiment, at least two of the classes are selected from transplant rejection, transplant dysfunction with no rejection and normal transplant function. In another embodiment, at least three of the classes are transplant rejection, transplant dysfunction with no rejection and normal transplant function.

In another aspect, a system comprising: a) a digital processing device comprising an operating system configured to perform executable instructions and a memory device; b) a computer program including instructions executable by the digital processing device to classify a sample from a transplant recipient comprising: i) a software module configured to receive a gene expression profile of one or more genes from the sample from the transplant recipient; ii) a software module configured to analyze the gene expression profile from the transplant recipient; and iii) a software module configured to classify the sample from the transplant recipient based on a classification system comprising three or more classes. In another embodiment, at least one of the classes is selected from transplant rejection, transplant dysfunction with no rejection and normal transplant function. In another embodiment, at least two of the classes are selected from transplant rejection, transplant dysfunction with no rejection and normal transplant function. In another embodiment, all three of the classes are selected from transplant rejection, transplant dysfunction with no rejection and normal transplant function.

In another aspect, analyzing the gene expression profile from the transplant recipient comprises applying an algorithm. In another embodiment, analyzing the gene expression profile comprises normalizing the gene expression profile from the transplant recipient. In another embodiment, normalizing the gene expression profile does not comprise quantile normalization.

INCORPORATION BY REFERENCE

All publications and patent applications mentioned in this specification are herein incorporated by reference in their entireties to the same extent as if each individual publication or patent application was specifically and individually incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Overview

The present disclosure provides novel methods for characterizing and/or analyzing samples, and related kits, compositions and systems, particularly in a minimally invasive manner. Methods of classifying one or more samples from one or more subjects are provided, as well as methods of determining, predicting and/or monitoring an outcome or status of an organ transplant, and related kits, compositions and systems. The methods, kits, compositions, and systems provided herein are particularly useful for distinguishing between two or more conditions or disorders associated with a transplanted organ or tissue. For example, they may be used to distinguish between acute transplant rejection (AR), acute dysfunction with no rejection (ADNR), and normally functioning transplants (TX). Often, a three-way analysis or classifier is used in the methods provided herein.

This disclosure may be particularly useful for kidney transplant recipients with elevated serum creatinine levels, since elevated creatinine may be indicative of AR or ADNR. The methods provided herein may inform the treatment of such patiecants and assist with medical decisions such as whether to continue or change immunosuppressive therapies. In some cases, the methods provided herein may inform decisions as to whether to increase immunosuppression to treat immune-mediated rejection if detected or to decrease immunosuppression (e.g., to protect the patient from unintended toxicities of immunosuppressive drugs when the testing demonstrates more immunosuppression is not required). The methods disclosed herein (e.g., serial blood monitoring for rejection) may allow clinicians to make a change in an immunosuppression regimen (e.g., an increase, decrease or other modification in immunosuppression) and then follow the impact of the change on the blood profile for rejection as a function of time for each individual patient through serial monitoring of a bodily fluid, such as by additional blood drawings.

Figure 1:
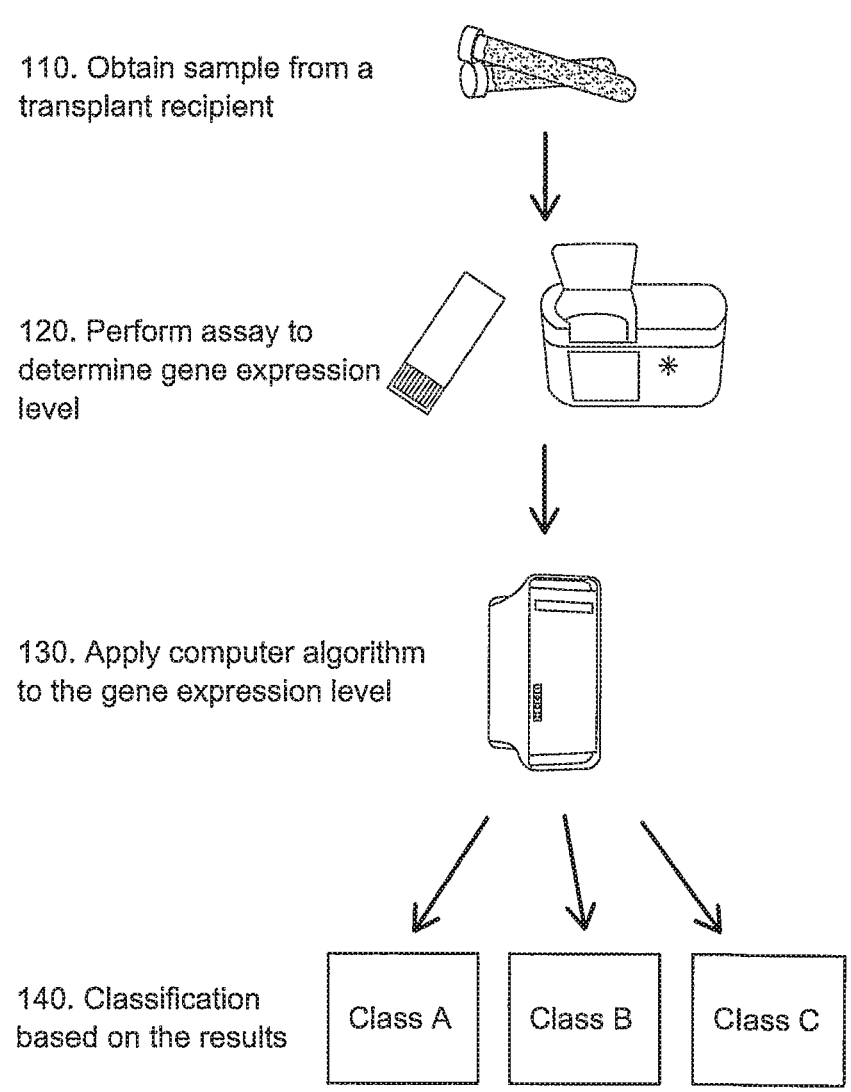
FIG. 1 shows a schematic overview of certain methods in the disclosure.

An overview of certain methods in the disclosure is provided in FIG. 1. In some instances, a method comprises obtaining a sample from a transplant recipient in a minimally invasive manner (110), such as via a blood draw, urine capture, saliva sample, throat culture, etc. The sample may comprise gene expression products (e.g., polypeptides, RNA, mRNA isolated from within cells or a cell-free source) associated with the status of the transplant (e.g., AR, ADNR, normal transplant function, etc.). In some instances, the method may involve reverse-transcribing RNA within the sample to obtain cDNA that can be analyzed using the methods described herein. The method may also comprise assaying the level of the gene expression products (or the corresponding DNA) using methods such as microarray or sequencing technology (120). The method may also comprise applying an algorithm to the assayed gene expression levels (130), wherein the algorithm is capable of distinguishing signatures for two or more transplantation conditions (e.g., AR, ADNR, TX, SCAR, CAN/IFTA, etc.) such as two or more non-normal transplant conditions (e.g., AR vs ADNR). Often, the algorithm is a trained algorithm obtained by the methods provided herein. In some instances, the algorithm is a three-way classifier and is capable of performing multi-class classification of the sample (140). The method may further comprise detecting, diagnosing, predicting, or monitoring the condition (e.g., AR, ADNR, TX, SCAR, CAN/IFTA etc.) of the transplant recipient. The methods may further comprise continuing, stopping or changing a therapeutic regimen based on the results of the assays described herein.

The methods, systems, kits and compositions provided herein may also be used to generate or validate an algorithm capable of distinguishing between at least two conditions of a transplant recipient (e.g., AR, ADNR, TX, SCAR, CAN/IFTA, etc.). The algorithm may be produced based on gene expression levels in various cohorts or sub-cohorts described herein.

Figure 2:
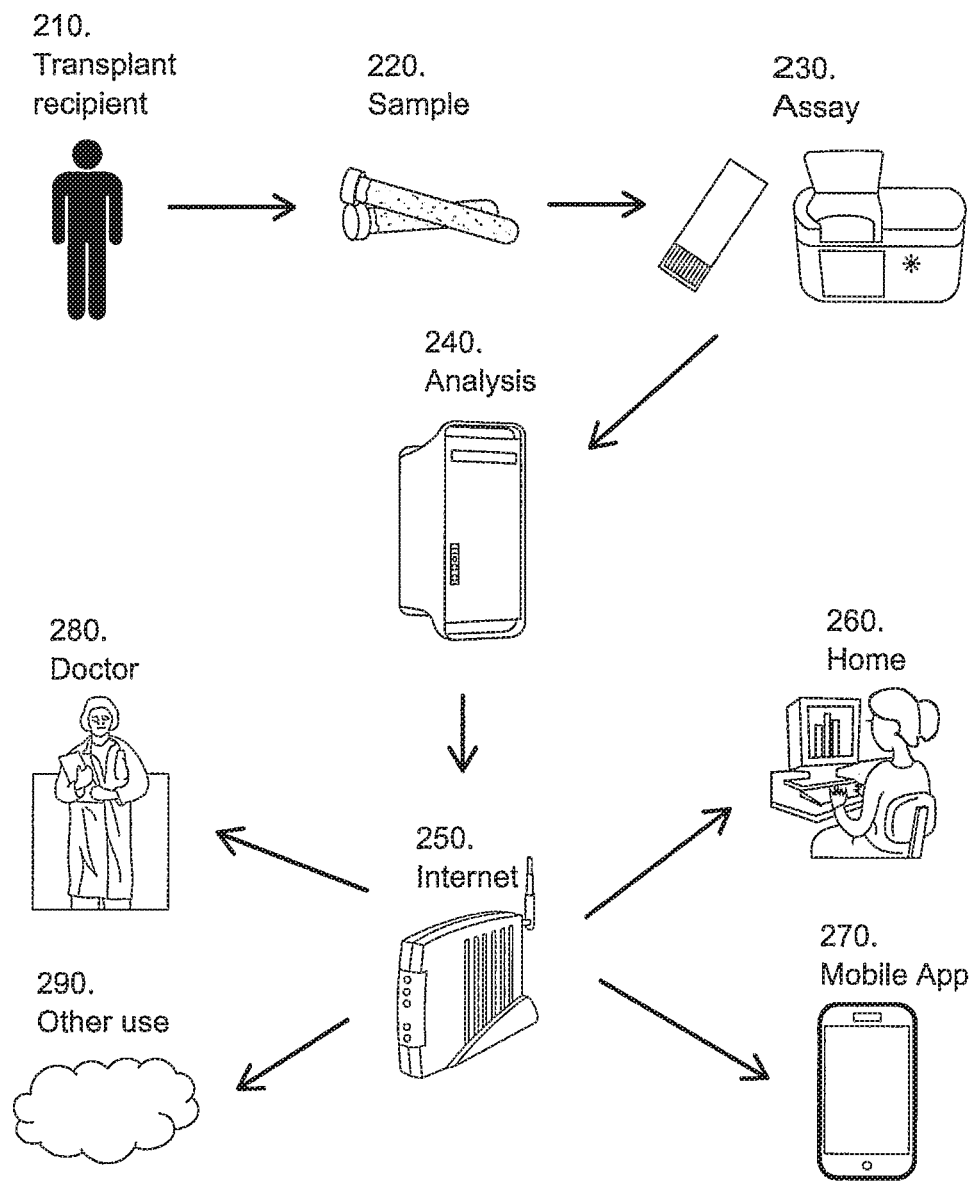
FIG. 2 shows a schematic overview of certain methods of acquiring samples, analyzing results, transmitting reports over a computer network.

The methods, systems, kits and compositions provided herein may also be capable of generating and transmitting results through a computer network. As shown in FIG. 2, a sample (220) is first collected from a subject (e.g. transplant recipient, 210). The sample is assayed (230) and gene expression products are generated. A computer system (240) is used in analyzing the data and making classification of the sample. The result is capable of being transmitted to different types of end users via a computer network (250). In some instances, the subject (e.g. patient) may be able to access the result by using a standalone software and/or a web-based application on a local computer capable of accessing the internet (260). In some instances, the result can be accessed via a mobile application (270) provided to a mobile digital processing device (e.g. mobile phone, tablet, etc.). In some instances, the result may be accessed by physicians and help them identify and track conditions of their patients (280). In some instances, the result may be used for other purposes (290) such as education and research.

Subjects

Often, the methods are used on a subject, preferably human, that is a transplant recipient. The methods may be used for detecting or predicting a condition of the transplant recipient such as acute rejection (AR), acute dysfunction with no rejection (ADNR), chronic allograft nephropathy (CAN), interstitial fibrosis and tubular atrophy (IF/TA), subclinical rejection acute rejection (SCAR), hepatitis C virus recurrence (HCV-R), etc. In some cases, the condition may be AR. In some cases, the condition may be ADNR. In some cases, the condition may be SCAR. In some cases, the condition may be transplant dysfunction. In some cases, the condition may be transplant dysfunction with no rejection. In some cases, the condition may be acute transplant dysfunction.

Typically, when the patient does not exhibit symptoms or test results of organ dysfunction or rejection, the transplant is considered a normal functioning transplant (TX: Transplant eXcellent). An unhealthy transplant recipient may exhibit signs of organ dysfunction and/or rejection (e.g., an increasing serum creatinine). However, a subject (e.g., kidney transplant recipient) with subclinical rejection may have normal and stable organ function (e.g. normal creatinine level and normal eGFR). In these subjects, at the present time, rejection may be diagnosed histologically through a biopsy. A failure to recognize, diagnose and treat subclinical AR before significant tissue injury has occurred and the transplant shows clinical signs of dysfunction could be a major cause of irreversible organ damage. Moreover, a failure to recognize a chronic, subclinical immune-mediated organ damage and a failure to make appropriate changes in immunosuppressive therapy to restore a state of effective immunosuppression in that patient could contribute to late organ transplant failure. The methods disclosed herein can reduce or eliminate these and other problems associated with transplant rejection or failure.

Acute rejection (AR) occurs when transplanted tissue is rejected by the recipient's immune system, which damages or destroys the transplanted tissue unless immunosuppression is achieved. T-cells, B-cells and other immune cells as well as possibly antibodies of the recipient may cause the graft cells to lyse or produce cytokines that recruit other inflammatory cells, eventually causing necrosis of allograft tissue. In some instances, AR may be diagnosed by a biopsy of the transplanted organ. In the case of kidney transplant recipients, AR may be associated with an increase in serum creatinine levels. The treatment of AR may include using immunosuppressive agents, corticosteroids, polyclonal and monoclonal antibodies, engineered and naturally occurring biological molecules, and antiproliferatives. AR more frequently occurs in the first three to 12 months after transplantation but there is a continued risk and incidence of AR for the first five years post transplant and whenever a patient's immunosuppression becomes inadequate for any reason for the life of the transplant.

Acute dysfunction with no rejection (ADNR) is an abrupt decrease or loss of organ function without histological evidence of rejection from a transplant biopsy. Kidney transplant recipients with ADNR will often exhibit elevated creatinine levels. Unfortunately, the levels of kidney dysfunction based on serum creatinines are usually not significantly different between AR and ADNR subjects.

Another condition that can be associated with a kidney transplant is chronic allograft nephropathy (CAN), which is characterized by a gradual decline in kidney function and, typically, accompanied by high blood pressure and hematuria. Histopathology of patients with CAN is characterized by interstitial fibrosis, tubular atrophy, fibrotic intimal thickening of arteries and glomerulosclerosis typically described as IFTA. CAN/IFTA usually happens months to years after the transplant though increased amounts of IFTA can be present early in the first year post transplant in patients that have received kidneys from older or diseased donors or when early severe ischemia perfusion injury or other transplant injury occurs. CAN is a clinical phenotype characterized by a progressive decrease in organ transplant function. In contrast, IFTA is a histological phenotype currently diagnosed by an organ biopsy. In kidney transplants, interstitial fibrosis (IF) is usually considered to be present when the supporting connective tissue in the renal parenchyma exceeds 5% of the cortical area. Tubular atrophy (TA) refers to the presence of tubules with thick redundant basement membranes, or a reduction of greater than 50% in tubular diameter compared to surrounding non-atrophic tubules. In certain instances, finding interstitial fibrosis and tubular atrophy (IFTA) on the biopsy may be early indicators that predict the later organ dysfunction associated with the clinical phenotype of CAN. Immunologically, CAN/IFTA usually represents a failure of effective longterm immunosuppression and mechanistically it is immune-mediated chronic rejection (CR) and can involve both cell and antibody-mediated mechanisms of tissue injury as well as activation of complement and other blood coagulation mechanisms and can also involve inflammatory cytokine-mediated tissue activation and injury.

Subclinical rejection (SCAR) is generally a condition that is histologically identified as acute rejection but without concurrent functional deterioration. For kidney transplant recipients, subclinical rejection (SCAR) is histologically defined acute rejection that is characterized by tubulointerstitial mononuclear infiltration identified from a biopsy specimen, but without concurrent functional deterioration (variably defined as a serum creatinine not exceeding about 10%, 20% or 25% of baseline values). A SCAR subject typically shows normal and/or stable serum creatinine levels. SCAR is usually diagnosed through biopsies that are taken at a fixed time after transplantation (e.g. protocol biopsies or serial monitoring biopsies) which are not driven by clinical indications but rather by standards of care. SCAR may be subclassified by some into acute SCAR (SCAR) or a milder form called borderline SCAR (suspicious for acute rejection) based on the biopsy histology.

A subject therefore may be a transplant recipient that has, or is at risk of having a condition such as AR, ADNR, TX, CAN, IFTA, or SCAR. In some instances, a normal serum creatinine level and/or a normal estimated glomerular filtration rate (eGFR) may indicate healthy transplant (TX) or subclinical rejection (SCAR). For example, typical reference ranges for serum creatinine are 0.5 to 1.0 mg/dL for women and 0.7 to 1.2 mg/dL for men, though typical kidney transplant patients have creatinines in the 0.8 to 1.5 mg/dL range for women and 1.0 to 1.9 mg/dL range for men. This may be due to the fact that most kidney transplant patients have a single kidney. In some instances, the trend of serum creatinine levels over time can be used to evaluate the recipient's organ function. This is why it may be important to consider both "normal" serum creatinine levels and "stable" serum creatinine levels in making clinical judgments, interpreting testing results, deciding to do a biopsy or making therapy change decisions including changing immunosuppressive drugs. For example, the transplant recipient may show signs of a transplant dysfunction or rejection as indicated by an elevated serum creatinine level and/or a decreased eGFR. In some instances, a transplant subject with a particular transplant condition (e.g., AR, ADNR, CAN, etc.) may have an increase of a serum creatinine level of at least 0.1 mg/dL, 0.2 mg/dL, 0.3 mg/dL, 0.4 mg/dL, 0.5 mg/dL, 0.6 mg/dL, 0.7 mg/dL 0.8 mg/dL, 0.9 mg/dL, 1.0 mg/dL, 1.1 mg/dL, 1.2 mg/dL, 1.3 mg/dL, 1.4 mg/dL, 1.5 mg/dL, 1.6 mg/dL, 1.7 mg/dL, 1.8 mg/dL, 1.9 mg/dL, 2.0 mg/dL, 2.1 mg/dL, 2.2 mg/dL, 2.3 mg/dL, 2.4 mg/dL, 2.5 mg/dL, 2.6 mg/dL, 2.7 mg/dL, 2.8 mg/dL, 2.9 mg/dL, 3.0 mg/dL, 3.1 mg/dL, 3.2 mg/dL, 3.3 mg/dL, 3.4 mg/dL, 3.5 mg/dL, 3.6 mg/dL, 3.7 mg/dL, 3.8 mg/dL, 3.9 mg/dL, or 4.0 mg/dL. In some instances, a transplant subject with a certain transplant condition (e.g., AR, ADNR, CAN, etc.) may have an increase of a serum creatinine level of at least 10%, 20%, 30%, 40%, 50%, 60%, 70%, 80%, 90%, or 100% from baseline. In some instances, a transplant subject with a certain transplant condition (e.g., AR, ADNR, CAN, etc.) may have an increase of a serum creatinine level of at least 1-fold, 2-fold, 3-fold, 4-fold, 5-fold, 6-fold, 7-fold, 8-fold, 9-fold, or 10-fold from baseline. In some cases, the increase in serum creatinine (e.g., any increase in the concentration of serum creatinine described herein) may occur over about 0.25 days, 0.5 days, 0.75 days, 1 day, 1.25 days, 1.5 days, 1.75 days, 2.0 days, 3.0 days, 4.0 days, 5.0 days, 6.0 days, 7.0 days, 8.0 days, 9.0 days, 10.0 days, 15 days, 30 days, 1 month, 2 months, 3 months, 4 months, 5 months, or 6 months, or more. In some instances, a transplant subject with a particular transplant condition (e.g., AR, ADNR, CAN, etc.) may have a decrease of a eGFR of at least 10%, 20%, 30%, 40%, 50%, 60%, 70%, 80%, 90%, or 100% from baseline. In some cases, the decrease in eGFR may occur over 0.25 days, 0.5 days, 0.75 days, 1 day, 1.25 days, 1.5 days, 1.75 days, 2.0 days, 3.0 days, 4.0 days, 5.0 days, 6.0 days, 7.0 days, 8.0 days, 9.0 days, 10.0 days, 15 days, 30 days, 1 month, 2 months, 3 months, 4 months, 5 months, or 6 months, or more. In some instances, diagnosing, predicting, or monitoring the status or outcome of a transplant or condition comprises determining transplant recipient-specific baselines and/or thresholds.

In some cases, the methods provided herein are used on a subject who has not yet received a transplant, such as a subject who is awaiting a tissue or organ transplant. In other cases, the subject is a transplant donor. In some cases, the subject has not received a transplant and is not expected to receive such transplant. In some cases, the subject may be a subject who is suffering from diseases requiring monitoring of certain organs for potential failure or dysfunction. In some cases, the subject may be a healthy subject.

A transplant recipient may be a recipient of a solid organ or a fragment of a solid organ. The solid organ may be a lung, kidney, heart, liver, pancreas, large intestine, small intestine, gall bladder, reproductive organ or a combination thereof. Preferably, the transplant recipient is a kidney transplant or allograft recipient. In some instances, the transplant recipient may be a recipient of a tissue or cell. The tissue or cell may be amnion, skin, bone, blood, marrow, blood stem cells, platelets, umbilical cord blood, cornea, middle ear, heart valve, vein, cartilage, tendon, ligament, nerve tissue, embryonic stem (ES) cells, induced pluripotent stem cells (IPSCs), stem cells, adult stem cells, hematopoietic stem cells, or a combination thereof.

The donor organ, tissue, or cells may be derived from a subject who has certain similarities or compatibilities with the recipient subject. For example, the donor organ, tissue, or cells may be derived from a donor subject who is age-matched, ethnicity-matched, gender-matched, blood-type compatible, or HLA-type compatible with the recipient subject.

The transplant recipient may be a male or a female. The transplant recipient may be patients of any age. For example, the transplant recipient may be a patient of less than about 10 years old. For example, the transplant recipient may be a patient of at least about 0, 5, 10, 20, 30, 40, 50, 60, 70, 80, 90, or 100 years old. The transplant recipient may be in utero. Often, the subject is a patient or other individual undergoing a treatment regimen, or being evaluated for a treatment regimen (e.g., immunosuppressive therapy). However, in some instances, the subject is not undergoing a treatment regimen. A feature of the graft tolerant phenotype detected or identified by the subject methods is that it is a phenotype which occurs without immunosuppressive therapy, e.g., it is present in a host that is not undergoing immunosuppressive therapy such that immunosuppressive agents are not being administered to the host.

In various embodiments, the subjects suitable for methods of the invention are patients who have undergone an organ transplant within 6 hours, 12 hours, 1 day, 2 days, 3 days, 4 days, 5 days, 10 days, 15 days, 20 days, 25 days, 1 month, 2 months, 3 months, 4 months, 5 months, 7 months, 9 months, 11 months, 1 year, 2 years, 4 years, 5 years, 10 years, 15 years, 20 years or longer of prior to receiving a classification disclosed herein (e.g., a classification obtained by the methods disclosed herein). Some of the methods further comprise changing the treatment regime of the patient responsive to the detecting, prognosing, diagnosing or monitoring step. In some of these methods, the subject can be one who has received a drug before performing the methods, and the change in treatment comprises administering an additional drug, administering a higher or lower dose of the same drug, stopping administration of the drug, or replacing the drug with a different drug or therapeutic intervention.

The subjects can include transplant recipients or donors or healthy subjects. The methods can be useful on human subjects who have undergone a kidney transplant although can also be used on subjects who have gone other types of transplant (e.g., heart, liver, lung, stem cell, etc.). The subjects may be mammals or non-mammals. The methods can be useful on non-humans who have undergone kidney or other transplant. Preferably, the subjects are a mammal, such as, a human, non-human primate (e.g., apes, monkeys, chimpanzees), cat, dog, rabbit, goat, horse, cow, pig, rodent, mouse, SCID mouse, rat, guinea pig, or sheep. Even more preferably, the subject is a human. The subject may be male or female; the subject may be a fetus, infant, child, adolescent, teenager or adult.

In some methods, species variants or homologs of these genes can be used in a non-human animal model. Species variants may be the genes in different species having greatest sequence identity and similarity in functional properties to one another. Many of such species variants human genes may be listed in the Swiss-Prot database.

Samples

Methods for detecting molecules (e.g., nucleic acids, proteins, etc.) in a subject who has received a transplant (e.g., organ transplant, tissue transplant, stem cell transplant) in order to detect, diagnose, monitor, predict, or evaluate the status or outcome of the transplant are described in this disclosure. In some cases, the molecules are circulating molecules. In some cases, the molecules are expressed in blood cells. In some cases, the molecules are cell-free circulating nucleic acids.

The methods, kits, and systems disclosed herein may be used to classify one or more samples from one or more subjects. A sample may be any material containing tissues, cells, nucleic acids, genes, gene fragments, expression products, polypeptides, exosomes, gene expression products, or gene expression product fragments of a subject to be tested. Methods for determining sample suitability and/or adequacy are provided. A sample may include but is not limited to, tissue, cells, or biological material from cells or derived from cells of an individual. The sample may be a heterogeneous or homogeneous population of cells or tissues. In some cases, the sample is from a single patient. In some cases, the method comprises analyzing multiple samples at once, e.g., via massively parallel sequencing.

The sample is preferably a bodily fluid. The bodily fluid may be sweat, saliva, tears, urine, blood, menses, semen, and/or spinal fluid. In preferred embodiments, the sample is a blood sample. The sample may comprise one or more peripheral blood lymphocytes. The sample may be a whole blood sample. The blood sample may be a peripheral blood sample. In some cases, the sample comprises peripheral blood mononuclear cells (PBMCs); in some cases, the sample comprises peripheral blood lymphocytes (PBLs). The sample may be a serum sample. In some instances, the sample is a tissue sample or an organ sample, such as a biopsy.

The methods, kits, and systems disclosed herein may comprise specifically detecting, profiling, or quantitating molecules (e.g., nucleic acids, DNA, RNA, polypeptides, etc.) that are within the biological samples. In some instances, genomic expression products, including RNA, or polypeptides, may be isolated from the biological samples. In some cases, nucleic acids, DNA, RNA, polypeptides may be isolated from a cell-free source. In some cases, nucleic acids, DNA, RNA, polypeptides may be isolated from cells derived from the transplant recipient.

The sample may be obtained using any method known to the art that can provide a sample suitable for the analytical methods described herein. The sample may be obtained by a non-invasive method such as a throat swab, buccal swab, bronchial lavage, urine collection, scraping of the skin or cervix, swabbing of the cheek, saliva collection, feces collection, menses collection, or semen collection. The sample may be obtained by a minimally-invasive method such as a blood draw. The sample may be obtained by venipuncture. In other instances, the sample is obtained by an invasive procedure including but not limited to: biopsy, alveolar or pulmonary lavage, or needle aspiration. The method of biopsy may include surgical biopsy, incisional biopsy, excisional biopsy, punch biopsy, shave biopsy, or skin biopsy. The sample may be formalin fixed sections. The method of needle aspiration may further include fine needle aspiration, core needle biopsy, vacuum assisted biopsy, or large core biopsy. In some embodiments, multiple samples may be obtained by the methods herein to ensure a sufficient amount of biological material. In some instances, the sample is not obtained by biopsy. In some instances, the sample is not a kidney biopsy.

Sample Data

The methods, kits, and systems disclosed herein may comprise data pertaining to one or more samples or uses thereof. The data may be expression level data. The expression level data may be determined by microarray, SAGE, sequencing, blotting, or PCR amplification (e.g. RT-PCR, quantitative PCR, etc.). In some cases, the expression level is determined by sequencing (e.g., RNA or DNA sequencing). The expression level data may be determined by microarray. Exemplary microarrays include but are not limited to the Affymetrix Human Genome U133 Plus 2.0 GeneChip or the HT HG-U133+ PM Array Plate.

In some cases, arrays (e.g., Illumina arrays) may use different probes attached to different particles or beads. In such arrays, the identity of which probe is attached to which particle or beads is usually determinable from an encoding system. The probes can be oligonucleotides. In some cases, the probes may comprise several match probes with perfect complementarity to a given target mRNA, optionally together with mismatch probes differing from the match probes. See, e.g., (Lockhart, et al., Nature Biotechnology 14:1675-1680 (1996); and Lipschutz, et al., Nature Genetics Supplement 21: 20-24, 1999). Such arrays may also include various control probes, such as a probe complementary to a housekeeping gene likely to be expressed in most samples. Regardless of the specifics of array design, an array generally contains one or more probes either perfectly complementary to a particular target mRNA or sufficiently complementary to the target mRNA to distinguish it from other mRNAs in the sample. The presence of such a target mRNA can be determined from the hybridization signal of such probes, optionally by comparison with mismatch or other control probes included in the array. Typically, the target bears a fluorescent label, in which case hybridization intensity can be determined by, for example, a scanning confocal microscope in photon counting mode. Appropriate scanning devices are described by e.g., U.S. Pat. Nos. 5,578,832, and 5,631,734. The intensity of labeling of probes hybridizing to a particular mRNA or its amplification product may provide a raw measure of expression level.

The data pertaining to the sample may be compared to data pertaining to one or more control samples, which may be samples from the same patient at different times. In some cases, the one or more control samples may comprise one or more samples from healthy subjects, unhealthy subjects, or a combination thereof. The one or more control samples may comprise one or more samples from healthy subjects, subjects suffering from transplant dysfunction with no rejection, subjects suffering from transplant rejection, or a combination thereof. The healthy subjects may be subjects with normal transplant function. The data pertaining to the sample may be sequentially compared to two or more classes of samples. The data pertaining to the sample may be sequentially compared to three or more classes of samples. The classes of samples may comprise control samples classified as being from subjects with normal transplant function, control samples classified as being from subjects suffering from transplant dysfunction with no rejection, control samples classified as being from subjects suffering from transplant rejection, or a combination thereof.

Biomarkers/Gene Expression Products

Biomarker refers to a measurable indicator of some biological state or condition. In some instances, a biomarker can be a substance found in a subject, a quantity of the substance, or some other indicator. For example, a biomarker may be the amount of RNA, mRNA, tRNA, miRNA, mitochondrial RNA, siRNA, polypeptides, proteins, DNA, cDNA and/or other gene expression products in a sample. In some instances, gene expression products may be proteins or RNA. In some instances, RNA may be an expression product of non-protein coding genes such as ribosomal RNA (rRNA), transfer RNA (tRNA), micro RNA (miRNA), or small nuclear RNA (snRNA) genes. In some instances, RNA may be messenger RNA (mRNA). In certain examples, a biomarker or gene expression product may be DNA complementary or corresponding to RNA expression products in a sample.

The methods, compositions and systems as described here also relate to the use of biomarker panels and/or gene expression products for purposes of identification, diagnosis, classification, treatment or to otherwise characterize various conditions of organ transplant comprising AR, ANDR, TX, IFTA, CAN, SCAR, hepatitis C virus recurrence (HCV-R). Sets of biomarkers and/or gene expression products useful for classifying biological samples are provided, as well as methods of obtaining such sets of biomarkers. Often, the pattern of levels of gene expression biomarkers in a panel (also known as a signature) is determined and then used to evaluate the signature of the same panel of biomarkers in a sample, such as by a measure of similarity between the sample signature and the reference signature. In some instances, biomarker panels or gene expression products may be chosen to distinguish acute rejection (AR) from transplant dysfunction with no acute rejection (ADNR) expression profiles. In some instances, biomarker panels or gene expression products may be chosen to distinguish acute rejection (AR) from normally functioning transplant (TX) expression profiles. In some instances, biomarker panels or gene expression products may be selected to distinguish acute dysfunction with no transplant rejection (ADNR) from normally functioning transplant (TX) expression profiles. In some instances, biomarker panels or gene expression products may be selected to distinguish transplant dysfunction from acute rejection (AR) expression profiles. In certain examples, this disclosure provides methods of reclassifying an indeterminate biological sample from subjects into a healthy, acute rejection or acute dysfunction no rejection categories, and related kits, compositions and systems.

The expression level may be normalized. In some instances, normalization may comprise quantile normalization. Normalization may comprise frozen robust multichip average (fRMA) normalization.

Determining the expression level may comprise normalization by frozen robust multichip average (fRMA). Determining the expression level may comprise reverse transcribing the RNA to produce cRNA.

The methods provided herein may comprise identifying a condition from one or more gene expression products from Table 1a, 1b, 1c, 1d, 8, 9, 10b, 12b, 14b, 16b, 17b, or 18b, in any combination. In some cases, AR of a kidney transplant (or other organ transplant) can be detected from one or more gene expression products from Table 1a, 1b, 1c, 1d, 8, 10b, or 12b, in any combination. In some cases, ADNR of a kidney transplant (or other organ transplant) can be detected from one or more gene expression products from Table 1a, 1b, 1c, 1d, 10b, or 12b, in any combination. In some cases, TX (or normal functioning) of a kidney transplant (or other organ transplant) can be detected from one or more gene expression products from Table 1a, 1b, 1c, 1d, 8, 9, 10b, 12b, or 14b, in any combination. In some cases, SCAR of kidney transplant (or other organ transplant) can be detected from one or more gene expression products from Table 8 or 9, in any combination. In some instances, AR of a liver transplant (or other organ transplant) can be detected from one or more gene expression products from Table 16b, 17b, or 18b, in any combination. In some instances, ADNR of liver can be detected from one or more gene expression products from Table 16b. In some cases, TX of liver can be detected from one or more gene expression products from Table 16b. In some cases, HCV of liver can be detected from one or more gene expression products from Table 17b or 18b, in any combination. In some cases, HCV+AR of liver can be detected from one or more gene expression products from Table 17b or 18b, in any combination.

The methods provided herein may also comprise identifying a condition from one or more gene expression products from a tissue biopsy sample. From example, AR of kidney biopsy can be detected from one or more gene expression products from Table 10b or 12b, in any combination. ADNR of kidney biopsy can be detected from one or more gene expression products from Table 10b or 12b, in any combination. CAN of kidney biopsy can be detected from one or more gene expression products from Table 12b or 14b, in any combination. TX of kidney biopsy can be detected from one or more gene expression products from Table 10b, 12b, or 14b, in any combination. AR of liver biopsy can be detected from one or more gene expression products from Table 18b. HCV of liver biopsy can be detected from one or more gene expression products from Table 18b. HCV+AR of liver biopsy can be detected from one or more gene expression products from Table 18b.

The gene expression product may be a peptide or RNA. At least one of the gene expression products may correspond to a gene found in Table 1a. The gene expression product may be a peptide or RNA. At least one of the gene expression products may correspond to a gene found in Table 1c. At least one of the gene expression products may correspond to a gene found in Table 1a, 1b, 1c or 1d, in any combination. At least one of the gene expression products may correspond to a gene found in Table 1a, 1b, 1c, 1d, 8, 9, 10b, 12b, 14b, 16b, 17b, or 18b, in any combination. The gene expression products may correspond to 1, 2, 3, 4, 5, 6, 7, 8, 9, 10, 11, 12, 13, 14, 15, 16, 17, 18, 19, 20 or more genes found in Table 1a. The gene expression products may correspond to 1, 2, 3, 4, 5, 6, 7, 8, 9, 10, 11, 12, 13, 14, 15, 16, 17, 18, 19, 20 or more genes found in Table 1c. The gene expression products may correspond to 1, 2, 3, 4, 5, 6, 7, 8, 9, 10, 11, 12, 13, 14, 15, 16, 17, 18, 19, 20 or more genes found in Table 1a, 1b, 1c, or 1d, in any combination. The gene expression products may correspond to 1, 2, 3, 4, 5, 6, 7, 8, 9, 10, 11, 12, 13, 14, 15, 16, 17, 18, 19, 20 or more genes found in Table 1a, 1b, 1c, 1d, 8, 9, 10b, 12b, 14b, 16b, 17b, or 18b, in any combination. The gene expression products may correspond to 10, 20, 30, 40, 50, 60, 70, 80, 90, 100, 110, 120, 130, 140, 150, 160, 170, 180, 190, 200 or more genes found in Table 1a. The gene expression products may correspond to 10, 20, 30, 40, 50, 60, 70, 80, 90, 100, 110, 120, 130, 140, 150, 160, 170, 180, 190, 200 or more genes found in Table 1c. The gene expression products may correspond to 10, 20, 30, 40, 50, 60, 70, 80, 90, 100, 110, 120, 130, 140, 150, 160, 170, 180, 190, 200 or more genes found in Table 1a, 1b, 1c, or 1d, in any combination. The gene expression products may correspond to 10, 20, 30, 40, 50, 60, 70, 80, 90, 100, 110, 120, 130, 140, 150, 160, 170, 180, 190, 200 or more genes found in Table 1a, 1b, 1c, 1d, 8, 9, 10b, 12b, 14b, 16b, 17b, or 18b, in any combination. The gene expression products may correspond to 10, 20, 30, 40, 50, 60, 70, 80, 90, 100, 110, 120, 130, 140, 150, 160, 170, 180, 190, 200 or less genes found in Table 1a. The gene expression products may correspond to 10, 20, 30, 40, 50, 60, 70, 80, 90, 100, 110, 120, 130, 140, 150, 160, 170, 180, 190, 200 or less genes found in Table 1c. The gene expression products may correspond to 10, 20, 30, 40, 50, 60, 70, 80, 90, 100, 110, 120, 130, 140, 150, 160, 170, 180, 190, 200 or less genes found in Table 1a, 1b, 1c, or 1d, in any combination. The gene expression products may correspond to 10, 20, 30, 40, 50, 60, 70, 80, 90, 100, 110, 120, 130, 140, 150, 160, 170, 180, 190, 200 or less genes found in Table 1a, 1b, 1c, 1d, 8, 9, 10b, 12b, 14b, 16b, 17b, or 18b, in any combination. The gene expression products may correspond to 100, 200, 300, 400, 500, 600, 700, 800, 900, 1000, 1100, 1200, 1300, 1400, 1500, 1600, 1700, 1800, 1900, 2000 or more genes found in Table 1a. The gene expression products may correspond to 100, 200, 300, 400, 500, 600, 700, 800, 900, 1000, 1100, 1200, 1300, 1400, 1500, 1600, 1700, 1800, 1900, 2000 or more genes found in Table 1c. The gene expression products may correspond to 100, 200, 300, 400, 500, 600, 700, 800, 900, 1000, 1100, 1200, 1300, 1400, 1500, 1600, 1700, 1800, 1900, 2000 or more genes found in Table 1a, 1b, 1c, or 1d, in any combination. The gene expression products may correspond to 100, 200, 300, 400, 500, 600, 700, 800, 900, 1000, 1100, 1200, 1300, 1400, 1500, 1600, 1700, 1800, 1900, 2000 or more genes found in Table 1a, 1b, 1c, 1d, 8, 9, 10b, 12b, 14b, 16b, 17b, or 18b, in any combination. The gene expression products may correspond to 10 or more genes found in Table 1a. The gene expression products may correspond to 10 or more genes found in Table 1c. The gene expression products may correspond to 10 or more genes found in Table 1a, 1b, 1c, or 1d, in any combination. The gene expression products may correspond to 10 or more genes found in Table 1a, 1b, 1c, 1d, 8, 9, 10b, 12b, 14b, 16b, 17b, or 18b, in any combination. The gene expression products may correspond to 25 or more genes found in Table 1a. The gene expression products may correspond to 25 or more genes found in Table 1c. The gene expression products may correspond to 25 or more genes found in Table 1a, 1b, 1c, or 1d, in any combination. The gene expression products may correspond to 25 or more genes found in Table 1a, 1b, 1c, 1d, 8, 9, 10b, 12b, 14b, 16b, 17b, or 18b, in any combination. The gene expression products may correspond to 50 or more genes found in Table 1a. The gene expression products may correspond to 50 or more genes found in Table 1c. The gene expression products may correspond to 50 or more genes found in Table 1a, 1b, 1c, or 1d, in any combination. The gene expression products may correspond to 50 or more genes found in Table 1a, 1b, 1c, 1d, 8, 9, 10b, 12b, 14b, 16b, 17b, or 18b, in any combination. The gene expression products may correspond to 100 or more genes found in Table 1a. The gene expression products may correspond to 100 or more genes found in Table 1c. The gene expression products may correspond to 100 or more genes found in Table 1a, 1b, 1c, or 1d, in any combination. The gene expression products may correspond to 100 or more genes found in Table 1a, 1b, 1c, 1d, 8, 9, 10b, 12b, 14b, 16b, 17b, or 18b, in any combination. The gene expression products may correspond to 200 or more genes found in Table 1a. The gene expression products may correspond to 200 or more genes found in Table 1c. The gene expression products may correspond to 200 or more genes found in Table 1a, 1b, 1c, or 1d in any combination. The gene expression products may correspond to 200 or more genes found in Table 1a, 1b, 1c, 1d, 8, 9, 10b, 12b, 14b, 16b, 17b, or 18b, in any combination.

At least a subset the gene expression products may correspond to the genes found in Table 1a. At least a subset the gene expression products may correspond to the genes found in Table 1c. At least a subset the gene expression products may correspond to the genes found in Table 1a, 1b, 1c, or 1d, in any combination. At least a subset the gene expression products may correspond to the genes found in Table 1a, 1b, 1c, 1d, 8, 9, 10b, 12b, 14b, 16b, 17b, or 18b, in any combination. At least about 1%, 2%, 3%, 4%, 5%, 6%, 7%, 8%, 9%, 10%, 11%, 12%, 13%, 14%, 15%, 16%, 17%, 18%, 19%, 20% or more of the gene expression products may correspond to the genes found in Table 1a. At least about 1%, 2%, 3%, 4%, 5%, 6%, 7%, 8%, 9%, 10%, 11%, 12%, 13%, 14%, 15%, 16%, 17%, 18%, 19%, 20% or more of the gene expression products may correspond to the genes found in Table 1c. At least about 1%, 2%, 3%, 4%, 5%, 6%, 7%, 8%, 9%, 10%, 11%, 12%, 13%, 14%, 15%, 16%, 17%, 18%, 19%, 20% or more of the gene expression products may correspond to the genes found in Table 1a, 1b, 1c, or 1d, in any combination. At least about 1%, 2%, 3%, 4%, 5%, 6%, 7%, 8%, 9%, 10%, 11%, 12%, 13%, 14%, 15%, 16%, 17%, 18%, 19%, 20% or more of the gene expression products may correspond to the genes found in Table 1a, 1b, 1c, 1d, 8, 9, 10b, 12b, 14b, 16b, 17b, or 18b, in any combination. At least about 10%, 15%, 20%, 25%, 30%, 35%, 40%, 45%, 50%, 55%, 60%, 65%, 70%, 75%, 80%, 85%, 90%, 95%, 97%, or 100% of the gene expression products may correspond to the genes found in Table 1a. At least about 10%, 15%, 20%, 25%, 30%, 35%, 40%, 45%, 50%, 55%, 60%, 65%, 70%, 75%, 80%, 85%, 90%, 95%, 97%, or 100% of the gene expression products may correspond to the genes found in Table 1c. At least about 10%, 15%, 20%, 25%, 30%, 35%, 40%, 45%, 50%, 55%, 60%, 65%, 70%, 75%, 80%, 85%, 90%, 95%, 97%, or 100% of the gene expression products may correspond to the genes found in Table 1a, 1b, 1c, or 1d, in any combination. At least about 10%, 15%, 20%, 25%, 30%, 35%, 40%, 45%, 50%, 55%, 60%, 65%, 70%, 75%, 80%, 85%, 90%, 95%, 97%, or 100% of the gene expression products may correspond to the genes found in Table 1a, 1b, 1c, 1d, 8, 9, 10b, 12b, 14b, 16b, 17b, or 18b, in any combination. At least about 5% of the gene expression products may correspond to the genes found in Table 1a. At least about 5% of the gene expression products may correspond to the genes found in Table 1c. At least about 5% of the gene expression products may correspond to the genes found in Table 1a, 1b, 1c, or 1d, in any combination. At least about 5% of the gene expression products may correspond to the genes found in Table 1a, 1b, 1c, 1d, 8, 9, 10b, 12b, 14b, 16b, 17b, or 18b, in any combination. At least about 10% of the gene expression products may correspond to the genes found in Table 1a. At least about 10% of the gene expression products may correspond to the genes found in Table 1c. At least about 10% of the gene expression products may correspond to the genes found in Table 1a, 1b, 1c, or 1d, in any combination. At least about 10% of the gene expression products may correspond to the genes found in Table 1a, 1b, 1c, 1d, 8, 9, 10b, 12b, 14b, 16b, 17b, or 18b, in any combination. At least about 25% of the gene expression products may correspond to the genes found in Table 1a. At least about 25% of the gene expression products may correspond to the genes found in Table 1c. At least about 25% of the gene expression products may correspond to the genes found in Table 1a, 1b, 1c, or 1d, in any combination. At least about 25% of the gene expression products may correspond to the genes found in Table 1a, 1b, 1c, 1d, 8, 9, 10b, 12b, 14b, 16b, 17b, or 18b, in any combination. At least about 30% of the gene expression products may correspond to the genes found in Table 1a. At least about 30% of the gene expression products may correspond to the genes found in Table 1c. At least about 30% of the gene expression products may correspond to the genes found in Table 1a, 1b, 1c, or 1d, in any combination. At least about 30% of the gene expression products may correspond to the genes found in Table 1a, 1b, 1c, 1d, 8, 9, 10b, 12b, 14b, 16b, 17b, or 18b, in any combination.

In another aspect, the invention provides arrays, which contain a support or supports bearing a plurality of nucleic acid probes complementary to a plurality of mRNAs fewer than 5000 in number. Typically, the plurality of mRNAs includes mRNAs expressed by at least five genes selected from Table 1a. In another embodiment, the plurality of mRNAs includes mRNAs expressed by at least five genes selected from Table 1c. The plurality of mRNAs may also include mRNAs expressed by at least five genes selected from Table 1a, 1b, 1c, or 1d, in any combination. The plurality of mRNAs may also include mRNAs expressed by at least five genes selected from Table 1a, 1b, 1c, 1d, 8, 9, 10b, 12b, 14b, 16b, 17b, or 18b, in any combination. In some embodiments, the plurality of mRNAs are fewer than 1000 or fewer than 100 in number. In some embodiments, the plurality of nucleic acid probes are attached to a planar support or to beads. In a related aspect, the invention provides arrays that contain a support or supports bearing a plurality of ligands that specifically bind to a plurality of proteins fewer than 5000 in number. The plurality of proteins typically includes at least five proteins encoded by genes selected from Table 1a. The plurality of proteins typically includes at least five proteins encoded by genes selected from Table 1c. The plurality of proteins typically includes at least five proteins encoded by genes selected from Table 1a, 1b, 1c, or 1d, in any combination. The plurality of proteins typically includes at least five proteins encoded by genes selected from Table 1a, 1b, 1c, 1d, 8, 9, 10b, 12b, 14b, 16b, 17b, or 18b, in any combination. In some embodiments, the plurality of proteins are fewer than 1000 or fewer than 100 in number. In some embodiments, the plurality of ligands are attached to a planar support or to beads. In some embodiments, the at least five proteins are encoded by genes selected from Table 1a. In some embodiments, the at least five proteins are encoded by genes selected from Table 1c. In some embodiments, the at least five proteins are encoded by genes selected from Table 1a, 1b, 1c, or 1d, in any combination. In some embodiments, the at least five proteins are encoded by genes selected from Table 1a, 1b, 1c, 1d, 8, 9, 10b, 12b, 14b, 16b, 17b, or 18b, in any combination. In some embodiments, the ligands are different antibodies that bind to different proteins of the plurality of proteins.

Methods, kits, and systems disclosed herein may have a plurality of genes associated with one or more biomarkers selected from gene expression products corresponding to genes listed in Table 1a. Methods, kits, and systems disclosed herein may have a plurality of genes associated with one or more biomarkers selected from gene expression products corresponding to genes listed in Table 1c. Methods, kits, and systems disclosed herein may also have a plurality of genes associated with one or more biomarkers selected from gene expression products corresponding to genes listed in Table 1a, 1b, 1c, or 1d, in any combination. Methods, kits, and systems disclosed herein may also have a plurality of genes associated with one or more biomarkers selected from gene expression products corresponding to genes listed in Table 1a, 1b, 1c, 1d, 8, 9, 10b, 12b, 14b, 16b, 17b, or 18b, in any combination. In some instances, there may be genes selected from 1, 2, 3, 4, 5, 6, 7, 8, 9, 10, 11, 12, 13, 14, 15 or 16 or more biomarker panels and can have from 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200 or more gene expression products from each biomarker panel, in any combination. In some instances, the biomarkers within each panel are interchangeable (modular). The plurality of biomarkers in all panels can be substituted, increased, reduced, or improved to accommodate the classification system described herein. In some embodiments, the set of genes combined give a specificity or sensitivity of greater than 70%, 75%, 80%, 85%, 86%, 87%, 88%, 89%, 90%, 91%, 92%, 93%, 94%, 95%, 96%, 97%, 98%, 99%, or 99.5%, or a positive predictive value or negative predictive value of at least 95%, 95.5%, 96%, 96.5%, 97%, 97.5%, 98%, 98.5%, 99%, 99.5% or more.

Classifiers may comprise 1, 2, 3, 4, 5, 6, 7, 8, 9, 10, 11, 12, 13, 14, 15, 16, 17, 18, 19, 20 biomarkers disclosed in Table 1a. Classifiers may comprise 1, 2, 3, 4, 5, 6, 7, 8, 9, 10, 11, 12, 13, 14, 15, 16, 17, 18, 19, 20 biomarkers disclosed in Table 1c. Classifiers may comprise 1, 2, 3, 4, 5, 6, 7, 8, 9, 10, 11, 12, 13, 14, 15, 16, 17, 18, 19, 20 biomarkers disclosed in Table 1a, 1b, 1c, or 1d, in any combination. Classifiers may comprise 1, 2, 3, 4, 5, 6, 7, 8, 9, 10, 11, 12, 13, 14, 15, 16, 17, 18, 19, 20 biomarkers disclosed in Table 1a, 1b, 1c, 1d, 8, 9, 10b, 12b, 14b, 16b, 17b, or 18b, in any combination. Classifiers may comprise 10, 20, 30, 40, 50, 60, 70, 80, 90, 100, 110, 120, 130, 140, 150, 160, 170, 180, 190, 200 biomarkers disclosed in Table 1a. Classifiers may comprise 10, 20, 30, 40, 50, 60, 70, 80, 90, 100, 110, 120, 130, 140, 150, 160, 170, 180, 190, 200 biomarkers disclosed in Table 1c. Classifiers may comprise 10, 20, 30, 40, 50, 60, 70, 80, 90, 100, 110, 120, 130, 140, 150, 160, 170, 180, 190, 200 biomarkers disclosed in Table 1a, 1b, 1c, or 1d, in any combination. Classifiers may comprise 10, 20, 30, 40, 50, 60, 70, 80, 90, 100, 110, 120, 130, 140, 150, 160, 170, 180, 190, 200 biomarkers disclosed in Table 1a, 1b, 1c, 1d, 8, 9, 10b, 12b, 14b, 16b, 17b, or 18b, in any combination. Classifiers may comprise 100, 200, 300, 400, 500, 600, 700, 800, 900, 1000, 1100, 1200, 1300, 1400, 1500, 1600, 1700, 1800, 1900, 2000 biomarkers disclosed in Table 1a. Classifiers may comprise 100, 200, 300, 400, 500, 600, 700, 800, 900, 1000, 1100, 1200, 1300, 1400, 1500, 1600, 1700, 1800, 1900, 2000 biomarkers disclosed in Table 1c. Classifiers may comprise 100, 200, 300, 400, 500, 600, 700, 800, 900, 1000, 1100, 1200, 1300, 1400, 1500, 1600, 1700, 1800, 1900, 2000 biomarkers disclosed in Table 1a, 1b, 1c, or 1d, in any combination. Classifiers may comprise 100, 200, 300, 400, 500, 600, 700, 800, 900, 1000, 1100, 1200, 1300, 1400, 1500, 1600, 1700, 1800, 1900, 2000 biomarkers disclosed in Table 1a, 1b, 1c, 1d, 8, 9, 10b, 12b, 14b, 16b, 17b, or 18b, in any combination.

At least about 1%, 2%, 3%, 4%, 5%, 6%, 7%, 8%, 9%, 10%, 11%, 12%, 13%, 14%, 15%, 16%, 17%, 18%, 19%, or 20% of the biomarkers from the classifiers may be selected from biomarkers disclosed in Table 1a. At least about 1%, 2%, 3%, 4%, 5%, 6%, 7%, 8%, 9%, 10%, 11%, 12%, 13%, 14%, 15%, 16%, 17%, 18%, 19%, or 20% of the biomarkers from the classifiers may be selected from biomarkers disclosed in Table 1c. At least about 1%, 2%, 3%, 4%, 5%, 6%, 7%, 8%, 9%, 10%, 11%, 12%, 13%, 14%, 15%, 16%, 17%, 18%, 19%, or 20% of the biomarkers from the classifiers may be selected from biomarkers disclosed in Table 1a, 1b, 1c, or 1d, in any combination. At least about 1%, 2%, 3%, 4%, 5%, 6%, 7%, 8%, 9%, 10%, 11%, 12%, 13%, 14%, 15%, 16%, 17%, 18%, 19%, or 20% of the biomarkers from the classifiers may be selected from biomarkers disclosed in Table 1a, 1b, 1c, 1d, 8, 9, 10b, 12b, 14b, 16b, 17b, or 18b, in any combination. At least about 22%, 25%, 27%, 30%, 32%, 35%, 37%, 40%, 42%, 45%, 47%, 50%, 52%, 55%, 57%, 60%, 62%, 65%, 67%, 70%, 72%, 75%, 77%, 80%, 82%, 85%, 87%, 90%, 92%, 95%, or 97% of the biomarkers from the classifiers may be selected from biomarkers disclosed in Table 1a. At least about 22%, 25%, 27%, 30%, 32%, 35%, 37%, 40%, 42%, 45%, 47%, 50%, 52%, 55%, 57%, 60%, 62%, 65%, 67%, 70%, 72%, 75%, 77%, 80%, 82%, 85%, 87%, 90%, 92%, 95%, or 97% of the biomarkers from the classifiers may be selected from biomarkers disclosed in Table 1c. At least about 22%, 25%, 27%, 30%, 32%, 35%, 37%, 40%, 42%, 45%, 47%, 50%, 52%, 55%, 57%, 60%, 62%, 65%, 67%, 70%, 72%, 75%, 77%, 80%, 82%, 85%, 87%, 90%, 92%, 95%, or 97% of the biomarkers from the classifiers may be selected from biomarkers disclosed in Table 1a, 1b, 1c, or 1d, in any combination. At least about 22%, 25%, 27%, 30%, 32%, 35%, 37%, 40%, 42%, 45%, 47%, 50%, 52%, 55%, 57%, 60%, 62%, 65%, 67%, 70%, 72%, 75%, 77%, 80%, 82%, 85%, 87%, 90%, 92%, 95%, or 97% of the biomarkers from the classifiers may be selected from biomarkers disclosed in Table 1a, 1b, 1c, 1d, 8, 9, 10b, 12b, 14b, 16b, 17b, or 18b, in any combination. At least about 3% of the biomarkers from the classifiers may be selected from biomarkers disclosed in Table 1a. At least about 3% of the biomarkers from the classifiers may be selected from biomarkers disclosed in Table 1c. At least about 3% of the biomarkers from the classifiers may be selected from biomarkers disclosed in Table 1a, 1b, 1c, or 1d, in any combination. At least about 3% of the biomarkers from the classifiers may be selected from biomarkers disclosed in Table 1a, 1b, 1c, 1d, 8, 9, 10b, 12b, 14b, 16b, 17b, or 18b, in any combination. At least about 5% of the biomarkers from the classifiers may be selected from biomarkers disclosed in Table 1a. At least about 5% of the biomarkers from the classifiers may be selected from biomarkers disclosed in Table 1c. At least about 5% of the biomarkers from the classifiers may be selected from biomarkers disclosed in Table 1a, 1b, 1c, or 1d, in any combination. At least about 5% of the biomarkers from the classifiers may be selected from biomarkers disclosed in Table 1a, 1b, 1c, 1d, 8, 9, 10b, 12b, 14b, 16b, 17b, or 18b, in any combination. At least about 10% of the biomarkers from the classifiers may be selected from biomarkers disclosed in Table 1a. At least about 10% of the biomarkers from the classifiers may be selected from biomarkers disclosed in Table 1c. At least about 10% of the biomarkers from the classifiers may be selected from biomarkers disclosed in Table 1a, 1b, 1c, or 1d, in any combination. At least about 10% of the biomarkers from the classifiers may be selected from biomarkers disclosed in Table 1a, 1b, 1c, 1d, 8, 9, 10b, 12b, 14b, 16b, 17b, or 18b, in any combination.

Classifier probe sets may comprise one or more oligonucleotides. The oligonucleotides may comprise at least a portion of a sequence that can hybridize to one or more biomarkers from the panel of biomarkers. Classifier probe sets may comprise 1, 2, 3, 4, 5, 6, 7, 8, 9, 10, 11, 12, 13, 14, 15, 16, 17, 18, 19, 20 or more oligonucleotides, wherein at least a portion of the oligonucleotide can hybridize to at least a portion of at least 1, 2, 3, 4, 5, 6, 7, 8, 9, 10, 11, 12, 13, 14, 15, 16, 17, 18, 19, 20 or more biomarkers from the panel of biomarkers. Classifier probe sets may comprise 10, 20, 30, 40, 50, 60, 70, 80, 90, 100, 110, 120, 130, 140, 150, 160, 170, 180, 190, 200 or more oligonucleotides, wherein at least a portion of the oligonucleotide can hybridize to at least a portion of at least 10, 20, 30, 40, 50, 60, 70, 80, 90, 100, 110, 120, 130, 140, 150, 160, 170, 180, 190, 200 or more biomarkers from the panel of biomarkers. Classifier probe sets may comprise 10, 20, 30, 40, 50, 60, 70, 80, 90, 100, 110, 120, 130, 140, 150, 160, 170, 180, 190, 200 or fewer oligonucleotides, wherein at least a portion of the oligonucleotide can hybridize to fewer than 10, 20, 30, 40, 50, 60, 70, 80, 90, 100, 110, 120, 130, 140, 150, 160, 170, 180, 190, 200 or more biomarkers from the panel of biomarkers. Classifier probe sets may comprise 100, 200, 300, 400, 500, 600, 700, 800, 900, 1000, 1100, 1200, 1300, 1400, 1500, 1600, 1700, 1800, 1900, 2000 or more oligonucleotides, wherein at least a portion of the oligonucleotide can hybridize to at least a portion of at least 100, 200, 300, 400, 500, 600, 700, 800, 900, 1000, 1100, 1200, 1300, 1400, 1500, 1600, 1700, 1800, 1900, 2000 or more biomarkers from the panel of biomarkers.

Training of multi-dimensional classifiers (e.g., algorithms) may be performed on numerous samples. For example, training of the multi-dimensional classifier may be performed on at least about 10, 20, 30, 40, 50, 60, 70, 80, 90, 100, 110, 120, 130, 140, 150, 160, 170, 180, 190, 200 or more samples. Training of the multi-dimensional classifier may be performed on at least about 200, 210, 220, 230, 240, 250, 260, 270, 280, 290, 300, 350, 400, 450, 500 or more samples. Training of the multi-dimensional classifier may be performed on at least about 525, 550, 600, 650, 700, 750, 800, 850, 900, 950, 1000, 1100, 1200, 1300, 1400, 1500, 1600, 1700, 1800, 2000 or more samples.

The total sample population may comprise samples obtained by venipuncture. Alternatively, the total sample population may comprise samples obtained by venipuncture, needle aspiration, fine needle aspiration, or a combination thereof. The total sample population may comprise samples obtained by venipuncture, needle aspiration, fine needle aspiration, core needle biopsy, vacuum assisted biopsy, large core biopsy, incisional biopsy, excisional biopsy, punch biopsy, shave biopsy, skin biopsy, or a combination thereof. In some embodiments, the samples are not obtained by biopsy. The percent of the total sample population that is obtained by venipuncture may be greater than about 1%, 5%, 10%, 15%, 20%, 25%, 30%, 35%, 40%, 50%, 55%, 60%, 65%, 70%, 75%, 80%, 85%, 90%, or 95%. The percent of the total sample population that is obtained by venipuncture may be greater than about 1%. The percent of the total sample population that is obtained by venipuncture may be greater than about 5%. The percent of the total sample population that is obtained by venipuncture may be greater than about 10%

There may be a specific (or range of) difference in gene expression between subtypes or sets of samples being compared to one another. In some examples, the gene expression of some similar subtypes are merged to form a super-class that is then compared to another subtype, or another super-class, or the set of all other subtypes. In some embodiments, the difference in gene expression level is at least about 5%, 10%, 15%, 20%, 25%, 30%, 35%, 40%, 45%, or 50% or more. In some embodiments, the difference in gene expression level is at least about 2, 3, 4, 5, 6, 7, 8, 9, 10 fold or more.

The present invention may initialize gene expression products corresponding to one or more biomarkers selected from gene expression products derived from genes listed in Table 1a. The present invention may initialize gene expression products corresponding to one or more biomarkers selected from gene expression products derived from genes listed in Table 1c. The present invention may initialize gene expression products corresponding to one or more biomarkers selected from gene expression products derived from genes listed in Table 1a, 1b, 1c, or 1d, in any combination. The present invention may initialize gene expression products corresponding to one or more biomarkers selected from gene expression products derived from genes listed in Table 1a, 1b, 1c, 1d, 8, 9, 10b, 12b, 14b, 16b, 17b, or 18b, in any combination. The methods, compositions and systems provided herein may include expression products corresponding to any or all of the biomarkers selected from gene expression products derived from genes listed in Table 1a, as well as any subset thereof, in any combination. The methods, compositions and systems provided herein may include expression products corresponding to any or all of the biomarkers selected from gene expression products derived from genes listed in Table 1c, as well as any subset thereof, in any combination. The methods, compositions and systems provided herein may include expression products corresponding to any or all of the biomarkers selected from gene expression products derived from genes listed in Table 1a, 1b, 1c, or 1d, in any combination, as well as any subset thereof, in any combination. The methods, compositions and systems provided herein may include expression products corresponding to any or all of the biomarkers selected from gene expression products derived from genes listed in Table 1a, 1b, 1c, 1d, 8, 9, 10b, 12b, 14b, 16b, 17b, or 18b, in any combination, as well as any subset thereof, in any combination. For example, the methods may use gene expression products corresponding to at least about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 of the markers provided Table 1a. In another embodiment, the methods use gene expression products corresponding to at least about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 of the markers provided Table 1c. In another example, the methods may use gene expression products corresponding to at least about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 of the markers provided Table 1a, 1b, 1c, or 1d, in any combination. In another example, the methods may use gene expression products corresponding to at least about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 of the markers provided Table 1a, 1b, 1c, 1d, 8, 9, 10b, 12b, 14b, 16b, 17b, or 18b, in any combination. The methods may use gene expression products corresponding to at least about 110, 120, 130, 140, 150, 160, 170, 180, 190, 200, 210, 220, 230, 240, 250, 260, 270, 280, 290, 300 or more of the markers provided in gene expression products derived from genes listed in Table 1a. The methods may use gene expression products corresponding to at least about 110, 120, 130, 140, 150, 160, 170, 180, 190, 200, 210, 220, 230, 240, 250, 260, 270, 280, 290, 300 or more of the markers provided in gene expression products derived from genes listed in Table 1c. The methods may use gene expression products corresponding to at least about 110, 120, 130, 140, 150, 160, 170, 180, 190, 200, 210, 220, 230, 240, 250, 260, 270, 280, 290, 300 or more of the markers provided in gene expression products derived from genes listed in Table 1a, 1b, 1c, or 1d, in any combination. The methods may use gene expression products corresponding to at least about 110, 120, 130, 140, 150, 160, 170, 180, 190, 200, 210, 220, 230, 240, 250, 260, 270, 280, 290, 300 or more of the markers provided in gene expression products derived from genes listed in Table 1a, 1b, 1c, 1d, 8, 9, 10b, 12b, 14b, 16b, 17b, or 18b, in any combination.

Further disclosed herein are classifier sets and methods of producing one or more classifier sets. The classifier set may comprise one or more genes. The classifier set may comprise 1, 2, 3, 4, 5, 6, 7, 8, 9, 10, 11, 12, 13, 14, 15, 16, 17, 18, 19, 20 or more genes. The classifier set may comprise 10, 20, 30, 40, 50, 60, 70, 80, 90, 100, 110, 120, 130, 140, 150, 160, 170, 180, 190, 200 or more genes. The classifier set may comprise 100, 200, 300, 400, 500, 600, 700, 800, 900, 1000, 1100, 1200, 1300, 1400, 1500, 1600, 1700, 1800, 1900, 2000 or more genes. The classifier set may comprise 1000, 2000, 3000, 4000, 5000, 6000, 7000, 8000, 9000, 10000, 11000, 12000, 13000, 14000, 15000, 16000, 17000, 18000, 19000, 20000 or more genes. The classifier set may comprise 10000, 20000, 30000, 40000, 50000, 60000, 70000, 80000, 90000, 100000, 110000, 120000, 130000, 140000, 150000, 160000, 170000, 180000, 190000, 200000 or more genes. The classifier set may comprise 10 or more genes. The classifier set may comprise 30 or more genes. The classifier set may comprise 60 or more genes. The classifier set may comprise 100 or more genes. The classifier set may comprise 125 or more genes. The classifier set may comprise 150 or more genes. The classifier set may comprise 200 or more genes. The classifier set may comprise 250 or more genes. The classifier set may comprise 300 or more genes.

The classifier set may comprise one or more differentially expressed genes. The classifier set may comprise one or more differentially expressed genes. The classifier set may comprise 1, 2, 3, 4, 5, 6, 7, 8, 9, 10, 11, 12, 13, 14, 15, 16, 17, 18, 19, 20 or more differentially expressed genes. The classifier set may comprise 10, 20, 30, 40, 50, 60, 70, 80, 90, 100, 110, 120, 130, 140, 150, 160, 170, 180, 190, 200 or more differentially expressed genes. The classifier set may comprise 100, 200, 300, 400, 500, 600, 700, 800, 900, 1000, 1100, 1200, 1300, 1400, 1500, 1600, 1700, 1800, 1900, 2000 or more differentially expressed genes. The classifier set may comprise 1000, 2000, 3000, 4000, 5000, 6000, 7000, 8000, 9000, 10000, 11000, 12000, 13000, 14000, 15000, 16000, 17000, 18000, 19000, 20000 or more differentially expressed genes. The classifier set may comprise 10000, 20000, 30000, 40000, 50000, 60000, 70000, 80000, 90000, 100000, 110000, 120000, 130000, 140000, 150000, 160000, 170000, 180000, 190000, 200000 or more differentially expressed genes. The classifier set may comprise 10 or more differentially expressed genes. The classifier set may comprise 30 or more differentially expressed genes.

The classifier set may comprise 60 or more differentially expressed genes. The classifier set may comprise 100 or more differentially expressed genes. The classifier set may comprise 125 or more differentially expressed genes. The classifier set may comprise 150 or more differentially expressed genes. The classifier set may comprise 200 or more differentially expressed genes. The classifier set may comprise 250 or more differentially expressed genes. The classifier set may comprise 300 or more differentially expressed genes.

In some instances, the method provides a number, or a range of numbers, of biomarkers or gene expression products that are used to characterize a sample. Examples of classification panels may be derived from genes listed in Table 1a. Examples of classification panels may be derived from genes listed in Table 1c. Examples of classification panels may be derived from genes listed in Table 1a, 1b, 1c, or 1d, in any combination. Examples of classification panels may be derived from genes listed in Table 1a, 1b, 1c, 1d, 8, 9, 10b, 12b, 14b, 16b, 17b, or 18b, in any combination. However, the present disclosure is not meant to be limited solely to the biomarkers disclosed herein. Rather, it is understood that any biomarker, gene, group of genes or group of biomarkers identified through methods described herein is encompassed by the present invention. In some embodiments, the method involves measuring (or obtaining) the levels of two or more gene expression products that are within a biomarker panel and/or within a classification panel. For example, in some embodiments, a biomarker panel or a gene expression product may contain at least about 1, 2, 3, 4, 5, 6, 7, 8, 9, 10, 11, 12, 13, 14, 15, 16, 17, 18, 19, 20, 25, 30, 33, 35, 38, 40, 43, 45, 47, 50, 52, 55, 57, 60, 62, 65, 67, 70, 72, 75, 77, 80, 85, 89, 92, 95, 97, 100, 103, 107, 110, 113, 117, 122, 128, 132, 138, 140, 142, 145, 147, 150, 155, 160, 165, 170, 175, 180, 183, 185, 187, 190, 192, 195, 197, 200, 210, 220, 230, 240, 250, 260, 270, 280, 290 or 300 or more genes chosen from Table 1a. In some embodiments, a biomarker panel or a gene expression product may contain at least about 1, 2, 3, 4, 5, 6, 7, 8, 9, 10, 11, 12, 13, 14, 15, 16, 17, 18, 19, 20, 25, 30, 33, 35, 38, 40, 43, 45, 47, 50, 52, 55, 57, 60, 62, 65, 67, 70, 72, 75, 77, 80, 85, 89, 92, 95, 97, 100, 103, 107, 110, 113, 117, 122, 128, 132, 138, 140, 142, 145, 147, 150, 155, 160, 165, 170, 175, 180, 183, 185, 187, 190, 192, 195, 197, 200, 210, 220, 230, 240, 250, 260, 270, 280, 290 or 300 or more genes chosen from Table 1c. In some embodiments, a biomarker panel or a gene expression product may contain at least about 1, 2, 3, 4, 5, 6, 7, 8, 9, 10, 11, 12, 13, 14, 15, 16, 17, 18, 19, 20, 25, 30, 33, 35, 38, 40, 43, 45, 47, 50, 52, 55, 57, 60, 62, 65, 67, 70, 72, 75, 77, 80, 85, 89, 92, 95, 97, 100, 103, 107, 110, 113, 117, 122, 128, 132, 138, 140, 142, 145, 147, 150, 155, 160, 165, 170, 175, 180, 183, 185, 187, 190, 192, 195, 197, 200, 210, 220, 230, 240, 250, 260, 270, 280, 290 or 300 or more genes chosen from Table 1a, 1b, 1c, or 1d, in any combination. In some embodiments, a biomarker panel or a gene expression product may contain at least about 1, 2, 3, 4, 5, 6, 7, 8, 9, 10, 11, 12, 13, 14, 15, 16, 17, 18, 19, 20, 25, 30, 33, 35, 38, 40, 43, 45, 47, 50, 52, 55, 57, 60, 62, 65, 67, 70, 72, 75, 77, 80, 85, 89, 92, 95, 97, 100, 103, 107, 110, 113, 117, 122, 128, 132, 138, 140, 142, 145, 147, 150, 155, 160, 165, 170, 175, 180, 183, 185, 187, 190, 192, 195, 197, 200, 210, 220, 230, 240, 250, 260, 270, 280, 290 or 300 or more genes chosen from Table 1a, 1b, 1c, 1d, 8, 9, 10b, 12b, 14b, 16b, 17b, or 18b, in any combination. In some embodiments, a biomarker panel or a gene expression product may contain no more than about 1, 2, 3, 4, 5, 6, 7, 8, 9, 10, 11, 12, 13, 14, 15, 16, 17, 18, 19, 20, 25, 30, 33, 35, 38, 40, 43, 45, 47, 50, 52, 55, 57, 60, 62, 65, 67, 70, 72, 75, 77, 80, 85, 89, 92, 95, 97, 100, 103, 107, 110, 113, 117, 122, 128, 132, 138, 140, 142, 145, 147, 150, 155, 160, 165, 170, 175, 180, 183, 185, 187, 190, 192, 195, 197, 200, 210, 220, 230, 240, 250, 260, 270, 280, 290 or 300 or more genes chosen from Table 1a. In some embodiments, a biomarker panel or a gene expression product may contain no more than about 1, 2, 3, 4, 5, 6, 7, 8, 9, 10, 11, 12, 13, 14, 15, 16, 17, 18, 19, 20, 25, 30, 33, 35, 38, 40, 43, 45, 47, 50, 52, 55, 57, 60, 62, 65, 67, 70, 72, 75, 77, 80, 85, 89, 92, 95, 97, 100, 103, 107, 110, 113, 117, 122, 128, 132, 138, 140, 142, 145, 147, 150, 155, 160, 165, 170, 175, 180, 183, 185, 187, 190, 192, 195, 197, 200, 210, 220, 230, 240, 250, 260, 270, 280, 290 or 300 or more genes chosen from Table 1c. In some embodiments, a biomarker panel or a gene expression product may contain no more than about 1, 2, 3, 4, 5, 6, 7, 8, 9, 10, 11, 12, 13, 14, 15, 16, 17, 18, 19, 20, 25, 30, 33, 35, 38, 40, 43, 45, 47, 50, 52, 55, 57, 60, 62, 65, 67, 70, 72, 75, 77, 80, 85, 89, 92, 95, 97, 100, 103, 107, 110, 113, 117, 122, 128, 132, 138, 140, 142, 145, 147, 150, 155, 160, 165, 170, 175, 180, 183, 185, 187, 190, 192, 195, 197, 200, 210, 220, 230, 240, 250, 260, 270, 280, 290 or 300 or more genes chosen from Table 1a, 1b, 1c, or 1d, in any combination. In some embodiments, a biomarker panel or a gene expression product may contain no more than about 1, 2, 3, 4, 5, 6, 7, 8, 9, 10, 11, 12, 13, 14, 15, 16, 17, 18, 19, 20, 25, 30, 33, 35, 38, 40, 43, 45, 47, 50, 52, 55, 57, 60, 62, 65, 67, 70, 72, 75, 77, 80, 85, 89, 92, 95, 97, 100, 103, 107, 110, 113, 117, 122, 128, 132, 138, 140, 142, 145, 147, 150, 155, 160, 165, 170, 175, 180, 183, 185, 187, 190, 192, 195, 197, 200, 210, 220, 230, 240, 250, 260, 270, 280, 290 or 300 or more genes chosen from Table 1a, 1b, 1c, 1d, 8, 9, 10b, 12b, 14b, 16b, 17b, or 18b, in any combination. In other embodiments, a biomarker panel or a gene expression product may contain about 1, 2, 3, 4, 5, 6, 7, 8, 9, 10, 11, 12, 13, 14, 15, 16, 17, 18, 19, 20, 25, 30, 33, 35, 38, 40, 43, 45, 47, 50, 52, 55, 57, 60, 62, 65, 67, 70, 72, 75, 77, 80, 85, 89, 92, 95, 97, 100, 103, 107, 110, 113, 117, 122, 128, 132, 138, 140, 142, 145, 147, 150, 155, 160, 165, 170, 175, 180, 183, 185, 187, 190, 192, 195, 197, 200, 210, 220, 230, 240, 250, 260, 270, 280, 290 or 300 total genes chosen from Table 1a. In other embodiments, a biomarker panel or a gene expression product may contain about 1, 2, 3, 4, 5, 6, 7, 8, 9, 10, 11, 12, 13, 14, 15, 16, 17, 18, 19, 20, 25, 30, 33, 35, 38, 40, 43, 45, 47, 50, 52, 55, 57, 60, 62, 65, 67, 70, 72, 75, 77, 80, 85, 89, 92, 95, 97, 100, 103, 107, 110, 113, 117, 122, 128, 132, 138, 140, 142, 145, 147, 150, 155, 160, 165, 170, 175, 180, 183, 185, 187, 190, 192, 195, 197, 200, 210, 220, 230, 240, 250, 260, 270, 280, 290 or 300 total genes chosen from Table 1c. In other embodiments, a biomarker panel or a gene expression product may contain about 1, 2, 3, 4, 5, 6, 7, 8, 9, 10, 11, 12, 13, 14, 15, 16, 17, 18, 19, 20, 25, 30, 33, 35, 38, 40, 43, 45, 47, 50, 52, 55, 57, 60, 62, 65, 67, 70, 72, 75, 77, 80, 85, 89, 92, 95, 97, 100, 103, 107, 110, 113, 117, 122, 128, 132, 138, 140, 142, 145, 147, 150, 155, 160, 165, 170, 175, 180, 183, 185, 187, 190, 192, 195, 197, 200, 210, 220, 230, 240, 250, 260, 270, 280, 290 or 300 total genes chosen from Table 1a, 1b, 1c, or 1d, in any combination. In other embodiments, a biomarker panel or a gene expression product may contain about 1, 2, 3, 4, 5, 6, 7, 8, 9, 10, 11, 12, 13, 14, 15, 16, 17, 18, 19, 20, 25, 30, 33, 35, 38, 40, 43, 45, 47, 50, 52, 55, 57, 60, 62, 65, 67, 70, 72, 75, 77, 80, 85, 89, 92, 95, 97, 100, 103, 107, 110, 113, 117, 122, 128, 132, 138, 140, 142, 145, 147, 150, 155, 160, 165, 170, 175, 180, 183, 185, 187, 190, 192, 195, 197, 200, 210, 220, 230, 240, 250, 260, 270, 280, 290 or 300 total genes chosen from Table 1a, 1b, 1c, 1d, 8, 9, 10b, 12b, 14b, 16b, 17b, or 18b, in any combination.

Measuring Expression Levels

The methods, kits and systems disclosed herein may be used to obtain or to determine an expression level for one or more gene products in a subject. In some instances, the expression level is used to develop or train an algorithm or classifier provided herein. In some instances, where the subject is a patient, such as a transplant recipient; gene expression levels are measured in a sample from the transplant recipient and a classifier or algorithm (e.g., trained algorithm) is applied to the resulting data in order to detect, predict, monitor, or estimate the risk of a transplant condition (e.g., acute rejection).

The expression level of the gene products (e.g., RNA, cDNA, polypeptides) may be determined using any method known in the art. In some instances, the expression level of the gene products (e.g., nucleic acid gene products such as RNA) is measured by microarray, sequencing, electrophoresis, automatic electrophoresis, SAGE, blotting, polymerase chain reaction (PCR), digital PCR, RT-PCR, and/or quantitative PCR (qPCR). In certain preferred embodiments, the expression level is determined by microarray. For example, the microarray may be an Affymetrix Human Genome U133 Plus 2.0 GeneChip or a HT HG-U133+ PM Array Plate.

In certain preferred embodiments, the expression level of the gene products (e.g., RNA) is determined by sequencing, such as by RNA sequencing or by DNA sequencing (e.g., of cDNA generated from reverse-transcribing RNA (e.g., mRNA) from a sample). Sequencing may be performed by any available method or technique. Sequencing methods may include: high-throughput sequencing, pyrosequencing, classic Sangar sequencing methods, sequencing-by-ligation, sequencing by synthesis, sequencing-by-hybridization, RNA-Seq (Illumina), Digital Gene Expression (Helicos), next generation sequencing, single molecule sequencing by synthesis (SMSS) (Helicos), Ion Torrent Sequencing Machine (Life Technologies/Thermo-Fisher), massively-parallel sequencing, clonal single molecule Array (Solexa), shotgun sequencing, Maxim-Gilbert sequencing, primer walking, and any other sequencing methods known in the art.

Measuring gene expression levels may comprise reverse transcribing RNA (e.g., mRNA) within a sample in order to produce cDNA. The cDNA may then be measured using any of the methods described herein (e.g., PCR, digital PCR, qPCR, microarray, SAGE, blotting, sequencing, etc.). In some instances, the method may comprise reverse transcribing RNA originating from the subject (e.g., transplant recipient) to produce cDNA, which is then measured such as by microarray, sequencing, PCR, and/or any other method available in the art.

In some instances, the gene products may be polypeptides. In such instances, the methods may comprise measuring polypeptide gene products. Methods of measuring or detecting polypeptides may be accomplished using any method or technique known in the art. Examples of such methods include proteomics, expression proteomics, mass spectrometry, 2D PAGE, 3D PAGE, electrophoresis, proteomic chips, proteomic microarrays, and/or Edman degradation reactions.

The expression level may be normalized (e.g., signal normalization). In some instances, signal normalization (e.g., quantile normalization) is performed on an entire cohort. In general, quantile normalization is a technique for making two or more distributions identical in statistical properties. However, in settings where samples must be processed individually or in small batches, data sets that are normalized separately are generally not comparable. In some instances provided herein, the expression level of the gene products is normalized using frozen RMA (fRMA). fRMA is particularly useful because it overcomes these obstacles by normalization of individual arrays to large publicly available microarray databases allowing for estimates of probe-specific effects and variances to be pre-computed and "frozen" (McCall et al. 2010, Biostatistics, 11(2): 242-253; McCall et al. 2011, BMC bioinformatics, 12:369). In some instances, a method provided herein does not comprise performing a normalization step. In some instances, a method provided herein does not comprise performing quantile normalization. In some cases, the normalization does not comprise quantile normalization. In certain preferred embodiments, the methods comprise frozen robust multichip average (fRMA) normalization.

In some cases, analysis of expression levels initially provides a measurement of the expression level of each of several individual genes. The expression level can be absolute in terms of a concentration of an expression product, or relative in terms of a relative concentration of an expression product of interest to another expression product in the sample. For example, relative expression levels of genes can be expressed with respect to the expression level of a house-keeping gene in the sample. Relative expression levels can also be determined by simultaneously analyzing differentially labeled samples hybridized to the same array. Expression levels can also be expressed in arbitrary units, for example, related to signal intensity.

Biomarker Discovery and Validation

Figure 3:
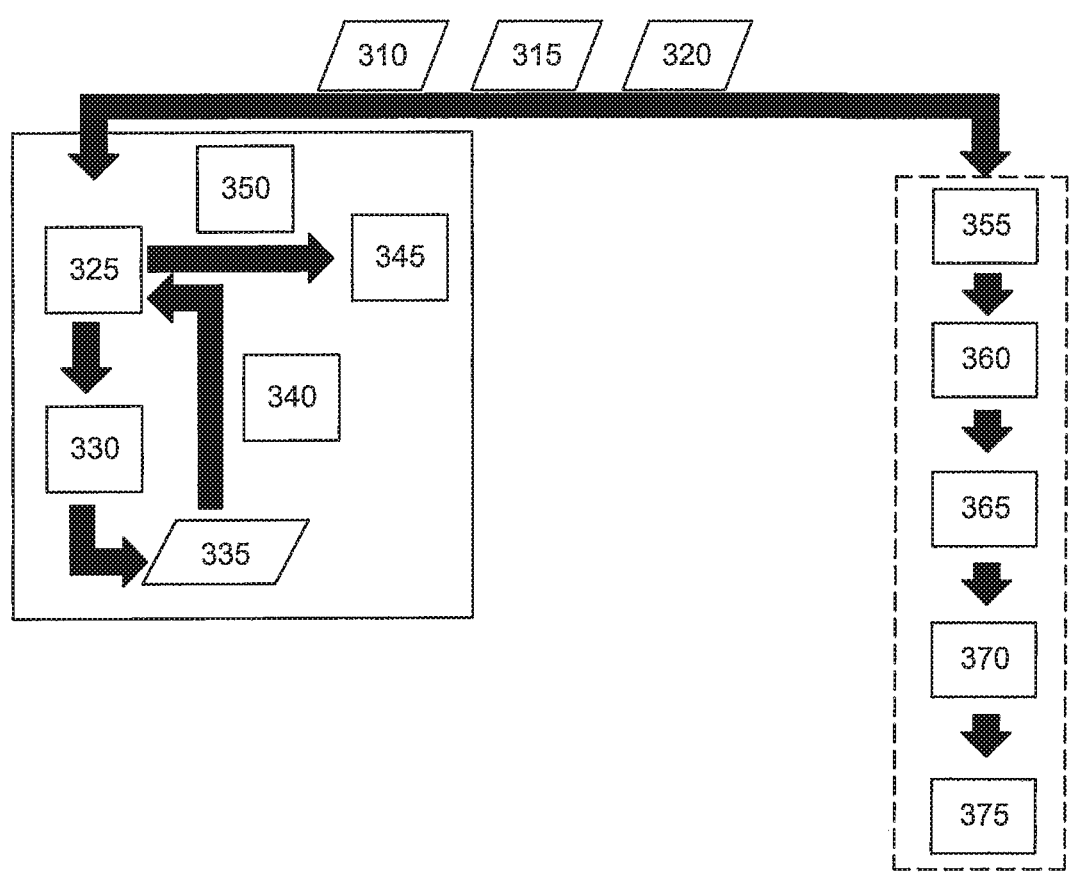
FIG. 3 shows a schematic of the workflows for cohort and bootstrapping strategies for biomarker discovery and validation.

Exemplary workflows for cohort and bootstrapping strategies for biomarker discovery and validation are depicted in FIG. 3. As shown in FIG. 3, the cohort-based method of biomarker discovery and validation is outlined by the solid box and the bootstrapping method of biomarker discovery and validation is outlined in the dotted box. For the cohort-based method, samples for acute rejection (n=63) (310), acute dysfunction no rejection (n=39) (315), and normal transplant function (n=46) (320) are randomly split into a discovery cohort (n=75) (325) and a validation cohort (n=73) (345). The samples from the discovery cohort are analyzed using a 3-class univariate F-test (1000 random permutations, FDR <10%; BRB ArrayTools) (330). The 3-class univariate F-test analysis of the discovery cohort yielded 2977 differentially expressed probe sets (Table 1) (335). Algorithms such as the Nearest Centroid, Diagonal Linear Discriminant Analysis, and Support Vector Machines, are used to create a 3-way classifier for AR, ADNR and TX in the discovery cohort (340). The 25-200 classifiers are "locked" (350). The "locked" classifiers are validated by samples from the validation cohort (345). For the bootstrapping method, 3-class univariate F-test is performed on the whole data set of samples (n=148) (1000 random permutations, FDR <10%; BRB ArrayTools) (355). The significantly expressed genes are selected to produce a probe set (n=200, based on the nearest centroid (NC), diagonal linear discriminant analysis (DLDA), or support vector machines (SVM)). Optimism-corrected AUCs are obtained for the 200-probe set classifier discovered with the 2 cohort-based strategy (360). AUCs are obtained for the full data set (365). Optimism-corrected AUCs are obtained for the 200-probe set classifier by Bootstrapping from 1000 samplings of the full data set with replacement (370). Optimism-corrected AUCs are obtained for nearest centroid (NC), diagonal linear discriminant analysis (DLDA), or support vector machines (SVM) using the original 200 SVM classifier (375).

In some instances, the cohort-based method comprises biomarker discovery and validation. Transplant recipients with known conditions (e.g. AR, ADNR, CAN, SCAR, TX) are randomly split into a discovery cohort and a validation cohort. One or more gene expression products may be measured for all the subjects in both cohorts. In some instances, at least 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, 500, 550, 600, 650, 700, 750, 800, 850, 900, 950, 1000, 1500, 2000, 2500 or more gene expression products are measured for all the subjects. In some instances, the gene expression products with different conditions (e.g. AR, ADNR, CAN, SCAR, TX) in the discovery cohort are compared and differentially expressed probe sets are discovered as biomarkers. For example, the discovery cohort in FIG. 3 yielded 2977 differentially expressed probe sets (Table 1). In some instances, the difference in gene expression level is at least 10%, 15%, 20%, 25%, 30%, 35%, 40%, 45% or 50% or more. In some instances, the difference in gene expression level is at least 2, 3, 4, 5, 6, 7, 8, 9, 10 fold or more. In some instances, the accuracy is calculated using a trained algorithm. For example, the present invention may provide gene expression products corresponding to genes selected from Table 1a. The present invention may also provide gene expression products corresponding to genes selected from Table 1c. In some instances, the accuracy is calculated using a trained algorithm. For example, the present invention may provide gene expression products corresponding to genes selected from Table 1a, 1b, 1c, or 1d, in any combination. In some instances, the accuracy is calculated using a trained algorithm. For example, the present invention may provide gene expression products corresponding to genes selected from Table 1a, 1b, 1c, 1d, 8, 9, 10b, 12b, 14b, 16b, 17b, or 18b, in any combination. In some instances, the identified probe sets may be used to train an algorithm for purposes of identification, diagnosis, classification, treatment or to otherwise characterize various conditions (e.g. AR, ADNR, CAN, SCAR, TX) of organ transplant.

The differentially expressed probe sets and/or algorithm may be subject to validation. In some instances, classification of the transplant condition may be made by applying the probe sets and/or algorithm generated from the discovery cohort to the gene expression products in the validation cohort. In some instances, the classification may be validated by the known condition of the subject. For example, in some instances, the subject is identified with a particular condition (e.g. AR, ADNR, CAN, SCAR, TX) with an accuracy of greater than 60%, 65%, 70%, 75%, 80%, 85%, 90%, 95%, 99% or more. In some instances, the subject is identified with a particular condition (e.g. AR, ADNR, CAN, SCAR, TX) with a sensitivity of greater than 60%, 65%, 70%, 75%, 80%, 85%, 90%, 95%, 99% or more. In some instances, the subject is identified with a particular condition (e.g. AR, ADNR, CAN, SCAR, TX) with a specificity of greater than 60%, 65%, 70%, 75%, 80%, 85%, 90%, 95%, 99% or more. In some instances, biomarkers and/or algorithms may be used in identification, diagnosis, classification and/or prediction of the transplant condition of a subject. For example, biomarkers and/or algorithms may be used in classification of transplant conditions for an organ transplant patient, whose condition may be unknown.

Biomarkers that have been validated and/or algorithms may be used in identification, diagnosis, classification and/or prediction of transplant conditions of subjects. In some instances, gene expression products of the organ transplant subjects may be compared with one or more different sets of biomarkers. The gene expression products for each set of biomarkers may comprise one or more reference gene expression levels. The reference gene expression levels may correlate with a condition (e.g. AR, ADNR, CAN, SCAR, TX) of an organ transplant.

The expression level may be compared to gene expression data for two or more biomarkers in a sequential fashion. Alternatively, the expression level is compared to gene expression data for two or more biomarkers simultaneously. Comparison of expression levels to gene expression data for sets of biomarkers may comprise the application of a classifier. For example, analysis of the gene expression levels may involve sequential application of different classifiers described herein to the gene expression data. Such sequential analysis may involve applying a classifier obtained from gene expression analysis of cohorts of transplant recipients with a first status or outcome (e.g., transplant rejection), followed by applying a classifier obtained from analysis of a mixture of different samples, some of such samples obtained from healthy transplant recipients, transplant recipients experiencing transplant rejection, and/or transplant recipients experiencing organ dysfunction with no transplant rejection. Alternatively, sequential analysis involves applying at least two different classifiers obtained from gene expression analysis of transplant recipients, wherein at least one of the classifiers correlates to transplant dysfunction with no rejection.

Classifiers and Classifier Probe Sets

Disclosed herein is the use of a classification system comprises one or more classifiers. In some instances, the classifier is a 2-, 3-, 4-, 5-, 6-, 7-, 8-, 9-, or 10-way classifier. In some instances, the classifier is a 15-, 20-, 25-, 30-, 35-, 40-, 45-, 50-, 55-, 60-, 65-, 70-, 75-, 80-, 85-, 90-, 95-, or 100-way classifier. In some preferred embodiments, the classifier is a three-way classifier. In some embodiments, the classifier is a four-way classifier.

A two-way classifier may classify a sample from a subject into one of two classes. In some instances, a two-way classifier may classify a sample from an organ transplant recipient into one of two classes comprising acute rejection (AR) and normal transplant function (TX). In some instances, a two-way classifier may classify a sample from an organ transplant recipient into one of two classes comprising acute rejection (AR) and acute dysfunction with no rejection (ADNR). In some instances, a two-way classifier may classify a sample from an organ transplant recipient into one of two classes comprising normal transplant function (TX) and acute dysfunction with no rejection (ADNR). In some instances, a three-way classifier may classify a sample from a subject into one of three classes. A three-way classifier may classify a sample from an organ transplant recipient into one of three classes comprising acute rejection (AR), acute dysfunction with no rejection (ADNR) and normal transplant function (TX). In some instances, a three-way classifier may a sample from an organ transplant recipient into one of three classes wherein the classes can include a combination of any one of acute rejection (AR), acute dysfunction with no rejection (ADNR), normal transplant function (TX), chronic allograft nephropathy (CAN), interstitial fibrosis and/or tubular atrophy (IF/TA), or Subclinical Acute Rejection (SCAR). In some cases, the three-way classifier may classify a sample as AR/HCV-R/Tx. In some cases, the classifier is a four-way classifier. In some cases, the four-way classifier may classify a sample as AR, HCV-R, AR+HCV, or TX.

Classifiers and/or classifier probe sets may be used to either rule-in or rule-out a sample as healthy. For example, a classifier may be used to classify a sample as being from a healthy subject. Alternatively, a classifier may be used to classify a sample as being from an unhealthy subject. Alternatively, or additionally, classifiers may be used to either rule-in or rule-out a sample as transplant rejection. For example, a classifier may be used to classify a sample as being from a subject suffering from a transplant rejection. In another example, a classifier may be used to classify a sample as being from a subject that is not suffering from a transplant rejection. Classifiers may be used to either rule-in or rule-out a sample as transplant dysfunction with no rejection. For example, a classifier may be used to classify a sample as being from a subject suffering from transplant dysfunction with no rejection. In another example, a classifier may be used to classify a sample as not being from a subject suffering from transplant dysfunction with no rejection.

Classifiers used in sequential analysis may be used to either rule-in or rule-out a sample as healthy, transplant rejection, or transplant dysfunction with no rejection. For example, a classifier may be used to classify a sample as being from an unhealthy subject. Sequential analysis with a classifier may further be used to classify the sample as being from a subject suffering from a transplant rejection. Sequential analysis may end with the application of a "main" classifier to data from samples that have not been ruled out by the preceding classifiers. For example, classifiers may be used in sequential analysis of ten samples. The classifier may classify 6 out of the 10 samples as being from healthy subjects and 4 out of the 10 samples as being from unhealthy subjects. The 4 samples that were classified as being from unhealthy subjects may be further analyzed with the classifiers. Analysis of the 4 samples may determine that 3 of the 4 samples are from subjects suffering from a transplant rejection. Further analysis may be performed on the remaining sample that was not classified as being from a subject suffering from a transplant rejection. The classifier may be obtained from data analysis of gene expression levels in multiple types of samples. The classifier may be capable of designating a sample as healthy, transplant rejection or transplant dysfunction with no rejection.

Classifier probe sets, classification systems and/or classifiers disclosed herein may be used to either classify (e.g., rule-in or rule-out) a sample as healthy or unhealthy. Sample classification may comprise the use of one or more additional classifier probe sets, classification systems and/or classifiers to further analyze the unhealthy samples. Further analysis of the unhealthy samples may comprise use of the one or more additional classifier probe sets, classification systems and/or classifiers to either classify (e.g., rule-in or rule-out) the unhealthy sample as transplant rejection or transplant dysfunction with no rejection. Sample classification may end with the application of a classifier probe set, classification system and/or classifier to data from samples that have not been ruled out by the preceding classifier probe sets, classification systems and/or classifiers. The classifier probe set, classification system and/or classifier may be obtained from data analysis of gene expression levels in multiple types of samples. The classifier probe set, classification system and/or classifier may be capable of designating a sample as healthy, transplant rejection or transplant dysfunction which may include transplant dysfunction with no rejection. Alternatively, the classifier probe set, classification system and/or classifier is capable of designating an unhealthy sample as transplant rejection or transplant dysfunction with no rejection.

The differentially expressed genes may be genes that may be differentially expressed in a plurality of control samples. For example, the plurality of control samples may comprise two or more samples that may be differentially classified as acute rejection, acute dysfunction no rejection or normal transplant function. The plurality of control samples may comprise three or more samples that may be differentially classified. The samples may be differentially classified based on one or more clinical features. The one or more clinical features may comprise status or outcome of a transplanted organ. The one or more clinical features may comprise diagnosis of transplant rejection. The one or more clinical features may comprise diagnosis of transplant dysfunction. The one or more clinical features may comprise one or more symptoms of the subject from which the sample is obtained from. The one or more clinical features may comprise age and/or gender of the subject from which the sample is obtained from. The one or more clinical features may comprise response to one or more immunosuppressive regimens. The one or more clinical features may comprise a number of immunosuppressive regimens.

The classifier set may comprise one or more genes that may be differentially expressed in two or more control samples. The two or more control samples may be differentially classified. The two or more control samples may be differentially classified as acute rejection, acute dysfunction no rejection or normal transplant function. The classifier set may comprise one or more genes that may be differentially expressed in three or more control samples. The three or more control samples may be differentially classified.

The method of producing a classifier set may comprise comparing two or more gene expression profiles from two or more control samples. The two or more gene expression profiles from the two or more control samples may be normalized. The two or more gene expression profiles may be normalized by different tools including use of frozen robust multichip average (fRMA). In some instances, the two or more gene expression profiles are not normalized by quantile normalization.

The method of producing a classifier set may comprise applying an algorithm to two or more expression profiles from two or more control samples. The classifier set may comprise one or more genes selected by application of the algorithm to the two or more expression profiles. The method of producing the classifier set may further comprise generating a shrunken centroid parameter for the one or more genes in the classifier set.

The classifier set may be generated by statistical bootstrapping. Statistical bootstrapping may comprise creating multiple computational permutations and cross validations using a control sample set.

Disclosed herein is the use of a classifier probe set for determining an expression level of one or more genes in preparation of a kit for classifying a sample from a subject, wherein the classifier probe set is based on a classification system comprising three or more classes. At least two of the classes may be selected from transplant rejection, transplant dysfunction with no rejection and normal transplant function. All three classes may be selected from transplant rejection, transplant dysfunction with no rejection and normal transplant function.

Further disclosed herein is a classifier probe set for use in classifying a sample from a subject, wherein the classifier probe set is based on a classification system comprising three or more classes. At least two of the classes may be selected from transplant rejection, transplant dysfunction with no rejection and normal transplant function. All three classes may be selected from transplant rejection, transplant dysfunction with no rejection and normal transplant function.

Further disclosed herein is the use of a classification system comprising three or more classes in preparation of a probe set for classifying a sample from a subject. At least two of the classes may be selected from transplant rejection, transplant dysfunction with no rejection and normal transplant function. At least three of the three or more classes may be selected from transplant rejection, transplant dysfunction with no rejection and normal transplant function. Often, the classes are different classes.

Further disclosed herein are classification systems for classifying one or more samples from one or more subjects. The classification system may comprise three or more classes. At least two of the classes may be selected from transplant rejection, transplant dysfunction with no rejection and normal transplant function. All three classes may be selected from transplant rejection, transplant dysfunction with no rejection and normal transplant function.

Classifiers may comprise panels of biomarkers. Expression profiling based on panels of biomarkers may be used to characterize a sample as healthy, transplant rejection and/or transplant dysfunction with no rejection. Panels may be derived from analysis of gene expression levels of cohorts containing healthy transplant recipients, transplant recipients experiencing transplant rejection and/or transplant recipients experiencing transplant dysfunction with no rejection. Panels may be derived from analysis of gene expression levels of cohorts containing transplant recipients experiencing transplant dysfunction with no rejection. Exemplary panels of biomarkers can be derived from genes listed in Table 1a. Exemplary panels of biomarkers can also be derived from genes listed in Table 1c. Exemplary panels of biomarkers can be derived from genes listed in Table 1a, 1b, 1c, or 1d, in any combination. Exemplary panels of biomarkers can be derived from genes listed in Table 1a, 1b, 1c, 1d, 8, 9, 10b, 12b, 14b, 16b, 17b, or 18b, in any combination.

Sample Cohorts

In some embodiments, the methods, kits and systems of the present invention seek to improve upon the accuracy of current methods of classifying samples obtained from transplant recipients. In some embodiments, the methods provide improved accuracy of identifying samples as normal function (e.g., healthy), transplant rejection or transplant dysfunction with no rejection. In some embodiments, the methods provide improved accuracy of identifying samples as normal function (e.g., healthy), AR or ADNR. Improved accuracy may be obtained by using algorithms trained with specific sample cohorts, high numbers of samples, samples from individuals located in diverse geographical regions, samples from individuals with diverse ethnic backgrounds, samples from individuals with different genders, and/or samples from individuals from different age groups.

The sample cohorts may be from female, male or a combination thereof. In some cases, the sample cohorts are from at least about 1, 2, 3, 4, 5, 6, 7, 8, 9, 10, 11, 12, 13, 14, 15, 20, 25, 30, 35, 40, 45, 50, 55, 60, 65, 70, 75, or 80 or more different geographical locations. The geographical locations may comprise sites spread out across a nation, a continent, or the world. Geographical locations include, but are not limited to, test centers, medical facilities, medical offices, hospitals, post office addresses, zip codes, cities, counties, states, nations, and continents. In some embodiments, a classifier that is trained using sample cohorts from the United States may need to be retrained for use on sample cohorts from other geographical regions (e.g., Japan, China, Europe, etc.). In some cases, the sample cohorts are from at least about 1, 2, 3, 4, 5, 6, 7, 8, 9, 10, 11, 12, 13, 14, 15, or 20 or more different ethnic groups. In some embodiments, a classifier that is trained using sample cohorts from a specific ethnic group may need to be retrained for use on sample cohorts from other ethnic groups. In some cases, the sample cohorts are from at least about 1, 2, 3, 4, 5, 6, 7, 8, 9, 10 or more different age groups. The age groups may be grouped into 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more years, or a combination thereof. Age groups may include, but are not limited to, under 10 years old, 10-15 years old, 15-20 years old, 20-25 years old, 25-30 years old, 30-35 years old, 35-40 years old, 40-45 years old, 45-50 years old, 50-55 years old, 55-60 years old, 60-65 years old, 65-70 years old, 70-75 years old, 75-80 years old, and over 80 years old. In some embodiments, a classifier that is trained using sample cohorts from a specific age group (e.g., 30-40 years old) may need to be retrained for use on sample cohorts from other age groups (e.g., 20-30 years old, etc.).

Methods of Classifying Samples

The samples may be classified simultaneously. The samples may be classified sequentially. The two or more samples may be classified at two or more time points. The samples may be obtained at 1, 2, 3, 4, 5, 6, 7, 8, 9, 10, 11, 12, 13, 14, 15, 16, 17, 18, 19, 20 or more time points. The samples may be obtained at 10, 20, 30, 40, 50, 60, 70, 80, 90, 100, 110, 120, 130, 140, 150, 160, 170, 180, 190, 200 or more time points. The samples may be obtained at 100, 200, 300, 400, 500, 600, 700, 800, 900, 1000, 1100, 1200, 1300, 1400, 1500, 1600, 1700, 1800, 1900, 2000 or more time points. The two or more time points may be 1, 2, 3, 4, 5, 6, 7, 8, 9, 10, 11, 12, 13, 14, 15, 16, 17, 18, 19, 20 or more minutes apart. The two or more time points may be 1, 2, 3, 4, 5, 6, 7, 8, 9, 10, 11, 12, 13, 14, 15, 16, 17, 18, 19, 20 or more hours apart. The two or more time points may be 1, 2, 3, 4, 5, 6, 7, 8, 9, 10, 11, 12, 13, 14, 15, 16, 17, 18, 19, 20 or more days apart. The two or more time points may be 1, 2, 3, 4, 5, 6, 7, 8, 9, 10, 11, 12, 13, 14, 15, 16, 17, 18, 19, 20 or more weeks apart. The two or more time points may be 1, 2, 3, 4, 5, 6, 7, 8, 9, 10, 11, 12, 13, 14, 15, 16, 17, 18, 19, 20 or more months apart. The two or more time points may be 1, 2, 3, 4, 5, 6, 7, 8, 9, 10, 11, 12, 13, 14, 15, 16, 17, 18, 19, 20 or more years apart. The two or more time points may be at least about 6 hours apart. The two or more time points may be at least about 12 hours apart. The two or more time points may be at least about 24 hours apart. The two or more time points may be at least about 2 days apart. The two or more time points may be at least about 1 week apart. The two or more time points may be at least about 1 month apart. The two or more time points may be at least about 3 months apart. The two or more time points may be at least about 6 months apart. The three or more time points may be at the same interval. For example, the first and second time points may be 1 month apart and the second and third time points may be 1 month apart. The three or more time points may be at different intervals. For example, the first and second time points may be 1 month apart and the second and third time points may be 3 months apart.

Methods of simultaneous classifier-based analysis of one or more samples may comprise applying one or more algorithm to data from one or more samples to simultaneously produce one or more lists, wherein the lists comprise one or more samples classified as being from healthy subjects (e.g. subjects with a normal functioning transplant (TX)), unhealthy subjects, subjects suffering from transplant rejection, subjects suffering from transplant dysfunction, subjects suffering from acute rejection (AR), subjects suffering from acute dysfunction with no rejection (ADNR), subjects suffering from chronic allograft nephropathy (CAN), subjects suffering from interstitial fibrosis and/or tubular atrophy (IF/TA), and/or subjects suffering from subclinical acute rejection (SCAR).

Methods of sequential classifier-based analysis of one or more samples may comprise (a) applying a first algorithm to data from one or more samples to produce a first list; and (b) applying a second algorithm to data from the one or more samples that were excluded from the first list to produce a second list. The first list or the second list may comprise one or more samples classified as being from healthy subjects (e.g. subjects with a normal functioning transplant (TX)). The first list or the second list may comprise one or more samples classified as being from unhealthy subjects. The first list or the second list may comprise one or more samples classified as being from subjects suffering from transplant rejection. The first list or the second list may comprise one or more samples classified as being from subjects suffering from transplant dysfunction. The first list or the second list may comprise one or more samples classified as being from subjects suffering from acute rejection (AR). The first list or the second list may comprise one or more samples classified as being from subjects suffering from acute dysfunction with no rejection (ADNR). The first list or the second list may comprise one or more samples classified as being from subjects suffering from chronic allograft nephropathy (CAN). The first list or the second list may comprise one or more samples classified as being from subjects suffering from interstitial fibrosis and/or tubular atrophy (IF/TA). The first list or the second list may comprise one or more samples classified as being from subjects suffering from subclinical acute rejection (SCAR). For example, a sequential classifier-based analysis may comprise (a) applying a first algorithm to data from one or more samples to produce a first list, wherein the first list comprises one or more samples classified as being from healthy subjects; and (b) applying a second algorithm to data from the one or more samples that were excluded from the first list to produce a second list, wherein the second list comprises one or more samples classified as being from subjects suffering from transplant rejection.

The methods may undergo further iteration. One or more additional lists may be produced by applying one or more additional algorithms. The first algorithm, second algorithm, and/or one or more additional algorithms may be the same. The first algorithm, second algorithm, and/or one or more additional algorithms may be different. In some instances, the one or more additional lists may be produced by applying one or more additional algorithms to data from one or more samples from one or more previous lists. The one or more additional lists may comprise one or more samples classified as being from healthy subjects (e.g. subjects with a normal functioning transplant (TX)). The one or more additional lists may comprise one or more samples classified as being from unhealthy subjects. The one or more additional lists may comprise one or more samples classified as being from subjects suffering from transplant rejection. The one or more additional lists may comprise one or more samples classified as being from subjects suffering from transplant dysfunction. The one or more additional lists may comprise one or more samples classified as being from subjects suffering from acute rejection (AR). The one or more additional lists may comprise one or more samples classified as being from subjects suffering from acute dysfunction with no rejection (ADNR). The one or more additional lists may comprise one or more samples classified as being from subjects suffering from chronic allograft nephropathy (CAN). The one or more additional lists may comprise one or more samples classified as being from subjects suffering from interstitial fibrosis and/or tubular atrophy (IF/TA). The one or more additional lists may comprise one or more samples classified as being from subjects suffering from subclinical acute rejection (SCAR).

This disclosure also provides one or more steps or analyses that may be used in addition to applying a classifier or algorithm to expression level data from a sample, such as a clinical sample. Such series of steps may include, but are not limited to, initial cytology or histopathology study of the sample, followed by analysis of gene (or other biomarker) expression levels in the sample. In some embodiments, the one or more steps or analyses (e.g., cytology or histopathology study) occur prior to the step of applying any of the classifier probe sets or classification systems described herein. The one or more steps or analyses (e.g., cytology or histopathology study) may occur concurrently with the step of applying any of the classifier probe sets or classification systems described herein. Alternatively, the one or more steps or analyses (e.g., cytology or histopathology study) may occur after the step of applying any of the classifier probe sets or classification systems described herein.

Sequential classifier-based analysis of the samples may occur in various orders. For example, sequential classifier-based analysis of one or more samples may comprise classifying samples as healthy or unhealthy, followed by classification of unhealthy samples as transplant rejection or non-transplant rejection, followed by classification of non-transplant rejection samples as transplant dysfunction or transplant dysfunction with no rejection. In another example, sequential classifier-based analysis of one or more samples may comprise classifying samples as transplant dysfunction or no transplant dysfunction, followed by classification of transplant dysfunction samples as transplant rejection or no transplant rejection. The no transplant dysfunction samples may further be classified as healthy. In another example, sequential classifier-based analysis comprises classifying samples as transplant rejection or no transplant rejection, followed by classification of the no transplant rejection samples as healthy or unhealthy. The unhealthy samples may be further classified as transplant dysfunction or no transplant dysfunction. Sequential classifier-based analysis may comprise classifying samples as transplant rejection or no transplant rejection, followed by classification of the no transplant rejection samples as transplant dysfunction or no transplant dysfunction. The no transplant dysfunction samples may further be classified as healthy or unhealthy. The unhealthy samples may further be classified as transplant rejection or no transplant rejection. The unhealthy samples may further be classified as chronic allograft nephropathy/interstitial fibrosis and tubular atrophy (CAN/IFTA) or no CAN/IFTA. The unhealthy samples may further be classified as transplant dysfunction or no transplant dysfunction. The transplant dysfunction samples may be further classified as transplant dysfunction with no rejection or transplant dysfunction with rejection. The transplant dysfunction samples may be further classified as transplant rejection or no transplant rejection. The transplant rejection samples may further be classified as chronic allograft nephropathy/interstitial fibrosis and tubular atrophy (CAN/IFTA) or no CAN/IFTA.

Algorithms

The methods, kits, and systems disclosed herein may comprise one or more algorithms or uses thereof. The one or more algorithms may be used to classify one or more samples from one or more subjects. The one or more algorithms may be applied to data from one or more samples. The data may comprise gene expression data. The data may comprise sequencing data. The data may comprise array hybridization data.

The methods disclosed herein may comprise assigning a classification to one or more samples from one or more subjects. Assigning the classification to the sample may comprise applying an algorithm to the expression level. In some cases, the gene expression levels are inputted to a trained algorithm for classifying the sample as one of the conditions comprising AR, ADNR, or TX.

The algorithm may provide a record of its output including a classification of a sample and/or a confidence level. In some instances, the output of the algorithm can be the possibility of the subject of having a condition, such as AR, ADNR, or TX. In some instances, the output of the algorithm can be the risk of the subject of having a condition, such as AR, ADNR, or TX. In some instances, the output of the algorithm can be the possibility of the subject of developing into a condition in the future, such as AR, ADNR, or TX.

The algorithm may be a trained algorithm. The algorithm may comprise a linear classifier. The linear classifier may comprise one or more linear discriminant analysis, Fisher's linear discriminant, Naïve Bayes classifier, Logistic regression, Perceptron, Support vector machine, or a combination thereof. The linear classifier may be a Support vector machine (SVM) algorithm.

The algorithm may comprise one or more linear discriminant analysis (LDA), Basic perceptron, Elastic Net, logistic regression, (Kernel) Support Vector Machines (SVM), Diagonal Linear Discriminant Analysis (DLDA), Golub Classifier, Parzen-based, (kernel) Fisher Discriminant Classifier, k-nearest neighbor, Iterative RELIEF, Classification Tree, Maximum Likelihood Classifier, Random Forest, Nearest Centroid, Prediction Analysis of Microarrays (PAM), k-medians clustering, Fuzzy C-Means Clustering, Gaussian mixture models, or a combination thereof. The algorithm may comprise a Diagonal Linear Discriminant Analysis (DLDA) algorithm. The algorithm may comprise a Nearest Centroid algorithm. The algorithm may comprise a Random Forest algorithm. The algorithm may comprise a Prediction Analysis of Microarrays (PAM) algorithm.

The methods disclosed herein may comprise use of one or more classifier equations. Classifying the sample may comprise a classifier equation. The classifier equation may be Equation 1:

$$\delta_k(x^*) = \sum_{i=1}^{p} \frac{(x_i^* - \bar{x}'_{ik})^2}{(s_i + s_0)^2} - 2\log \pi_k,$$

wherein:
k is a number of possible classes;
$\delta_k$ may be the discriminant score for class k;
$x^*_i$ represents the expression level of gene i;
$x^*$ represents a vector of expression levels for all p genes to be used for classification drawn from the sample to be classified;
$\bar{x}'_k$ may be a shrunken centroid calculated from a training data and a shrinkage factor;
$\bar{x}'_{ik}$: may be a component of $\bar{x}'_k$ corresponding to gene i;
$s_i$ is a pooled within-class standard deviation for gene i in the training data;
$s_0$ is a specified positive constant; and
$\pi_k$ represents a prior probability of a sample belonging to class k.

Assigning the classification may comprise calculating a class probability. Calculating the class probability $\hat{p}_k(x^*)$ may be calculated by Equation 2:

$$\hat{p}_k(x^*) = \frac{e^{-\frac{1}{2}\delta_k(x^*)}}{\sum_{l=1}^{K} e^{-\frac{1}{2}\delta_l(x^*)}}.$$

Assigning the classification may comprise a classification rule. The classification rule $C(x^*)$ may be expressed by Equation 3:

$$C(x^*) = \underset{k \in \{1,K\}}{\mathrm{argmax}} \hat{p}_k(x^*).$$

Classification of Samples

The classifiers disclosed herein may be used to classify one or more samples. The classifiers disclosed herein may be used to classify 1, 2, 3, 4, 5, 6, 7, 8, 9, 10, 11, 12, 13, 14, 15, 16, 17, 18, 19, 20 or more samples. The classifiers disclosed herein may be used to classify 10, 20, 30, 40, 50, 60, 70, 80, 90, 100, 110, 120, 130, 140, 150, 160, 170, 180, 190, 200 or more samples. The classifiers disclosed herein may be used to classify 100, 200, 300, 400, 500, 600, 700, 800, 900, 1000, 1100, 1200, 1300, 1400, 1500, 1600, 1700, 1800, 1900, 2000 or more samples. The classifiers disclosed herein may be used to classify 1000, 2000, 3000, 4000, 5000, 6000, 7000, 8000, 9000, 10000, 11000, 12000, 13000, 14000, 15000, 16000, 17000, 18000, 19000, 20000 or more samples. The classifiers disclosed herein may be used to classify 10000, 20000, 30000, 40000, 50000, 60000, 70000, 80000, 90000, 100000, 110000, 120000, 130000, 140000, 150000, 160000, 170000, 180000, 190000, 200000 or more samples. The classifiers disclosed herein may be used to classify at least about 5 samples. The classifiers disclosed herein may be used to classify at least about 10 samples. The classifiers disclosed herein may be used to classify at least about 20 samples. The classifiers disclosed herein may be used to classify at least about 30 samples. The classifiers disclosed herein may be used to classify at least about 50 samples. The classifiers disclosed herein may be used to classify at least about 100 samples. The classifiers disclosed herein may be used to classify at least about 200 samples.

Two or more samples may be from the same subject. The samples may be from two or more different subjects. The samples may be from 1, 2, 3, 4, 5, 6, 7, 8, 9, 10, 11, 12, 13, 14, 15, 16, 17, 18, 19, 20 or more subjects. The samples may be from 10, 20, 30, 40, 50, 60, 70, 80, 90, 100, 110, 120, 130, 140, 150, 160, 170, 180, 190, 200 or more subjects. The samples may be from 100, 200, 300, 400, 500, 600, 700, 800, 900, 1000, 1100, 1200, 1300, 1400, 1500, 1600, 1700, 1800, 1900, 2000 or more subjects. The samples may be from 1000, 2000, 3000, 4000, 5000, 6000, 7000, 8000, 9000, 10000, 11000, 12000, 13000, 14000, 15000, 16000, 17000, 18000, 19000, 20000 or more subjects. The samples may be from 1000, 2000, 3000, 4000, 5000, 6000, 7000, 8000, 9000, 10000, 11000, 12000, 13000, 14000, 15000, 16000, 17000, 18000, 19000, 20000 or more subjects. The samples may be from 2 or more subjects. The samples may be from 5 or more subjects. The samples may be from 10 or more subjects. The samples may be from 20 or more subjects. The samples may be from 50 or more subjects. The samples may be from 70 or more subjects. The samples may be from 80 or more subjects. The samples may be from 100 or more subjects. The samples may be from 200 or more subjects. The samples may be from 300 or more subjects. The samples may be from 500 or more subjects.

The two or more samples may be obtained at the same time point. The two or more samples may be obtained at two or more different time points. The samples may be obtained at 1, 2, 3, 4, 5, 6, 7, 8, 9, 10, 11, 12, 13, 14, 15, 16, 17, 18, 19, 20 or more time points. The samples may be obtained at 10, 20, 30, 40, 50, 60, 70, 80, 90, 100, 110, 120, 130, 140, 150, 160, 170, 180, 190, 200 or more time points. The samples may be obtained at 100, 200, 300, 400, 500, 600, 700, 800, 900, 1000, 1100, 1200, 1300, 1400, 1500, 1600, 1700, 1800, 1900, 2000 or more time points. The two or more time points may be 1, 2, 3, 4, 5, 6, 7, 8, 9, 10, 11, 12, 13, 14, 15, 16, 17, 18, 19, 20 or more minutes apart. The two or more time points may be 1, 2, 3, 4, 5, 6, 7, 8, 9, 10, 11, 12, 13, 14, 15, 16, 17, 18, 19, 20 or more hours apart. The two or more time points may be 1, 2, 3, 4, 5, 6, 7, 8, 9, 10, 11, 12, 13, 14, 15, 16, 17, 18, 19, 20 or more days apart. The two or more time points may be 1, 2, 3, 4, 5, 6, 7, 8, 9, 10, 11, 12, 13, 14, 15, 16, 17, 18, 19, 20 or more weeks apart. The two or more time points may be 1, 2, 3, 4, 5, 6, 7, 8, 9, 10, 11, 12, 13, 14, 15, 16, 17, 18, 19, 20 or more months apart. The two or more time points may be 1, 2, 3, 4, 5, 6, 7, 8, 9, 10, 11, 12, 13, 14, 15, 16, 17, 18, 19, 20 or more years apart. The two or more time points may be at least about 6 hours apart. The two or more time points may be at least about 12 hours apart. The two or more time points may be at least about 24 hours apart. The two or more time points may be at least about 2 days apart. The two or more time points may be at least about 1 week apart. The two or more time points may be at least about 1 month apart. The two or more time points may be at least about 3 months apart. The two or more time points may be at least about 6 months apart. The three or more time points may be at the same interval. For example, the first and second time points may be 1 month apart and the second and third time points may be 1 month apart. The three or more time points may be at different intervals. For example, the first and second time points may be 1 month apart and the second and third time points may be 3 months apart.

Further disclosed herein are methods of classifying one or more samples from one or more subjects. The method of classifying one or more samples from one or more subjects may comprise (a) obtaining an expression level of one or more gene expression products of a sample from a subject; and (b) identifying the sample as normal transplant function if the gene expression level indicates a lack of transplant rejection and/or transplant dysfunction. The subject may be a transplant recipient. The subject may be a transplant donor. The subject may be a healthy subject. The subject may be an unhealthy subject. The method may comprise determining an expression level of one or more gene expression products in one or more samples from one or more subjects. The one or more subjects may be transplant recipients, transplant donors, or combination thereof. The one or more subjects may be healthy subjects, unhealthy subjects, or a combination thereof. The method may further comprise identifying the sample as transplant dysfunction if the gene expression level indicates transplant rejection and/or transplant dysfunction. The method may further comprise identifying the sample as transplant dysfunction with no rejection if the gene expression level indicates transplant dysfunction and a lack transplant rejection. The method may further comprise identifying the sample as transplant rejection if the gene expression level indicates transplant rejection and/or transplant dysfunction. The expression level may be obtained by sequencing. The expression level may be obtained by RNA-sequencing. The expression level may be obtained by array. The array may be a microarray. The microarray may be a peg array. The peg array may be a Gene 1.1$^{ST}$ peg array. The peg array may be a Hu133 Plus 2.0PM peg array. The peg array may be a HT HG-U133+ PM Array. The sample may be a blood sample. The sample may comprise one or more peripheral blood lymphocytes. The blood sample may be a peripheral blood sample. The sample may be a serum sample. The sample may be a plasma sample. The expression level may be based on detecting and/or measuring one or more RNA. Identifying the sample may comprise use of one or more classifier probe sets. Identifying the sample may comprise use of one or more algorithms. Identifying the sample may comprise use of one or more classification systems. The classification system may comprise a three-way classification. The three-way classification may comprise normal transplant function, transplant dysfunction with no rejection, transplant rejection, or a combination thereof. The three-way classification may comprise normal transplant function, transplant dysfunction with no rejection, and transplant rejection. The method may further comprise generating one or more reports based on the identification of the sample. The method may further comprise transmitting one or more reports comprising information pertaining to the identification of the sample to the subject or a medical representative of the subject.

The method of classifying a sample may comprise (a) obtaining an expression level of one or more gene expression products of a sample from a subject; and (b) identifying the sample as transplant rejection if the gene expression level indicative of transplant rejection and/or transplant dysfunction. The one or more subjects may be transplant recipients. The subject may be a transplant recipient. The subject may be a transplant donor. The subject may be a healthy subject. The subject may be an unhealthy subject. The method may comprise determining an expression level of one or more gene expression products in one or more samples from one or more subjects. The one or more subjects may be transplant recipients, transplant donors, or combination thereof. The one or more subjects may be healthy subjects, unhealthy subjects, or a combination thereof. The method may further comprise identifying the sample as transplant dysfunction if the gene expression level indicates transplant rejection and/or transplant dysfunction. The method may further comprise identifying the sample as transplant dysfunction with no rejection if the gene expression level indicates transplant dysfunction and a lack of transplant rejection. The method may further comprise identifying the sample as normal function if the gene expression level indicates a lacks of transplant rejection and transplant dysfunction. The expression level may be obtained by sequencing. The expression level may be obtained by RNA-sequencing. The expression level may be obtained by array. The array may be a microarray. The microarray may be a peg array. The peg array may be a Gene 1.1$^{ST}$ peg array. The peg array may be a Hu133 Plus 2.0PM peg array. The peg array may be a HT HG-U133+ PM Array. The sample may be a blood sample. The sample may comprise one or more peripheral blood lymphocytes. The blood sample may be a peripheral blood sample. The sample may be a serum sample. The sample may be a plasma sample. The expression level may be based on detecting and/or measuring one or more RNA. Identifying the sample may comprise use of one or more classifier probe sets. Identifying the sample may comprise use of one or more algorithms. Identifying the sample may comprise use of one or more classification systems. The classification system may comprise a three-way classification. The three-way classification may comprise normal transplant function, transplant dysfunction with no rejection, transplant rejection, or a combination thereof. The three-way classification may comprise normal transplant function, transplant dysfunction with no rejection, and transplant rejection. The method may further comprise generating one or more reports based on the identification of the sample. The method may further comprise transmitting one or more reports comprising information pertaining to the identification of the sample to the subject or a medical representative of the subject.

The method of classifying a sample may comprise (a) obtaining an expression level of one or more gene expression products of a sample from a subject; and (b) identifying the sample as transplant dysfunction with no rejection wherein the gene expression level indicative of transplant dysfunction and the gene expression level indicates a lack of transplant rejection. The subject may be a transplant recipient. The subject may be a transplant donor. The subject may be a healthy subject. The subject may be an unhealthy subject. The method may comprise determining an expression level of one or more gene expression products in one or more samples from one or more subjects. The one or more subjects may be transplant recipients, transplant donors, or combination thereof. The one or more subjects may be healthy subjects, unhealthy subjects, or a combination thereof. The method may further comprise identifying the sample as normal transplant function if the gene expression level indicates a lack of transplant dysfunction. The method may further comprise identifying the sample as transplant rejection if the gene expression level indicates transplant rejection and/or transplant dysfunction. The expression level may be obtained by sequencing. The expression level may be obtained by RNA-sequencing. The expression level may be obtained by array. The array may be a microarray. The microarray may be a peg array. The peg array may be a Gene 1.1$^{ST}$ peg array. The peg array may be a Hu133 Plus 2.0PM peg array. The peg array may be a HT HG-U133+ PM Array. The sample may be a blood sample. The sample may comprise one or more peripheral blood lymphocytes. The blood sample may be a peripheral blood sample. The sample may be a serum sample. The sample may be a plasma sample. The expression level may be based on detecting and/or measuring one or more RNA. Identifying the sample may comprise use of one or more classifier probe sets. Identifying the sample may comprise use of one or more algorithms. Identifying the sample may comprise use of one or more classification systems. The classification system may comprise a three-way classification. The three-way classification may comprise normal transplant function, transplant dysfunction with no rejection, transplant rejection, or a combination thereof. The three-way classification may comprise normal transplant function, transplant dysfunction with no rejection, and transplant rejection. The method may further comprise generating one or more reports based on the identification of the sample. The method may further comprise transmitting one or more reports comprising information pertaining to the identification of the sample to the subject or a medical representative of the subject.

The method of classifying a sample may comprise (a) determining an expression level of one or more gene expression products in a sample from a subject; and (b) assigning a classification to the sample based on the level of expression of the one or more gene products, wherein the classification comprises transplant dysfunction with no rejection. In some embodiments, the gene expression products are associated with one or more biomarkers selected from gene expression products corresponding to genes listed in Table 1a. In some embodiments, the gene expression products are associated with one or more biomarkers selected from gene expression products corresponding to genes listed in Table 1c. In some embodiments, the gene expression products are associated with one or more biomarkers selected from gene expression products corresponding to genes listed in Table 1a, 1b, 1c, or 1d, in any combination. In some embodiments, the gene expression products are associated with one or more biomarkers selected from gene expression products corresponding to genes listed in Table 1a, 1b, 1c, 1d, 8, 9, 10b, 12b, 14b, 16b, 17b, or 18b, in any combination. The subject may be a transplant recipient. The subject may be a transplant donor. The subject may be a healthy subject. The subject may be an unhealthy subject. The method may comprise determining an expression level of one or more gene expression products in one or more samples from one or more subjects. The one or more subjects may be transplant recipients, transplant donors, or combination thereof. The one or more subjects may be healthy subjects, unhealthy subjects, or a combination thereof. The method may further comprise classifying the sample as transplant dysfunction. The method may further comprise classifying the sample as transplant dysfunction with no rejection. The method may further comprise classifying the sample as normal function. The method may further comprise classifying the sample as transplant rejection. The expression level may be obtained by sequencing. The expression level may be obtained by RNA-sequencing. The expression level may be obtained by array. The array may be a microarray. The microarray may be a peg array. The peg array may be a Gene 1.1$^{ST}$ peg array. The peg array may be a Hu133 Plus 2.0PM peg array. The peg array may be a HT HG-U133+ PM Array. The sample may be a blood sample. The sample may comprise one or more peripheral blood lymphocytes. The blood sample may be a peripheral blood sample. The sample may be a serum sample. The sample may be a plasma sample. The expression level may be based on detecting and/or measuring one or more RNA. Classifying the sample may comprise use of one or more classifier probe sets. Classifying the sample may comprise use of one or more algorithms. The classification system may further comprise normal transplant function. The classification system may further comprise transplant rejection. The classification system may further comprise CAN. The classification system may further comprise IF/TA. The classification system may comprise a three-way classification. The three-way classification may comprise normal transplant function, transplant dysfunction with no rejection, transplant rejection, or a combination thereof. The three-way classification may comprise normal transplant function, transplant dysfunction with no rejection, and transplant rejection. The method may further comprise generating one or more reports based on the identification of the sample. The method may further comprise transmitting one or more reports comprising information pertaining to the identification of the sample to the subject or a medical representative of the subject.

The method of classifying a sample may comprise (a) determining an expression level of one or more gene expression products in a sample from a subject; and (b) assigning a classification to the sample based on the level of expression of the one or more gene products, wherein the classification comprises transplant rejection, transplant dysfunction with no rejection and normal transplant function. In some embodiments, the gene expression products are associated with one or more biomarkers selected from gene expression products corresponding to genes listed in Table 1a. In some embodiments, the gene expression products are associated with one or more biomarkers selected from gene expression products corresponding to genes listed in Table 1c. In some embodiments, the gene expression products are associated with one or more biomarkers selected from gene expression products corresponding to genes listed in Table 1a, 1b, 1c, or 1d, in any combination. In some embodiments, the gene expression products are associated with one or more biomarkers selected from gene expression products corresponding to genes listed in Table 1a, 1b, 1c, 1d, 8, 9, 10b, 12b, 14b, 16b, 17b, or 18b, in any combination. The subject may be a transplant recipient. The subject may be a transplant donor. The subject may be a healthy subject. The subject may be an unhealthy subject. The method may comprise determining an expression level of one or more gene expression products in one or more samples from one or more subjects. The one or more subjects may be transplant recipients, transplant donors, or combination thereof. The one or more subjects may be healthy subjects, unhealthy subjects, or a combination thereof. The method may further comprise classifying the sample as transplant dysfunction. The method may further comprise classifying the sample as transplant dysfunction with no rejection. The method may further comprise classifying the sample as normal function. The method may further comprise classifying the sample as transplant rejection. The expression level may be obtained by sequencing. The expression level may be obtained by RNA-sequencing. The expression level may be obtained by array. The array may be a microarray. The microarray may be a peg array. The peg array may be a Gene $1.1^{ST}$ peg array. The peg array may be a Hu133 Plus 2.0PM peg array. The peg array may be a HT HG-U133+ PM Array. The sample may be a blood sample. The sample may comprise one or more peripheral blood lymphocytes. The blood sample may be a peripheral blood sample. The sample may be a serum sample. The sample may be a plasma sample. The expression level may be based on detecting and/or measuring one or more RNA. Classifying the sample may comprise use of one or more classifier probe sets. Classifying the sample may comprise use of one or more algorithms. The classification system may further comprise CAN. The classification system may further comprise IF/TA. The method may further comprise generating one or more reports based on the identification of the sample. The method may further comprise transmitting one or more reports comprising information pertaining to the identification of the sample to the subject or a medical representative of the subject.

The method of classifying a sample may comprise (a) determining a level of expression of a plurality of genes in a sample from a subject; and (b) classifying the sample by applying an algorithm to the expression level data from step (a), wherein the algorithm is not validated by a cohort-based analysis of an entire cohort. In some embodiments, the plurality of genes is associated with one or more biomarkers selected from gene expression products corresponding to genes listed in Table 1a. In some embodiments, the plurality of genes is associated with one or more biomarkers selected from gene expression products corresponding to genes listed in Table 1c. In some embodiments, the plurality of genes is associated with one or more biomarkers selected from gene expression products corresponding to genes listed in Table 1a, 1b, 1c, or 1d, in any combination. In some embodiments, the plurality of genes is associated with one or more biomarkers selected from gene expression products corresponding to genes listed in Table 1a, 1b, 1c, 1d, 8, 9, 10b, 12b, 14b, 16b, 17b, or 18b, in any combination. The subject may be a transplant recipient. The subject may be a transplant donor. The subject may be a healthy subject. The subject may be an unhealthy subject. The method may comprise determining an expression level of one or more gene expression products in one or more samples from one or more subjects. The one or more subjects may be transplant recipients, transplant donors, or combination thereof. The one or more subjects may be healthy subjects, unhealthy subjects, or a combination thereof. The method may further comprise classifying the sample as transplant dysfunction. The method may further comprise classifying the sample as transplant dysfunction with no rejection. The method may further comprise classifying the sample as normal function. The method may further comprise classifying the sample as transplant rejection. The expression level may be obtained by sequencing. The expression level may be obtained by RNA-sequencing. The expression level may be obtained by array. The array may be a microarray. The microarray may be a peg array. The peg array may be a Gene $1.1^{ST}$ peg array. The peg array may be a Hu133 Plus 2.0PM peg array. The sample may be a blood sample. The sample may comprise one or more peripheral blood lymphocytes. The blood sample may be a peripheral blood sample. The sample may be a serum sample. The sample may be a plasma sample. The expression level may be based on detecting and/or measuring one or more RNA. Classifying the sample may comprise use of one or more classifier probe sets. Classifying the sample may comprise use of one or more algorithms. Classifying the sample may comprise use of a classification system. The classification system may further comprise normal transplant function. The classification system may further comprise transplant rejection. The classification system may further comprise CAN. The classification system may further comprise IF/TA. The classification system may comprise a three-way classification. The three-way classification may comprise normal transplant function, transplant dysfunction with no rejection, transplant rejection, or a combination thereof. The three-way classification may comprise normal transplant function, transplant dysfunction with no rejection, and transplant rejection. The method may further comprise generating one or more reports based on the identification of the sample. The method may further comprise transmitting one or more reports comprising information pertaining to the identification of the sample to the subject or a medical representative of the subject. The algorithm may be validated by analysis of less than or equal to about 97%, 95%, 93%, 90%, 87%, 85%, 83%, 80%, 77%, 75%, 73%, 70%, 67%, 65%, 53%, 60%, 57%, 55%, 53%, 50%, 47%, 45%, 43%, 40%, 37%, 35%, 33%, 30%, 27%, 25%, 23%, 20%, 17%, 15%, 13%, 10%, 9%, 8%, 7%, 6%, 5%, 4%, or 3% of the entire cohort. The algorithm may be validated by analysis of less than or equal to about 70% of the entire cohort. The algorithm may be validated by analysis of less than or equal to about 60% of the entire cohort. The algorithm may be validated by analysis of less than or equal to about 50% of the entire cohort. The algorithm may be validated by analysis of less than or equal to about 40% of the entire cohort.

The method of classifying a sample may comprise (a) determining a level of expression of a plurality of genes in a sample from a subject; and (b) classifying the sample by applying an algorithm to the expression level data from step (a), wherein the algorithm is validated by a combined analysis of expression level data from a plurality of samples, wherein the plurality of samples comprises at least one sample with an unknown phenotype and at least one sample with a known phenotype. In some embodiments, the plurality of genes is associated with one or more biomarkers selected from gene expression products corresponding to genes listed in Table 1a. In some embodiments, the plurality of genes is associated with one or more biomarkers selected from gene expression products corresponding to genes listed in Table 1c. In some embodiments, the plurality of genes is associated with one or more biomarkers selected from gene expression products corresponding to genes listed in Table 1a, 1b, 1c, or 1d, in any combination. In some embodiments, the plurality of genes is associated with one or more biomarkers selected from gene expression products corresponding to genes listed in Table 1a, 1b, 1c, 1d, 8, 9, 10b, 12b, 14b, 16b, 17b, or 18b, in any combination. The subject may be a transplant recipient. The subject may be a transplant donor. The subject may be a healthy subject. The subject may be an unhealthy subject. The method may comprise determining an expression level of one or more gene expression products in one or more samples from one or more subjects. The one or more subjects may be transplant recipients, transplant donors, or combination thereof. The one or more subjects may be healthy subjects, unhealthy subjects, or a combination thereof. The method may further comprise classifying the sample as transplant dysfunction. The method may further comprise classifying the sample as transplant dysfunction with no rejection. The method may further comprise classifying the sample as normal function. The method may further comprise classifying the sample as transplant rejection. The expression level may be obtained by sequencing. The expression level may be obtained by RNA-sequencing. The expression level may be obtained by array. The array may be a microarray. The microarray may be a peg array. The peg array may be a Gene $1.1^{ST}$ peg array. The peg array may be a Hu133 Plus 2.0PM peg array. The sample may be a blood sample. The sample may comprise one or more peripheral blood lymphocytes. The blood sample may be a peripheral blood sample. The sample may be a serum sample. The sample may be a plasma sample. The expression level may be based on detecting and/or measuring one or more RNA. Classifying the sample may comprise use of one or more classifier probe sets. Classifying the sample may comprise use of one or more algorithms. Classifying the sample may comprise use of a classification system. The classification system may further comprise normal transplant function. The classification system may further comprise transplant rejection. The classification system may further comprise CAN. The classification system may further comprise IF/TA. The classification system may comprise a three-way classification. The three-way classification may comprise normal transplant function, transplant dysfunction with no rejection, transplant rejection, or a combination thereof. The three-way classification may comprise normal transplant function, transplant dysfunction with no rejection, and transplant rejection. The method may further comprise generating one or more reports based on the identification of the sample. The method may further comprise transmitting one or more reports comprising information pertaining to the identification of the sample to the subject or a medical representative of the subject. At least about 1%, 2%, 3%, 4%, 5%, 6%, 7%, 8%, 9%, 10%, 12%, 15%, 17%, 20%, 23%, 25%, 27%, 30% or more of the samples from the plurality of samples may have an unknown phenotype. At least about 35%, 40%, 45%, 50%, 55%, 57%, 60%, 65%, 70%, 75%, 80%, 85%, 90%, 95%, 97% or more of the samples from the plurality of samples may have an unknown phenotype. At least about 1%, 2%, 3%, 4%, 5%, 6%, 7%, 8%, 9%, 10%, 12%, 15%, 17%, 20%, 23%, 25%, 27%, 30% or more of the samples from the plurality of samples may have a known phenotype. At least about 35%, 40%, 45%, 50%, 55%, 57%, 60%, 65%, 70%, 75%, 80%, 85%, 90%, 95%, 97% or more of the samples from the plurality of samples may have a known phenotype.

The method of classifying one or more samples from one or more subjects may comprise (a) determining an expression level of one or more gene expression products in a sample from a subject; and (b) assigning a classification to the sample based on the level of expression of the one or more gene products, wherein the classification comprises transplant rejection, transplant dysfunction with no rejection and normal transplant function. The subject may be a transplant recipient. The subject may be a transplant donor. The subject may be a healthy subject. The subject may be an unhealthy subject. The method may comprise determining an expression level of one or more gene expression products in one or more samples from one or more subjects. The one or more subjects may be transplant recipients, transplant donors, or combination thereof. The one or more subjects may be healthy subjects, unhealthy subjects, or a combination thereof. The method may further comprise classifying the sample as transplant dysfunction. The method may further comprise classifying the sample as transplant dysfunction with no rejection. The method may further comprise classifying the sample as normal function. The method may further comprise classifying the sample as transplant rejection. The expression level may be obtained by sequencing. The expression level may be obtained by RNA-sequencing. The expression level may be obtained by array. The array may be a microarray. The microarray may be a peg array. The peg array may be a Gene $1.1^{ST}$ peg array. The peg array may be a Hu133 Plus 2.0PM peg array. The sample may be a blood sample. The sample may comprise one or more peripheral blood lymphocytes. The blood sample may be a peripheral blood sample. The sample may be a serum sample. The sample may be a plasma sample. The expression level may be based on detecting and/or measuring one or more RNA. Identifying the sample may comprise use of one or more classifier probe sets. Classifying the sample may comprise use of one or more algorithms. The classification may further comprise CAN. The classification may further comprise IF/TA. The method may further comprise generating one or more reports based on the classification of the sample. The method may further comprise transmitting one or more reports comprising information pertaining to the identification of the sample to the subject or a medical representative of the subject.

Classifying the sample may be based on the expression level of 10, 20, 30, 40, 50, 60, 70, 80, 90, 100 or more gene products. Classifying the sample may be based on the expression level of 100, 200, 300, 400, 500, 600, 700, 800, 900, 1000 or more gene products. Classifying the sample may be based on the expression level of 1000, 2000, 3000, 4000, 5000, 6000, 7000, 8000, 9000, 10000 or more gene products. Classifying the sample may be based on the expression level of 10000, 20000, 30000, 40000, 50000, 60000, 70000, 80000, 90000, 100000 or more gene products. Classifying the sample may be based on the expression level of 25 or more gene products. Classifying the sample may be based on the expression level of 50 or more gene products. Classifying the sample may be based on the expression level of 100 or more gene products. Classifying the sample may be based on the expression level of 200 or more gene products. Classifying the sample may be based on the expression level of 300 or more gene products.

Classifying the sample may comprise statistical bootstrapping.

Clinical Applications

The methods, compositions, systems and kits provided herein can be used to detect, diagnose, predict or monitor a condition of a transplant recipient. In some instances, the methods, compositions, systems and kits described herein provide information to a medical practitioner that can be useful in making a therapeutic decision. Therapeutic decisions may include decisions to: continue with a particular therapy, modify a particular therapy, alter the dosage of a particular therapy, stop or terminate a particular therapy, altering the frequency of a therapy, introduce a new therapy, introduce a new therapy to be used in combination with a current therapy, or any combination of the above. In some cases, the methods provided herein can be applied in an experimental setting, e.g., clinical trial. In some instances, the methods provided herein can be used to monitor a transplant recipient who is being treated with an experimental agent such as an immunosuppressive drug or compound. In some instances, the methods provided herein can be useful to determine whether a subject can be administered an experimental agent (e.g., an agonist, antagonist, peptidomimetic, protein, peptide, nucleic acid, small molecule, or other drug candidate) to reduce the risk of rejection. Thus, the methods described herein can be useful in determining if a subject can be effectively treated with an experimental agent and for monitoring the subject for risk of rejection or continued rejection of the transplant.

Additionally or alternatively, the physician can change the treatment regime being administered to the patient. A change in treatment regime can include administering an additional or different drug, or administering a higher dosage or frequency of a drug already being administered to the patient. Many different drugs are available for treating rejection, such as immunosuppressive drugs used to treat transplant rejection calcineurin inhibitors (e.g., cyclosporine, tacrolimus), mTOR inhibitors (e.g., sirolimus and everolimus), anti-proliferatives (e.g., azathioprine, mycophenolic acid), corticosteroids (e.g., prednisolone and hydrocortisone) and antibodies (e.g., basiliximab, daclizumab, Orthoclone, anti-thymocyte globulin and anti-lymphocyte globulin). Conversely, if the value or other designation of aggregate expression levels of a patient indicates the patient does not have or is at reduced risk of transplant rejection, the physician need not order further diagnostic procedures, particularly not invasive ones such as biopsy. Further, the physician can continue an existing treatment regime, or even decrease the dose or frequency of an administered drug.

In some cases, a clinical trial can be performed on a drug in similar fashion to the monitoring of an individual patient described above, except that drug is administered in parallel to a population of transplant patients, usually in comparison with a control population administered a placebo.

Detecting/Diagnosing a Condition of a Transplant Recipient

The methods, compositions, systems and kits provided herein are particularly useful for detecting or diagnosing a condition of a transplant recipient such as a condition the transplant recipient has at the time of testing. Exemplary conditions that can be detected or diagnosed with the present methods include organ transplant rejection, acute rejection (AR), chronic rejection, Acute Dysfunction with No Rejection (ADNR), normal transplant function (TX) and/or Sub-Clinical Acute Rejection (SCAR). The methods provided herein are particularly useful for transplant recipients who have received a kidney transplant. Exemplary conditions that can be detected or diagnosed in such kidney transplant recipients include: AR, chronic allograft nephropathy (CAN), ADNR, SCAR, IF/TA, and TX.

The diagnosis or detection of condition of a transplant recipient may be particularly useful in limiting the number of invasive diagnostic interventions that are administered to the patient. For example, the methods provided herein may limit or eliminate the need for a transplant recipient (e.g., kidney transplant recipient) to receive a biopsy (e.g., kidney biopsies) or to receive multiple biopsies. In some instances, the methods provided herein may also help interpreting a biopsy result, especially when the biopsy result is inconclusive.

In a further embodiment, the methods provided herein can be used alone or in combination with other standard diagnosis methods currently used to detect or diagnose a condition of a transplant recipient, such as but not limited to results of biopsy analysis for kidney allograft rejection, results of histopathology of the biopsy sample, serum creatinine level, creatinine clearance, ultrasound, radiological imaging results for the kidney, urinalysis results, elevated levels of inflammatory molecules such as neopterin, and lymphokines, elevated plasma interleukin (IL)-1 in azathioprine-treated patients, elevated IL-2 in cyclosporine-treated patients, elevated IL-6 in serum and urine, intrarenal expression of cytotoxic molecules (granzyme B and perforin) and immunoregulatory cytokines (IL-2, -4, -10, interferon gamma and transforming growth factor-b1).

The methods provided herein are useful for distinguishing between two or more conditions or disorders (e.g., AR vs ADNR, SCAR vs ADNR, etc.). In some instances, the methods are used to determine whether a transplant recipient has AR, ADNR or TX. In some instances, the methods are used to determine whether a transplant recipient has AR, ADNR, SCAR and/or TX, or any subset or combination thereof. In some instances, the methods are used to determine whether a transplant recipient has AR, ADNR, SCAR, TX, HCV, or any subset or combination thereof. As previously described, elevated serum creatinine levels from baseline levels in kidney transplant recipients may be indicative of AR or ADNR. In preferred embodiments, the methods provided herein are used to distinguish AR from ADNR in a kidney transplant recipient. In some preferred embodiments, the methods provided herein are used to distinguish AR from ADNR in a liver transplant recipient. In some instances, the methods are used to determine whether a transplant recipient has AR, ADNR, SCAR, TX, acute transplant dysfunction, transplant dysfunction, transplant dysfunction with no rejection, or any subset or combination thereof. In some instances, the methods provided herein are used to distinguish AR from HCV from HCV+AR in a liver transplant recipient. In some instances, the methods provided herein are used to distinguish AR from HCV-R from HCV-R+AR in a liver transplant recipient. In some instances, the methods provided herein are used to distinguish HCV-R from HCV-R+AR in a liver transplant recipient. In some instances, the methods provided herein are used to distinguish AR from ADNR from CAN a kidney transplant recipient.

In some instances, the methods are used to distinguish between AR and ADNR in a kidney transplant recipient. In some instances, the methods are used to distinguish between AR and SCAR in a kidney transplant recipient. In some instances, the methods are used to distinguish between AR, TX, and SCAR in a kidney transplant recipient. In some instances, the methods are used to determine whether a kidney transplant recipient has AR, ADNR or TX. In some instances, the methods are used to determine whether a kidney transplant recipient has AR, ADNR, SCAR, CAN or TX, or any combination thereof. In some instances, the methods are used to distinguish between AR, ADNR, and CAN in a kidney transplant recipient.

In some instances, the methods provided herein are used to detect or diagnose AR in a transplant recipient (e.g., kidney transplant recipient) in the early stages of AR, in the middle stages of AR, or the end stages of AR. In some instances, the methods provided herein are used to detect or diagnose ADNR in a transplant recipient (e.g., kidney transplant recipient) in the early stages of ADNR, in the middle stages of ADNR, or the end stages of ADNR. In some instances, the methods are used to diagnose or detect AR, ADNR, IFTA, CAN, TX, SCAR, or other disorders in a transplant recipient with an accuracy, error rate, sensitivity, positive predictive value, or negative predictive value provided herein.

Predicting a Condition of a Transplant Recipient

In some embodiments, the methods provided herein can predict AR, CAN, ADNR, and/or SCAR prior to actual onset of the conditions. In some instances, the methods provided herein can predict AR, IFTA, CAN, ADNR, SCAR or other disorders in a transplant recipient at least 1 day, 5 days, 10 days, 30 days, 50 days or 100 days prior to onset. In other instances, the methods provided herein can predict AR, IFTA, CAN, ADNR, SCAR or other disorders in a transplant recipient at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days prior to onset. In other instances, the methods provided herein can predict AR, IFTA, CAN, ADNR, SCAR or other disorders in a transplant recipient at least 1, 2, 3, 4, 5, 6, 7, 8, 9, 10, 11, 12 months prior to onset.

Monitoring a Condition of a Transplant Recipient

Provided herein are methods, systems, kits and compositions for monitoring a condition of a transplant recipient. Often, the monitoring is conducted by serial testing, such as serial non-invasive tests, serial minimally-invasive tests (e.g., blood draws), serial invasive tests (biopsies), or some combination thereof. Preferably, the monitoring is conducted by administering serial non-invasive tests or serial minimally-invasive tests (e.g., blood draws).

In some instances, the transplant recipient is monitored as needed using the methods described herein. Alternatively the transplant recipient may be monitored hourly, daily, weekly, monthly, yearly or at any pre-specified intervals. In some instances, the transplant recipient is monitored at least once every 1, 2, 3, 4, 5, 6, 7, 8, 9, 10, 11, 12, 13, 14, 15, 16, 17, 18, 19, 20, 21, 22, 23 or 24 hours. In some instances the transplant recipient is monitored at least once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days. In some instances, the transplant recipient is monitored at least once every 1, 2, 3, 4, 5, 6, 7, 8, 9, 10, 11, 12 months. In some instances, the transplant recipient is monitored at least once every 1, 2, 3, 4, 5, 6, 7, 8, 9, 10 years or longer, for the lifetime of the patient and the graft.

In some instances, gene expression levels in the patients can be measured, for example, within, one month, three months, six months, one year, two years, five years or ten years after a transplant. In some methods, gene expression levels are determined at regular intervals, e.g., every 3 months, 6 months or every year post-transplant, either indefinitely, or until evidence of a condition is observed, in which case the frequency of monitoring is sometimes increased. In some methods, baseline values of expression levels are determined in a subject before a transplant in combination with determining expression levels at one or more time points thereafter.

The results of diagnosing, predicting, or monitoring a condition of a transplant recipient may be useful for informing a therapeutic decision such as determining or monitoring a therapeutic regimen. In some instances, determining a therapeutic regimen may comprise administering a therapeutic drug. In some instances, determining a therapeutic regimen comprises modifying, continuing, initiating or stopping a therapeutic regimen. In some instances, determining a therapeutic regimen comprises treating the disease or condition. In some instances, the therapy is an immunosuppressive therapy. In some instances, the therapy is an anti-microbial therapy. In other instances, diagnosing, predicting, or monitoring a disease or condition comprises determining the efficacy of a therapeutic regimen or determining drug resistance to the therapeutic regimen.

Modifying the therapeutic regimen may comprise terminating a therapy. Modifying the therapeutic regimen may comprise altering a dosage of a therapy. Modifying the therapeutic regimen may comprise altering a frequency of a therapy. Modifying the therapeutic regimen may comprise administering a different therapy. In some instances, the results of diagnosing, predicting, or monitoring a condition of a transplant recipient may be useful for informing a therapeutic decision such as removal of the transplant. In some instances, the removal of the transplant can be an immediate removal. In other instances, the therapeutic decision can be a retransplant. Other examples of therapeutic regimen can include a blood transfusion in instances where the transplant recipient is refractory to immunosuppressive or antibody therapy.

Examples of therapeutic regimen can include administering compounds or agents that are e.g., compounds or agents having immunosuppressive properties (e.g., a calcineurin inhibitor, cyclosporine A or FK 506); a mTOR inhibitor (e.g., rapamycin, 40-O-(2-hydroxyethyl)-rapamycin, CCI779, ABT578, AP23573, biolimus-7 or biolimus-9); an ascomycin having immuno-suppressive properties (e.g., ABT-281, ASM981, etc.); corticosteroids; cyclophosphamide; azathioprene; methotrexate; leflunomide; mizoribine; mycophenolic acid or salt; mycophenolate mofetil; 15-deoxyspergualine or an immunosuppressive homologue, analogue or derivative thereof; a PKC inhibitor (e.g., as disclosed in WO 02/38561 or WO 03/82859); a JAK3 kinase inhibitor (e.g., N-benzyl-3,4-dihydroxy-benzylidene-cyano-acetamide a-cyano-(3,4-dihydroxy)-]N-benzylcinnamamide (Tyrphostin AG 490), prodigiosin 25-C(PNU156804), [4-(4'-hydroxyphenyl)-amino-6,7-dimethoxyquinazoline] (WHI-P131), [4-(3'-bromo-4'-hydroxylphenyl)-amino-6,7-dimethoxyquinazoline] (WHI-P154), [4-(3',5'-dibromo-4'-hydroxylphenyl)-amino-6,7-dimethoxyquinazoline] WHI-P97, KRX-211, 3-{(3R,4R)-4-methyl-3-[methyl-(7H-pyrrolo[2,3-d]pyrimidin-4-yl)-amino]-piperidin-1-yl}-3-oxo-propionitrile, in free form or in a pharmaceutically acceptable salt form, e.g., mono-citrate (also called CP-690, 550), or a compound as disclosed in WO 04/052359 or WO 05/066156); a SIP receptor agonist or modulator (e.g., FTY720 optionally phosphorylated or an analog thereof, e.g., 2-amino-2-[4-(3-benzyloxyphenylthio)-2-chlorophenyl]ethyl-1,3-propanediol optionally phosphorylated or 1-{4-[1-(4-cyclohexyl-3-trifluoromethyl-benzyloxyimino)-ethyl]-2-ethyl-benzyl}-azetidine-3-carboxylic acid or its pharmaceutically acceptable salts); immunosuppressive monoclonal antibodies (e.g., monoclonal antibodies to leukocyte receptors, e.g., MHC, CD2, CD3, CD4, CD7, CD8, CD25, CD28, CD40, CD45, CD52, CD58, CD80, CD86 or their ligands); other immunomodulatory compounds (e.g., a recombinant binding molecule having at least a portion of the extracellular domain of CTLA4 or a mutant thereof, e.g., an at least extracellular portion of CTLA4 or a mutant thereof joined to a non-CTLA4 protein sequence, e.g., CTLA4Ig (for ex. designated ATCC 68629) or a mutant thereof, e.g., LEA29Y); adhesion molecule inhibitors (e.g., LFA-1 antagonists, ICAM-1 or -3 antagonists, VCAM-4 antagonists or VLA-4 antagonists). These compounds or agents may also be used alone or in combination. Immunosuppressive protocols can differ in different clinical settings. In some instances, in AR, the first-line treatment is pulse methylprednisolone, 500 to 1000 mg, given intravenously daily for 3 to 5 days. In some instances, if this treatment fails, than OKT3 or polyclonal anti-T cell antibodies will be considered. In other instances, if the transplant recipient is still experiencing AR, antithymocyte globulin (ATG) may be used.

Kidney Transplants

The methods, compositions, systems and kits provided herein are particularly useful for detecting or diagnosing a condition of a kidney transplant. Kidney transplantation may be needed when a subject is suffering from kidney failure, wherein the kidney failure may be caused by hypertension, diabetes melitus, kidney stone, inherited kidney disease, inflammatory disease of the nephrons and glomeruli, side effects of drug therapy for other diseases, etc. Kidney transplantation may also be needed by a subject suffering from dysfunction or rejection of a transplanted kidney.

Kidney function may be assessed by one or more clinical and/or laboratory tests such as complete blood count (CBC), serum electrolytes tests (including sodium, potassium, chloride, bicarbonate, calcium, and phosphorus), blood urea test, blood nitrogen test, serum creatinine test, urine electrolytes tests, urine creatinine test, urine protein test, urine fractional excretion of sodium (FENA) test, glomerular filtration rate (GFR) test. Kidney function may also be assessed by a renal biopsy. Kidney function may also be assessed by one or more gene expression tests. The methods, compositions, systems and kits provided herein may be used in combination with one or more of the kidney tests mentioned herein. The methods, compositions, systems and kits provided herein may be used before or after a kidney transplant. In some instances, the method may be used in combination with complete blood count. In some instances, the method may be used in combination with serum electrolytes (including sodium, potassium, chloride, bicarbonate, calcium, and phosphorus). In some instances, the method may be used in combination with blood urea test. In some instances, the method may be used in combination with blood nitrogen test. In some instances, the method may be used in combination with a serum creatinine test. In some instances, the method may be used in combination with urine electrolytes tests. In some instances, the method may be used in combination with urine creatinine test. In some instances, the method may be used in combination with urine protein test. In some instances, the method may be used in combination with urine fractional excretion of sodium (FENA) test. In some instances, the method may be used in combination with glomerular filtration rate (GFR) test. In some instances, the method may be used in combination with a renal biopsy. In some instances, the method may be used in combination with one or more other gene expression tests. In some instances, the method may be used when the result of the serum creatinine test indicates kidney dysfunction and/or transplant rejection. In some instances, the method may be used when the result of the glomerular filtration rate (GFR) test indicates kidney dysfunction and/or transplant rejection. In some instances, the method may be used when the result of the renal biopsy indicates kidney dysfunction and/or transplant rejection. In some instances, the method may be used when the result of one or more other gene expression tests indicates kidney dysfunction and/or transplant rejection.

Sensitivity, Specificity, and Accuracy

The methods, kits, and systems disclosed herein for use in identifying, classifying or characterizing a sample may be characterized by having a specificity of at least about 50%. The specificity of the method may be at least about 50%, 53%, 55%, 57%, 60%, 63%, 65%, 67%, 70%, 72%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. The specificity of the method may be at least about 63%. The specificity of the method may be at least about 68%. The specificity of the method may be at least about 72%. The specificity of the method may be at least about 77%. The specificity of the method may be at least about 80%. The specificity of the method may be at least about 83%. The specificity of the method may be at least about 87%. The specificity of the method may be at least about 90%. The specificity of the method may be at least about 92%.

In some embodiments, the present invention provides a method of identifying, classifying or characterizing a sample that gives a sensitivity of at least about 50% using the methods disclosed herein. The sensitivity of the method may be at least about 50%, 53%, 55%, 57%, 60%, 63%, 65%, 67%, 70%, 72%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. The sensitivity of the method may be at least about 63%. The sensitivity of the method may be at least about 68%. The sensitivity of the method may be at least about 72%. The sensitivity of the method may be at least about 77%. The sensitivity of the method may be at least about 80%. The sensitivity of the method may be at least about 83%. The sensitivity of the method may be at least about 87%. The sensitivity of the method may be at least about 90%. The sensitivity of the method may be at least about 92%.

The methods, kits and systems disclosed herein may improve upon the accuracy of current methods of monitoring or predicting a status or outcome of an organ transplant. The methods, kits, and systems disclosed herein for use in identifying, classifying or characterizing a sample may be characterized by having an accuracy of at least about 50%. The accuracy of the methods, kits, and systems disclosed herein may be at least about 50%, 53%, 55%, 57%, 60%, 63%, 65%, 67%, 70%, 72%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. The accuracy of the methods, kits, and systems disclosed herein may be at least about 63%. The accuracy of the methods, kits, and systems disclosed herein may be at least about 68%. The accuracy of the methods, kits, and systems disclosed herein may be at least about 72%. The accuracy of the method may be at least about 77%. The accuracy of the methods, kits, and systems disclosed herein may be at least about 80%. The accuracy of the methods, kits, and systems disclosed herein may be at least about 83%. The accuracy of the methods, kits, and systems disclosed herein may be at least about 87%. The accuracy of the methods, kits, and systems disclosed herein may be at least about 90%. The accuracy of the method may be at least about 92%.

The methods, kits, and/or systems disclosed herein for use in identifying, classifying or characterizing a sample may be characterized by having a specificity of at least about 50% and/or a sensitivity of at least about 50%. The specificity may be at least about 50% and/or the sensitivity may be at least about 70%. The specificity may be at least about 70% and/or the sensitivity may be at least about 70%. The specificity may be at least about 70% and/or the sensitivity may be at least about 50%. The specificity may be at least about 60% and/or the sensitivity may be at least about 70%. The specificity may be at least about 70% and/or the sensitivity may be at least about 60%. The specificity may be at least about 75% and/or the sensitivity may be at least about 75%.

The methods, kits, and systems for use in identifying, classifying or characterizing a sample may be characterized by having a negative predictive value (NPV) greater than or equal to 90%. The NPV may be at least about 90%, 91%, 92%, 93%, 94%, 95%, 95.2%, 95.5%, 95.7%, 96%, 96.2%, 96.5%, 96.7%, 97%, 97.2%, 97.5%, 97.7%, 98%, 98.2%, 98.5%, 98.7%, 99%, 99.2%, 99.5%, 99.7%, or 100%. The NPV may be greater than or equal to 95%. The NPV may be greater than or equal to 96%. The NPV may be greater than or equal to 97%. The NPV may be greater than or equal to 98%.

The methods, kits, and/or systems disclosed herein for use in identifying, classifying or characterizing a sample may be characterized by having a positive predictive value (PPV) of at least about 30%. The PPV may be at least about 32%, 35%, 40%, 45%, 50%, 55%, 60%, 65%, 70%, 75%, 80%, 85%, 90%, 95%, 95.2%, 95.5%, 95.7%, 96%, 96.2%, 96.5%, 96.7%, 97%, 97.2%, 97.5%, 97.7%, 98%, 98.2%, 98.5%, 98.7%, 99%, 99.2%, 99.5%, 99.7%, or 100%. The PPV may be greater than or equal to 95%. The PPV may be greater than or equal to 96%. The PPV may be greater than or equal to 97%. The PPV may be greater than or equal to 98%.

The methods, kits, and/or systems disclosed herein for use in identifying, classifying or characterizing a sample may be characterized by having a NPV may be at least about 90% and/or a PPV may be at least about 30%. The NPV may be at least about 90% and/or the PPV may be at least about 50%. The NPV may be at least about 90% and/or the PPV may be at least about 70%. The NPV may be at least about 95% and/or the PPV may be at least about 30%. The NPV may be at least about 95% and/or the PPV may be at least about 50%. The NPV may be at least about 95% and/or the PPV may be at least about 70%.

The methods, kits, and systems disclosed herein for use in identifying, classifying or characterizing a sample may be characterized by having an error rate of less than about 30%, 25%, 20%, 19%, 18%, 17%, 16%, 15%, 14%, 13%, 12%, 11%, 10%, 9.5%, 9%, 8.5%, 8%, 7.5%, 7%, 6.5%, 6%, 5.5%, 5%, 4.5%, 4%, 3.5%, 3%, 2.5%, 2%, 1.5%, or 1%. The methods, kits, and systems disclosed herein may be characterized by having an error rate of less than about 1%, 0.9%, 0.8%, 0.7%, 0.6%, 0.5%, 0.4%, 0.3%, 0.2%, 0.1% or 0.005%. The methods, kits, and systems disclosed herein may be characterized by having an error rate of less than about 10%. The method may be characterized by having an error rate of less than about 5%. The methods, kits, and systems disclosed herein may be characterized by having an error rate of less than about 3%. The methods, kits, and systems disclosed herein may be characterized by having an error rate of less than about 1%. The methods, kits, and systems disclosed herein may be characterized by having an error rate of less than about 0.5%.

The methods, kits, and systems disclosed herein for use in diagnosing, prognosing, and/or monitoring a status or outcome of a transplant in a subject in need thereof may be characterized by having an accuracy of at least about 50%, 55%, 57%, 60%, 62%, 65%, 67%, 70%, 72%, 75%, 77%, 80%, 82%, 85%, 87%, 90%, 92%, 95%, or 97%. The methods, kits, and systems disclosed herein may be characterized by having an accuracy of at least about 70%. The methods, kits, and systems disclosed herein may be characterized by having an accuracy of at least about 80%. The methods, kits, and systems disclosed herein may be characterized by having an accuracy of at least about 85%. The methods, kits, and systems disclosed herein may be characterized by having an accuracy of at least about 90%. The methods, kits, and systems disclosed herein may be characterized by having an accuracy of at least about 95%.

The methods, kits, and systems disclosed herein for use in diagnosing, prognosing, and/or monitoring a status or outcome of a transplant in a subject in need thereof may be characterized by having a specificity of at least about 50%, 55%, 57%, 60%, 62%, 65%, 67%, 70%, 72%, 75%, 77%, 80%, 82%, 85%, 87%, 90%, 92%, 95%, or 97%. The methods, kits, and systems disclosed herein may be characterized by having a specificity of at least about 70%. The methods, kits, and systems disclosed herein may be characterized by having a specificity of at least about 80%. The methods, kits, and systems disclosed herein may be characterized by having a specificity of at least about 85%. The methods, kits, and systems disclosed herein may be characterized by having a specificity of at least about 90%. The methods, kits, and systems disclosed herein may be characterized by having a specificity of at least about 95%.

The methods, kits, and systems disclosed herein for use in diagnosing, prognosing, and/or monitoring a status or outcome of a transplant in a subject in need thereof may be characterized by having a sensitivity of at least about 50%, 55%, 57%, 60%, 62%, 65%, 67%, 70%, 72%, 75%, 77%, 80%, 82%, 85%, 87%, 90%, 92%, 95%, or 97%. The methods, kits, and systems disclosed herein may be characterized by having a sensitivity of at least about 70%. The methods, kits, and systems disclosed herein may be characterized by having a sensitivity of at least about 80%. The methods, kits, and systems disclosed herein may be characterized by having a sensitivity of at least about 85%. The methods, kits, and systems disclosed herein may be characterized by having a sensitivity of at least about 90%. The methods, kits, and systems disclosed herein may be characterized by having a sensitivity of at least about 95%.

The methods, kits, and systems disclosed herein for use in diagnosing, prognosing, and/or monitoring a status or outcome of a transplant in a subject in need thereof may be characterized by having an error rate of less than about 30%, 25%, 20%, 19%, 18%, 17%, 16%, 15%, 14%, 13%, 12%, 11%, 10%, 9.5%, 9%, 8.5%, 8%, 7.5%, 7%, 6.5%, 6%, 5.5%, 5%, 4.5%, 4%, 3.5%, 3%, 2.5%, 2%, 1.5%, or 1%. The methods, kits, and systems disclosed herein may be characterized by having an error rate of less than about 1%, 0.9%, 0.8%, 0.7%, 0.6%, 0.5%, 0.4%, 0.3%, 0.2%, 0.1% or 0.005%. The methods, kits, and systems disclosed herein may be characterized by having an error rate of less than about 10%. The method may be characterized by having an error rate of less than about 5%. The methods, kits, and systems disclosed herein may be characterized by having an error rate of less than about 3%. The methods, kits, and systems disclosed herein may be characterized by having an error rate of less than about 1%. The methods, kits, and systems disclosed herein may be characterized by having an error rate of less than about 0.5%.

The classifier, classifier set, classifier probe set, classification system may be characterized by having a accuracy for distinguishing two or more conditions (AR, ANDR, TX, CAN) of at least about 50%, 55%, 57%, 60%, 62%, 65%, 67%, 70%, 72%, 75%, 77%, 80%, 82%, 85%, 87%, 90%, 92%, 95%, or 97%. The classifier, classifier set, classifier probe set, classification system may be characterized by having a sensitivity for distinguishing two or more conditions (AR, ANDR, TX, CAN) of at least about 50%, 55%, 57%, 60%, 62%, 65%, 67%, 70%, 72%, 75%, 77%, 80%, 82%, 85%, 87%, 90%, 92%, 95%, or 97%. The classifier, classifier set, classifier probe set, classification system may be characterized by having a selectivity for distinguishing two or more conditions (AR, ANDR, TX, CAN) of at least about 50%, 55%, 57%, 60%, 62%, 65%, 67%, 70%, 72%, 75%, 77%, 80%, 82%, 85%, 87%, 90%, 92%, 95%, or 97%.

Computer Program

The methods, kits, and systems disclosed herein may include at least one computer program, or use of the same. A computer program may include a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. The computer program will normally provide a sequence of instructions from one location or a plurality of locations. In various embodiments, a computer program includes, in part or in whole, one or more web applications, one or more mobile applications, one or more standalone applications, one or more web browser plug-ins, extensions, add-ins, or add-ons, or combinations thereof.

Further disclosed herein are systems for classifying one or more samples and uses thereof. The system may comprise (a) a digital processing device comprising an operating system configured to perform executable instructions and a memory device; (b) a computer program including instructions executable by the digital processing device to classify a sample from a subject comprising: (i) a first software module configured to receive a gene expression profile of one or more genes from the sample from the subject; (ii) a second software module configured to analyze the gene expression profile from the subject; and (iii) a third software module configured to classify the sample from the subject based on a classification system comprising three or more classes. At least one of the classes may be selected from transplant rejection, transplant dysfunction with no rejection and normal transplant function. At least two of the classes may be selected from transplant rejection, transplant dysfunction with no rejection and normal transplant function. All three of the classes may be selected from transplant rejection, transplant dysfunction with no rejection and normal transplant function. Analyzing the gene expression profile from the subject may comprise applying an algorithm. Analyzing the gene expression profile may comprise normalizing the gene expression profile from the subject. In some instances, normalizing the gene expression profile does not comprise quantile normalization.

Figure 4:
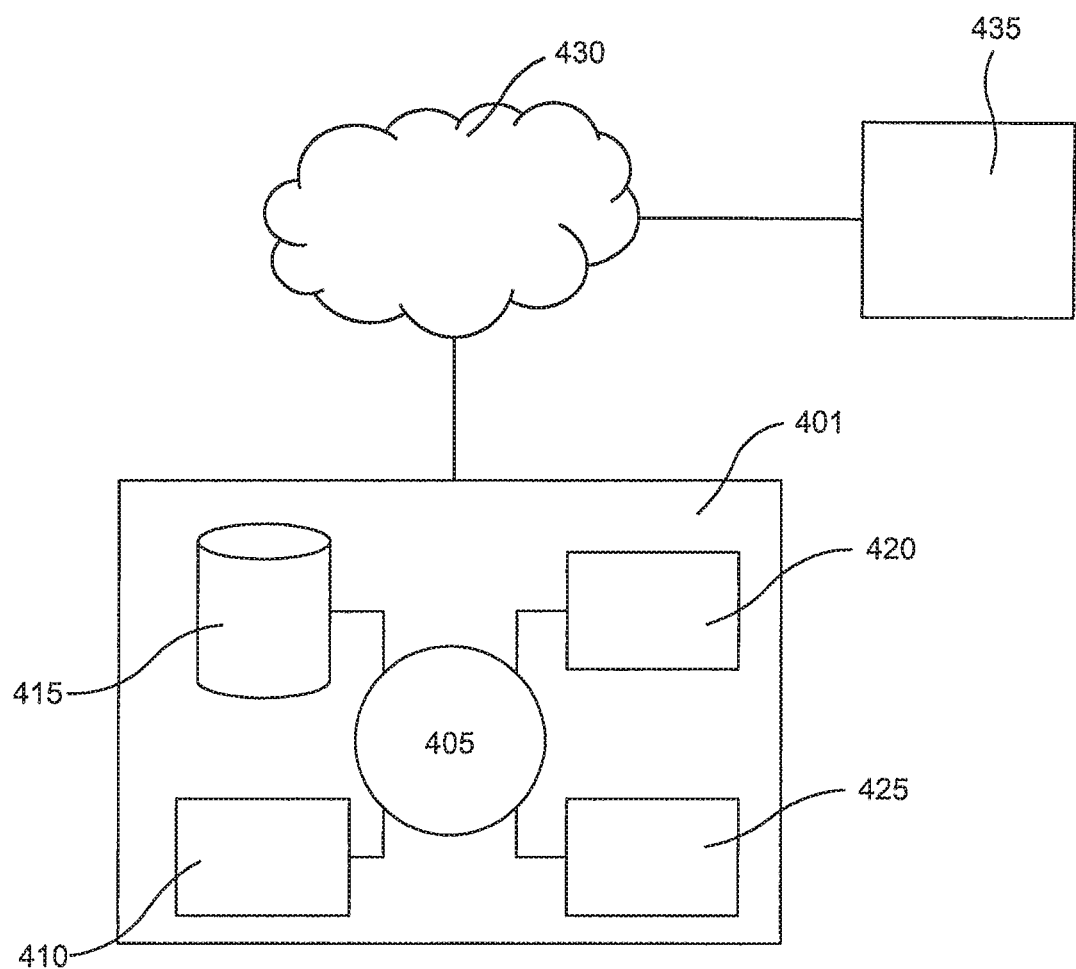
FIG. 4 shows a graph of the Area Under the Curve (AUCs) for the normal transplant function (TX) versus acute rejection (AR), normal transplant function (TX) versus acute dysfunction no rejection (ADNR), and the acute rejection (AR) versus acute dysfunction no rejection (ADNR) comparisons for the locked nearest centroid (NC) classifier in the validation cohort.

FIG. 4 shows a computer system (also "system" herein) 401 programmed or otherwise configured for implementing the methods of the disclosure, such as producing a selector set and/or for data analysis. The system 401 includes a central processing unit (CPU, also "processor" and "computer processor" herein) 405, which can be a single core or multi core processor, or a plurality of processors for parallel processing. The system 401 also includes memory 410 (e.g., random-access memory, read-only memory, flash memory), electronic storage unit 415 (e.g., hard disk), communications interface 420 (e.g., network adapter) for communicating with one or more other systems, and peripheral devices 425, such as cache, other memory, data storage and/or electronic display adapters. The memory 410, storage unit 415, interface 420 and peripheral devices 425 are in communication with the CPU 405 through a communications bus (solid lines), such as a motherboard. The storage unit 415 can be a data storage unit (or data repository) for storing data. The system 401 is operatively coupled to a computer network ("network") 430 with the aid of the communications interface 420. The network 430 can be the Internet, an internet and/or extranet, or an intranet and/or extranet that is in communication with the Internet. The network 430 in some instances is a telecommunication and/or data network. The network 430 can include one or more computer servers, which can enable distributed computing, such as cloud computing. The network 430 in some instances, with the aid of the system 401, can implement a peer-to-peer network, which may enable devices coupled to the system 401 to behave as a client or a server.

The system 401 is in communication with a processing system 435. The processing system 435 can be configured to implement the methods disclosed herein. In some examples, the processing system 435 is a nucleic acid sequencing system, such as, for example, a next generation sequencing system (e.g., Illumina sequencer, Ion Torrent sequencer, Pacific Biosciences sequencer). The processing system 435 can be in communication with the system 401 through the network 430, or by direct (e.g., wired, wireless) connection. The processing system 435 can be configured for analysis, such as nucleic acid sequence analysis.

Methods as described herein can be implemented by way of machine (or computer processor) executable code (or software) stored on an electronic storage location of the system 401, such as, for example, on the memory 410 or electronic storage unit 415. During use, the code can be executed by the processor 405. In some examples, the code can be retrieved from the storage unit 415 and stored on the memory 410 for ready access by the processor 405. In some situations, the electronic storage unit 415 can be precluded, and machine-executable instructions are stored on memory 410.

Digital Processing Device

The methods, kits, and systems disclosed herein may include a digital processing device, or use of the same. In further embodiments, the digital processing device includes one or more hardware central processing units (CPU) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

The digital processing device will normally include an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

The device generally includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

A display to send visual information to a user will normally be initialized. Examples of displays include a cathode ray tube (CRT, a liquid crystal display (LCD), a thin film transistor liquid crystal display (TFT-LCD, an organic light emitting diode (OLED) display. In various further embodiments, on OLED display is a passive-matrix OLED (PMOLED) or active-matrix OLED (AMOLED) display. In some embodiments, the display may be a plasma display, a video projector or a combination of devices such as those disclosed herein.

The digital processing device would normally include an input device to receive information from a user. The input device may be, for example, a keyboard, a pointing device including, by way of non-limiting examples, a mouse, trackball, track pad, joystick, game controller, or stylus; a touch screen, or a multi-touch screen, a microphone to capture voice or other sound input, a video camera to capture motion or visual input or a combination of devices such as those disclosed herein.

Non-Transitory Computer Readable Storage Medium

The methods, kits, and systems disclosed herein may include one or more non-transitory computer readable storage media encoded with a program including instructions executable by the operating system to perform and analyze the test described herein; preferably connected to a networked digital processing device. The computer readable storage medium is a tangible component of a digital that is optionally removable from the digital processing device. The computer readable storage medium includes, by way of non-limiting examples, CD-ROMs, DVDs, flash memory devices, solid state memory, magnetic disk drives, magnetic tape drives, optical disk drives, cloud computing systems and services, and the like. In some instances, the program and instructions are permanently, substantially permanently, semi-permanently, or non-transitorily encoded on the media.

A non-transitory computer-readable storage media may be encoded with a computer program including instructions executable by a processor to create or use a classification system. The storage media may comprise (a) a database, in a computer memory, of one or more clinical features of two or more control samples, wherein (i) the two or more control samples may be from two or more subjects; and (ii) the two or more control samples may be differentially classified based on a classification system comprising three or more classes; (b) a first software module configured to compare the one or more clinical features of the two or more control samples; and (c) a second software module configured to produce a classifier set based on the comparison of the one or more clinical features.

At least two of the classes may be selected from transplant rejection, transplant dysfunction with no rejection and normal transplant function. All three classes may be selected from transplant rejection, transplant dysfunction with no rejection and normal transplant function. The storage media may further comprise one or more additional software modules configured to classify a sample from a subject. Classifying the sample from the subject may comprise a classification system comprising three or more classes. At least two of the classes may be selected from transplant rejection, transplant dysfunction with no rejection and normal transplant function. All three classes may be selected from transplant rejection, transplant dysfunction with no rejection and normal transplant function.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Web Browser Plug-in

In some embodiments, the computer program includes a web browser plug-in. In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

The methods, kits, and systems disclosed herein may include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

The methods, kits, and systems disclosed herein may comprise one or more databases, or use of the same. In view of the disclosure provided herein, those of skill in the art will recognize that many databases are suitable for storage and retrieval of information pertaining to gene expression profiles, sequencing data, classifiers, classification systems, therapeutic regimens, or a combination thereof. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

Data Transmission

The methods, kits, and systems disclosed herein may be used to transmit one or more reports. The one or more reports may comprise information pertaining to the classification and/or identification of one or more samples from one or more subjects. The one or more reports may comprise information pertaining to a status or outcome of a transplant in a subject. The one or more reports may comprise information pertaining to therapeutic regimens for use in treating transplant rejection in a subject in need thereof. The one or more reports may comprise information pertaining to therapeutic regimens for use in treating transplant dysfunction in a subject in need thereof. The one or more reports may comprise information pertaining to therapeutic regimens for use in suppressing an immune response in a subject in need thereof.

The one or more reports may be transmitted to a subject or a medical representative of the subject. The medical representative of the subject may be a physician, physician's assistant, nurse, or other medical personnel. The medical representative of the subject may be a family member of the subject. A family member of the subject may be a parent, guardian, child, sibling, aunt, uncle, cousin, or spouse. The medical representative of the subject may be a legal representative of the subject.

The term "about," as used herein and throughout the disclosure, generally refers to a range that may be 15% greater than or 15% less than the stated numerical value within the context of the particular usage. For example, "about 10" would include a range from 8.5 to 11.5.

The term "or" as used herein and throughout the disclosure, generally means "and/or".

EXAMPLES

The following illustrative examples are representative of embodiments of the software applications, systems, and methods described herein and are not meant to be limiting in any way.

Example 1

Introduction

Improvements in kidney transplantation have resulted in significant reductions in clinical acute rejection (AR) (8-14%) (Meier-Kriesche et al. 2004, Am J Transplant, 4(3): 378-383). However, histological AR without evidence of kidney dysfunction (i.e. subclinical AR) occurs in >15% of protocol biopsies done within the first year. Without a protocol biopsy, patients with subclinical AR would be treated as excellent functioning transplants (TX). Biopsy studies also document significant rates of progressive interstitial fibrosis and tubular atrophy in >50% of protocol biopsies starting as early as one year post transplant.

Two factors contribute to AR: the failure to optimize immunosuppression and individual patient non-adherence. Currently, there is no validated test to measure or monitor the adequacy of immunosuppression; the failure of which is often first manifested directly as an AR episode. Subsequently, inadequate immunosuppression results in chronic rejection and allograft failure. The current standards for monitoring kidney transplant function are serum creatinine and estimated glomerular filtration rates (eGFR). Unfortunately, serum creatinine and eGFR are relatively insensitive markers requiring significant global injury before changing and are influenced by multiple non-immunological factors.

Performing routine protocol biopsies is one strategy to diagnose and treat AR prior to extensive injury. A study of 28 patients one week post-transplant with stable creatinines showed that 21% had unsuspected "borderline" AR and 25% had inflammatory tubulitis (Shapiro et al. 2001, Am J Transplant, 1(1): 47-50). Other studies reveal a 29% prevalence of subclinical rejection (Hymes et al. 2009, Pediatric transplantation, 13(7): 823-826) and that subclinical rejection with chronic allograft nephropathy was a risk factor for late graft loss (Moreso et al. 2006, Am J Transplant, 6(4):

747-752). A study of 517 renal transplants followed after protocol biopsies showed that finding subclinical rejection significantly increased the risk of chronic rejection (Moreso et al. 2012, Transplantation 93(1): 41-46).

We originally reported a peripheral blood gene expression signature by DNA microarrays to diagnose AR (Flechner et al. 2004, Am J Transplant, 4(9): 1475-1489). Subsequently, others have reported qPCR signatures of AR in peripheral blood based on genes selected from the literature or using microarrays (Gibbs et al. 2005, Transpl Immunol, 14(2): 99-108; Li et al. 2012, Am J Transplant, 12(10): 2710-2718; Sabek et al. 2002, Transplantation, 74(5): 701-707; Sarwal et al. 2003, N Engl J Med, 349(2): 125-138; Simon et al. 2003, Am J Transplant, 3(9): 1121-1127; Vasconcellos et al. 1998, Transplantation, 66(5): 562-566). As the biomarker field has evolved, validation requires independently collected sample cohorts and avoidance of over-training during classifier discovery (Lee et al. 2006, Pharm Res, 23(2): 312-328; Chau et at 2008, Clin Cancer Res, 14(19): 5967-5976). Another limitation is that the currently published biomarkers are designed for 2-way classifications, AR vs. TX, when many biopsies reveal additional ADNR.

We prospectively followed over 1000 kidney transplants from 5 different clinical centers (Transplant Genomics Collaborative Group) to identify 148 instances of unequivocal biopsy-proven AR (n=63), ADNR (n=39), and TX (n=45). Global gene expression profiling was done on peripheral blood using DNA microarrays and robust 3-way class prediction tools (Dabney et al. 2005, Bioinformatics, 21(22): 4148-4154; Shen et al. 2006, Bioinformatics, 22(21): 2635-2642; Zhu et al. 2009, BMC bioinformatics, 10 Suppl 1:S21). Classifiers were comprised of the 200 highest value probe sets ranked by the prediction accuracies with each tool were created with three different classifier tools to insure that our results were not subject to bias introduced by a single statistical method. Importantly, even using three different tools, the 200 highest value probe set classifiers identified were essentially the same. These 200 classifiers had sensitivity, specificity, positive predictive accuracy (PPV), negative predictive accuracy (NPV) and Area Under the Curve (AUC) for the Validation cohort depending on the three different prediction tools used ranging from 82-100%, 76-95%, 76-95%, 79-100%, 84-100% and 0.817-0.968, respectively. Next, the Harrell bootstrapping method (Miao et al. 2013, SAS Global Forum, San Francisco; 2013) based on sampling with replacement was used to demonstrate that these results, regardless of the tool used, were not the consequence of statistical over-fitting. Finally, to model the use of our test in real clinical practice, we developed a novel one-by-one prediction strategy in which we created a large reference set of 118 samples and then randomly took 10 samples each from the AR, ADNR and TX cohorts in the Validation set. These were then blinded to phenotype and each sample was tested by itself against the entire reference set to model practice in a real clinical situation where there is only a single new patient sample obtained at any given time.

Materials and Methods
Patient Populations:

We studied 46 kidney transplant patients with well-functioning grafts and biopsy-proven normal histology (TX; controls), 63 patients with biopsy-proven acute kidney rejection (AR) and 39 patients with acute kidney dysfunction without histological evidence of rejection (ADNR). Inclusion/exclusion criteria are in Table 2. Subjects were enrolled serially as biopsies were performed by 5 different clinical centers (Scripps Clinic, Cleveland Clinic, St. Vincent Medical Center, University of Colorado and Mayo Clinic Arizona). Human Subjects Research Protocols approved at each Center and by the Institutional Review Board of The Scripps Research Institute covered all studies.

Pathology:

All subjects had kidney biopsies (either protocol or "for cause") graded for evidence of acute rejection by the Banff 2007 criteria (Solez et al. 2008, Am J Transplant, 8(4): 753-760). All biopsies were read by local pathologists and then reviewed and graded in a blinded fashion by a single pathologist at an independent center (LG). The local and single pathologist readings were then reviewed by DRS to standardize and finalize the phenotypes prior to cohort construction and any diagnostic classification analysis. C4d staining was done per the judgment of the local clinicians and pathologists on 69 of the 148 samples (47%; Table 3). Positive was defined as linear, diffuse staining of peritubular capillaries. Donor specific antibodies were not measured on these patients and thus, we cannot exclude the new concept of C4d negative antibody-mediated rejection (Sis et at 2009, Am J Transplant, 9(10): 2312-2323; Wiebe et al. 2012, Am J Transplant, 12(5): 1157-1167).

Gene Expression Profiling and Statistical Analysis:

RNA was extracted from Paxgene tubes using the Paxgene Blood RNA system (PreAnalytix) and GlobinClear (Ambion). Biotinylated cRNA was prepared with Ambion MessageAmp Biotin H kit (Ambion) and hybridized to Affymetrix Human Genome U133 Plus 2.0 GeneChips. Normalized Signals were generated using frozen RMA (fRMA) in R (McCall et al. 2010, Biostatistics, 11(2): 242-253; McCall et al. 2011, BMC bioinformatics, 12:369). The complete strategy used to discover, refine and validate the biomarker panels is shown in FIG. 1. Class predictions were performed with multiple tools: Nearest Centroids, Support Vector Machines (SVM) and Diagonal Linear Discriminant Analysis (DLDA). Predictive accuracy is calculated as true positives+true negatives/true positives+false positives+false negatives+true negatives. Other diagnostic metrics given are sensitivity, specificity, Postive Predictive Value (PPV), Negative Predictive Value (NPV) and Area Under the Curve (AUC). Receiver Operating Characteristic (ROC) curves were generated using pROC in R (Robin et al. 2011, BMC bioinformatics, 12:77). Clinical study parameters were tested by multivariate logistic regression with an adjusted (Wald test) p-value and a local false discovery rate calculation (q-value). Chi Square analysis was done using GraphPad. CEL files and normalized signal intensities are posted in NIH Gene Expression Omnibus (GEO) (accession number GSE15296).

Results
Patient Population

Subjects were consented and biopsied in a random and prospective fashion at five Centers (n=148; Table 3). Blood was collected at the time of biopsy. TX represented protocol biopsies of transplants with excellent, stable graft function and normal histology (n=45). AR patients were biopsied "for cause" based on elevated serum creatinine (n=63). We excluded subjects with recurrent kidney disease, BKV or other infections. ADNRs were biopsied "for cause" based on suspicion of AR but had no AR by histology (n=39). Differences in steroid use (less in TX) reflect more protocol biopsies done at a steroid-free center. As expected, creatinines were higher in AR and ADNR than TX. Creatinine was the only significant variable by multivariable logistic regression by either phenotype or cohort. C4d staining, when done, was negative in TX and ADNR. C4d staining was done in 56% of AR subjects by the judgment of the pathologists and was positive in 12/3 6 (33%) of this selected group.

Three-Way Predictions

We randomly split the data from 148 samples into two cohorts, Discovery and Validationas shown in FIG. 1. Discovery was 32 AR, 20 ADNR, 23 TX and Validation was 32 AR, 19 ADNR, 22 TX. Normalization used Frozen Robust Multichip Average (fRMA) (McCall et al. 2010, Biostatistics, 11(2): 242-253; McCall et al. 2011, BMC bioinformatics, 12:369). Probe sets with median $Log_2$ signals less than 5.20 in >70% of samples were eliminated. A 3-class univariate F-test was done on the Discovery cohort (1000 random permutations, FDR <10%; BRB ArrayTools) yielding 2977 differentially expressed probe sets using the Hu133 Plus 2.0 cartridge arrays plates (Table 1b). In another experiment, 4132 differentially expressed probe sets were yield using the HT HG-U133+ PM array plates (Table 1d). The Nearest Centroid algorithm (Dabney et al. 2005, Bioinformatics, 21(22): 4148-4154) was used to create a 3-way classifier for AR, ADNR and TX in the Discovery cohort revealing 200 high-value probe sets (Table 1a: using the Hu133 Plus 2.0 cartridge arrays plates; Table 1c: using the HT HG-U133+ PM array plates) defined by having the lowest class predictive error rates (Table 4; see also Supplemental Statistical Methods).

Figure 5:
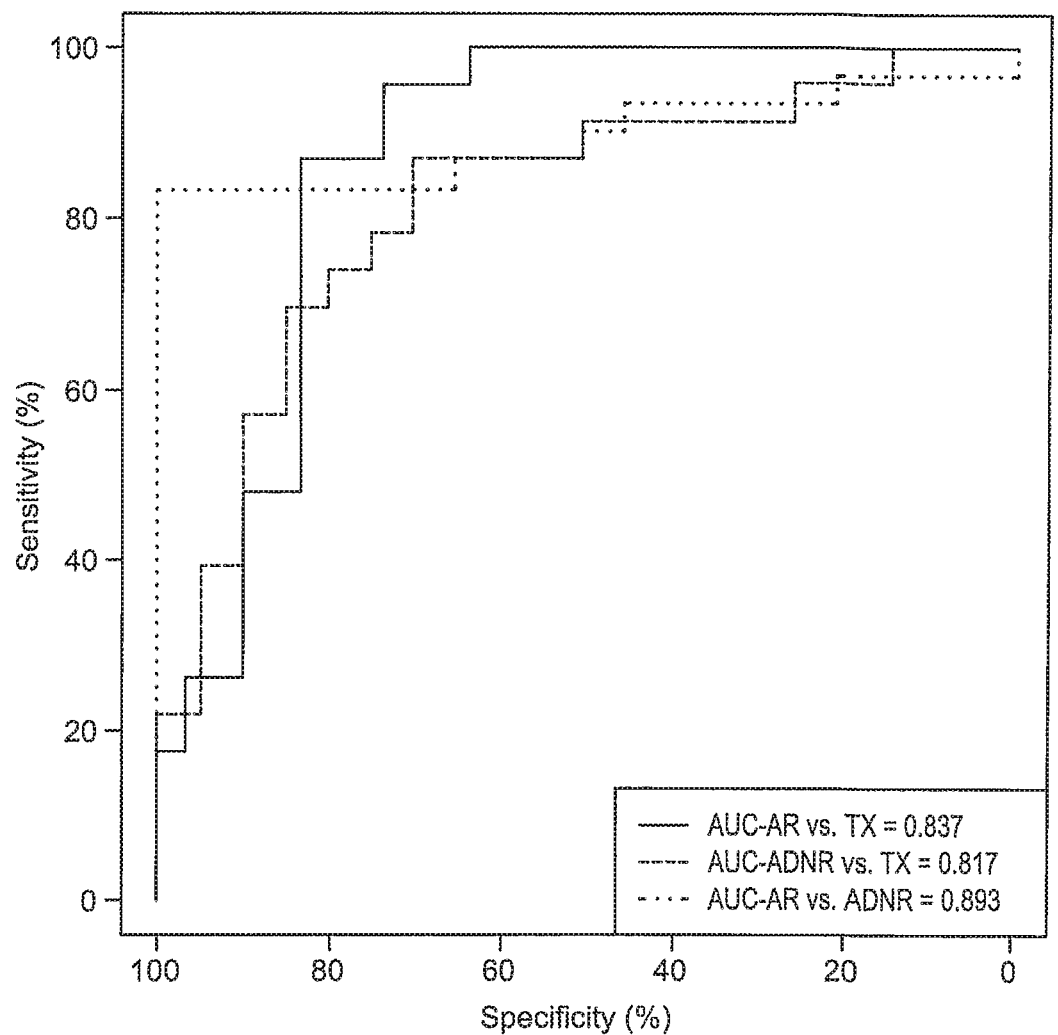
FIG. 5 shows a graph of the Area Under the Curve (AUCs) for the normal transplant function (TX) versus acute rejection (AR), normal transplant function (TX) versus acute dysfunction no rejection (ADNR), and the acute rejection (AR) versus acute dysfunction no rejection (ADNR) using the locked nearest centroid (NC) classifier on 30 blinded validation acute rejection (AR), acute dysfunction no rejection (ADNR) and normal function (TX) samples using the one-by-one strategy.

Thustesting our locked classifier in the validation cohort demonstrated predictive accuracies of 83%, 82% and 90% for the TX vs. AR, TX vs. ADNR and AR vs. ADNR respectively (Table 4). The AUCs for the TX vs. AR, TX vs. ADNR and the AR vs. ADNR comparisons were 0.837, 0.817 and 0.893, respectively as shown in FIG. 5. The sensitivity, specificity, PPV, NPV for the three comparisons were in similar ranges and are shown in Table 4. To determine a possible minimum classifier set, we ranked the 200 probe sets by p values and tested the top 25, 50, 100 and 200 (Table 4). The conclusion is that given the highest value classifiers discovered using unbiased whole genome profiling, the total number of classifiers necessary for testing may be 25. However, below that number the performance of our 3-way classifier falls off to about 50% AUC at 10 or lower (data not shown).

Alternative Prediction Tools

Robust molecular diagnostic strategies should work using multiple tools. Therefore, we repeated the entire 3-way locked discovery and validation process using DLDA and Support Vector Machines (Table 5). All the tools perform nearly equally well with 100-200 classifiers though small differences were observed.

Figure 7:
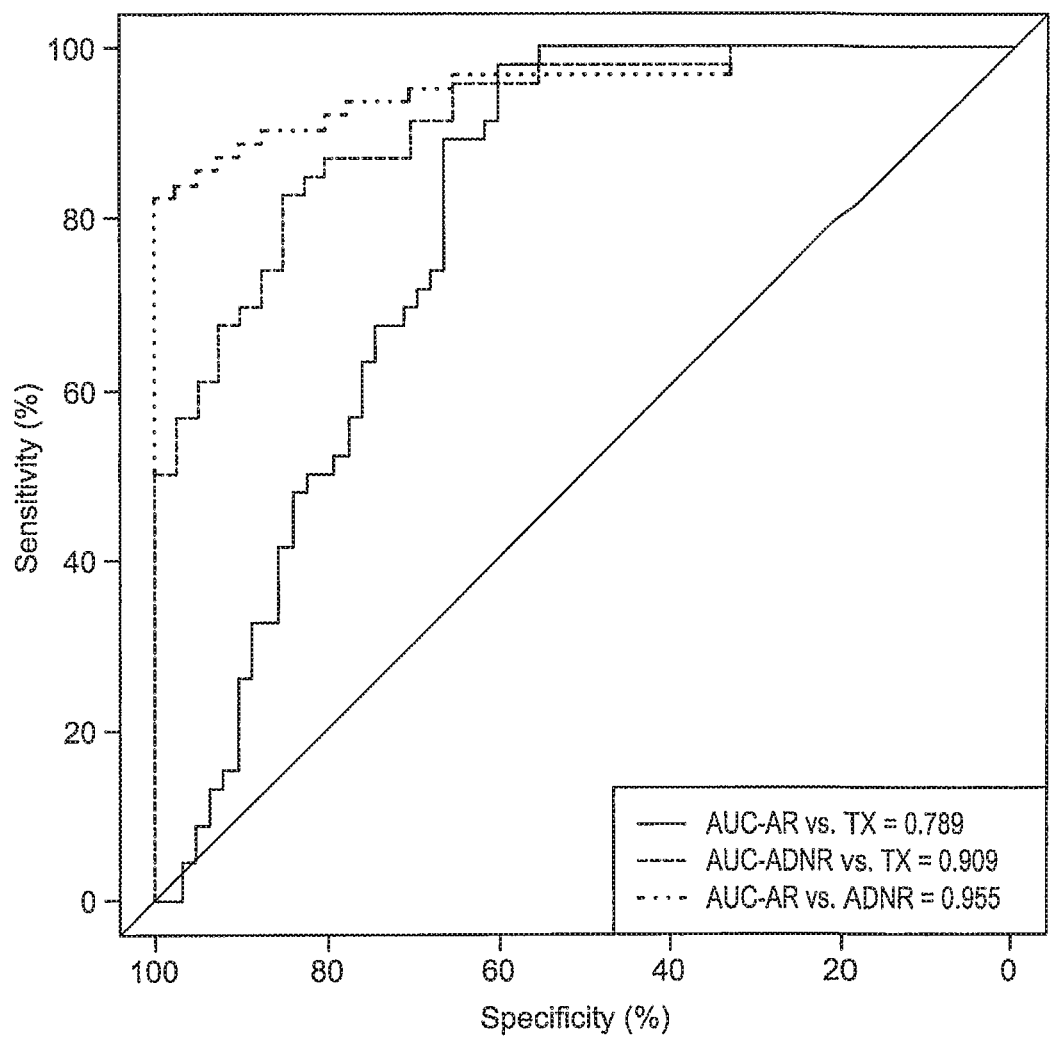
FIG. 7 shows a graph of AUCs for the 200-classifier set obtained from the full study sample set of 148 samples. These results demonstrate that there is no over-fitting of the classifier.

It is also important to test whether a new classifier is subject to statistical over-fitting that would inflate the claimed predictive results. This testing can be done with the method of Harrell et al. using bootstrapping where the original data set is sampled 1000 times with replacement and the AUCs calculated for each (Miao et at 2013, SAS Global Forum, San Francisco; 2013). The original AUCs minus the calculated AUCs for each tool create the corrections in the AUCs for "optimism" in the original predictions that adjust for potential over-fitting (Table 6). Therefore we combined the Discovery and Validation cohorts and performed a 3-class univariate F-test on the whole data set of 148 samples (1000 random permutations, FDR <10%; BRB ArrayTools). This yielded 2666 significantly expressed genes from which we selected the top 200 by p-values. Results using NC, SVM and DLDA with these 200 probe sets are shown in Table 6. Optimism-corrected AUCs from 0.823-0.843 were obtained for the 200-probe set classifier discovered with the 2 cohort-based strategy. Results for the 200-classifier set obtained from the full study sample set of 148 were 0.851-0.866. These results demonstrate that over-fitting is not a major problem as would be expected from a robust set of classifiers (FIG. 7). These results translate to sensitivity, specificity, PPV and NPV of 81%, 93%, 92% and 84% for AR vs. TX; 90%, 85%, 86% and 90% for ADNR vs. TX and 85%, 96%, 95% and 87% for AR vs. ADNR.

Validation in One-by-One Predictions

Figure 6:
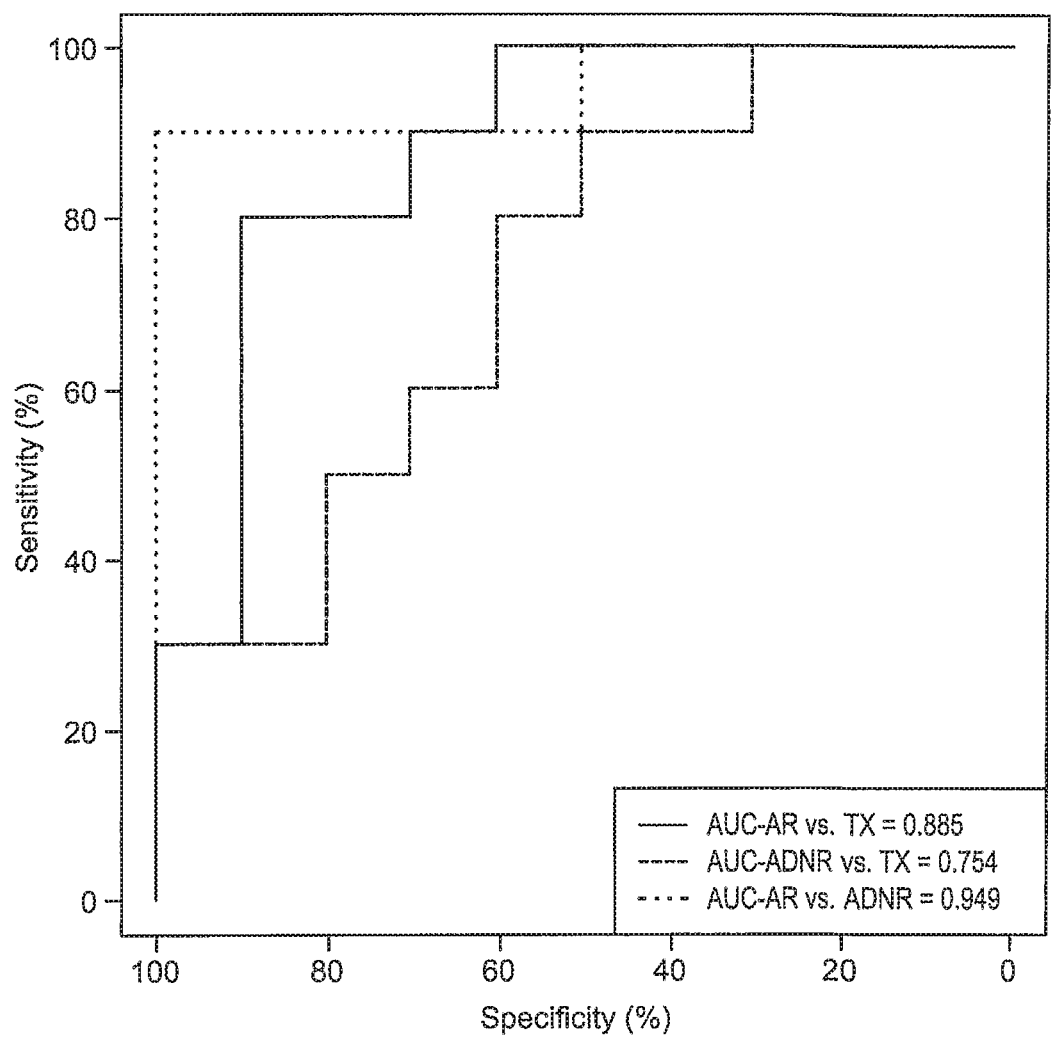
FIG. 6 shows a system for implementing the methods of the disclosure.

In clinical practice the diagnostic value of a biomarker is challenged each time a single patient sample is acquired and analyzed. Thus, prediction strategies based on large cohorts of known clinical classifications do not address the performance of biomarkers in their intended application. Two problems exist with cohort-based analysis. First, signal normalization is typically done on the entire cohort, which is not the case in a clinical setting for one patient. Quantile normalization is a robust method but has 2 drawbacks; it cannot be used in clinical settings where samples must be processed individually or in small batches and data sets normalized separately are not comparable. Frozen RMA (fRMA) overcomes these limitations by normalization of individual arrays to large publicly available microarray databases allowing for estimates of probe-specific effects and variances to be pre-computed and "frozen" (McCall et al. 2010, Biostatistics, 11(2): 242-253; McCall et al. 2011, BMC bioinformatics, 12:369). The second problem with cohort analysis is that all the clinical phenotypes are already known and classification is done on the entire cohort. To address these challenges, we removed 30 random samples from the Validation cohort (10 AR, 10 ADNR, 10 TX), blinded their classifications and left a Reference cohort of 118 samples with known phenotypes. Classification was done by adding one blinded sample at a time to the Reference cohort. Using the 200-gene, 3-way classifier derived in NC, we demonstrated an overall predictive accuracy of 80% and individual accuracies of 80% AR, 90% ADNR and 70% TX and AUCs of 0.885, 0.754 and 0.949 for the AR vs. TX, ADNR vs. TX and the AR vs. ADNR comparisons, respectively as shown in FIG. 6.

Discussion

Ideally, molecular markers will serve as early warnings for immune-mediated injury, before renal function deteriorates, and also permit optimization of immunosuppression. We studied a total of 148 subjects with biopsy-proven phenotypes identified in 5 different clinical centers by following over 1000 transplant patients. Global RNA expression of peripheral blood was used to profile 63 patients with biopsy-proven AR, 39 patients with ADNR and 46 patients with excellent function and normal histology (TX).

We addressed several important and often overlooked aspects of biomarker discovery. To avoid over training, we used a discovery cohort to establish the predictive equation and its corresponding classifiers, then locked these down and allowed no further modification. We then tested the diagnostic on our validation cohort. To demonstrate the robustness of our approach, we used multiple, publically available prediction tools to establish that our results are not simply tool-dependent artifacts. We used the bootstrapping method of Harrell to calculate optimism-corrected AUCs and demonstrated that our predictive accuracies are not inflated by over-fitting. We also modeled the actual clinical application of this diagnostic, with a new strategy optimized to normalizing individual samples by fRMA. We then used 30 blinded samples from the validation cohort and tested them one-by-one. Finally, we calculated the statistical power of our analysis and determined that we have greater than 90% power at a significance level of p<0.001. We concluded that peripheral blood gene expression profiling can be used to diagnose AR and ADNR in patients with acute kidney transplant dysfunction. An interesting finding is that we got the same results using the classic two-cohort strategy (discovery vs. validation) as we did using the entire sample set and creating our classifiers with the same tools but using the Harrell bootstrapping method to control for over-fitting. Thus, the current thinking that all biomarker signatures require independent validation cohorts may need to be reconsidered.

In the setting of acute kidney transplant dysfunction, we are the first to address the common clinical challenge of distinguishing AR from ADNR by using 3-way instead of 2-way classification algorithms.

Additional methods may comprise a prospective, blinded study. The biomarkers may be further validated using a prospective, blinded study. Methods may comprise additional samples. The additional samples may be used to classify the different subtypes of T cell-mediated, histologically-defined AR. The methods may further comprise use of one or more biopsies. The one or more biopsies may be used to develop detailed histological phenotyping. The methods may comprise samples obtained from subjects of different ethnic backgrounds. The methods may comprise samples obtained from subjects treated with various therapies (e.g., calcineurin inhibitors, mycophenolic acid derivatives, and steroids. The methods may comprise samples obtained from one or more clinical centers. The use of samples obtained from two or more clinical centers may be used to identify any differences in the sensitivity and/or specificity of the methods to classify and/or characterize one or more samples. The use of samples obtained from two or more clinical centers may be used to determine the effect of race and/or therapy on the sensitivity and/or specificity of the methods disclosed herein. The use of multiple samples may be used to determine the impact of bacterial and/or viral infections on the sensitivity and/or specificity of the methods disclosed herein.

The samples may comprise pure ABMR (antibody mediated rejection). The samples may comprise mixed ABMR/TCMR (T-cell mediated rejection). In this example, we had 12 mixed ABMR/TCMR instances but only 1 of the 12 was misclassified for AR. About 30% of our AR subjects had biopsies with positive C4d staining. However, supervised clustering to detect outliers did not indicate that our signatures were influenced by C4d status. At the time this study was done it was not common practice to measure donor-specific antibodies. However, we note the lack of correlation with C4d status for our data.

The methods disclosed herein may be used to determine a mechanism of ADNR since these patients were biopsied based on clinical judgments of suspected AR after efforts to exclude common causes of acute transplant dysfunction. While our results from this example do not address this question, it is evident that renal transplant dysfunction is common to both AR and ADNR. The levels of kidney dysfunction based on serum creatinines were not significantly different between AR and ADNR subjects. Thus, these gene expression differences are not based simply on renal function or renal injury. Also, the biopsy histology for the ADNR patients revealed nonspecific and only focal tubular necrosis, interstitial edema, scattered foci of inflammatory cells that did not rise to even borderline AR and nonspecific arteriolar changes consistent but not diagnostic of CNI toxicity.

Biopsy-based diagnosis may be subject to the challenge of sampling errors and differences between the interpretations of individual pathologists (Mengel at 2007, Am J Transplant, 7(10): 2221-2226). To mitigate this limitation, we used the Banff schema classification and an independent central biopsy review of all samples to establish the phenotypes. Another question is how these signatures would reflect known causes of acute kidney transplant dysfunction (e.g. urinary tract infection, CMV and BK nephropathy). Our view is that there are already well-established, clinically validated and highly sensitive tests available to diagnose each of these. Thus, for implementation and interpretation of our molecular diagnostic for AR and ADNR clinicians would often do this kind of laboratory testing in parallel. In complicated instances a biopsy will still be required, though we note that a biopsy is also not definitive for sorting out AR vs. BK nephropathy.

The methods may be used for molecular diagnostics to predict outcomes like AR, especially diagnose subclinical AR, prior to enough tissue injury to result in kidney transplant dysfunction. The methods may be used to measure and ultimately optimize the adequacy of long term immunosuppression by serial monitoring of blood gene expression. The design of the present study involved blood samples collected at the time of biopsies. The methods may be used to predict AR or ADNR. The absence of an AR gene profile in a patient sample may be a first measure of adequate immunosuppression and may be integrated into a serial blood monitoring protocol. Demonstrating the diagnosis of subclinical AR and the predictive capability of our classifiers may create the first objective measures of adequate immunosuppression. One potential value of our approach using global gene expression signatures developed by DNA microarrays rather than highly reduced qPCR signatures is that these more complicated predictive and immunosuppression adequacy signatures can be derived later from prospective studies like CTOT08. In turn, an objective metric for the real-time efficacy of immunosuppression may allow the individualization of drug therapy and enable the long term serial monitoring necessary to optimize graft survival and minimize drug toxicity.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

Supplemental Statistical Methods

All model selection was done in Partek Genomics Suite v6.6 using the Partek user guide model selection, 2010: Nearest Centroid The Nearest Centroid classification method was based on [Tibshirani, R., Hastie, T., Narasimham, B., and Chu, G (2003): Class Prediction by Nearest Shrunken Centroids, with Applications to DNA Microarrays. Statist. Sci. Vol. 18 (1):104-117] and [Tou, J. T., and Gonzalez, R. C. (1974): Pattern Recognition Principals, Addison-Wesley, Reading, Massachusetts]. The centroid classifications were done by assigning equal prior probabilities.

Support Vector Machines

Support Vector Machines (SVMs) attempt to find a set of hyperplanes (one for each pair of classes) that best classify the data. It does this by maximizing the distance of the hyperplanes to the closest data points on both sides. Partek uses the one-against-one method as described in "A comparison of methods for multi-class support vector machines" (C. W. Hsu and C. J. Lin. IEEE Transactions on Neural Networks, 13(2002), 415-425).

To run model selection with SVM cost with shrinking was used. Cost of 1 to 1000 with Step 100 was chosen to run several models. The radial basis kernel (gamma) was used. The kernel parameters were 1/number of columns.

Diagonal Linear Discriminant Analysis

The Discriminant Analysis method can do predictions based on the class variable.

The linear with equal prior probability method was chosen.

Linear Discriminant Analysis is performed in Partek using these steps:

Calculation of a common (pooled) covariance matrix and within-group means

Calculation of the set of linear discriminant functions from the common covariance and the within-group means Classification using the linear discriminant functions The common covariance matrix is a pooled estimate of the within-group covariance matrices:

$$\Sigma SWi$$

$$S=i$$

$$\Sigma ni-Ci$$

Thus, for linear discriminant analysis, the linear discriminant function for class i is defined as: $d(x) = -1 (x-m)t S-1 (x-m) + \ln P(w)$.

Optimism-Corrected AUC's

The steps for estimating the optimism-corrected AUCs are based on the work of F. Harrell published in [*Regression Modeling Strategies: With applications to linear models, logistic regression, and survival analysis*. Springer, New York (2001)].

The basic approach is described in [Miao Y M, Cenzer I S, Kirby K A, Boscardin J W. Estimating Harrell's Optimism on Predictive Indices Using Bootstrap Samples. SAS Global Forum 2013; San Francisco]:

1. Select the predictors and fit a model using the full dataset and a particular variable selection method. From that model, calculate the apparent discrimination (capp).
2. Generate M=100 to 200 datasets of the same sample size (n) using bootstrap samples with replacement.
3. For each one of the new datasets m . . . M, select predictors and fit the model using the exact same algorithmic approach as in step 1 and calculate the discrimination (cboot (m)).
4. For each one of the new models, calculate its discrimination back on the original data set (corig(m)). For this step, the regression coefficients can either be fixed to their values from step 3 to determine the joint degree of over-fitting from both selection and estimation or can be re-estimated to determine the degree of over-fitting from selection only.
5. For each one of the bootstrap samples, the optimism in the fit is o(m)=corig(m)–cboot(m). The average of these values is the optimism of the original model.
6. The optimism-corrected performance of the original model is then cadj=capp–o. This value is a nearly unbiased estimate of the expected values of the optimism that would be obtained in external validation.

We adapted this model in Partek Genomics Suite using 1000 samplings with replacement of our dataset (n=148). An original AUC was calculated on the full dataset, and then the average of the M=1000 samplings was also estimated. The difference between the original and the estimated AUC's was designated as the optimism and this was subtracted from the original AUC to arrive at the "optimism-corrected AUC". In the text, we specifically compared the AUC's that we reported by testing our locked 200-probe set classifiers on only our Validation cohort (see Table 4) to the optimism-corrected AUC's (see Table 5). The results demonstrate little difference consistent with the conclusion that our high predictive accuracies are not the result of over-fitting.

TABLE 1a

The top 200 gene probeset used in the 3-Way AR, ADNR TX ANOVA Analysis (using the Hu133 Plus 2.0 cartridge arrays plates)

| | Parametric p-value | Geom mean of intensities in class 1 | Geom mean of intensities in class 2 | Geom mean of intensities in class 3 | ProbeSet | Symbol | Name | EntrezID | DefinedGenelist | Pairwise significant |
|---|---|---|---|---|---|---|---|---|---|---|
| 1 | <1e−07 | 6.48 | 7.08 | 7.13 | 212167_s_at | SMARCB1 | SWI/SNF related, matrix associated, actin dependent regulator of chromatin, subfamily b, member 1 | 6598 | Chromatin Remodeling by hSWI/SNF ATP-dependent Complexes | (1, 2), (1, 3) |
| 2 | <1e−07 | 9.92 | 9.42 | 10.14 | 201444_s_at | ATP6AP2 | ATPase, H+ transporting, lysosomal accessory protein 2 | 10159 | | (2, 1), (2, 3) |

TABLE 1a-continued

The top 200 gene probeset used in the 3-Way AR, ADNR TX ANOVA Analysis (using the Hu133 Plus 2.0 cartridge arrays plates)

| | Parametric p-value | Geom mean of intensities in class 1 | Geom mean of intensities in class 2 | Geom mean of intensities in class 3 | ProbeSet | Symbol | Name | EntrezID | DefinedGenelist | Pairwise significant |
|---|---|---|---|---|---|---|---|---|---|---|
| 3 | <1e−07 | 5.21 | 5.01 | 5.68 | 227658_s_at | PLEKHA3 | pleckstrin homology domain containing, family A (phosphoinositide binding specific) member 3 | 65977 | | (1, 3), (2, 3) |
| 4 | 1.00E−07 | 6.73 | 7.62 | 7.73 | 201746_at | TP53 | tumor protein p53 | 7157 | Apoptotic Signaling in Response to DNA Damage, ATM Signaling Pathway, BTG family proteins and cell cycle regulation, Cell Cycle: G1/S Check Point, Cell Cycle: G2/M Checkpoint, Chaperones modulate interferon Signaling Pathway, CTCF: First Multivalent Nuclear Factor, Double Stranded RNA Induced Gene Expression, Estrogen-responsive protein Efp controls cell cycle and breast tumors growth, Hypoxia and p53 in the Cardiovascular system, Overview of telomerase protein component gene hTert Transcriptional Regulation, p53 Signaling Pathway, RB Tumor Suppressor/Checkpoint Signaling in response to DNA damage, Regulation of cell cycle progression by Plk3, Regulation of transcriptional activity by PML, Role of BRCA1, BRCA2 and ATR in Cancer Susceptibility, Telomeres, Telomerase, Cellular Aging, and Immortality, Tumor Suppressor Arf Inhibits Ribosomal Biogenesis, Amyotrophic lateral sclerosis (ALS), Apoptosis, Cell cycle, Colorectal cancer, Huntington\'s disease, MAPK signaling pathway, Wnt sign . . . | (1, 2), (1, 3) |

TABLE 1a-continued

The top 200 gene probeset used in the 3-Way AR, ADNR TX ANOVA Analysis (using the Hu133 Plus 2.0 cartridge arrays plates)

| | Parametric p-value | Geom mean of intensities in class 1 | Geom mean of intensities in class 2 | Geom mean of intensities in class 3 | ProbeSet | Symbol | Name | EntrezID | DefinedGenelist | Pairwise significant |
|---|---|---|---|---|---|---|---|---|---|---|
| 5 | 1.00E−07 | 6.64 | 6.07 | 6.87 | 218292_s_at | PRKAG2 | protein kinase, AMP-activated, gamma 2 non-catalytic subunit | 51422 | ChREBP regulation by carbohydrates and cAMP, Reversal of Insulin Resistance by Leptin, Adipocytokine signaling pathway, Insulin signaling pathway | (2, 1), (2, 3) |
| 6 | 1.00E−07 | 11.08 | 11.9 | 12.02 | 1553551_s_at | ND2 | MTND2 | 4536 | | (1, 2), (1, 3) |
| 7 | 2.00E−07 | 8.6 | 9.41 | 9.21 | 210996_s_at | YWHAE | tyrosine 3-monooxygenase/tryptophan 5-monooxygenase activation protein, epsilon polypeptide | 7531 | Cell cycle | (1, 2), (1, 3) |
| 8 | 2.00E−07 | 5.89 | 6.92 | 6.23 | 243037_at | | | | | (1, 2), (3, 2) |
| 9 | 2.00E−07 | 7.61 | 7 | 7.81 | 200890_s_at | SSR1 | signal sequence receptor, alpha | 6745 | | (2, 1), (2, 3) |
| 10 | 2.00E−07 | 5.18 | 6.71 | 6.12 | 1570571_at | CCDC91 | coiled-coil domain containing 91 | 55297 | | (1, 2), (1, 3) |
| 11 | 3.00E−07 | 7.01 | 6.55 | 7.21 | 233748_x_at | PRKAG2 | protein kinase, AMP-activated, gamma 2 non-catalytic subunit | 51422 | ChREBP regulation by carbohydrates and cAMP, Reversal of Insulin Resistance by Leptin, Adipocytokine signaling pathway, Insulin signaling pathway | (2, 1), (2, 3) |
| 12 | 3.00E−07 | 7.96 | 7.29 | 7.86 | 224455_s_at | ADPGK | ADP-dependent glucokinase | 83440 | | (2, 1), (2, 3) |
| 13 | 3.00E−07 | 8.42 | 7.93 | 8.41 | 223931_s_at | CHFR | checkpoint with forkhead and ring finger domains, E3 ubiquitin protein ligase | 55743 | Tryptophan metabolism | (2, 1), (2, 3) |
| 14 | 3.00E−07 | 4.84 | 5.44 | 5.11 | 236766_at | | | | | (1, 2), (1, 3), (3, 2) |
| 15 | 3.00E−07 | 7.95 | 8.72 | 7.73 | 242068_at | | | | | (1, 2), (3, 2) |
| 16 | 3.00E−07 | 6.96 | 6.58 | 7.31 | 215707_s_at | PRNP | prion protein | 5621 | Prion Pathway, Neurodegenerative Disorders, Prion disease | (2, 1), (2, 3) |
| 17 | 3.00E−07 | 6.68 | 7.73 | 7.4 | 1558220_at | | | | | (1, 2), (1, 3) |
| 18 | 3.00E−07 | 6.53 | 6.19 | 6.87 | 203100_s_at | CDYL | chromodomain protein, Y-like | 9425 | | (2, 1), (2, 3) |
| 19 | 3.00E−07 | 6.19 | 5.66 | 6.28 | 202278_s_at | SPTLC1 | serine palmitoyltransferase, long chain base subunit 1 | 10558 | Sphingolipid metabolism | (2, 1), (2, 3) |
| 20 | 4.00E−07 | 7.73 | 7.83 | 6.71 | 232726_at | | | | | (3, 1), (3, 2) |
| 21 | 4.00E−07 | 9.78 | 9.22 | 9.81 | 218178_s_at | CHMP1B | charged multivesicular body protein 1B | 57132 | | (2, 1), (2, 3) |
| 22 | 4.00E−07 | 7.08 | 6.35 | 7.25 | 223585_x_at | KBTBD2 | kelch repeat and BTB (POZ) domain containing 2 | 25948 | | (2, 1), (2, 3) |
| 23 | 4.00E−07 | 4.85 | 4.53 | 5.49 | 224407_s_at | MST4 | serine/threonine protein kinase MST4 | 51765 | | (1, 3), (2, 3) |
| 24 | 4.00E−07 | 9.49 | 9.74 | 8.95 | 239597_at | | | | | (3, 1), (3, 2) |
| 25 | 4.00E−07 | 4.3 | 4.76 | 4.42 | 239987_at | | | | | (1, 2), (3, 2) |

TABLE 1a-continued

The top 200 gene probeset used in the 3-Way AR, ADNR TX ANOVA Analysis (using the Hu133 Plus 2.0 cartridge arrays plates)

| | Parametric p-value | Geom mean of intensities in class 1 | Geom mean of intensities in class 2 | Geom mean of intensities in class 3 | ProbeSet | Symbol | Name | EntrezID | DefinedGenelist | Pairwise significant |
|---|---|---|---|---|---|---|---|---|---|---|
| 26 | 5.00E−07 | 5.49 | 6.06 | 5.84 | 243667_at | | | | | (1, 2), (1, 3) |
| 27 | 6.00E−07 | 8.08 | 7.32 | 7.95 | 209287_s_at | CDC42EP3 | CDC42 effector protein (Rho GTPase binding) 3 | 10602 | | (2, 1), (2, 3) |
| 28 | 6.00E−07 | 7.81 | 7.17 | 8 | 212008_at | UBXN4 | UBX domain protein 4 | 23190 | | (2, 1), (2, 3) |
| 29 | 6.00E−07 | 4.88 | 4.57 | 5.27 | 206288_at | PGGT1B | protein geranylgeranyl-transferase type I, beta subunit | 5229 | | (1, 3), (2, 3) |
| 30 | 6.00E−07 | 9.75 | 9.98 | 9.26 | 238883_at | | | | | (3, 1), (3, 2) |
| 31 | 7.00E−07 | 6.19 | 5.42 | 6.79 | 207794_at | CCR2 | chemokine (C-C motif) receptor 2 | 729230 | | (2, 1), (2, 3) |
| 32 | 7.00E−07 | 8.17 | 8.58 | 7.98 | 242143_at | | | | | (1, 2), (3, 2) |
| 33 | 7.00E−07 | 4.52 | 5.01 | 5.07 | 205964_at | ZNF426 | zinc finger protein 426 | 79088 | | (1, 2), (1, 3) |
| 34 | 8.00E−07 | 6.68 | 5.68 | 6.75 | 1553685_s_at | SP1 | Sp1 transcription factor | 6667 | Agrin in Postsynaptic Differentiation, Effects of calcineurin in Keratinocyte Differentiation, Human Cytomegalovirus and Map Kinase Pathways, Keratinocyte Differentiation, MAPKinase Signaling Pathway, Mechanism of Gene Regulation by Peroxisome Proliferators via PPARa(alpha), Overview of telomerase protein component gene hTert Transcriptional Regulation, Overview of telomerase RNA component gene hTerc Transcriptional Regulation, TGF-beta signaling pathway | (2, 1), (2, 3) |
| 35 | 8.00E−07 | 5.08 | 5.8 | 6.03 | 219730_at | MED18 | mediator complex subunit 18 | 54797 | | (1, 2), (1, 3) |
| 36 | 9.00E−07 | 5.74 | 6.07 | 5.74 | 233004_x_at | | | | | (1, 2), (3, 2) |
| 37 | 9.00E−07 | 5.5 | 6.4 | 6.06 | 242797_x_at | | | | | (1, 2), (1, 3) |
| 38 | 9.00E−07 | 8.4 | 8.03 | 8.65 | 200778_s_at | 2-Sep | septin 2 | 4735 | | (2, 1), (2, 3) |
| 39 | 1.00E−06 | 7.64 | 6.65 | 7.91 | 211559_s_at | CCNG2 | cyclin G2 | 901 | | (2, 1), (2, 3) |
| 40 | 1.00E−06 | 6.71 | 7.3 | 7.23 | 221090_s_at | OGFOD1 | 2-oxoglutarate and iron-dependent oxygenase domain containing 1 | 55239 | | (1, 2), (1, 3) |
| 41 | 1.00E−06 | 4.36 | 5.14 | 4.87 | 240232_at | | | | | (1, 2), (1, 3) |
| 42 | 1.10E−06 | 6.55 | 6.86 | 7.12 | 221650_s_at | MED18 | mediator complex subunit 18 | 54797 | | (1, 2), (1, 3), (2, 3) |
| 43 | 1.10E−06 | 8 | 8.48 | 8.26 | 214670_at | ZKSCAN1 | zinc finger with KRAB and SCAN domains 1 | 7586 | | (1, 2), (1, 3), (3, 2) |

TABLE 1a-continued

The top 200 gene probeset used in the 3-Way AR, ADNR TX ANOVA Analysis (using the Hu133 Plus 2.0 cartridge arrays plates)

| | Parametric p-value | Geom mean of intensities in class 1 | Geom mean of intensities in class 2 | Geom mean of intensities in class 3 | ProbeSet | Symbol | Name | EntrezID | DefinedGenelist | Pairwise significant |
|---|---|---|---|---|---|---|---|---|---|---|
| 44 | 1.20E−06 | 6.55 | 6.17 | 7.04 | 202089_s_at | SLC39A6 | solute carrier family 39 (zinc transporter), member 6 | 25800 | | (1, 3), (2, 3) |
| 45 | 1.20E−06 | 7.05 | 6.31 | 7.45 | 211825_s_at | FLI1 | Friend leukemia virus integration 1 | 2313 | | (2, 1), (2, 3) |
| 46 | 1.20E−06 | 6.05 | 6.85 | 6.71 | 243852_at | LUC7L2 | LUC7-like 2 (*S. cerevisiae*) | 51631 | | (1, 2), (1, 3) |
| 47 | 1.20E−06 | 8.27 | 7.44 | 8.6 | 207549_x_at | CD46 | CD46 molecule, complement regulatory protein | 4179 | Complement and coagulation cascades | (2, 1), (2, 3) |
| 48 | 1.30E−06 | 4.7 | 5.52 | 4.65 | 242737_at | | | | | (1, 2), (3, 2) |
| 49 | 1.30E−06 | 4.93 | 4.67 | 4.57 | 239189_at | CASKIN1 | CASK interacting protein 1 | 57524 | | (2, 1), (3, 1) |
| 50 | 1.30E−06 | 7.66 | 8.08 | 7.47 | 232180_at | UGP2 | UDP-glucose pyrophosphorylase 2 | 7360 | Galactose metabolism, Nucleotide sugars metabolism, Pentose and glucuronate interconversions, Starch and sucrose metabolism | (1, 2), (3, 2) |
| 51 | 1.40E−06 | 7.47 | 6.64 | 7.31 | 210971_s_at | ARNTL | aryl hydrocarbon receptor nuclear translocator-like | 406 | Circadian Rhythms | (2, 1), (2, 3) |
| 52 | 1.40E−06 | 8.66 | 8.99 | 8.1 | 232307_at | | | | | (3, 1), (3, 2) |
| 53 | 1.40E−06 | 7.06 | 6.48 | 7.56 | 222699_s_at | PLEKHF2 | pleckstrin homology domain containing, family F (with FYVE domain) member 2 | 79666 | | (2, 1), (2, 3) |
| 54 | 1.60E−06 | 6.59 | 6.62 | 6.13 | 234435_at | | | | | (3, 1), (3, 2) |
| 55 | 1.60E−06 | 3.94 | 3.51 | 4.17 | 207117_at | ZNF117 | zinc finger protein 117 | 51351 | | (2, 1), (2, 3) |
| 56 | 1.60E−06 | 7.57 | 7.25 | 8.26 | 1553530_a_at | ITGB1 | integrin, beta 1 (fibronectin receptor, beta polypeptide, antigen CD29 includes MDF2, MSK12) | 3688 | Adhesion and Diapedesis of Lymphocytes, Adhesion Molecules on Lymphocyte, Agrin in Postsynaptic Differentiation, Aspirin Blocks Signaling Pathway Involved in Platelet Activation, B Cell Survival Pathway, Cells and Molecules involved in local acute inflammatory response, Eph Kinases and ephrins support platelet aggregation, Erk and PI-3 Kinase Are Necessary for Collagen Binding in Corneal Epithelia, Erk1/Erk2 Mapk Signaling pathway, Integrin Signaling Pathway, mCalpain and friends in Cell motility, Monocyte and its Surface | (1, 3), (2, 3) |

TABLE 1a-continued

The top 200 gene probeset used in the 3-Way AR, ADNR TX ANOVA Analysis (using the Hu133 Plus 2.0 cartridge arrays plates)

| | Parametric p-value | Geom mean of intensities in class 1 | Geom mean of intensities in class 2 | Geom mean of intensities in class 3 | ProbeSet | Symbol | Name | EntrezID | DefinedGenelist | Pairwise significant |
|---|---|---|---|---|---|---|---|---|---|---|
| 57 | 1.60E−06 | 5.67 | 5.02 | 6.16 | 214786_at | MAP3K1 | mitogen-activated protein kinase kinase kinase 1, E3 ubiquitin protein ligase | 4214 | Molecules, PTEN dependent cell cycle arrest and apoptosis, Ras-Independent pathway in NK cell-mediated cytotoxicity, Signaling of Hepatocyte Growth Factor Receptor, Trefoil Factors Initiate Mucosal Healing, uCalpain and friends in Cell spread, Axon guidance, Cell adhesion molecules (CAMs), ECM-receptor interaction, Focal adhesion, Leukocyte transendothelial migration, Regulation of actin cytoskeleton Angiotensin II mediated activation of JNK Pathway via Pyk2 dependent signaling, BCR Signaling Pathway, CD40L Signaling Pathway, Ceramide Signaling Pathway, EGF Signaling Pathway, FAS signaling pathway (CD95), Fc Epsilon Receptor I Signaling in Mast Cells, fMLP induced chemokine gene expression in HMC-1 cells, HIV-I Nef: negative effector of Fas and TNF, Human Cytomegalovirus and Map Kinase Pathways, Inhibition of Cellular Proliferation by Gleevec, Keratinocyte Differentiation, Links between Pyk2 and Map Kinases, Map Kinase Inactivation of SMRT Corepressor, MAPKinase Signaling Pathway, Neuropeptides VIP and PACAP inhibit the apoptosis of activated T cells, NF-kB Signaling Pathway, p38 MAPK Signaling Pathway, PDGF Signaling Pathway, Rac 1 cell motility signaling pathway, Role of | (2, 1), (2, 3) |

TABLE 1a-continued

The top 200 gene probeset used in the 3-Way AR, ADNR TX ANOVA Analysis (using the Hu133 Plus 2.0 cartridge arrays plates)

| | Parametric p-value | Geom mean of intensities in class 1 | Geom mean of intensities in class 2 | Geom mean of intensities in class 3 | ProbeSet | Symbol | Name | EntrezID | DefinedGenelist | Pairwise significant |
|---|---|---|---|---|---|---|---|---|---|---|
| 58 | 1.70E−06 | 7.49 | 7.27 | 7.73 | 222729_at | FBXW7 | F-box and WD repeat domain containing 7, E3 ubiquitin protein ligase | 55294 | MAL in Rho-Mediated Activation of SRF, Signal transduction through IL1R, T Cell Receptor Signaling Pathway, The 4-1BB-dependent immune response, TNF/Stress Related Signaling, TNFR1 Signaling Pathway, TNFR2 Sig . . . Cyclin E Destruction Pathway, Neurodegenerative Disorders, Ubiquitin mediated proteolysis | (2, 1), (2, 3) |
| 59 | 1.80E−06 | 7.73 | 7.41 | 8.08 | 208310_s_at | | | | | (2, 1), (2, 3) |
| 60 | 1.80E−06 | 9.06 | 9.28 | 8.54 | 242471_at | SRGAP2B | SLIT-ROBO Rho GTPase activating protein 2B | 647135 | | (3, 1), (3, 2) |
| 61 | 1.80E−06 | 7.84 | 8.15 | 7.5 | 238812_at | | | | | (3, 1), (3, 2) |
| 62 | 1.80E−06 | 6.64 | 7.28 | 7.08 | 206240_s_at | ZNF136 | zinc finger protein 136 | 7695 | | (1, 2), (1, 3) |
| 63 | 1.80E−06 | 10.29 | 9.86 | 10.35 | 1555797_a_at | ARPC5 | actin related protein 2/3 complex, subunit 5, 16 kDa | 10092 | Regulation of actin cytoskeleton | (2, 1), (2, 3) |
| 64 | 1.90E−06 | 5.05 | 5.49 | 5.24 | 215068_s_at | FBXL18 | F-box and leucine-rich repeat protein 18 | 80028 | | (1, 2), (3, 2) |
| 65 | 2.00E−06 | 6.84 | 6.08 | 7.16 | 204426_at | TMED2 | transmembrane emp24 domain trafficking protein 2 | 10959 | | (2, 1), (2, 3) |
| 66 | 2.00E−06 | 5.6 | 5.19 | 5.13 | 234125_at | | | | | (2, 1), (3, 1) |
| 67 | 2.10E−06 | 9.87 | 9.38 | 10.27 | 200641_s_at | YWHAZ | tyrosine 3-monooxygenase/tryptophan 5-monooxygenase activation protein, zeta polypeptide | 7534 | Cell cycle | (2, 1), (2, 3) |
| 68 | 2.10E−06 | 7.6 | 6.83 | 7.89 | 214544_s_at | SNAP23 | synaptosomal-associated protein, 23 kDa | 8773 | SNARE interactions in vesicular transport | (2, 1), (2, 3) |
| 69 | 2.10E−06 | 9.57 | 10.14 | 9.29 | 238558_at | | | | | (1, 2), (3, 2) |
| 70 | 2.20E−06 | 6.79 | 7.12 | 6.72 | 221071_at | | | | | (1, 2), (3, 2) |
| 71 | 2.40E−06 | 6.98 | 6.38 | 7.29 | 232591_s_at | TMEM30A | transmembrane protein 30A | 55754 | | (2, 1), (2, 3) |
| 72 | 2.40E−06 | 7.22 | 7.49 | 6.35 | 1569477_at | | | | | (3, 1), (3, 2) |
| 73 | 2.60E−06 | 7.97 | 7.26 | 8.22 | 211574_s_at | CD46 | CD46 molecule, complement regulatory protein | 4179 | Complement and coagulation cascades | (2, 1), (2, 3) |
| 74 | 2.60E−06 | 7.63 | 7.37 | 8.18 | 201627_s_at | INSIG1 | insulin induced gene 1 | 3638 | | (1, 3), (2, 3) |
| 75 | 2.60E−06 | 5.27 | 5.97 | 5.53 | 215866_at | | | | | (1, 2), (3, 2) |
| 76 | 2.80E−06 | 9.6 | 9.77 | 9.42 | 201986_at | MED13 | mediator complex subunit 13 | 9969 | | (3, 2) |
| 77 | 2.80E−06 | 9.21 | 8.85 | 9.44 | 200753_x_at | SRSF2 | serine/arginine-rich splicing factor 2 | 6427 | Spliceosomal Assembly | (2, 1), (2, 3) |

TABLE 1a-continued

The top 200 gene probeset used in the 3-Way AR, ADNR TX ANOVA Analysis (using the Hu133 Plus 2.0 cartridge arrays plates)

| | Parametric p-value | Geom mean of intensities in class 1 | Geom mean of intensities in class 2 | Geom mean of intensities in class 3 | ProbeSet | Symbol | Name | EntrezID | DefinedGenelist | Pairwise significant |
|---|---|---|---|---|---|---|---|---|---|---|
| 78 | 3.00E−06 | 4.65 | 4.75 | 5.36 | 214959_s_at | API5 | apoptosis inhibitor 5 | 8539 | | (1, 3), (2, 3) |
| 79 | 3.10E−06 | 7.39 | 8.28 | 7.81 | 217704_x_at | SUZ12P1 | suppressor of zeste 12 homolog pseudogene 1 | 440423 | | (1, 2), (3, 2) |
| 80 | 3.30E−06 | 7.38 | 7.93 | 7 | 244535_at | | | | | (1, 2), (3, 2) |
| 81 | 3.40E−06 | 7.17 | 6.66 | 7.86 | 210786_s_at | FLI1 | Friend leukemia virus integration 1 | 2313 | | (1, 3), (2, 3) |
| 82 | 3.40E−06 | 7.33 | 7.87 | 7.47 | 235035_at | SLC35E1 | solute carrier family 35, member E1 | 79939 | | (1, 2), (3, 2) |
| 83 | 3.40E−06 | 10.42 | 10.84 | 10.08 | 241681_at | | | | | (1, 2), (3, 2) |
| 84 | 3.40E−06 | 7.13 | 6.16 | 7.1 | 212720_at | PAPOLA | poly(A) polymerase alpha | 10914 | Polyadenylation of mRNA | (2, 1), (2, 3) |
| 85 | 3.50E−06 | 5.81 | 5.47 | 6.03 | 205408_at | MLLT10 | myeloid/lymphoid or mixed-lineage leukemia (trithorax homolog, Drosophila); translocated to, 10 | 8028 | | (2, 1), (2, 3) |
| 86 | 3.50E−06 | 5.51 | 6.12 | 5.83 | 238418_at | SLC35B4 | solute carrier family 35, member B4 | 84912 | | (1, 2), (1, 3) |
| 87 | 3.50E−06 | 6.03 | 7.01 | 6.37 | 1564424_at | | | | | (1, 2), (3, 2) |
| 88 | 3.60E−06 | 8.65 | 9.02 | 8.39 | 243030_at | | | | | (1, 2), (3, 2) |
| 89 | 3.60E−06 | 5.52 | 5.25 | 5.78 | 215207_x_at | | | | | (2, 1), (2, 3) |
| 90 | 3.90E−06 | 6.77 | 7.36 | 7.21 | 235058_at | | | | | (1, 2), (1, 3) |
| 91 | 4.20E−06 | 8.15 | 7.94 | 8.48 | 202092_s_at | ARL2BP | ADP-ribosylation factor-like 2 binding protein | 23568 | | (1, 3), (2, 3) |
| 92 | 4.40E−06 | 8.55 | 8.24 | 8.6 | 202162_s_at | CNOT8 | CCR4-NOT transcription complex, subunit 8 | 9337 | | (2, 1), (2, 3) |
| 93 | 4.40E−06 | 8.21 | 8.1 | 8.68 | 201259_s_at | SYPL1 | synaptophysin-like 1 | 6856 | | (1, 3), (2, 3) |
| 94 | 4.40E−06 | 7.68 | 7.79 | 7.2 | 236168_at | | | | | (3, 1), (3, 2) |
| 95 | 4.40E−06 | 6.72 | 7.58 | 6.89 | 1553252_a_at | BRWD3 | bromodomain and WD repeat domain containing 3 | 254065 | | (1, 2), (3, 2) |
| 96 | 4.50E−06 | 6.71 | 7.67 | 7.19 | 244872_at | RBBP4 | retinoblastoma binding protein 4 | 5928 | The PRC2 Complex Sets Long-term Gene Silencing Through Modification of Histone Tails | (1, 2), (3, 2) |
| 97 | 4.50E−06 | 5.58 | 6.53 | 6.36 | 215390_at | | | | | (1, 2), (1, 3) |
| 98 | 4.60E−06 | 4.93 | 6.29 | 5.36 | 1566966_at | | | | | (1, 2), (3, 2) |
| 99 | 4.90E−06 | 5.46 | 5.07 | 5.68 | 225700_at | GLCCI1 | glucocorticoid induced transcript 1 | 113263 | | (2, 1), (2, 3) |
| 100 | 5.00E−06 | 4.96 | 5.17 | 4.79 | 236324_at | MBP | myelin basic protein | 4155 | | (1, 2), (3, 2) |
| 101 | 5.10E−06 | 8.08 | 7.26 | 8.33 | 222846_at | RAB8B | RAB8B, member RAS oncogene family | 51762 | | (2, 1), (2, 3) |
| 102 | 5.10E−06 | 6.24 | 5.75 | 6.58 | 1564053_a_at | YTHDF3 | YTH domain family, member 3 | 253943 | | (2, 1), (2,3) |

TABLE 1a-continued

The top 200 gene probeset used in the 3-Way AR, ADNR TX ANOVA Analysis (using the Hu133 Plus 2.0 cartridge arrays plates)

| | Parametric p-value | Geom mean of intensities in class 1 | Geom mean of intensities in class 2 | Geom mean of intensities in class 3 | ProbeSet | Symbol | Name | EntrezID | DefinedGenelist | Pairwise significant |
|---|---|---|---|---|---|---|---|---|---|---|
| 103 | 5.20E−06 | 7 | 6.36 | 7.35 | 216100_s_at | TOR1AIP1 | torsin A interacting protein 1 | 26092 | | (2, 1), (2, 3) |
| 104 | 5.20E−06 | 6.15 | 5.97 | 6.63 | 1565269_s_at | ATF1 | activating transcription factor 1 | 466 | TNF/Stress Related Signaling | (1, 3), (2, 3) |
| 105 | 5.30E−06 | 8.13 | 7.73 | 8.57 | 220477_s_at | TMEM230 | transmembrane protein 230 | 29058 | | (2, 3) |
| 106 | 5.30E−06 | 7.45 | 8.09 | 7.72 | 1559490_at | LRCH3 | leucine-rich repeats and calponin homology (CH) domain containing 3 | 84859 | | (1, 2), (3, 2) |
| 107 | 5.30E−06 | 7.44 | 8.05 | 7.44 | 225490_at | ARID2 | AT rich interactive domain 2 (ARID, RFX-like) | 196528 | | (1, 2), (3, 2) |
| 108 | 5.50E−06 | 7.49 | 8.18 | 7.83 | 244766_at | | | | | (1, 2), (3, 2) |
| 109 | 5.50E−06 | 7.71 | 8.41 | 8 | 242673_at | | | | | (1, 2), (3, 2) |
| 110 | 5.60E−06 | 8.97 | 8.59 | 9.24 | 202164_s_at | CNOT8 | CCR4-NOT transcription complex, subunit 8 | 9337 | | (2, 1), (2, 3) |
| 111 | 5.70E−06 | 7.75 | 8.26 | 7.52 | 222357_at | ZBTB20 | zinc finger and BTB domain containing 20 | 26137 | | (1, 2), (3, 2) |
| 112 | 5.90E−06 | 5.07 | 5.52 | 4.71 | 240594_at | | | | | (1, 2), (3, 2) |
| 113 | 6.00E−06 | 7.78 | 7.45 | 7.96 | 1554577_a_at | PSMD10 | proteasome (prosome, macropain) 26S subunit, non-ATPase, 10 | 5716 | | (2, 1), (2, 3) |
| 114 | 6.00E−06 | 6.55 | 7.03 | 6.58 | 215137_at | | | | | (1, 2), (3, 2) |
| 115 | 6.10E−06 | 9.46 | 9.66 | 9.05 | 243527_at | | | | | (3, 1), (3, 2) |
| 116 | 6.30E−06 | 7.8 | 7.27 | 8.15 | 214449_s_at | RHOQ | ras homolog family member Q | 23433 | Insulin signaling pathway | (2, 1), (2,3) |
| 117 | 6.30E−06 | 7.3 | 7.92 | 7.44 | 216197_at | ATF7IP | activating transcription factor 7 interacting protein | 5572 | | (1, 2), (3, 2) |
| 118 | 6.40E−06 | 7.38 | 8.17 | 7.51 | 1558569_at | LOC100131541 | uncharacterized LOC100131541 | 100131541 | | (1, 2), (3, 2) |
| 119 | 6.50E−06 | 4.79 | 5.23 | 4.55 | 244030_at | STYX | serine/threonine/tyrosine interacting protein | 6815 | | (1, 3), (2, 3) |
| 120 | 6.70E−06 | 7.2 | 7.95 | 7.27 | 244010_at | | | | | (1, 2), (3, 2) |
| 121 | 7.20E−06 | 6.36 | 6.78 | 6.05 | 232002_at | | | | | (1, 2), (3, 2) |
| 122 | 7.20E−06 | 6.11 | 6.95 | 6.18 | 243051_at | CNIH4 | cornichon homolog 4 (Drosophila) | 29097 | | (1, 2), (3, 2) |
| 123 | 7.20E−06 | 5.89 | 6.55 | 6.32 | 212394_at | EMC1 | ER membrane protein complex subunit 1 | 23065 | | (1, 2), (1, 3) |
| 124 | 7.30E−06 | 5.6 | 6.37 | 5.86 | 1553407_at | MACF1 | microtubule-actin crosslinking factor 1 | 23499 | | (1, 2), (3, 2) |
| 125 | 7.50E−06 | 5.08 | 5.84 | 5.74 | 214123_s_at | NOP14-AS1 | NOP14 antisense RNA 1 | 317648 | | (1, 2), (1, 3) |
| 126 | 7.50E−06 | 4.89 | 5.65 | 5.06 | 1564438_at | | | | | (1, 2), (3, 2) |
| 127 | 7.60E−06 | 8.54 | 8.88 | 8.22 | 229858_at | | | | | (3, 2) |

TABLE 1a-continued

The top 200 gene probeset used in the 3-Way AR, ADNR TX ANOVA Analysis (using the Hu133 Plus 2.0 cartridge arrays plates)

| | Parametric p-value | Geom mean of intensities in class 1 | Geom mean of intensities in class 2 | Geom mean of intensities in class 3 | ProbeSet | Symbol | Name | EntrezID | DefinedGenelist | Pairwise significant |
|---|---|---|---|---|---|---|---|---|---|---|
| 128 | 7.60E−06 | 9.26 | 8.77 | 9.49 | 215933_s_at | HHEX | hematopoietically expressed homeobox | 3087 | Maturity onset diabetes of the young | (2, 1), (2, 3) |
| 129 | 7.60E−06 | 7.97 | 8.14 | 7.59 | 239234_at | | | | | (3, 1), (3, 2) |
| 130 | 7.70E−06 | 9.71 | 9.93 | 9.17 | 238619_at | | | | | (3, 1), (3, 2) |
| 131 | 7.70E−06 | 5.46 | 6.05 | 5.61 | 1559039_at | DHX36 | DEAH (Asp-Glu-Ala-His) box polypeptide 36 | 170506 | | (1, 2), (3, 2) |
| 132 | 7.70E−06 | 9.19 | 8.57 | 9.36 | 222859_s_at | DAPP1 | dual adaptor of phosphotyrosine and 3-phosphoinositides | 27071 | | (2, 1), (2, 3) |
| 133 | 7.80E−06 | 7.76 | 7.35 | 8.07 | 210285_x_at | WTAP | Wilms tumor 1 associated protein | 9589 | | (2, 1), (2, 3) |
| 134 | 7.90E−06 | 5.64 | 5.2 | 5.67 | 238816_at | PSEN1 | presenilin 1 | 5663 | Generation of amyloid b-peptide by PS1, g-Secretase mediated ErbB4 Signaling Pathway, HIV-I Nef: negative effector of Fas and TNF, Presenilin action in Notch and Wnt signaling, Proteolysis and Signaling Pathway of Notch, Alzheimer\'s disease, Neurodegenerative Disorders, Notch signaling pathway, Wnt signaling pathway | (2, 1), (2, 3) |
| 135 | 7.90E−06 | 5.6 | 5.42 | 5.26 | 239112_at | | | | | (2, 1), (3, 1), (3, 2) |
| 136 | 8.40E−06 | 6.99 | 6.66 | 7.22 | 211536_x_at | MAP3K7 | mitogen-activated protein kinase kinase kinase 7 | 6885 | ALK in cardiac myocytes, FAS signaling pathway (CD95), MAPKinase Signaling Pathway, NFkB activation by Nontypeable Hemophilus influenzae, NF-kB Signaling Pathway, p38 MAPK Signaling Pathway, Signal transduction through IL1R, TGF beta signaling pathway, Thrombin signaling and protease-activated receptors, TNFR1 Signaling Pathway, Toll-Like Receptor Pathway, WNT Signaling Pathway, Adherens junction, MAPK signaling pathway, Toll-like receptor signaling pathway, Wnt signaling pathway | (2, 1), (2, 3) |
| 137 | 8.40E−06 | 7.82 | 8.34 | 7.98 | 228070_at | PPP2R5E | protein phosphatase 2, regulatory subunit B', epsilon isoform | 5529 | | (1, 2), (3, 2) |

TABLE 1a-continued

The top 200 gene probeset used in the 3-Way AR, ADNR TX ANOVA Analysis (using the Hu133 Plus 2.0 cartridge arrays plates)

| | Parametric p-value | Geom mean of intensities in class 1 | Geom mean of intensities in class 2 | Geom mean of intensities in class 3 | ProbeSet | Symbol | Name | EntrezID | DefinedGenelist | Pairwise significant |
|---|---|---|---|---|---|---|---|---|---|---|
| 138 | 8.60E−06 | 5.38 | 5.07 | 5.54 | 220285_at | FAM108B1 | family with sequence similarity 108, member B1 | 51104 | | (2, 1), (2,3) |
| 139 | 8.60E−06 | 8.07 | 7.56 | 8.2 | 210284_s_at | TAB2 | TGF-beta activated kinase 1/MAP3K7 binding protein 2 | 2311 | MAPK signaling pathway, Toll-like receptor signaling pathway | (2, 1), (2, 3) |
| 140 | 8.60E−06 | 5.22 | 4.5 | 5.59 | 1558014_s_at | FAR1 | fatty acyl CoA reductase 1 | 84188 | | (2, 1), (2, 3) |
| 141 | 8.60E−06 | 6.25 | 6.53 | 6.04 | 240247_at | | | | | (1, 2), (3, 2) |
| 142 | 8.80E−06 | 6.64 | 6.6 | 7.21 | 235177_at | METTL21A | methyltransferase like 21A | 151194 | | (1, 3), (2, 3) |
| 143 | 8.90E−06 | 6.46 | 7.47 | 6.7 | 1569540_at | | | | | (1, 2), (3, 2) |
| 144 | 8.90E−06 | 6.8 | 6.34 | 7.16 | 224642_at | FYTTD1 | forty-two-three domain containing 1 | 84248 | | (2, 1), (2, 3) |
| 145 | 8.90E−06 | 7.94 | 7.19 | 8.19 | 204427_s_at | TMED2 | transmembrane emp24 domain trafficking protein 2 | 10959 | | (2, 1), (2, 3) |
| 146 | 8.90E−06 | 9.75 | 9.99 | 9.23 | 233867_at | | | | | (3, 1), (3, 2) |
| 147 | 9.00E−06 | 10.08 | 10.61 | 10.12 | 212852_s_at | TROVE2 | TROVE domain family, member 2 | 6738 | | (1, 2), (3, 2) |
| 148 | 9.20E−06 | 7.39 | 7.76 | 7.12 | 215221_at | | | | | (1, 2), (3, 2) |
| 149 | 9.30E−06 | 9.17 | 9.71 | 9.05 | 231866_at | LNPEP | leucyl/cystinyl aminopeptidase | 4012 | | (1, 2), (3, 2) |
| 150 | 9.50E−06 | 5.34 | 5.61 | 5.22 | 217293_at | | | | | (1, 2), (3, 2) |
| 151 | 9.50E−06 | 7.2 | 6.59 | 7.35 | 224311_s_at | CAB39 | calcium binding protein 39 | 51719 | mTOR signaling pathway | (2, 1), (2, 3) |
| 152 | 9.60E−06 | 8.5 | 9 | 8.52 | 231716_at | RC3H2 | ring finger and CCCH-type domains 2 | 54542 | | (1, 2), (3, 2) |
| 153 | 9.70E−06 | 6.99 | 7.48 | 6.92 | 1565692_at | | | | | (1, 2), (3, 2) |
| 154 | 9.70E−06 | 8.45 | 8.64 | 7.76 | 232174_at | | | | | (3, 1), (3, 2) |
| 155 | 9.70E−06 | 6.72 | 7.22 | 6.23 | 243827_at | | | | | (3, 2) |
| 156 | 9.90E−06 | 5.13 | 6.2 | 5.51 | 217536_x_at | | | | | (1, 2), (3, 2) |
| 157 | 1.00E−05 | 9 | 8.88 | 9.33 | 206052_s_at | SLBP | stem-loop binding protein | 7884 | | (1, 3), (2, 3) |
| 158 | 1.00E−05 | 7.26 | 6.61 | 7.55 | 209131_s_at | SNAP23 | synaptosomal-associated protein, 23 kDa | 8773 | SNARE interactions in vesicular transport | (2, 1), (2, 3) |
| 159 | 1.00E−05 | 4.46 | 5.13 | 4.73 | 1568801_at | VWA9 | von Willebrand factor A domain containing 9 | 81556 | | (1, 2), (3, 2) |
| 160 | 1.00E−05 | 8.01 | 7.85 | 8.32 | 211061_s_at | MGAT2 | mannosyl (alpha-1,6-)-glycoprotein beta-1,2-N-acetylglucos-aminyltransferase | 4247 | Glycan structures-biosynthesis 1, N-Glycan biosynthesis | (1, 3), (2, 3) |
| 161 | 1.01E−05 | 8.55 | 8.23 | 8.9 | 223010_s_at | OCIAD1 | OCIA domain containing 1 | 54940 | | (2, 3) |
| 162 | 1.01E−05 | 6.75 | 7.5 | 7.6 | 207460_at | GZMM | granzyme M (lymphocyte met-ase 1) | 3004 | | (1, 2), (1, 3) |
| 163 | 1.02E−05 | 4.77 | 4.59 | 5.46 | 1553176_at | SH2D1B | SH2 domain containing 1B | 117157 | Natural killer cell mediated cytotoxicity | (1, 3), (2, 3) |
| 164 | 1.02E−05 | 6.36 | 6.24 | 6.62 | 211033_s_at | PEX7 | peroxisomal biogenesis factor 7 | 5191 | | (1, 3), (2, 3) |
| 165 | 1.04E−05 | 7.01 | 7.75 | 7.77 | 203547_at | CD4 | CD4 molecule | 920 | Activation of Csk by cAMP-dependent Protein Kinase | (1, 2), (1, 3) |

TABLE 1a-continued

The top 200 gene probeset used in the 3-Way AR, ADNR TX ANOVA Analysis (using the Hu133 Plus 2.0 cartridge arrays plates)

| | Parametric p-value | Geom mean of intensities in class 1 | Geom mean of intensities in class 2 | Geom mean of intensities in class 3 | ProbeSet | Symbol | Name | EntrezID | DefinedGenelist | Pairwise significant |
|---|---|---|---|---|---|---|---|---|---|---|
| | | | | | | | | | Inhibits Signaling through the T Cell Receptor, Antigen Dependent B Cell Activation, Bystander B Cell Activation, Cytokines and Inflammatory Response, HIV Induced T Cell Apoptosis, HIV-1 defeats host-mediated resistance by CEM15, IL 17 Signaling Pathway, IL 5 Signaling Pathway, Lck and Fyn tyrosine kinases in initiation of TCR Activation, NO2-dependent IL 12 Pathway in NK cells, Regulation of hematopoiesis by cytokines, Selective expression of chemokine receptors during T-cell polarization, T Helper Cell Surface Molecules, Antigen processing and presentation, Cell adhesion molecules (CAMs), Hematopoietic cell lineage, T cell receptor signaling pathway | |
| 166 | 1.04E−05 | 8.82 | 8.4 | 9.05 | 200776_s_at | BZW1 | basic leucine zipper and W2 domains 1 | 9689 | | (2, 1), (2, 3) |
| 167 | 1.07E−05 | 6.71 | 7.95 | 7.51 | 207735_at | RNF125 | ring finger protein 125, E3 ubiquitin protein ligase | 54941 | | (1, 2), (1, 3) |
| 168 | 1.08E−05 | 6.5 | 7.08 | 6.99 | 46947_at | GNL3L | guanine nucleotide binding protein-like 3 (nucleolar)-like | 54552 | | (1, 2), (1, 3) |
| 169 | 1.08E−05 | 7.92 | 8.54 | 8.12 | 240166_x_at | TRMT10B | tRNA methyltransferase 10 homolog B (*S. cerevisiae*) | 158234 | | (1, 2), (3, 2) |
| 170 | 1.13E−05 | 8.39 | 7.96 | 8.54 | 1555780_a_at | RHEB | Ras homolog enriched in brain | 6009 | mTOR Signaling Pathway, Insulin signaling pathway, mTOR signaling pathway | (2, 1), (2, 3) |
| 171 | 1.14E−05 | 8.37 | 8.82 | 8.56 | 214948_s_at | TMF1 | TATA element modulatory factor 1 | 7110 | | (1, 2), (3,2) |
| 172 | 1.15E−05 | 6.77 | 7.43 | 7.07 | 221191_at | STAG3L1 | stromal antigen 3-like 1 | 54441 | | (1, 2), (3, 2) |
| 173 | 1.16E−05 | 5.47 | 4.68 | 5.89 | 201295_s_at | WSB1 | WD repeat and SOCS box containing 1 | 26118 | | (2, 1), (2, 3) |

TABLE 1a-continued

The top 200 gene probeset used in the 3-Way AR, ADNR TX ANOVA Analysis (using the Hu133 Plus 2.0 cartridge arrays plates)

| | Parametric p-value | Geom mean of intensities in class 1 | Geom mean of intensities in class 2 | Geom mean of intensities in class 3 | ProbeSet | Symbol | Name | EntrezID | DefinedGenelist | Pairwise significant |
|---|---|---|---|---|---|---|---|---|---|---|
| 174 | 1.18E−05 | 7.31 | 6.73 | 7.62 | 211302_s_at | PDE4B | phosphodiesterase 4B, cAMP-specific | 5142 | Purine metabolism | (2, 1), (2, 3) |
| 175 | 1.19E−05 | 9.02 | 9.36 | 8.68 | 227576_at | | | | | (3, 2) |
| 176 | 1.23E−05 | 7.34 | 7.82 | 7.28 | 1553349_at | ARID2 | AT rich interactive domain 2 (ARID, RFX-like) | 196528 | | (1, 2), (3, 2) |
| 177 | 1.23E−05 | 8.56 | 9.02 | 8.26 | 242405_at | | | | | (1, 2), (3, 2) |
| 178 | 1.24E−05 | 5.32 | 6.33 | 5.71 | 238723_at | ATXN3 | ataxin 3 | 4287 | | (1, 2), (3, 2) |
| 179 | 1.25E−05 | 6.97 | 7.45 | 6.59 | 241508_at | | | | | (1, 2), (3, 2) |
| 180 | 1.27E−05 | 7.73 | 7.49 | 7.74 | 225374_at | | | | | (2, 1), (2, 3) |
| 181 | 1.29E−05 | 8.64 | 9.09 | 8.43 | 244414_at | | | | | (1, 2), (3, 2) |
| 182 | 1.29E−05 | 7.52 | 6.99 | 7.57 | 202213_s_at | CUL4B | cullin 4B | 8450 | | (2, 1), (2, 3) |
| 183 | 1.29E−05 | 5.63 | 5.52 | 5.19 | 243002_at | | | | | (3, 1), (3, 2) |
| 184 | 1.34E−05 | 4.51 | 5.32 | 4.8 | 210384_at | PRMT2 | protein arginine methyltransferase 2 | 3275 | Aminophosphonate metabolism, Androgen and estrogen metabolism, Histidine metabolism, Nitrobenzene degradation, Selenoamino acid metabolism, Tryptophan metabolism, Tyrosine metabolism | (1, 2), (3, 2) |
| 185 | 1.35E−05 | 4.65 | 4.25 | 4.81 | 1569952_x_at | | | | | (2, 1), (2, 3) |
| 186 | 1.36E−05 | 12.44 | 12.13 | 12.55 | 202902_s_at | CTSS | cathepsin S | 1520 | Antigen processing and presentation | (2, 1), (2, 3) |
| 187 | 1.37E−05 | 7.56 | 7.92 | 7.09 | 239561_at | | | | | (3, 2) |
| 188 | 1.37E−05 | 6.8 | 7.38 | 7.18 | 218555_at | ANAPC2 | anaphase promoting complex subunit 2 | 29882 | Cell cycle, Ubiquitin mediated proteolysis | (1, 2), (1, 3) |
| 189 | 1.38E−05 | 8.03 | 7.89 | 8.57 | 200946_x_at | GLUD1 | glutamate dehydrogenase 1 | 2746 | Arginine and proline metabolism, D-Glutamine and D-glutamate metabolism, Glutamate metabolism, Nitrogen metabolism, Urea cycle and metabolism of amino groups | (1, 3), (2, 3) |
| 190 | 1.39E−05 | 5.15 | 4.77 | 5.96 | 221268_s_at | SGPP1 | sphingosine-1-phosphate phosphatase 1 | 81537 | Sphingolipid metabolism | (1, 3), (2, 3) |
| 191 | 1.40E−05 | 5.36 | 6.5 | 5.8 | 216166_at | | | | | (1, 2), (3, 2) |
| 192 | 1.41E−05 | 7.07 | 7.64 | 7.09 | 1553909_x_at | FAM178A | family with sequence similarity 178, member A | 55719 | | (1, 2), (3, 2) |
| 193 | 1.42E−05 | 7.23 | 6.95 | 7.5 | 1554747_a_at | 2-Sep | septin 2 | 4735 | | (2, 3) |
| 194 | 1.45E−05 | 6.04 | 6.69 | 6.38 | 242751_at | | | | | (1, 2) |
| 195 | 1.46E−05 | 7.74 | 8.22 | 7.79 | 239363_at | | | | | (1, 2), (3, 2) |
| 196 | 1.47E−05 | 5.57 | 5.19 | 5.76 | 222645_s_at | KCTD5 | potassium channel tetramerisation domain containing 5 | 54442 | | (2, 1), (2, 3) |

TABLE 1a-continued

The top 200 gene probeset used in the 3-Way AR, ADNR TX ANOVA Analysis (using the Hu133 Plus 2.0 cartridge arrays plates)

| | Parametric p-value | Geom mean of intensities in class 1 | Geom mean of intensities in class 2 | Geom mean of intensities in class 3 | ProbeSet | Symbol | Name | EntrezID | DefinedGenelist | Pairwise significant |
|---|---|---|---|---|---|---|---|---|---|---|
| 197 | 1.53E−05 | 3.93 | 3.73 | 4.26 | 210875_s_at | ZEB1 | zinc finger E-box binding homeobox 1 | 6935 | SUMOylation as a mechanism to modulate CtBP-dependent gene responses | (1, 3), (2, 3) |
| 198 | 1.55E−05 | 8.42 | 8 | 8.63 | 1567458_s_at | RAC1 | ras-related C3 botulinum toxin substrate 1 (rho family, small GTP binding protein Rac1) | 5879 | Agrin in Postsynaptic Differentiation, Angiotensin II mediated activation of JNK Pathway via Pyk2 dependent signaling, BCR Signaling Pathway, fMLP induced chemokine gene expression in HMC-1 cells, How does *salmonella* hijack a cell, Influence of Ras and Rho proteins on G1 to S Transition, Links between Pyk2 and Map Kinases, MAPKinase Signaling Pathway, p38 MAPK Signaling Pathway, Phosphoinositides and their downstream targets., Phospholipids as signalling intermediaries, Rac 1 cell motility signaling pathway, Ras Signaling Pathway, Ras-Independent pathway in NK cell-mediated cytotoxicity, Role of MAL in Rho-Mediated Activation of SRF, Role of PI3K subunit p85 in regulation of Actin Organization and Cell Migration, T Cell Receptor Signaling Pathway, Transcription factor CREB and its extracellular signals, Tumor Suppressor Arf Inhibits Ribosomal Biogenesis, uCalpain and friends in Cell spread, Y branching of actin filaments, Adherens junction, Axon guidance, B cell receptor signaling pat . . . | (2, 1), (2, 3) |
| 199 | 1.56E−05 | 9 | 9.37 | 8.89 | 233893_s_at | UVSSA | UV-stimulated scaffold protein A | 57654 | | (1, 2), (3, 2) |
| 200 | 1.59E−05 | 5.95 | 6.42 | 6.55 | 226539_s_at | | | | | (1, 2), (1, 3) |

TABLE 1b

The 2977 gene probeset used in the 3-Way AR, ADNR TX ANOVA
Analysis (using the Hu133 Plus 2.0 cartridge arrays plates)

| | | | | | |
|---|---|---|---|---|---|
| SMARCB1 | 233900_at | RNPC3 | FLJ44342 | 1563715_at | 244088_at |
| ATP6AP2 | KCNC4 | COQ9 | CNIH | ZBTB20 | OXTR |
| PLEKHA3 | GLRX3 | HSPD1 | HMGXB4 | BLOC1S3 | 220687_at |
| TP53 | BCL2L11 | NFYA | GJC2 | GMCL1 | TLE4 |
| PRKAG2 | HNRPDL | TNRC18 | 236370_at | SRSF3 | 1556655_s_at |
| ND2 | XRN2 | 238745_at | SH2B3 | 227730_at | TMEM161B |
| YWHAE | EXOC3 | 215595_x_at | 232834_at | CLIP1 | FTSJD1 |
| 243037_at | RNGTT | 228799_at | OTUB2 | 236742_at | AAGAB |
| SSR1 | ENY2 | 1555485_s_at | LINC00028 | MAT2B | 1570335_at |
| CCDC91 | KLHL36 | SEMA7A | INTS1 | 217185_s_at | CIZ1 |
| PRKAG2 | UBR4 | ZNF160 | DIS3 | MTUS2 | ZNF45 |
| ADPGK | RALB | G6PD | ATP2A3 | MOB3B | 215650_at |
| CHFR | UBE2D3 | 1556205_at | LOC100128822 | 1558922_at | UBTF |
| 236766_at | DR1 | DSTN | PRKAR2A | 233376_at | ZNF555 |
| 242068_at | CLEC7A | HSF1 | 214027_x_at | SLC16A7 | MED28 |
| PRNP | SDHD | NPHP4 | TCF4 | 241106_at | SIGLEC10 |
| 1558220_at | 1565701_at | 242126_at | CCDC115 | IRAK3 | TM6SF2 |
| CDYL | 216813_at | SRSF11 | 244677_at | 242362_at | PACSIN2 |
| SPTLC1 | C2orf72 | 231576_at | SRP72 | ADAMTS16 | DLX3 |
| 232726_at | 236109_at | RBM4 | 221770_at | KIAA1715 | PKM |
| CHMP1B | 240262_at | FAM175B | 1556003_a_at | 202648_at | SUMO3 |
| KBTBD2 | 1563364_at | ZNF592 | 1559691_at | PTPRO | GATM |
| MST4 | 235263_at | RAPGEF2 | KANK2 | ADAM12 | NECAP1 |
| 239597_at | PRR12 | MALAT1 | PEX7 | XBP1 | LPPR3 |
| 239987_at | CBFB | 216621_at | PTGS2 | 222180_at | CAMK2D |
| 243667_at | JAK1 | KIAA1683 | RDH11 | MGAT2 | CRH |
| CDC42EP3 | 240527_at | 1559391_s_at | PHF7 | CUBN | 243310_at |
| UBXN4 | 6-Sep | DR1 | 236446_at | ZNF626 | DYNC1H1 |
| PGGT1B | ITGB1 | ARF4 | 242027_at | CD84 | C17orf80 |
| 238883_at | 1562948_at | RAB39B | 1565877_at | LRRC8C | 233931_at |
| CCR2 | YRDC | GPR27 | ACBD3 | AMBP | C20orf78 |
| 242143_at | 1566001_at | HPS3 | SNAI3-AS1 | C3orf38 | MED13L |
| ZNF426 | SETD5 | 215900_at | 215630_at | ATG4C | 226587_at |
| SP1 | RNGTT | 220458_at | POLR1B | 217701_x_at | 226543_at |
| MED18 | 240789_at | ARFGAP3 | PON2 | LOC100996246 | LPP |
| 233004_x_at | 239227_at | 1566428_at | MED27 | 244473_at | LOC100131043 |
| 242797_x_at | 236802_at | EID2B | LOC100289058 | FOLR1 | AGA |
| 2-Sep | TM2D1 | 1559347_at | 1565976_at | 231682_at | STX11 |
| CCNG2 | TBX4 | ARPP19 | YEATS4 | NRP2 | 215586_at |
| OGFOD1 | 232528_at | IFRD1 | VIPR2 | PTPRD | 244177_at |
| 240232_at | TSEN15 | 1564227_at | 233761_at | RBBP6 | 240892_at |
| MED18 | MAP3K8 | 1561058_at | SLC25A16 | SMARCD2 | GPBP1L1 |
| ZKSCAN1 | TMEM206 | SFT2D3 | OSTC | CLEC4A | 242872_at |
| SLC39A6 | 239600_at | LOC646482 | ATP11B | RBM3 | 240550_at |
| FLI1 | TMOD3 | TMEM43 | C1orf43 | POLE3 | KIAA0754 |
| LUC7L2 | GLS | CSNK1A1 | CASK | MAPK9 | 213704_at |
| CD46 | RPS10 | 233816_at | PAXBP1 | ACTR10 | GABPA |
| 242737_at | TSN | C3orf17 | ADSSL1 | 1557551_at | 240347_at |
| CASKIN1 | C7orf53 | 239901_at | C11orf58 | ZNF439 | G3BP1 |
| UGP2 | MTMR1 | ABCC6 | 1569312_at | RTFDC1 | PIK3AP1 |
| ARNTL | TNPO1 | 7-Mar | STRN | ND6 | KRIT1 |
| 232307_at | 232882_at | NRIP2 | 243634_at | LIN7C | CGNL1 |
| PLEKHF2 | SSR1 | 1569930_at | 240392_at | CNOT7 | C11orf30 |
| 234435_at | 233223_at | DLAT | SDK2 | 237846_at | 1562059_at |
| ZNF117 | VNN3 | USP14 | WNK1 | GAPVD1 | SPG20 |
| ITGB1 | ARFGEF1 | UACA | AKAP10 | CDAN1 | 1561749_at |
| MAP3K1 | 244100_at | PGK1 | UNK | TECR | C16orf87 |
| FBXW7 | TMEM245 | CHRNB2 | GUCA1B | LINC00476 | 232234_at |
| 208310_s_at | CDC42EP3 | SUMF2 | PTPRH | 229448_at | MEGF9 |
| SRGAP2B | 244433_at | NEDD1 | 216756_at | ZBTB43 | RAD18 |
| 238812_at | MYCBP2 | MFN1 | 1557993_at | 230659_at | ZCCHC3 |
| ZNF136 | ATF5 | PIGY | MAEA | 1560199_x_at | TOR2A |
| ARPC5 | RBBP4 | 1564248_at | 215628_x_at | BET1L | SMIM14 |
| FBXL18 | 232929_at | APH1A | SPSB1 | PAFAH1B1 | SLMO2 |
| TMED2 | PCGF1 | DCTN1 | APC | 243350_at | NAA15 |
| 234125_at | 239567_at | KLHL42 | TIMM50 | TAF1B | ZNF80 |
| YWHAZ | 233799_at | OGFRL1 | 240080_at | MRPL42 | GKAP1 |
| SNAP23 | FBXO9 | FBXL14 | SLC38A9 | 232867_at | FBXO8 |
| 238558_at | SS18 | 240013_at | MON1A | ASIC4 | 233027_at |
| 221071_at | ARMC10 | SREK1IP1 | 239809_at | WNT7B | 237051_at |
| TMEM30A | 232700_at | CDH16 | 243088_at | ZNF652 | YJEFN3 |
| 1569477_at | UNKL | 234278_at | 233940_at | GMEB1 | 213048_s_at |
| CD46 | 1561389_at | LIX1L | KIAA1468 | BCAS4 | PPP1R12A |
| INSIG1 | SLC35B3 | NBR2 | 1563320_at | GFM1 | TCEB3 |
| 215866_at | 235912_at | SEC31A | APOL2 | IGHMBP2 | 201380_at |
| MED13 | 234759_at | MLX | FLJ12334 | BEX4 | LOC283788 |
| SRSF2 | SLC15A4 | ATP6V1H | FANCF | SNX24 | RNA45S5 |

TABLE 1b-continued

The 2977 gene probeset used in the 3-Way AR, ADNR TX ANOVA Analysis (using the Hu133 Plus 2.0 cartridge arrays plates)

| | | | | | |
|---|---|---|---|---|---|
| API5 | TMEM70 | USP36 | 242403_at | AKIRIN1 | RBBP4 |
| SUZ12P1 | RANBP9 | C2orf68 | ERLIN2 | ZNF264 | SNTB2 |
| 244535_at | NMD3 | LOC149373 | 241965_at | LYSMD2 | 234046_at |
| FLI1 | LARP1 | TMEM38B | SLC30A5 | RUFY2 | 231346_s_at |
| SLC35E1 | 240765_at | TNPO1 | 238024_at | 239925_at | AGFG2 |
| 241681_at | SCFD1 | RSU1 | 1562283_at | SPSB4 | NONO |
| PAPOLA | RAB28 | FXR1 | 216902_s_at | ZNF879 | THEMIS |
| MLLT10 | 242144_at | TET3 | SMAP1 | XIAP | NDUFS1 |
| SLC35B4 | PAFAH2 | MGC57346 | C6orf89 | SNX19 | RAB18 |
| 1564424_at | ZNF43 | 231107_at | FBXO33 | RER1 | NAP1L1 |
| 243030_at | CYP4V2 | PHF20 | ANKRD10 | 1566472_s_at | 235701_at |
| 215207_x_at | MREG | 1560332_at | INSIG1 | QSOX2 | 1557353_at |
| 235058_at | BECN1 | PAIP2 | 239106_at | DDR2 | HOPX |
| ARL2BP | LOXL2 | 235805_at | KIAA1161 | 1566491_at | CCT6A |
| CNOT8 | TPD52 | KRBA2 | 1563590_at | PRNP | VGLL4 |
| SYPL1 | API5 | BCKDHB | LOC100129175 | HNMT | EXOSC6 |
| 236168_at | 222282_at | VAV3 | DLGAP4 | GGA1 | TM2D3 |
| BRWD3 | HHEX | MC1R | ARID5A | AQR | BAZ2A |
| RBBP4 | 237048_at | HMGCR | SMAD6 | KIF3B | HIF1AN |
| 215390_at | 1562853_x_at | MBD4 | ZNF45 | SMO | MBD4 |
| 1566966_at | CCNL1 | PPP2R2A | SLC38A10 | 241303_x_at | DET1 |
| GLCCI1 | TIGD1 | 242480_at | GFM1 | MTPAP | 227383_at |
| MBP | 241391_at | INTS9 | 221579_s_at | 230998_at | 239005_at |
| RAB8B | DDX3X | ABHD6 | CCIN | 241159_x_at | PIGF |
| YTHDF3 | FTX | CEP350 | ASAP1-IT1 | TGDS | SREBF2 |
| TOR1AIP1 | HIBADH | RHEB | FAM126B | CRLS1 | TLE4 |
| ATF1 | PXK | 1559598_at | 232906_at | REXO1 | PLCB1 |
| TMEM230 | 231644_at | ING4 | RALGAPA2 | 1557699_x_at | DNAAF2 |
| LRCH3 | FPR2 | RHNO1 | SPCS1 | FAM208B | PALLD |
| ARID2 | CPSF2 | 1552867_at | MAGT1 | ZNF721 | USP28 |
| 244766_at | G2E3 | 212117_at | TMEM19 | PRDM11 | 217572_at |
| 242673_at | 237600_at | TLR8 | ZNF24 | 243869_at | C1orf86 |
| CNOT8 | 244357_at | 231324_at | NAIP | G2E3 | DAAM2 |
| ZBTB20 | 215577_at | DDA1 | 232134_at | 233270_x_at | GNB3 |
| 240594_at | CLEC7A | 243207_at | B2M | DMPK | RNF145 |
| PSMD10 | GAREML | 9-Sep | NPR3 | NLK | RANBP9 |
| 215137_at | 1566965_at | SRP72 | ATP6AP2 | TRIM28 | 1557543_at |
| 243527_at | TLK1 | 233832_at | 1563104_at | 238785_at | ZNF250 |
| RHOQ | 231281_at | GABBR1 | ERCC3 | 243691_at | PPP1R15B |
| ATF7IP | EXOC5 | TRIM50 | STEAP4 | LOC283482 | FLI1 |
| LOC100131541 | GHITM | KIAA1704 | 232937_at | LOC285300 | SMURF1 |
| STYX | ZCCHC9 | LRRFIP2 | 238892_at | 242310_at | EAF1 |
| 244010_at | ZNF330 | LIG4 | NDUFS4 | 239449_at | SUMO2 |
| 232002_at | TMEM230 | HECA | ERLEC1 | SOCS5 | MED21 |
| CNIH4 | ZNF207 | 243561_at | UBL3 | 233121_at | PIGR |
| EMC1 | LOC440993 | 215961_at | BBS12 | NUMBL | 240154_at |
| MACF1 | PAPOLA | BRAP | 242637_at | PCNP | UPF1 |
| NOP14-AS1 | CXorf36 | SURF4 | 231125_at | PRG3 | 217703_x_at |
| 1564438_at | AKAP13 | PANK2 | SMCHD1 | SRSF2 | SKAP2 |
| 229858_at | ASXL2 | 236338_at | PDE3B | MOAP1 | ARL6IP5 |
| HHEX | RAB14 | FNBP1 | TRPM7 | SPG11 | STIM2 |
| 239234_at | DIP2A | G2E3 | RPL18 | ZFP41 | WBP11 |
| 238619_at | 243391_x_at | FLT3LG | PTOV1 | CARD11 | ADAM10 |
| DHX36 | PBXIP1 | 233800_at | HAVCR2 | MFSD8 | PHF20L1 |
| DAPP1 | MFN1 | SMIM7 | 242890_at | EEF1D | CR1 |
| WTAP | DENND4C | ADRA2B | BFAR | NAPEPLD | STEAP4 |
| PSEN1 | SLC25A40 | PTPN23 | ARHGAP21 | GM2A | MAML2 |
| 239112_at | 242490_at | SNX2 | SRPK2 | EBAG9 | 236450_at |
| MAP3K7 | LMBR1 | P2RY10 | PRKCA | 242749_at | RTN4IP1 |
| PPP2R5E | CDK6 | ABHD15 | TRAPPC2L | PRKCA | 221454_at |
| FAM108B1 | TMEM19 | 1565804_at | LRRFIP1 | SUV39H1 | RMDN2 |
| TAB2 | 237310_at | 236966_at | CCDC6 | LOC100507281 | UFM1 |
| FAR1 | PIK3C3 | SRPK2 | 232344_at | PLXDC1 | 228911_at |
| 240247_at | ABI1 | 242865_at | TRAK1 | ZP1 | BEST1 |
| METTL21A | CHD8 | AGMAT | SRGN | HR | 239086_at |
| 1569540_at | SLC30A5 | GPHN | PAPOLA | RYBP | 216380_x_at |
| FYTTD1 | 216056_at | ZNF75D | ATXN7L1 | POPDC2 | KCTD5 |
| TMED2 | MAPKAPK5 | SON | TBATA | SNX2 | SFTPC |
| 233867_at | CSNK1A1 | AP1AR | TTC17 | BMP7 | KLF7 |
| TROVE2 | 243149_at | TXNDC12 | ELP6 | 226532_at | ERBB2IP |
| 215221_at | 1560349_at | 1569527_at | CACHD1 | MAN2A2 | 232622_at |
| LNPEP | SERBP1 | 237377_at | ELOVL5 | LOC100129726 | 234882_at |
| 217293_at | MDM4 | NPTN | 1563173_at | PDE1B | 225494_at |
| CAB39 | 217702_at | 239431_at | CHRNA6 | SCRN3 | OSGIN1 |
| RC3H2 | RPAP3 | 242132_x_at | SLC9A5 | FAM3C | SLC26A6 |
| 1565692_at | NR3C1 | AP1S2 | UBE4B | GPHA2 | MALT1 |
| 232174_at | SMAD4 | TMEM38B | 233674_at | USP38 | 216593_s_at |

TABLE 1b-continued

The 2977 gene probeset used in the 3-Way AR, ADNR TX ANOVA
Analysis (using the Hu133 Plus 2.0 cartridge arrays plates)

| | | | | | |
|---|---|---|---|---|---|
| 243827_at | FBXO11 | CDC42SE1 | CHRNE | IDH3A | 237176_at |
| 217536_x_at | SNAPC3 | TLR4 | TIMM23 | FGFR1OP2 | 1570087_at |
| SLBP | SVIL | C14orf169 | FCGR2C | DST | ENTPD2 |
| SNAP23 | TSPAN14 | BTF3L4 | 232583_at | NSMF | 232744_x_at |
| VWA9 | SERBP1 | AUH | KIAA2026 | 241786_at | NUDT6 |
| MGAT2 | 238544_at | RDX | 242551_at | WHSC1L1 | AGPAT1 |
| OCIAD1 | LRRFIP2 | 224175_s_at | MALAT1 | 234033_at | 242926_at |
| GZMM | SNAP29 | 240813_at | 229434_at | 244086_at | CLASP2 |
| SH2D1B | 215648_at | FGL1 | YWHAE | C14orf142 | 239241_at |
| PEX7 | PPTC7 | 235028_at | COPS8 | ME2 | MIR143HG |
| CD4 | 241932_at | SENP7 | 215599_at | NFYB | 232472_at |
| BZW1 | CNBP | 215386_at | KDM2A | AIF1L | FCAR |
| RNF125 | 239463_at | MGC34796 | TFAP2D | MALT1 | XPNPEP3 |
| GNL3L | POGZ | ME2 | PKHD1 | 226250_at | ACAD8 |
| TRMT10B | 215083_at | PPP6R1 | OGFOD1 | 233099_at | PARP15 |
| RHEB | TMEM64 | 211180_x_at | GPATCH2L | 237655_at | TMEM128 |
| TMF1 | ERP44 | GFM1 | DSTN | ZBED3 | PTPN7 |
| STAG3L1 | LOC100272216 | CEP120 | ZSCAN9 | BAZ1B | 215474_at |
| WSB1 | 1562062_at | MAN1A2 | MFSD11 | CDC42SE2 | 215908_at |
| PDE4B | 1559154_at | STX3 | SERPINI1 | ISG20 | AASDHPPT |
| 227576_at | CDC40 | 243469_at | XRCC3 | KLHDC8A | NCBP1 |
| ARID2 | PIGM | NDUFS1 | ADNP | DLAT | 233272_at |
| 242405_at | 238000_at | CAAP1 | LOC100506651 | DIABLO | 240870_at |
| ATXN3 | RAP2B | CHD4 | 242532_at | PDXDC1 | LPIN1 |
| 241508_at | 236685_at | ZNF644 | CD200R1 | PTGDR | AFG3L1P |
| 225374_at | GLIPR1 | FLJ13197 | ZMYND11 | 231992_x_at | CNEP1R1 |
| 244414_at | OGT | HSPA14 | PACRGL | 221381_s_at | PMS2P5 |
| CUL4B | CREB1 | CNNM2 | RNFT1 | ZNF277 | C14orf1 |
| 243002_at | YAF2 | SENP2 | CD58 | RBM47 | THOP1 |
| PRMT2 | 215385_at | KLF4 | USP42 | SYN1 | CLASP2 |
| 1569952_x_at | PPM1K | 1558410_s_at | 216745_x_at | SCP2 | 241477_at |
| CTSS | 1562324_a_at | 241837_at | 235493_at | 234159_at | 233733_at |
| 239561_at | SH2D1B | LOC100130654 | CLASP1 | FLJ10038 | SNX19 |
| ANAPC2 | GNAI3 | SNTB2 | HACL1 | FAM84B | ZNF554 |
| GLUD1 | AKAP11 | 233417_at | ANAPC7 | BRAP | G2E3 |
| SGPP1 | 1569578_at | 236149_at | LOC286437 | FOXJ1 | SLC30A1 |
| 216166_at | ATF7 | 237404_at | RPS12 | 244845_at | ATF7IP |
| FAM178A | 234260_at | DHRS4-AS1 | PALLD | 244550_at | 228746_s_at |
| 2-Sep | KLHDC10 | KHSRP | MTO1 | 244422_at | 232779_at |
| 242751_at | RFWD3 | SLC25A43 | 241114_s_at | RAB30 | 227052_at |
| 239363_at | STX16 | MESP1 | UBXN7 | TTLL5 | 240405_at |
| KCTD5 | CTBP2 | PSMD12 | 215376_at | NUCKS1 | ZNF408 |
| ZEB1 | FOXN3 | HMP19 | 241843_at | PRMT8 | PIP5K1A |
| RAC1 | 239861_at | 240020_at | TSR1 | 239659_at | CCPG1 |
| UVSSA | LOC100505876 | LRRFIP1 | CD164 | CENPL | ASCC1 |
| 226539_s_at | MLLT10 | TNPO1 | MRPS10 | THADA | LINC00527 |
| MS4A6A | 243874_at | GALNT7 | MACF1 | MRPS11 | UBQLN4 |
| CNOT4 | MDM4 | VPS37A | 213833_x_at | DBH | MAST4 |
| 1559491_at | TAOK1 | PPP2CA | 244665_at | LRRFIP1 | RAP1GAP |
| NOP16 | PIK3R5 | TFEC | HPN | 239445_at | SRSF4 |
| HIRIP3 | LINC00094 | ENTPD6 | PAK2 | 234753_x_at | LOC149401 |
| PTPN11 | 242369_x_at | M6PR | MOB1A | TSHZ2 | 11-Sep |
| GFM2 | 242357_x_at | TAF9B | MTMR9LP | GTSE1 | NIT1 |
| SMCR8 | 243035_at | 1564077_at | IGLJ3 | 243674_at | PTGS2 |
| ZNF688 | TMEM50B | PMAIP1 | ADNP2 | 237201_at | ACTG1 |
| KIAA0485 | XAGE3 | 234596_at | PLA2G4F | HSP90AB1 | ARHGEF1 |
| ABHD10 | FAS | 1558748_at | NRBF2 | 216285_at | TRIM8 |
| LOC729013 | FBXO9 | TMEM41A | SYTL3 | ACTR3 | TTC27 |
| 233440_at | 239655_at | MIER3 | C1orf174 | KRCC1 | GABPA |
| 224173_s_at | VAMP3 | UBAP2L | C16orf72 | RHOA | 243736_at |
| TAOK1 | 230918_at | NXT2 | ZNF836 | TRMT2B | TLR2 |
| SLC39A6 | ZNF615 | PRRT3 | KCNK3 | ADK | VPS35 |
| NAMPT | DLST | BRD3 | UBXN8 | PNRC1 | MED28 |
| CNBP | 231042_s_at | 243414_at | TIA1 | 216607_s_at | 242542_at |
| MBP | TNPO3 | MTMR2 | NCOA2 | GRM2 | 241893_at |
| PRKAR2A | CS | 243178_at | CEP135 | EIF3L | ZNF92 |
| GNL3L | CLTC-IT1 | TCF3 | BCL7B | 236704_at | GPC2 |
| YWHAZ | MEF2C | SFTPB | HELB | MYO9B | TSPAN16 |
| PPP6R2 | PACSIN3 | UBE2N | LOC642236 | NGFRAP1 | LOC100507602 |
| RSPRY1 | TROVE2 | 238836_at | PAK2 | PSPC1 | 1561155_at |
| MBNL1 | PPIF | RPRD1A | FPR2 | 239560_at | 218458_at |
| DENR | RBM15B | RDH11 | ITGA4 | ERCC8 | ZNF548 |
| DNAJB9 | 242793_at | WWP2 | MSI2 | VPS13D | ADAM17 |
| 216766_at | ARHGAP32 | CLYBL | SMPD1 | MTM1 | 1561067_at |
| CLINT1 | SHOX2 | 230240_at | TMEM92 | ANKRD13D | 207186_s_at |
| FBXO9 | 208811_s_at | VNN3 | ARHGAP26 | AKAP17A | MED29 |
| ATXN1 | 217055_x_at | PECR | ZBTB1 | LOC100506748 | DTD2 |

TABLE 1b-continued

The 2977 gene probeset used in the 3-Way AR, ADNR TX ANOVA Analysis (using the Hu133 Plus 2.0 cartridge arrays plates)

| | | | | | |
|---|---|---|---|---|---|
| 1570021_at | LMNA | HLA-DPA1 | GALNT9 | RCN2 | 242695_at |
| ARFGEF1 | PSEN1 | TPCN2 | CTNNB1 | NTN5 | 238040_at |
| 232333_at | CLCN7 | LARS | 227608_at | OAT | EIF1B-AS1 |
| GOSR1 | C15orf37 | ZDHHC8 | TMEM106C | ZNF562 | 1561181_at |
| FAM73A | TUG1 | BCL6 | PSD4 | 1560049_at | SERTAD2 |
| 244358_at | WDYHV1 | IMPACT | DYNLRB1 | 215861_at | 1561733_at |
| SPPL3 | SELT | 1558236_at | 237868_x_at | A2M | FGFR1 |
| ARFIP1 | BBIP1 | 235295_at | PADI2 | CADM3 | PSMD10 |
| SF3B3 | TMCO3 | APOBEC2 | RALGPS1 | CAMK2D | CCND3 |
| TMEM185A | FBXO22 | PIK3CG | ZNF790-AS1 | TRIM4 | DPYSL4 |
| LARP1 | PICALM | ZNF706 | 214194_at | CRYZL1 | ANGPTL4 |
| SETX | KLHL7 | 239396_at | FTCD | IL1R2 | CAPS |
| POLR3A | 233431_x_at | GATAD2B | 1570299_at | WNT10A | 238159_at |
| RSBN1 | TNPO3 | ZDHHC21 | WDR20 | SEH1L | 225239_at |
| SNX13 | SMAD4 | MED4 | 208638_at | 216789_at | STOX2 |
| ZNF542 | FAS | PRKACB | 9-Sep | JAK3 | 207759_s_at |
| 228623_at | RPL27A | HERPUD1 | KLHL20 | TFDP2 | LOC100996349 |
| 242688_at | 222295_x_at | PPFIA3 | SOS1 | C4orf29 | ZNF805 |
| 237881_at | GHITM | 222358_x_at | PTPN22 | TACC2 | LOC100131825 |
| 239414_at | IER5 | TUBGCP4 | CYB5R4 | FBXO33 | ZFP36L2 |
| RASSF5 | HSPD1 | 210338_s_at | 232601_at | GOPC | KIF1B |
| 222319_at | UEVLD | RABL5 | IMPAD1 | C1QBP | ZNF117 |
| PPP1R3B | LPXN | 242859_at | LOC100128751 | NXPH3 | SLC35D2 |
| TAOK1 | DENND2A | 1554948_at | CXCR4 | PLAUR | 235441_at |
| MAP2K4 | SPRTN | ZNF551 | PODNL1 | ZNF175 | 214996_at |
| NMT2 | SF3A2 | GPSM3 | ZNF567 | POLR2L | LOC100506127 |
| STX16 | DICER1 | 1556339_a_at | 242839_at | ZAN | BTBD7 |
| PDE7A | ANKRD17 | 236545_at | MAPRE2 | 239296_at | PNRC2 |
| RALGAPA2 | GOLGA7 | MKRN2 | PGM2 | TBX2 | 232991_at |
| MED1 | UBE2J1 | AGAP2 | PHF20L1 | TUBB | PRKCSH |
| PICALM | 215212_at | CCNK | TTF1 | 244847_at | PRM3 |
| BTG2 | 236944_at | 233103_at | ETV4 | MEA1 | GNAI3 |
| KIAA2018 | CREB1 | 239408_at | FAM159A | MLL | 243839_s_at |
| 230590_at | 232835_at | NXPE3 | EIF4E | SECISBP2L | PHTF2 |
| AP5M1 | LOC100631377 | 222306_at | 232535_at | MCRS1 | TSPYL5 |
| 217615_at | ZNF880 | ANGPTL1 | UBA1 | 219422_at | DCAF17 |
| 238519_at | TMEM63A | RYK | ZNF493 | USP7 | IDS |
| TBL1XR1 | AKAP7 | SCARB2 | 224105_x_at | TRDMT1 | 242413_at |
| MAT2A | LMBRD1 | 1557224_at | GPR137 | EFS | 213601_at |
| CDC42SE2 | 235138_at | DCUN1D4 | ZKSCAN5 | RAB30 | INSIG2 |
| 228105_at | POLK | STX7 | PRKAR2A | 1562468_at | AP1G2 |
| CHAMP1 | TBCC | CCT2 | SATB1 | 236592_at | SLC5A9 |
| ASAH1 | AK2 | 233107_at | ZNF346 | MNX1 | 215462_at |
| TAF8 | 216094_at | ZNF765 | ZFP90 | 236908_at | 240046_at |
| PAPOLG | TRAPPC11 | 239933_x_at | SPG11 | E2F5 | PTPLAD1 |
| 240500_at | CSNK1A1 | LOC283867 | ALPK1 | TRO | 1559117_at |
| 200041_s_at | PPP1R17 | TNKS2 | GOLGA2 | MAN2A1 | WARS2 |
| 233727_at | 244383_at | ZNF70 | PRRC2A | TPM2 | SMAD4 |
| DPP8 | CNOT2 | 239646_at | 216704_at | SH3BGRL | ZNF500 |
| MAP3K7 | 1569041_at | NUFIP1 | SMARCA2 | FAM81A | KCTD12 |
| SBNO1 | MBIP | FOXK2 | 233626_at | MAST4 | SRSF10 |
| VPS13D | 1555392_at | PRPF18 | 236404_at | FARSB | SAT1 |
| 1556657_at | RBM25 | DARS | LOC100507918 | HEATR3 | 1569538_at |
| TMEM170A | PRDX3 | TLK2 | NAP1L1 | 200653_s_at | REV1 |
| ZFAND5 | C1orf170 | 244219_at | FOPNL | SLC23A3 | 1558877_at |
| UBE2G1 | FOXP1-IT1 | LOC145474 | LINC00526 | LIN52 | 212929_s_at |
| 233664_at | ERO1L | 235422_at | ZMYND8 | PDIA6 | GRAMD4 |
| 1565743_at | TMCO1 | 244341_at | 240118_at | 242616_at | CNST |
| RAB5A | SORL1 | HERC4 | 242380_at | ZNF419 | NPY5R |
| 243524_at | BRI3BP | MAST4 | 1565975_at | SETDB2 | STK38 |
| ATG5 | PAFAH1B2 | TMED10 | MAP1A | XYLT2 | ZFAND1 |
| DSERG1 | TRIM32 | TRIM2 | TMEM50B | PDXDC1 | 240216_at |
| ZNF440 | 1567101_at | 236114_at | RABGAP1 | 1561128_at | P2RX6 |
| IL18BP | PDK4 | BAZ2A | GFM1 | 244035_at | 239876_at |
| F2RL1 | GOLGB1 | FAM206A | GLOD4 | GRIK2 | UBE2D2 |
| CRLS1 | PRRC2A | ZC2HC1A | NAPB | HNMT | UBE2W |
| 238277_at | ATM | 239923_at | HYMAI | SP6 | PLEKHB1 |
| COL7A1 | 209084_s_at | SWAP70 | PRKAB1 | 220719_at | 232400_at |
| MAP3K2 | 240252_at | 222197_s_at | 1559362_at | 244156_at | GJB1 |
| TMX1 | 1557520_a_at | LRBA | EXOC5 | 227777_at | UBA6 |
| MCFD2 | 216729_at | 203742_s_at | C12orf43 | PEX3 | FCF1 |
| SLMAP | ZCWPW1 | 235071_at | HAX1 | HDAC2 | 240241_at |
| CNOT1 | PRDX3 | 240520_at | CRISPLD2 | 229679_at | 242343_x_at |
| 242407_at | CWC25 | NDNL2 | TNPO1 | RCOR2 | ULK4 |
| CDC5L | KIF5B | RPS23 | ARF6 | EIF3M | GATC |
| DCTN4 | ETV5 | 235053_at | 239661_at | SNRPA1 | BET1 |
| TM6SF1 | 232264_at | ZNF565 | 1562600_at | RBM8A | HIPK2 |

TABLE 1b-continued

The 2977 gene probeset used in the 3-Way AR, ADNR TX ANOVA
Analysis (using the Hu133 Plus 2.0 cartridge arrays plates)

| | | | | | |
|---|---|---|---|---|---|
| ZFP3 | ARL8B | CCDC126 | MAF | EMX1 | GNB4 |
| SRSF1 | 1562033_at | VEZF1 | ETNK1 | USP46 | ERO1L |
| GDI2 | NIN | COPS8 | PSMD11 | KCNE3 | 220728_at |
| TERF2 | 1558093_s_at | NSUN4 | CNOT11 | EDC3 | MYOD1 |
| ATM | 236060_at | LOC283887 | MEGF9 | ALG13 | 1561318_at |
| 1558425_x_at | 243895_x_at | FBXO28 | NNT | NUDT7 | FAM213A |
| 234148_at | 244548_at | MRPL30 | LUZP1 | RAD1 | 1557688_at |
| ITGA4 | VTA1 | 215278_at | MFGE8 | EIF3B | 208810_at |
| 1556658_a_at | BRD2 | 243003_at | ZNF12 | RPL35A | RNF207 |
| POLR3E | UBXN2B | FNTA | KRAS | UBE2B | BHLHE40 |
| BRD2 | SLC33A1 | ZKSCAN4 | 1555522_s_at | MBD4 | S1PR1 |
| RECQL4 | SUZ12 | HSPH1 | PEX2 | BIRC3 | 233690_at |
| PTPRC | QRSL1 | OR4D1 | FOXP1 | 240665_at | ZNF93 |
| AURKAIP1 | ARNTL | 219112_at | 238769_at | 235123_at | BCR |
| TLR1 | LTBP4 | FAM170A | NIP7 | 242194_at | 1559663_at |
| 243203_at | CENPT | DDX51 | STAM2 | ARHGAP42 | 234942_s_at |
| PRPF4B | 1556352_at | CANX | PSMB4 | PQBP1 | CHN2 |
| 239603_x_at | TTYH2 | 208750_s_at | NUDT13 | 221079_s_at | 237013_at |
| ZBTB18 | RAB40B | 230350_at | 232338_at | GTF2H2 | SERPINB9 |
| SLC35A3 | TBL1XR1 | 234345_at | SSR3 | 229469_at | 244597_at |
| 239166_at | SPOP | SNX6 | RABEP1 | 244123_at | 230386_at |
| TM9SF2 | NKTR | DCAF8 | FCGR2C | MED28 | SH2B1 |
| 237185_at | ATP2A2 | ALG2 | 242691_at | ALDH3A2 | 234369_at |
| 233824_at | RNF130 | OSGIN2 | 230761_at | PLEKHG5 | CALU |
| COG8 | 234113_at | CCDC85C | 225642_at | 1569519_at | DNM2 |
| 215528_at | NEK4 | CNOT6L | ND4 | RASA1 | SRSF4 |
| CDV3 | ARPC5 | ERBB4 | DHDH | AKAP13 | TMEM134 |
| GINS4 | ZBTB44 | DNAJC16 | FABP6 | NT5DC1 | TTF2 |
| ATF1 | YTHDF2 | SPOPL | ZNF316 | ATP5F1 | E2F3 |
| IBTK | 1562412_at | FGD5-AS1 | G3BP1 | PMAIP1 | 239585_at |
| PRKAR1A | 242995_at | ZNF44 | KRCC1 | 212241_at | VANGL1 |
| PSME3 | TPD52 | 1568795_at | FOXK2 | HTR7 | CYP21A2 |
| PRKCB | EML4 | 1555014_x_at | MORF4L1 | TRIM65 | 214223_at |
| FAM27E3 | PLA2G12A | HADH | FAM105B | 244791_at | MTRF1L |
| 244579_at | CANX | DPT | TLN1 | CXorf56 | STARD4 |
| XYLT2 | 240666_at | GPSM3 | 220582_at | TAGLN | 207488_at |
| 5-Mar | PPP2R1B | TP73-AS1 | 241692_at | MRM1 | ZNF451 |
| DAZAP2 | 232919_at | 234488_s_at | SLC35F5 | ZNF503-AS2 | LOC728537 |
| CILP2 | SYNPO2 | 240529_at | AKAP10 | 1569234_at | MPZL2 |
| TMEM168 | ORAI2 | ZNF566 | USP34 | MAOB | ABCA11P |
| PDGFC | SETD5-AS1 | GTF3C5 | R3HDM1 | MTM1 | CSNK1G3 |
| MYCN | BARD1 | GSPT2 | SMG6 | CASC4 | CDRT15L2 |
| ZNF747 | ND4 | SAMD4B | PPP6R2 | TMEM214 | FAM204A |
| TTF1 | SLC5A8 | TFR2 | MRPS10 | LRCH3 | IGSF9B |
| 1566426_at | R3HDM1 | 236615_at | CREB1 | TBC1D16 | 232759_at |
| ARV1 | LYZ | 1554771_at | NUS1 | IQSEC2 | HSF2BP |
| PRKD3 | 241769_at | P2RY10 | MOB1A | MROH7 | REST |
| 1557538_at | TRIM15 | JKAMP | C16orf55 | CDK12 | GLYR1 |
| CACNA2D4 | 232290_at | DCAF16 | ANKFY1 | 230868_at | GPCPD1 |
| C22orf43 | AKAP13 | CCDC50 | FBXL5 | USP7 | WDR45B |
| SMCR8 | GDE1 | UBE3A | PLA2G7 | RFC3 | 231351_at |
| 236931_at | SLC30A5 | 236322_at | CNOT6L | FAM22F | 217679_x_at |
| RAB1A | 1565677_at | EIF4G2 | CUX1 | MDM4 | PARP10 |
| RAB9A | PKN1 | IPO13 | 1564378_a_at | 242527_at | RBBP5 |
| YWHAE | ACTR2 | PON2 | 215123_at | TRIP6 | 233570_at |
| DIS3 | GRB10 | 1561834_a_at | AKT2 | HAUS6 | 1570229_at |
| RAB1A | NADKD1 | COG6 | SLC5A5 | MRPL50 | CRYL1 |
| 213740_s_at | LRCH3 | GLB1L3 | XPO7 | 240399_at | KATNBL1 |
| 244019_at | LOC100132874 | TMEM64 | AP1S2 | 231934_at | PRSS3P2 |
| 1570439_at | RAB7L1 | MARS2 | NFKBIB | TRAK1 | 1-Sep |
| CACNA2D4 | ORC5 | RP2 | MLL2 | 240238_at | 1561195_at |
| GLUD2 | RNF170 | TGIF1 | NOC4L | 230630_at | LIN7C |
| BLOC1S6 | MS4A6A | PPARA | RPRD1A | RBM22 | 240319_at |
| LINC00667 | SLC35D2 | 233313_at | RBM7 | PIGM | 237575_at |
| SCAMP1 | TUBD1 | SMARCA4 | TTLL9 | TSHZ2 | S100A14 |
| MAP3K2 | SPOPL | ADO | ATPBD4 | SPAG9 | ARL6IP6 |
| IBA57 | SWAP70 | ADH5 | VASN | SPPL3 | ARF4 |
| ZCCHC10 | HIBADH | 243673_at | KLC4 | ABCB8 | P4HA2 |
| 1560741_at | TIMM17A | MOSPD2 | ABHD5 | COL17A1 | 1559702_at |
| FAM43A | DOCK4 | TAF9B | 214740_at | 230617_at | TMEM106B |
| ALS2CR8 | C9orf53 | YY1 | PTP4A2 | HADH | 236125_at |
| 233296_x_at | 1569311_at | MESDC1 | EPC1 | ATF6 | WTAP |
| INF2 | 231005_at | GON4L | MZT2B | 1554089_s_at | IGDCC3 |
| PRMT6 | C1orf228 | LARP4 | RASGRF1 | PLEKHA4 | ENDOV |
| IL13RA1 | NLGN3 | 217446_x_at | SETD5-AS1 | 200624_s_at | 1556931_at |
| SF3A2 | 1558670_at | RPP14 | 220691_at | TMEM239 | TP53AIP1 |
| FBXL12 | PAGR1 | RNF113A | FBXL20 | 237171_at | 242233_at |

TABLE 1b-continued

The 2977 gene probeset used in the 3-Way AR, ADNR TX ANOVA
Analysis (using the Hu133 Plus 2.0 cartridge arrays plates)

| | | | | | |
|---|---|---|---|---|---|
| 233554_at | RRAS2 | 1558237_x_at | SQSTM1 | MANEA | SPEN |
| 241867_at | PDE8A | PTGER1 | TRAPPC10 | CLDN16 | C16orf52 |
| OGFRL1 | IFNGR1 | 1561871_at | 1565762_at | LOC100506369 | SYMPK |
| 231191_at | UHRF1BP1L | LCMT2 | STX17 | C6orf120 | ITSN2 |
| 1560082_at | 240446_at | MED23 | PRKRA | ANKRD13C | RFC1 |
| RHEB | GBAS | 215874_at | MED30 | 1556373_a_at | ZC3H7A |
| RHOA | MRPS10 | TRAM1 | RHAG | 214658_at | TRIM23 |
| RRN3P3 | ANKS1B | ATPAF1 | PPID | 1561167_at | 240505_at |
| ELMSAN1 | 202374_s_at | NR2C2 | APP | 235804_at | DYRK1B |
| ADAT1 | 244382_at | ZNF451 | RERE | ASPHD1 | TOR1AIP1 |
| 242320_at | MCL1 | DENND6B | 1560862_at | PTEN | TMEM203 |
| 1555194_at | ZNF430 | FAM83G | 239453_at | CCNT2 | ASAH1 |
| 238108_at | SFRP1 | NAA40 | ERN2 | 237264_at | CUL4B |
| 240315_at | ARNT | TSPAN3 | 240279_at | ERICH1 | BZRAP1-AS1 |
| SCOC | ZNF318 | MLLT10 | 222371_at | TTC9C | MTSS1 |
| C15orf57 | ZFR | WDR4 | PEBP1 | IGIP | DNM1 |
| 1562067_at | MEF2A | 234609_at | AP1G1 | MGC70870 | ZNF777 |
| 235862_at | COL7A1 | NIPSNAP3A | TRIOBP | JAK2 | RALGAPA1 |
| UBE2D4 | ZNRF2 | ANKRD52 | RNF213 | 221242_at | IMPAD1 |
| 240478_at | RFC3 | TMEM251 | HNRNPM | LUC7L | 222315_at |
| 239409_at | FAM110A | 234590_x_at | EBPL | 217549_at | CDKN2AIP |
| ZNF146 | CRYBB3 | NAP1L1 | LOC142937 | LOC283174 | SCAMP1 |
| RASA2 | WDR19 | 242920_at | CEP57 | 234788_x_at | 216584_at |
| CSNK1A1 | RPS2 | FAM103A1 | 239121_at | UBE2D1 | 238656_at |
| B3GNT2 | ETNK1 | STK38L | C6orf106 | PTP4A1 | CAT |
| LOC100131067 | 227505_at | DNAJC10 | PPP1R12C | SMG5 | LOC100505876 |
| FDX1 | C2orf43 | ARFIP2 | ETNK1 | CEP350 | EMC4 |
| TADA3 | NCK1 | DEFB1 | IRF8 | 233473_x_at | GNAQ |
| IKZF1 | 222378_at | TMEM55A | TMEM88 | LMBRD2 | 228694_at |
| 242827_x_at | ST3GAL6 | SSBP2 | ENOPH1 | LOC100505555 | RICTOR |
| DNAJC14 | 222375_at | MAU2 | CEP68 | FAM45A | NDFIP2 |
| NEDD9 | ENTHD2 | OSBPL11 | WDR48 | HBP1 | 243473_at |
| CD47 | 1557270_at | PAFAH1B2 | PRKCH | PSME3 | ACYP2 |
| GSDMB | TPGS1 | NOL9 | ZNF224 | HNRNPUL1 | MTFR1 |
| FABP3 | PHLPP2 | POU5F1P4 | EPN1 | 244732_at | TRIM4 |
| DR1 | CYP2A6 | CHD9 | TET3 | LILRA2 | ZAN |
| FLT1 | ADAM10 | HEATR5B | PPP1R8 | ANTXR1 | 215986_at |
| PCBD2 | 202397_at | RPRD1A | USP9X | PATL1 | SRP72 |
| 1562194_at | MAVS | CAMSAP1 | CCL22 | 1562056_at | KLF4 |
| TRAPPC1 | PDIA6 | 1570408_at | WDR77 | 236438_at | DRAXIN |
| PRKCB | 234201_x_at | 239171_at | FAM175A | C9orf84 | NUP188 |
| APCDD1L-AS1 | VAMP2 | CCDC108 | INPP4A | OTOR | VAV3 |
| 243249_at | 239264_at | NLRP1 | HIGD1A | MRPL19 | YWHAZ |
| CHMP2B | IFNGR2 | 240165_at | MAVS | TGFB1 | CHD9 |
| ABCD3 | HNRNPC | 1554413_s_at | LYPLA1 | ARHGAP27 | 233960_s_at |
| DSTYK | ARHGAP26 | 1566959_at | FAM99B | FAM131C | 228812_at |
| CASP8 | 243568_at | GGT7 | CAT | SETBP1 | DLD |
| CUL4A | ATXN10 | RPS15 | RPS10P7 | ELP2 | SMIM15 |
| 233648_at | FOXP3 | 1565915_at | ETNK1 | 1557512_at | 1557724_a_at |
| 242558_at | 217164_at | 232584_at | SUMO2 | TRMT11 | NSMCE4A |
| 1557562_at | 222436_s_at | 233783_at | TCOF1 | 227556_at | ENDOG |
| MAGI1 | DNAJB11 | SNX5 | POGZ | ST8SIA4 | EVI5L |
| UBTD2 | 237311_at | 241460_at | RHOQ | PDLIM5 | FAM63A |
| EIF4E3 | SMAD7 | MUC3B | DKFZP547L112 | BTBD7 | IL1R2 |
| CFDP1 | 204347_at | 1556336_at | EDIL3 | 239613_at | MCTP2 |
| COG7 | UCHL5 | MOGAT2 | GHDC | UFL1 | 238807_at |
| 234645_at | MGA | 242476_at | COMMD10 | POLH | CADM1 |
| 243992_at | CSGALNACT1 | NICN1 | HAP1 | 237456_at | OBSCN |
| VAMP3 | NR5A1 | DDX42 | TMEM48 | 229717_at | HNRNPH1 |
| 243280_at | SEC23A | DNAJC10 | ANKZF1 | C17orf70 | NUCKS1 |
| NAA50 | C15orf57 | 1555996_s_at | MUC20 | 1566823_a_at | USP31 |
| AVL9 | SRSF5 | 241445_at | DDR1-AS1 | CTSC | HDGFRP2 |
| TOB2 | CTDSPL2 | 240008_at | RCN2 | 244674_at | XRCC6 |
| C5orf22 | 6-Mar | PRKAR1B | 240538_at | 242058_at | 226252_at |
| 236612_at | PCBP3 | LOC374443 | CHD2 | INTS10 | OXR1 |
| 1558710_at | 1556055_at | 231604_at | FASTKD3 | SARDH | ALPI |
| RAB3IP | SPTLC2 | B4GALT1 | 243286_at | SCLT1 | CASP8 |
| KLHL28 | PCMT1 | EXOC6 | CPNE6 | 229575_at | 6-Sep |
| CCNG2 | TMTC4 | LYRM4 | ZDHHC13 | NKTR | 232626_at |
| ZNF207 | SGK494 | ERVK13-1 | CD44 | SEZ6L2 | 211910_at |
| PEBP1 | 243860_at | NECAP2 | RECQL5 | ACHE | DNASE1L3 |
| ROCK1 | 244332_at | CCDC40 | SULT4A1 | TTC9B | NF1 |
| 242927_at | MBD2 | 237330_at | SEC23IP | SUPT6H | TTC5 |
| 241387_at | 235613_at | KIAA0141 | ID2 | GPR65 | 222156_x_at |
| ZNF304 | LOC100507283 | FAM174A | LINC00661 | FLNB | FAM181A |
| 227384_s_at | RAB22A | 241376_at | DRD2 | ATP9A | ATF1 |
| HOXB2 | PDCD6IP | TOR3A | FYTTD1 | PLAGL1 | RHOQ |

TABLE 1b-continued

The 2977 gene probeset used in the 3-Way AR, ADNR TX ANOVA Analysis (using the Hu133 Plus 2.0 cartridge arrays plates)

| | | | | | |
|---|---|---|---|---|---|
| AGGF1 | 9-Sep | 243454_at | MAPRE1 | LRRC37A3 | IL13RA1 |
| HIPK3 | ZBTB43 | SLC20A2 | POT1 | LINS | CCNY |
| SERP1 | 235847_at | ZNF655 | 242768_at | 1566166_at | CEP57 |
| TOR1AIP1 | VAMP4 | KCP | 243078_at | RICTOR | LOC729852 |
| 242824_at | 1556865_at | ZNF398 | RSBN1L | DCAF13 | PEX3 |
| IKBIP | GOLPH3 | BCLAF1 | UPRT | GRB10 | ARID4B |
| CHD7 | PEX12 | 243396_at | C19orf43 | 1560982_at | DCAF8 |
| SETD5 | KBTBD4 | 216567_at | PTER | PTP4A2 | 1557422_at |
| REPS1 | MLLT11 | COX2 | 239780_at | 1562051_at | SNAP23 |
| 233323_at | FLJ31813 | ATP11A | 239451_at | CCNL1 | OGFRL1 |
| TTBK2 | RAB6A | 216448_at | CADM3 | C17orf58 | 239164_at |
| 237895_at | PTPN11 | PDIA6 | 243512_x_at | GRIPAP1 | 207756_at |
| IL13RA1 | CHMP1B | UBE2D3 | ZBTB20 | SIAH1 | 242732_at |
| DIO3 | 242457_at | APPBP2 | 239555_at | 232788_at | NOL9 |
| 234091_at | CIAPIN1 | MCTP2 | 236610_at | RTCA | TCF3 |
| 233228_at | PRRC2A | ZNF708 | MIER3 | NENF | SAE1 |
| B4GALNT3 | 240775_at | MIA | SLC32A1 | 233922_at | ZNF280D |
| MED30 | 238712_at | XRCC1 | 215197_at | 216850_at | C12orf5 |
| 243826_at | 216465_at | RBM15 | ADD1 | SNX10 | 1556327_a_at |
| TANK | ZFYVE21 | PDP1 | 230980_x_at | BTBD18 | MMP28 |
| 232909_s_at | RQCD1 | CD9 | FAM184B | BRCC3 | ACSS1 |
| TNFRSF19 | SCAF11 | COMMD10 | FGF18 | FAHD2CP | ULK2 |
| 1569999_at | 1562063_x_at | KCTD18 | 234449_at | 243509_at | AGO1 |
| 1558418_at | SMARCC2 | HEATR5A | LACTB2 | TFB2M | TPI1 |
| UBE4B | XAB2 | NCOA2 | 1556778_at | PALM3 | TPSAB1 |
| 239557_at | SLC25A40 | TRAPPC13 | KDELR2 | 242386_x_at | CCDC28A |
| 232890_at | TSPAN12 | CELF2 | 238559_at | ATP5S | CEP152 |
| ITPR1 | KLHL9 | 206088_at | ZNF235 | DCTD | CDK9 |
| MEAF6 | 217653_x_at | PRSS53 | 239619_at | REL | RAE1 |
| 239331_at | U2SURP | SLC22A31 | GNL3L | TOMM22 | PROK2 |
| 243808_at | RALGAPA2 | POLK | 216656_at | SSTR5-AS1 | CCNY |
| ZNF580 | TPM3 | SEC24A | USP2 | LRMP | 233790_at |
| KLF9 | 244474_at | MFI2 | CGGBP1 | TTL | PLEKHG3 |
| 241788_x_at | LOC150381 | RUNX1-IT1 | SOAT1 | ALG13 | G3BP2 |
| 204006_s_at | | | | | |

3-class univariate F-test was done on the Discovery cohort (1000 random permutations and FDR <10%; BRB Array-Tools)
Number of significant genes by controlling the proportion of false positive genes: 2977
Sorted by p-value of the univariate test.
Class 1: ADNR; Class 2: AR; Class 3: TX.

With probability of 80% the first 2977 genes contain no more than 10% of false discoveries. Further extension of the list was halted because the list would contain more than 100 false discoveries
The 'Pairwise significant' column shows pairs of classes with significantly different gene expression at alpha=0.01. Class labels in a pair are ordered (ascending) by their averaged gene expression.

TABLE 1c

The top 200 gene probeset used in the 3-Way AR, ADNR TX ANOVA Analysis (using the HT HG-U133 + PM Array Plates)

| | 3-Way AR, ADNR TX ANOVA Analysis | | | p-value - |
|---|---|---|---|---|
| # | Probeset ID | Gene Symbol | Gene Title | phenotype |
| 1 | 213718_PM_at | RBM4 | RNA binding motif protein 4 | 5.39E−10 |
| 2 | 227878_PM_s_at | ALKBH7 | alkB, alkylation repair homolog 7 (*E. coli*) | 3.15E−08 |
| 3 | 214405_PM_at | 214405_PM_at_EST1 | EST1 | 3.83E−08 |
| 4 | 210792_PM_x_at | SIVA1 | SIVA1, apoptosis-inducing factor | 4.64E−08 |
| 5 | 214182_PM_at | 214182_PM_at_EST2 | EST2 | 6.38E−08 |
| 6 | 1554015_PM_a_at | CHD2 | chromodomain helicase DNA binding protein 2 | 6.50E−08 |
| 7 | 225839_PM_at | RBM33 | RNA binding motif protein 33 | 7.41E−08 |
| 8 | 1554014_PM_at | CHD2 | chromodomain helicase DNA binding protein 2 | 7.41E−08 |
| 9 | 214263_PM_x_at | POLR2C | polymerase (RNA) II (DNA directed) polypeptide C, 33 kDa | 7.47E−08 |
| 10 | 1556865_PM_at | 1556865_PM_at_EST3 | EST3 | 9.17E−08 |
| 11 | 203577_PM_at | GTF2H4 | general transcription factor IIH, polypeptide 4, 52 kDa | 9.44E−08 |
| 12 | 218861_PM_at | RNF25 | ring finger protein 25 | 1.45E−07 |
| 13 | 206061_PM_s_at | DICER1 | dicer 1, ribonuclease type III | 1.53E−07 |
| 14 | 225377_PM_at | C9orf86 | chromosome 9 open reading frame 86 | 1.58E−07 |

TABLE 1c-continued

The top 200 gene probeset used in the 3-Way AR, ADNR TX
ANOVA Analysis (using the HT HG-U133 + PM Array Plates)

| | 3-Way AR, ADNR TX ANOVA Analysis | | | p-value - |
| # | Probeset ID | Gene Symbol | Gene Title | phenotype |
| --- | --- | --- | --- | --- |
| 15 | 1553107_PM_s_at | C5orf24 | chromosome 5 open reading frame 24 | 2.15E−07 |
| 16 | 1557246_PM_at | KIDINS220 | kinase D-interacting substrate, 220 kDa | 2.43E−07 |
| 17 | 224455_PM_s_at | ADPGK | ADP-dependent glucokinase | 3.02E−07 |
| 18 | 201055_PM_s_at | HNRNPA0 | heterogeneous nuclear ribonucleoprotein A0 | 3.07E−07 |
| 19 | 236237_PM_at | 236237_PM_at_EST4 | EST4 | 3.30E−07 |
| 20 | 211833_PM_s_at | BAX | BCL2-associated X protein | 3.92E−07 |
| 21 | 1558111_PM_at | MBNL1 | muscleblind-like (*Drosophila*) | 3.93E−07 |
| 22 | 206113_PM_s_at | RAB5A | RAB5A, member RAS oncogene family | 3.95E−07 |
| 23 | 202306_PM_at | POLR2G | polymerase (RNA) II (DNA directed) polypeptide G | 4.83E−07 |
| 24 | 242268_PM_at | CELF2 | CUGBP, Elav-like family member 2 | 5.87E−07 |
| 25 | 223332_PM_x_at | RNF126 | ring finger protein 126 | 6.24E−07 |
| 26 | 1561909_PM_at | 1561909_PM_at_EST5 | EST5 | 6.36E−07 |
| 27 | 213940_PM_s_at | FNBP1 | formin binding protein 1 | 6.60E−07 |
| 28 | 210655_PM_s_at | FOXO3 /// FOXO3B | forkhead box O3 /// forkhead box O3B pseudogene | 6.82E−07 |
| 29 | 233303_PM_at | 233303_PM_at_EST6 | EST6 | 8.00E−07 |
| 30 | 244219_PM_at | 244219_PM_at_EST7 | EST7 | 9.55E−07 |
| 31 | 35156_PM_at | R3HCC1 | R3H domain and coiled-coil containing 1 | 1.02E−06 |
| 32 | 215210_PM_s_at | DLST | dihydrolipoamide S-succinyltransferase (E2 component of 2-oxo-glutarate complex) | 1.08E−06 |
| 33 | 1563431_PM_x_at | CALM3 | Calmodulin 3 (phosphorylase kinase, delta) | 1.15E−06 |
| 34 | 202858_PM_at | U2AF1 | U2 small nuclear RNA auxiliary factor 1 | 1.18E−06 |
| 35 | 1555536_PM_at | ANTXR2 | anthrax toxin receptor 2 | 1.21E−06 |
| 36 | 210313_PM_at | LILRA4 | leukocyte immunoglobulin-like receptor, subfamily A (with TM domain), member 4 | 1.22E−06 |
| 37 | 216997_PM_x_at | TLE4 | transducin-like enhancer of split 4 (E(sp1) homolog, *Drosophila*) | 1.26E−06 |
| 38 | 201072_PM_s_at | SMARCC1 | SWI/SNF related, matrix associated, actin dependent regulator of chromatin, subfamily c | 1.28E−06 |
| 39 | 223023_PM_at | BET1L | blocked early in transport 1 homolog (*S. cerevisiae*)-like | 1.36E−06 |
| 40 | 201556_PM_s_at | VAMP2 | vesicle-associated membrane protein 2 (synaptobrevin 2) | 1.39E−06 |
| 41 | 218385_PM_at | MRPS18A | mitochondrial ribosomal protein S18A | 1.44E−06 |
| 42 | 1555420_PM_a_at | KLF7 | Kruppel-like factor 7 (ubiquitous) | 1.50E−06 |
| 43 | 242726_PM_at | 242726_PM_at_EST8 | EST8 | 1.72E−06 |
| 44 | 233595_PM_at | USP34 | ubiquitin specific peptidase 34 | 1.79E−06 |
| 45 | 218218_PM_at | APPL2 | adaptor protein, phosphotyrosine interaction, PH domain and leucine zipper containing 2 | 1.80E−06 |
| 46 | 240991_PM_at | 240991_PM_at_EST9 | EST9 | 1.95E−06 |
| 47 | 210763_PM_x_at | NCR3 | natural cytotoxicity triggering receptor 3 | 2.05E−06 |
| 48 | 201009_PM_s_at | TXNIP | thioredoxin interacting protein | 2.10E−06 |
| 49 | 221855_PM_at | SDHAF1 | succinate dehydrogenase complex assembly factor 1 | 2.19E−06 |
| 50 | 241955_PM_at | HECTD1 | HECT domain containing 1 | 2.37E−06 |
| 51 | 213872_PM_at | C6orf62 | Chromosome 6 open reading frame 62 | 2.57E−06 |
| 52 | 243751_PM_at | 243751_PM_at_EST10 | EST10 | 2.60E−06 |
| 53 | 232908_PM_at | ATAD2B | ATPase family, AAA domain containing 2B | 2.64E−06 |
| 54 | 222413_PM_s_at | MLL3 | myeloid/lymphoid or mixed-lineage leukemia 3 | 2.74E−06 |
| 55 | 217550_PM_at | ATF6 | activating transcription factor 6 | 2.86E−06 |
| 56 | 223123_PM_s_at | C1orf128 | chromosome 1 open reading frame 128 | 2.87E−06 |
| 57 | 202283_PM_at | SERPINF1 | serpin peptidase inhibitor, clade F (alpha-2 antiplasmin, pigment epithelium derived fa | 2.87E−06 |
| 58 | 200813_PM_s_at | PAFAH1B1 | platelet-activating factor acetylhydrolase 1b, regulatory subunit 1 (45 kDa) | 3.10E−06 |
| 59 | 223312_PM_at | C2orf7 | chromosome 2 open reading frame 7 | 3.30E−06 |
| 60 | 217399_PM_s_at | FOXO3 /// FOXO3B | forkhead box O3 /// forkhead box O3B pseudogene | 3.31E−06 |
| 61 | 218571_PM_s_at | CHMP4A | chromatin modifying protein 4A | 3.47E−06 |
| 62 | 228727_PM_at | ANXA11 | annexin A11 | 3.73E−06 |

TABLE 1c-continued

The top 200 gene probeset used in the 3-Way AR, ADNR TX
ANOVA Analysis (using the HT HG-U133 + PM Array Plates)

| # | Probeset ID | Gene Symbol | Gene Title | p-value - phenotype |
|---|---|---|---|---|
| 63 | 200055_PM_at | TAF10 | TAF10 RNA polymerase II, TATA box binding protein (TBP)-associated factor, 30 kDa | 3.76E−06 |
| 64 | 242854_PM_x_at | DLEU2 | deleted in lymphocytic leukemia 2 (non-protein coding) | 3.84E−06 |
| 65 | 1562250_PM_at | 1562250_PM_at_EST11 | EST11 | 3.99E−06 |
| 66 | 208657_PM_s_at | SEPT9 | septin 9 | 4.12E−06 |
| 67 | 201394_PM_s_at | RBM5 | RNA binding motif protein 5 | 4.33E−06 |
| 68 | 200898_PM_s_at | MGEA5 | meningioma expressed antigen 5 (hyaluronidase) | 4.55E−06 |
| 69 | 202871_PM_at | TRAF4 | TNF receptor-associated factor 4 | 4.83E−06 |
| 70 | 1558527_PM_at | LOC100132707 | hypothetical LOC100132707 | 4.85E−06 |
| 71 | 203479_PM_s_at | OTUD4 | OTU domain containing 4 | 4.86E−06 |
| 72 | 219931_PM_s_at | KLHL12 | kelch-like 12 (*Drosophila*) | 4.88E−06 |
| 73 | 203496_PM_s_at | MED1 | mediator complex subunit 1 | 4.99E−06 |
| 74 | 216112_PM_at | 216112_PM_at_EST12 | EST12 | 5.22E−06 |
| 75 | 1557418_PM_at | ACSL4 | Acyl-CoA synthetase long-chain family member 4 | 5.43E−06 |
| 76 | 212113_PM_at | ATXN7L3B | ataxin 7-like 3B | 5.67E−06 |
| 77 | 204246_PM_s_at | DCTN3 | dynactin 3 (p22) | 5.68E−06 |
| 78 | 235868_PM_at | MGEA5 | Meningioma expressed antigen 5 (hyaluronidase) | 5.70E−06 |
| 79 | 232725_PM_s_at | MS4A6A | membrane-spanning 4-domains, subfamily A, member 6A | 5.73E−06 |
| 80 | 212886_PM_at | CCDC69 | coiled-coil domain containing 69 | 5.84E−06 |
| 81 | 226840_PM_at | H2AFY | H2A histone family, member Y | 5.86E−06 |
| 82 | 226825_PM_s_at | TMEM165 | transmembrane protein 165 | 5.96E−06 |
| 83 | 227924_PM_at | INO80D | INO80 complex subunit D | 6.18E−06 |
| 84 | 238816_PM_at | PSEN1 | presenilin 1 | 6.18E−06 |
| 85 | 224798_PM_s_at | C15orf17 | chromosome 15 open reading frame 17 | 6.31E−06 |
| 86 | 243295_PM_at | RBM27 | RNA binding motif protein 27 | 6.34E−06 |
| 87 | 207460_PM_at | GZMM | granzyme M (lymphocyte met-ase 1) | 6.46E−06 |
| 88 | 242131_PM_at | ATP6 | ATP synthase F0 subunit 6 | 6.56E−06 |
| 89 | 228637_PM_at | ZDHHC1 | zinc finger, DHHC-type containing 1 | 6.80E−06 |
| 90 | 233575_PM_s_at | TLE4 | transducin-like enhancer of split 4 (E(sp1) homolog, *Drosophila*) | 7.08E−06 |
| 91 | 215088_PM_s_at | SDHC | succinate dehydrogenase complex, subunit C, integral membrane protein, 15 kDa | 7.18E−06 |
| 92 | 209675_PM_s_at | HNRNPUL1 | heterogeneous nuclear ribonucleoprotein U-like 1 | 7.35E−06 |
| 93 | 37462_PM_i_at | SF3A2 | splicing factor 3a, subunit 2, 66 kDa | 7.38E−06 |
| 94 | 236545_PM_at | 236545_PM_at_EST13 | EST13 | 7.42E−06 |
| 95 | 232846_PM_s_at | CDH23 | cadherin-related 23 | 7.42E−06 |
| 96 | 242679_PM_at | LOC100506866 | hypothetical LOC100506866 | 7.52E−06 |
| 97 | 229860_PM_x_at | C4orf48 | chromosome 4 open reading frame 48 | 7.60E−06 |
| 98 | 243557_PM_at | 243557_PM_at_EST14 | EST14 | 7.62E−06 |
| 99 | 222638_PM_s_at | C6orf35 | chromosome 6 open reading frame 35 | 7.67E−06 |
| 100 | 209477_PM_at | EMD | emerin | 7.70E−06 |
| 101 | 213328_PM_at | NEK1 | NIMA (never in mitosis gene a)-related kinase 1 | 7.72E−06 |
| 102 | 1555843_PM_at | HNRNPM | Heterogeneous nuclear ribonucleoprotein M | 7.72E−06 |
| 103 | 241240_PM_at | 241240_PM_at_EST15 | EST15 | 7.74E−06 |
| 104 | 218600_PM_at | LIMD2 | LIM domain containing 2 | 7.81E−06 |
| 105 | 212994_PM_at | THOC2 | THO complex 2 | 7.84E−06 |
| 106 | 243046_PM_at | 243046_PM_at_EST16 | EST16 | 8.03E−06 |
| 107 | 211947_PM_s_at | BAT2L2 | HLA-B associated transcript 2-like 2 | 8.04E−06 |
| 108 | 238800_PM_s_at | ZCCHC6 | Zinc finger, CCHC domain containing 6 | 8.09E−06 |
| 109 | 228723_PM_at | 228723_PM_at_EST17 | EST17 | 8.11E−06 |
| 110 | 242695_PM_at | 242695_PM_at_EST18 | EST18 | 8.30E−06 |
| 111 | 216971_PM_s_at | PLEC | plectin | 8.39E−06 |
| 112 | 220746_PM_s_at | UIMC1 | ubiquitin interaction motif containing 1 | 8.44E−06 |
| 113 | 238840_PM_at | LRRFIP1 | leucine rich repeat (in FLU) interacting protein 1 | 8.59E−06 |
| 114 | 1556055_PM_at | 1556055_PM_at_EST19 | EST19 | 8.74E−06 |
| 115 | AFFX-M27830_5_at | AFFX-M27830_5_at_EST20 | EST20 | 9.08E−06 |
| 116 | 215248_PM_at | GRB10 | growth factor receptor-bound protein 10 | 9.43E−06 |
| 117 | 211192_PM_s_at | CD84 | CD84 molecule | 1.01E−05 |
| 118 | 214383_PM_x_at | KLHDC3 | kelch domain containing 3 | 1.04E−05 |

TABLE 1c-continued

The top 200 gene probeset used in the 3-Way AR, ADNR TX
ANOVA Analysis (using the HT HG-U133 + PM Array Plates)

| # | Probeset ID | Gene Symbol | Gene Title | p-value - phenotype |
|---|---|---|---|---|
| | 3-Way AR, ADNR TX ANOVA Analysis | | | |
| 119 | 208478_PM_s_at | BAX | BCL2-associated X protein | 1.08E-05 |
| 120 | 229422_PM_at | NRD1 | nardilysin (N-arginine dibasic convertase) | 1.12E-05 |
| 121 | 206636_PM_at | RASA2 | RAS p21 protein activator 2 | 1.14E-05 |
| 122 | 1559589_PM_a_at | 1559589_PM_a_at_EST21 | EST21 | 1.16E-05 |
| 123 | 229676_PM_at | MTPAP | Mitochondrial poly(A) polymerase | 1.18E-05 |
| 124 | 201369_PM_s_at | ZFP36L2 | zinc finger protein 36, C3H type-like 2 | 1.19E-05 |
| 125 | 215535_PM_s_at | AGPAT1 | 1-acylglycerol-3-phosphate O-acyltransferase 1 (lysophosphatidic acid acyltransferase, | 1.25E-05 |
| 126 | 212162_PM_at | KIDINS220 | kinase D-interacting substrate, 220 kDa | 1.26E-05 |
| 127 | 218893_PM_at | ISOC2 | isochorismatase domain containing 2 | 1.26E-05 |
| 128 | 204334_PM_at | KLF7 | Kruppel-like factor 7 (ubiquitous) | 1.26E-05 |
| 129 | 221598_PM_s_at | MED27 | mediator complex subunit 27 | 1.31E-05 |
| 130 | 221060_PM_s_at | TLR4 | toll-like receptor 4 | 1.32E-05 |
| 131 | 224821_PM_at | ABHD14B | abhydrolase domain containing 14B | 1.35E-05 |
| 132 | 244349_PM_at | 244349_PM_at_EST22 | EST22 | 1.38E-05 |
| 133 | 244418_PM_at | 244418_PM_at_EST23 | EST23 | 1.41E-05 |
| 134 | 225157_PM_at | MLXIP | MLX interacting protein | 1.42E-05 |
| 135 | 228469_PM_at | PPID | Peptidylprolyl isomerase D | 1.44E-05 |
| 136 | 224332_PM_s_at | MRPL43 | mitochondrial ribosomal protein L43 | 1.47E-05 |
| 137 | 1553588_PM_at | ND3 /// SH3KBP1 | NADH dehydrogenase, subunit 3 (complex I) /// SH3-domain kinase binding protein 1 | 1.48E-05 |
| 138 | 238468_PM_at | TNRC6B | trinucleotide repeat containing 6B | 1.49E-05 |
| 139 | 235727_PM_at | KLHL28 | kelch-like 28 (Drosophila) | 1.53E-05 |
| 140 | 218978_PM_s_at | SLC25A37 | solute carrier family 25, member 37 | 1.59E-05 |
| 141 | 221214_PM_s_at | NELF | nasal embryonic LHRH factor | 1.62E-05 |
| 142 | 204282_PM_s_at | FARS2 | phenylalanyl-tRNA synthetase 2, mitochondrial | 1.64E-05 |
| 143 | 236155_PM_at | ZCCHC6 | Zinc finger, CCCH domain containing 6 | 1.65E-05 |
| 144 | 224806_PM_at | TRIM25 | tripartite motif-containing 25 | 1.66E-05 |
| 145 | 202840_PM_at | TAF15 | TAF15 RNA polymerase II, TATA box binding protein (TBP)-associated factor, 68 kDa | 1.67E-05 |
| 146 | 207339_PM_s_at | LTB | lymphotoxin beta (TNF superfamily, member 3) | 1.68E-05 |
| 147 | 221995_PM_s_at | 221995_PM_s_at_EST24 | EST24 | 1.69E-05 |
| 148 | 242903_PM_at | IFNGR1 | interferon gamma receptor 1 | 1.70E-05 |
| 149 | 228826_PM_at | 228826_PM_at_EST25 | EST25 | 1.70E-05 |
| 150 | 220231_PM_at | C7orf16 | chromosome 7 open reading frame 16 | 1.71E-05 |
| 151 | 242861_PM_at | NEDD9 | neural precursor cell expressed, developmentally down-regulated 9 | 1.72E-05 |
| 152 | 202785_PM_at | NDUFA7 | NADH dehydrogenase (ubiquinone) 1 alpha subcomplex, 7, 14.5 kDa | 1.74E-05 |
| 153 | 205787_PM_x_at | ZC3H11A | zinc finger CCCH-type containing 11A | 1.76E-05 |
| 154 | 1554333_PM_at | DNAJA4 | DnaJ (Hsp40) homolog, subfamily A, member 4 | 1.77E-05 |
| 155 | 1563315_PM_s_at | ERICH1 | glutamate-rich 1 | 1.82E-05 |
| 156 | 202101_PM_s_at | RALB | v-ral simian leukemia viral oncogene homolog B (ras related; GTP binding protein) | 1.82E-05 |
| 157 | 210210_PM_at | MPZL1 | myelin protein zero-like 1 | 1.84E-05 |
| 158 | 217234_PM_s_at | EZR | ezrin | 1.85E-05 |
| 159 | 219222_PM_at | RBKS | ribokinase | 1.86E-05 |
| 160 | 213161_PM_at | TMOD1 /// TSTD2 | tropomodulin 1 /// thiosulfate sulfurtransferase (rhodanese)-like domain containing 2 | 1.88E-05 |
| 161 | 236497_PM_at | LOC729683 | hypothetical protein LOC729683 | 1.91E-05 |
| 162 | 203111_PM_s_at | PTK2B | PTK2B protein tyrosine kinase 2 beta | 1.93E-05 |
| 163 | 1554571_PM_at | APBB1IP | amyloid beta (A4) precursor protein-binding, family B, member 1 interacting protein | 1.97E-05 |
| 164 | 212007_PM_at | UBXN4 | UBX domain protein 4 | 1.98E-05 |
| 165 | 1569106_PM_s_at | SETD5 | SET domain containing 5 | 1.98E-05 |
| 166 | 243032_PM_at | 243032_PM_at_EST26 | EST26 | 2.00E-05 |
| 167 | 216380_PM_x_at | 216380_PM_x_at_EST27 | EST27 | 2.00E-05 |
| 168 | 217958_PM_at | TRAPPC4 | trafficking protein particle complex 4 | 2.10E-05 |
| 169 | 200884_PM_at | CKB | creatine kinase, brain | 2.11E-05 |
| 170 | 208852_PM_s_at | CANX | calnexin | 2.12E-05 |
| 171 | 1558624_PM_at | 1558624_PM_at_EST28 | EST28 | 2.19E-05 |
| 172 | 203489_PM_at | SIVA1 | SIVA1, apoptosis-inducing factor | 2.23E-05 |
| 173 | 240652_PM_at | 240652_PM_at_EST29 | EST29 | 2.25E-05 |

TABLE 1c-continued

The top 200 gene probeset used in the 3-Way AR, ADNR TX
ANOVA Analysis (using the HT HG-U133 + PM Array Plates)

| | 3-Way AR, ADNR TX ANOVA Analysis | | | p-value - |
| # | Probeset ID | Gene Symbol | Gene Title | phenotype |
| --- | --- | --- | --- | --- |
| 174 | 214639_PM_s_at | HOXA1 | homeobox A1 | 2.37E−05 |
| 175 | 203257_PM_s_at | C11orf49 | chromosome 11 open reading frame 49 | 2.45E−05 |
| 176 | 217507_PM_at | SLC11A1 | solute carrier family 11 (proton-coupled divalent metal ion transporters), member 1 | 2.56E−05 |
| 177 | 223166_PM_x_at | C9orf86 | chromosome 9 open reading frame 86 | 2.57E−05 |
| 178 | 206245_PM_s_at | IVNS1ABP | influenza virus NS1A binding protein | 2.62E−05 |
| 179 | 223290_PM_at | PDXP /// SH3BP1 | pyridoxal (pyridoxine, vitamin B6) phosphatase /// SH3-domain binding protein 1 | 2.64E−05 |
| 180 | 224732_PM_at | CHTF8 | CTF8, chromosome transmission fidelity factor 8 homolog (*S. cerevisiae*) | 2.69E−05 |
| 181 | 204560_PM_at | FKBP5 | FK506 binding protein 5 | 2.75E−05 |
| 182 | 1556283_PM_s_at | FGFR1OP2 | FGFR1 oncogene partner 2 | 2.75E−05 |
| 183 | 212451_PM_at | SECISBP2L | SECIS binding protein 2-like | 2.76E−05 |
| 184 | 208750_PM_s_at | ARF1 | ADP-ribosylation factor 1 | 2.81E−05 |
| 185 | 238987_PM_at | B4GALT1 | UDP-Gal:betaGlcNAc beta 1,4-galactosyltransferase, polypeptide 1 | 2.82E−05 |
| 186 | 227211_PM_at | PHF19 | PHD finger protein 19 | 2.84E−05 |
| 187 | 223960_PM_s_at | C16orf5 | chromosome 16 open reading frame 5 | 2.86E−05 |
| 188 | 223009_PM_at | C11orf59 | chromosome 11 open reading frame 59 | 2.88E−05 |
| 189 | 229713_PM_at | PIP4K2A | Phosphatidylinositol-5-phosphate 4-kinase, type II, alpha | 2.96E−05 |
| 190 | 1555330_PM_at | GCLC | glutamate-cysteine ligase, catalytic subunit | 2.96E−05 |
| 191 | 242288_PM_s_at | EMILIN2 | elastin microfibril interfacer 2 | 2.97E−05 |
| 192 | 207492_PM_at | NGLY1 | N-glycanase 1 | 2.98E−05 |
| 193 | 233292_PM_s_at | ANKHD1 /// ANKHD1-EIF4EBP3 | ankyrin repeat and KH domain containing 1 /// ANKHD1-EIF4EBP3 readthrough | 3.00E−05 |
| 194 | 1569600_PM_at | DLEU2 | Deleted in lymphocytic leukemia 2 (non-protein coding) | 3.00E−05 |
| 195 | 218387_PM_s_at | PGLS | 6-phosphogluconolactonase | 3.03E−05 |
| 196 | 239660_PM_at | RALGAPA2 | Ral GTPase activating protein, alpha subunit 2 (catalytic) | 3.07E−05 |
| 197 | 230733_PM_at | 230733_PM_at_EST30 | EST30 | 3.07E−05 |
| 198 | 1557804_PM_at | 1557804_PM_at_EST31 | EST31 | 3.11E−05 |
| 199 | 210969_PM_at | PKN2 | protein kinase N2 | 3.12E−05 |
| 200 | 233937_PM_at | GGNBP2 | gametogenetin binding protein 2 | 3.13E−05 |

TABLE 1d

The gene list of all 4132 genes analyzed in the 3-Way AR, ADNR
TX ANOVA Analysis (using the HT HG-U133 + PM Array Plates)

| | | | |
| --- | --- | --- | --- |
| RBM4 | IFT52 | TMSB4Y | SLAMF6 |
| ALKBH7 | 240759_PM_at | FLT3LG | LOC100287401 |
| 214405_PM_at_EST1 | EZR | MTMR2 | CFLAR |
| SIVA1 | DEXI | C8orf82 | PIGV |
| 214182_PM_at_EST2 | SMARCC2 | ELP4 | RB1CC1 |
| CHD2 | ADPGK | TEX264 | SLC25A37 |
| RBM33 | TACR1 | STX3 | CES2 |
| CHD2 | FLJ10661 | 208278_PM_s_at | CLYBL |
| POLR2C | ACSL4 | VPS25 | SDHD |
| 1556865_PM_at_EST3 | STAC3 | ISCA1 | TRAF3IP3 |
| GTF2H4 | PHF20 | SNCA | MRPL2 |
| RNF25 | UBXN7 | CCDC17 | CISH |
| DICER1 | SCFD1 | CCDC51 | FBXO9 |
| C9orf86 | 1559391_PM_s_at | MTPAP | LOC284454 |
| C5orf24 | 1570151_PM_at | 1566958_PM_at | CUL4B |
| KIDINS220 | MED13L | STRADB | PHTF1 |
| ADPGK | XCL1 | HEY1 | TACC1 |
| HNRNPA0 | 1563833_PM_at | LOC100129361 | RBM8A |
| 236237_PM_at_EST4 | CPEB4 | EHBP1 | PCMT1 |
| BAX | PFKFB2 | TMEM223 | LOC100507315 /// PPP2R5C |
| MBNL1 | 244357_PM_at | OGT | TNPO1 |
| RAB5A | DAAM2 | 231005_PM_at | FXR2 |
| POLR2G | CCDC57 | C16orf5 | SLC25A19 |
| CELF2 | CDKN1C | GNGT2 | RAB34 |

TABLE 1d-continued

The gene list of all 4132 genes analyzed in the 3-Way AR, ADNR TX ANOVA Analysis (using the HT HG-U133 + PM Array Plates)

| | | | |
|---|---|---|---|
| RNF126 | CTAGE5 | IKZF1 | IFT52 |
| 1561909_PM_at_EST5 | PTEN /// PTENP1 | 242008_PM_at | LCP1 |
| FNBP1 | DENND1C | STON2 | ZNF677 |
| FOXO3 /// FOXO3B | TAGAP | CALM1 | HCG22 |
| 233303_PM_at_EST6 | ANXA3 | 217347_PM_at | 1564155_PM_x_at |
| 244219_PM_at_EST7 | UBE2I | ID3 | OBFC2B |
| R3HCC1 | LOC728723 | TGIF2 | SRSF2 |
| DLST | 243695_PM_at | CELF2 | SORBS1 |
| CALM3 | C15orf57 | MAP3K13 | WDR82 |
| U2AF1 | ALG8 | SLC4A7 | ALOX5 |
| ANTXR2 | PSMD7 | CCDC97 | TES |
| LILRA4 | C9orf84 | UBE2J2 | CD46 |
| TLE4 | TSPAN18 | PATL1 | CALU |
| SMARCC1 | PIAS2 | DTX3 | ARHGDIA |
| BET1L | RNF145 | ZNF304 | SDCCAG8 |
| VAMP2 | C19orf43 | GDAP2 | C7orf26 |
| MRPS18A | 208324_PM_at | 227729_PM_at | SEMA4F |
| KLF7 | FCAR | TMED2 | TLR1 |
| 242726_PM_at_EST8 | LTN1 | C6orf125 | 222300_PM_at |
| USP34 | PKN2 | PGAP3 | NUDT4 |
| APPL2 | TTLL3 | ZMYND11 | MLL3 |
| 240991_PM_at_EST9 | NAA15 | CYB5B | SVIL |
| NCR3 | GNAQ | MBD6 | IFT46 |
| TXNIP | KLF6 | 241434_PM_at | ARIH2 |
| SDHAF1 | TOR1A | GHITM | NFYC |
| HECTD1 | SLC27A5 | 244555_PM_at | RABL2A /// RABL2B |
| C6orf62 | SLC2A11 | CTSB | 235661_PM_at |
| 243751_PM_at_EST10 | 240939_PM_x_at | LYRM7 | PTPRC |
| ATAD2B | LSMD1 | DNASE1 | 243031_PM_at |
| MLL3 | WAC | FECH | ESD |
| ATF6 | LOC100128590 | UBE2W | 244642_PM_at |
| C1orf128 | NSMAF | TLK1 | EDF1 |
| SERPINF1 | VAV3 | 229483_PM_at | C1orf159 |
| PAFAH1B1 | 239166_PM_at | MKLN1 | CHP |
| C2orf7 | ST8SIA4 | DERL2 | 1558385_PM_at |
| FOXO3 /// FOXO3B | ACTR10 | C11orf31 | 1557667_PM_at |
| CHMP4A | PXK | PHC3 | PDE6B |
| ANXA11 | DGUOK | PPM1L | MFAP1 |
| TAF10 | MTG1 | LOC100505764 | TMED4 |
| DLEU2 | 1557538_PM_at | ZNF281 | PPARA |
| 1562250_PM_at_EST11 | TXNL4B | JAK3 | ARHGAP24 |
| SEPT9 | 239723_PM_at | NME6 | PSMD9 |
| RBM5 | MAPKAPK2 | ZMAT3 | LOC100507006 |
| MGEA5 | CXXC5 | MADD | GLUD1 |
| TRAF4 | CHST2 | SLC2A8 | CCDC19 |
| LOC100132707 | GSTM1 | PALLD | AKR7A3 |
| OTUD4 | 210824_PM_at | LOC283392 | SCLY |
| KLHL12 | ADAM17 | 243105_PM_at | GCLC |
| MED1 | 244267_PM_at | FCAR | USP32 |
| 216112_PM_at_EST12 | LOC339862 | CNOT8 | GSPT1 |
| ACSL4 | 1561733_PM_at | 1555373_PM_at | RUFY2 |
| ATXN7L3B | PEX14 | HNRNPL | RHEBL1 |
| DCTN3 | EXOSC1 | LOC646014 | FAF1 |
| MGEA5 | 230354_PM_at | VAV3 | WSB1 |
| MS4A6A | ZBTB43 | LRBA | DNAJC7 |
| CCDC69 | C8orf60 | HGD | MGC16275 |
| H2AFY | C15orf54 | TADA2B | 1556508_PM_s_at |
| TMEM165 | CELF2 | 227223_PM_at | VAPA |
| INO80D | 241722_PM_x_at | SLC25A33 | RRAGC |
| PSEN1 | LIMD1 | LMBR1L | TDG |
| C15orf17 | OTUB1 | SPRED1 | ENO1 |
| RBM27 | KCTD10 | SEC24D | SIDT2 |
| GZMM | 1560443_PM_at | 239848_PM_at | UMPS |
| ATP6 | FBXO41 | 232867_PM_at | FLJ35816 |
| ZDHHC1 | DCAF6 /// ND4 | SLC35C2 | RPRD1A |
| TLE4 | PEPD | ANGEL1 | PPIB |
| SDHC | CERK | 242320_PM_at | ALAD |
| HNRNPUL1 | PTPMT1 | DSTYK | C10orf54 |
| SF3A2 | FAM189B | ERGIC2 | C16orf88 |
| 236545_PM_at_EST13 | TMED1 | QRSL1 | EPB41 |
| CDH23 | UBL4A | KDM2A | PRDX2 |
| LOC100506866 | SLC25A37 | MED6 | MMAB |
| C4orf48 | SUGT1 | ATP5D | PRDX3 |
| 243557_PM_at_EST14 | MPZL1 | RNF130 | FOXO3 |
| C6orf35 | GSTM2 | TCOF1 | 1560798_PM_at |
| EMD | MLL5 | ARHGEF2 | ENY2 |
| NEK1 | C19orf25 | REPIN1 | PTEN |

TABLE 1d-continued

The gene list of all 4132 genes analyzed in the 3-Way AR, ADNR
TX ANOVA Analysis (using the HT HG-U133 + PM Array Plates)

| | | | |
|---|---|---|---|
| HNRNPM | C6orf108 | MRPS27 | ZNF879 |
| 241240_PM_at_EST15 | FPR2 | RNASET2 | 233223_PM_at |
| LIMD2 | EXOSC9 | C9orf70 | AGAP10 /// AGAP4 /// AGAP9 /// BMS1P1 /// BMS1P5 /// LOC399753 |
| THOC2 | BMS1P1 ///BMS1P5 | 243671_PM_at | NUBPL |
| 243046_PM_at_EST16 | CCDC92 | GFM2 | C20orf4 |
| BAT2L2 | HIF1AN | ZNHIT1 | BBS2 |
| ZCCHC6 | IDS | ZNF554 | BTBD19 |
| 228723_PM_at_EST17 | 240108_PM_at | KIAA1609 | 230987_PM_at |
| 242695_PM_at_EST18 | BMP6 | ZNF333 | C1QBP |
| PLEC | AKR1B1 | CD59 | HIST1H3B |
| UIMC1 | NDUFB8 | UBXN1 | C16orf88 |
| LRRFIP1 | CCDC69 | LZTFL1 | RANGRF |
| 1556055_PM_at_EST19 | LRRFIP2 | C17orf79 | DSTN |
| AFFX-M27830_5_at_EST20 | OXR1 | PSMG2 | ADCY3 |
| GRB10 | MED20 | LOC151146 | SSH2 |
| CD84 | ADNP2 | C15orf26 | ATP5A1 |
| KLHDC3 | ADORA2A /// SPECC1L | SPRED1 | C20orf30 |
| BAX | HERC4 | ARAF | 1557410_PM_at |
| NRD1 | MAT2A | 241865_PM_at | 237517_PM_at |
| RASA2 | C20orf196 | 244249_PM_at | MYEOV2 |
| 1559589_PM_a_at_EST21 | ABTB1 | 243233_PM_at | 226347_PM_at |
| MTPAP | ZBTB3 | NAP1L4 | YTHDF3 |
| ZFP36L2 | COX5B | ANKRD55 | JMJD1C |
| AGPAT1 | SELM | DAD1 | ZNRD1 |
| KIDINS220 | DKC1 | MCTP2 | CAPNS2 |
| ISOC2 | PPP1R11 | 242134_PM_at | 229635_PM_at |
| KLF7 | SLC35B2 | NDUFA3 | 1569362_PM_at |
| MED27 | FAM159A | 243013_PM_at | 241838_PM_at |
| TLR4 | LOC100505501 | CDV3 | VAV2 |
| ABHD14B | 213574_PM_s_at | SRD5A1 | CYP2W1 |
| 244349_PM_at_EST22 | COX5B | 229327_PM_s_at | TBC1D14 |
| 244418_PM_at_EST23 | SRGN | ERICH1 | 244781_PM_x_at |
| MLXIP | SF3A2 | 230154_PM_at | NUDC |
| PPID | CLPP | APOB48R | C12orf45 |
| MRPL43 | ATP6V1C1 | ACSL1 | PTEN |
| ND3 /// SH3KBP1 | CARD16 /// CASP1 | C5orf56 | CAMTA1 |
| TNRC6B | CNPY3 | 232784_PM_at | 240798_PM_at |
| KLHL28 | HIRA | CD44 | TOMM22 |
| SLC25A37 | MBP | SNPH | 237165_PM_at |
| NELF | SLC41A3 | LPP | MRPL46 |
| FARS2 | NDUFA2 | ARPC5L | CSRNP2 |
| ZCCHC6 | GPN2 | 238183_PM_at | JAK1 |
| TRIM25 | 233094_PM_at | ZNF83 | ZNF2 |
| TAF15 | IL32 | 10-Sep | HLA-C |
| LTB | 241774_PM_at | BMPR2 | RPL10L |
| 221995_PM_s_at_EST24 | 1558371_PM_a_at | TMEM101 | TUG1 |
| IFNGR1 | SMEK1 | TRUB2 | 227121_PM_at |
| 228826_PM_at_EST25 | UBE4B | 216568_PM_x_at | LOC100287911 |
| C7orf16 | LOC100287482 | 244860_PM_at | KBTBD4 /// PTPMT1 |
| NEDD9 | PRPF18 | GNB1 | USP37 |
| NDUFA7 | 1556942_PM_at | H6PD | CTNNA1 |
| ZC3H11A | COX8A | LARP7 | LEPREL4 |
| DNAJA4 | NFAT5 | 1560102_PM_at | DNMT3A |
| ERICH1 | CDKN1C | PHF20L1 | CD81 |
| RALB | 236962_PM_at | CFLAR | 1557987_PM_at |
| MPZL1 | CCL28 | NIPAL3 | ZBTB20 |
| EZR | 1560026_PM_at | TSEN15 | FGD2 |
| RBKS | SURF2 | MAEA | DTX1 |
| TMOD1 /// TSTD2 | COG2 | EPRS | ST7 |
| LOC729683 | PYGM | SBNO1 | RBM42 |
| PTK2B | LOC401320 | SNTB2 | 242556_PM_at |
| APBB1IP | ZNF341 | TNPO2 | TOR3A |
| UBXN4 | 235107_PM_at | WDR77 | FHL1 |
| SETD5 | MDM4 | HBA1 /// HBA2 | MRPS22 |
| 243032_PM_at_EST26 | ADK | MAST4 | 231205_PM_at |
| 216380_PM_x_at_EST27 | RBPJ | RPP25 | 1557810_PM_at |
| TRAPPC4 | FAM162A | GKAP1 | ZNF569 |
| CKB | WDR11 | C19orf42 | UBE2F |
| CANX | 240695_PM_at | INVS | LOC283485 |
| 1558624_PM_at_EST28 | BIN2 | CYP3A43 | SCP2 |
| SIVA1 | 242279_PM_at | NHP2L1 | CSH2 |
| 240652_PM_at_EST29 | USP4 | PCCA | DVL2 |
| HOXA1 | C19orf20 | SAMM50 | CD164 |
| C11orf49 | 240220_PM_at | ENTPD1 | CFL1 |

TABLE 1d-continued

The gene list of all 4132 genes analyzed in the 3-Way AR, ADNR TX ANOVA Analysis (using the HT HG-U133 + PM Array Plates)

| | | | |
|---|---|---|---|
| SLC11A1 | ZNF689 | MED13L | INHBB |
| C9orf86 | 235999_PM_at | HLA-E | PAPOLA |
| IVNS1ABP | 235743_PM_at | NT5C2 | GSPT1 |
| PDXP /// SH3BP1 | 238420_PM_at | SNX5 | TUBGCP5 |
| CHTF8 | NUBP2 | FBXL3 | SPPL3 |
| FKBP5 | MSH6 | PSMD4 | PFDN6 |
| FGFR1OP2 | CFLAR | PSMF1 | NASP |
| SECISBP2L | ACAD9 | LOC100127983 | HAVCR2 |
| ARF1 | LOC284454 | DRAM1 | CDKN2A |
| B4GALT1 | PPM1K | CARD16 | SLC40A1 |
| PHF19 | 243149_PM_at | STAG3L4 | PRKDC |
| C16orf5 | SKP1 | GTDC1 | RRN3P2 |
| C11orf59 | MED13 | RINT1 | SLC8A1 |
| PIP4K2A | SNORD89 | CSTB | ILVBL |
| GCLC | 235288_PM_at | 244025_PM_at | 241184_PM_x_at |
| EMILIN2 | PCK2 | COL1A1 | GPR44 |
| NGLY1 | TXN2 | TTC1 | FAM195A |
| ANKHD1 /// ANKHD1-EIF4EBP3 | KHSRP | JAK2 | DENND3 |
| DLEU2 | ENTPD1 | UTRN | NOSIP |
| PGLS | C19orf60 | TMEM126B | 241466_PM_at |
| RALGAPA2 | TOX4 | 240538_PM_at | NCRNA00182 |
| 230733_PM_at_EST30 | CCDC13 | ZNF638 | CAB39 |
| 1557804_PM_at_EST31 | DGUOK | FAM178A | 215029_PM_at |
| PKN2 | SLC22A15 | ABTB1 | PGBD4 |
| GGNBP2 | SDHC | KIAA1704 /// LOC100507773 | FXN |
| SLC25A43 | PIGW | ELF1 | HEMGN |
| CHMP6 | LOC100287911 | G6PC3 | 1566473_PM_a_at |
| CSTF2T | 216589_PM_at | GYPB | FXYD2 |
| PELI3 | C1orf93 | CFLAR | C9orf30 |
| DNASE1L3 | PLXNA2 | SURF4 | ZNF532 |
| ARPC5L | 232354_PM_at | DUSP8 | GPR97 |
| ITSN2 | MPZL1 | ECHDC1 | ISCA2 |
| PURB | PKP4 | POLH | DHRS3 |
| 240870_PM_at | APOBEC3G | KRTAP1-3 | FBXW9 |
| ORAI1 | 239238_PM_at | 237655_PM_at | IKZF4 |
| SYNCRIP | ALPK1 | DYNLRB1 | ARHGEF10L |
| NUTF2 | NUMB | RPRD1A | SHPK |
| 238918_PM_at | DNAJB12 | C17orf104 | 237071_PM_at |
| CD58 | UCK1 | RAD50 | 237337_PM_at |
| DLEU2 | ASPH | STX8 | FCGR3A /// FCGR3B |
| SPTLC2 | FUS | AARSD1 | HIVEP3 |
| B3GALT4 | PRDM4 | CRCP | LOC728153 |
| 239405_PM_at | MBD3 | FBXO31 | SYTL3 |
| TSPAN14 | GGCX | GRAP2 | NUS1 /// NUS1P3 |
| AVEN | UBA7 | C18orf55 | HBA1 /// HBA2 |
| 213879_PM_at | NDUFA13 | OS9 | KPNB1 |
| DPH1 /// OVCA2 | CFLAR | 1565918_PM_a_at | RTN4IP1 |
| NACC1 | JAK1 | SF3B5 | IKZF1 |
| MTMR14 | SSR4 | 215212_PM_at | ZNF787 |
| SLC9A8 | SLC35B4 | 244341_PM_at | ACIN1 |
| MRPL52 | LARP4B | PECI | C12orf52 |
| BRD2 | AP2B1 | CORO1B | 216143_PM_at |
| ARF1 | 232744_PM_x_at | BACE2 | LOC646470 |
| RAD1 | MGC16142 | TMED8 | ALAS2 |
| 234278_PM_at | TFB1M | TCOF1 | CHMP4B |
| TECPR1 | C12orf39 | TBC1D12 | SEC24D |
| 9-Sep | STS | SYTL3 | PTGDS |
| NUDT18 | SUCLG1 | 239046_PM_at | DDX46 |
| HBD | PLEKHA9 | 230350_PM_at | ARHGAP24 |
| NARFL | ATXN7 | ZNF493 | CSF2RA |
| ARMCX6 | TMEM55B | RPL36AL | SMARCE1 |
| PPFIA1 | MAN2C1 | C15orf41 | GOLGA2P2Y /// GOLGA2P3Y |
| RALGAPA2 | MRPS17 /// ZNF713 | ANKRD19 | TPI1 |
| MED13L | 237185_PM_at | LOC144438 | CD83 |
| CELF2 | DPH1 /// OVCA2 | 222330_PM_at | RALGAPA1 |
| PELI1 | 235190_PM_at | CHMP7 | PGAM1 |
| MLXIP | KLHL8 | CPAMD8 | C7orf68 |
| 244638_PM_at | ABCG1 | 244454_PM_at | 238544_PM_at |
| HIPK1 | MTMR3 | LOC100130175 | C1orf135 |
| FNDC3B | DCAF7 | 239850_PM_at | TMOD1 |
| CCR9 | ARF4 | HDAC3 | DLD |
| HIPK2 | RUNX3 | SLC15A4 | PPP4R1L |
| TLR4 | 242106_PM_at | C12orf43 | FAM105A |
| HIPK1 | C11orf73 | LOC100288939 | 244648_PM_at |

TABLE 1d-continued

The gene list of all 4132 genes analyzed in the 3-Way AR, ADNR TX ANOVA Analysis (using the HT HG-U133 + PM Array Plates)

| | | | |
|---|---|---|---|
| SMG7 | EIF4E2 | AP1S1 | FAM45A |
| LLGL1 | DDX6 | 239379_PM_at | PARP2 |
| APH1A | RABL3 | FOXP2 | ESRRA |
| 241458_PM_at | ILKAP | GRHPR | CNTNAP3 |
| DICER1 | RBM47 | HAS3 | STYXL1 |
| C17orf49 | MDP1 | ZDHHC19 | ANKRD54 |
| VNN3 | NDUFAF3 | ZFP3 | 230395_PM_at |
| CDKN1C | TRAF3 | B3GNT6 | LOC100288618 |
| ZNF593 | IRF8 | ALG1 | GANAB |
| SMARCA2 | 217572_PM_at | CYP4V2 | 228390_PM_at |
| 241388_PM_at | TMEM93 | UBR5 | C22orf29 |
| IL1R2 | EZR | GFM1 | DCAF6 /// ND4 |
| BRD2 | GDF15 | 1565597_PM_at | BRCC3 |
| TPST1 | 243158_PM_at | BAGE2 /// MLL3 | SRSF3 |
| GAR1 | KIAA0141 | OGT | 227762_PM_at |
| PTPN1 | FHL3 | PLIN4 | KIAA1109 |
| RNF126 | SRSF9 | 231695_PM_at | ROPN1L |
| COQ6 | BCL6 | CBR3 | C17orf44 |
| SDHAF1 | 232081_PM_at | CALR | LAGE3 |
| ERLIN1 | ARL6IP4 | 1561893_PM_at | ALG2 |
| SMAD4 | LOC151438 | NFKBIE | 1569482_PM_at |
| ARHGAP26 | VPS39 | TMEM189 | LOC729683 |
| 241091_PM_at | C17orf90 | SSX2IP | 231652_PM_at |
| YY1AP1 | CD7 | SRP72 | STK24 |
| 1562265_PM_at | TLR8 | NDUFB10 | IPO4 |
| MYLIP | SLC2A4RG | CDC42EP3 | C9orf16 |
| HINT2 | LFNG | MYST3 | LOC100507602 |
| PHF20L1 | SSBP4 | MED7 | RNF115 |
| MCTP2 | ECHDC1 | 1570639_PM_at | 1556657_PM_at |
| 1554948_PM_at | 243837_PM_x_at | TMEM189-UBE2V1 /// UBE2V1 | |
| TBC1D5 | NUDT22 | HNRNPH2 | MLC1 |
| CR1 | CUEDC2 | KLRC3 | TBC1D25 |
| EDF1 | UBIAD1 | PHKA2 | FBLIM1 |
| GSTA4 | FAM134C | 240803_PM_at | 217152_PM_at |
| ZXDC | DCUN1D1 | CFLAR | ALOX5 |
| MPI | E2F2 | USP48 | VAMP3 |
| PKP4 | SIPA1L2 | WDR8 | DEFB122 |
| PATZ1 | ZNF561 | H1FX | 231934_PM_at |
| CCL5 | FAM113B | KLHL36 | 214731_PM_at |
| GTF2H2 | CDC42 | GRPEL1 | SUPT7L |
| PMM1 | TNPO3 | APITD1 | TOX |
| AHNAK | DUSP7 | NEK9 | PTEN |
| SH3BGRL | 1569528_PM_at | ZNF524 | SAMM50 |
| 1560926_PM_at | RPL18A /// RPL18AP3 | LPP | 241508_PM_at |
| ASH1L | NDUFC2 | MARCKSL1 | TPI1 |
| RBM3 | SHISA6 | NSFL1C | ZNF580 |
| NPM3 | ADAM10 | GLYR1 | 1569727_PM_at |
| 1561872_PM_at | ATL1 | ATP11B | 235959_PM_at |
| DGCR6L | NSFL1C | ZNF37BP | ASPH |
| TSC22D3 | NVL | TBL1Y | RPRD2 |
| POLR2C | COX2 | YWHAZ | USP28 |
| MIPEP | 1560868_PM_s_at | PRPF19 | 239571_PM_at |
| FKBP5 | C1orf128 | 1565894_PM_at | LAT /// SPNS1 |
| POLR3K | MED19 | RPS19 | EIF4E3 |
| TSC22D3 | MXD4 | 1564107_PM_at | CDS2 |
| CALM3 | TMEM179B | RASSF4 | CXorf40B |
| NUFIP2 | 243659_PM_at | ECHDC3 | TMEM161B |
| NCR3 | PREPL | N4BP2L1 | MRPL42 |
| UBE4B | PSEN1 | OLAH | C22orf32 |
| KCNK17 | HIRIP3 | HDAC4 | PIK3CA |
| TMEM69 | PRO2852 | KCNJ15 | HEY1 |
| 1557852_PM_at | MRPS24 | PRKAR2A | TTBK2 |
| RNASEH2C | NAF1 | CYSLTR1 | NAMPT |
| AGPAT1 | 241219_PM_at | 1559020_PM_a_at | AHDC1 |
| 1565614_PM_at | 241993_PM_x_at | TMEM48 | LYST |
| MED27 | TOM1L2 | PHC1 | 1559119_PM_at |
| PRPF6 | LYST | CABIN1 | 242611_PM_at |
| NDUFB6 | 242407_PM_at | OCIAD1 | PATL1 |
| SORL1 | LIMK2 | CCR2 | FAM82A2 |
| PATL1 | IL2RB | WDR48 | HSPA4 |
| 242480_PM_at | ADI1 | UBE2G1 | RHOF |
| 221205_PM_at | C12orf76 /// LOC100510175 | MLL4 | 240240_PM_at |
| UBE2D3 | PNPLA4 | ETV6 | GABRR2 |
| MBOAT2 | HIST1H1T | CENPB | AFG3L2 |
| ZNF576 | GOSR2 | EP400 | RGS14 |

TABLE 1d-continued

The gene list of all 4132 genes analyzed in the 3-Way AR, ADNR TX ANOVA Analysis (using the HT HG-U133 + PM Array Plates)

| | | | |
|---|---|---|---|
| U2AF1 | VSIG4 | 1560625_PM_s_at | SKP2 |
| U2AF1 | RPL23AP32 | KDM5A | SH3BGRL |
| TKTL1 | APC | CIAPIN1 | BEX4 |
| 240960_PM_at | MRPL12 | CEP170 /// CEP170P1 | PNPO |
| 243546_PM_at | SGSM3 | CASP2 | 239759_PM_at |
| IL6ST | LRP10 | ZNF696 | TMEM229B |
| PON2 | MMP8 | CFLAR | 1556043_PM_a_at |
| 213945_PM_s_at | ICMT | PLSCR3 | 241441_PM_at |
| LOC339290 | PACSIN2 | PDE7B | FPGS |
| CCL5 | DSTNP2 | C5orf4 | NR1I3 |
| C11orf83 | NFATC2IP | ELAC1 | DR1 |
| 243072_PM_at | ATP5D | SAMSN1 | POLA2 |
| 1559154_PM_at | FASTK | ZNF23 | ENSA |
| 215109_PM_at | ZBTB11 | SUMO3 | RGS10 |
| C5orf41 | PPP1R3B | MRPS12 | PDE6D |
| EGLN2 | 239124_PM_at | ZDHHC24 | PSMB5 |
| 1568852_PM_x_at | PLD4 | GLTPD1 | NDNL2 |
| UGP2 | NSUN4 | RBMX2 | CHD6 |
| TMEM141 | ARPC5L | ACRBP | RUVBL2 |
| KLRAQ1 | 242926_PM_at | NHP2 | MAP3K7 |
| MGEA5 | PEX7 | GNAQ | 242142_PM_at |
| C14orf118 | 226146_PM_at | C10orf46 | 240780_PM_at |
| KLHL8 | HIC1 | CRKL | LOC729082 |
| RERE | ANKRD11 | C6orf26 /// MSH5 | 241786_PM_at |
| CIAO1 | TNFRSF21 | FAM104A | ROBLD3 |
| SEC61B | ZMYM6 | TWISTNB | GSTO1 |
| INPP5D | 239901_PM_at | FAM50B | PDZD7 |
| SRI | IL12RB1 | TMEM201 | EIF3F |
| PATZ1 | KPNB1 | SNX13 | PSEN1 |
| 241590_PM_at | NCOA2 | PTPN9 | DUSP14 |
| ADAM17 | 238988_PM_at | MMACHC | GPBP1L1 |
| LAT2 | THOC4 | SAV1 | CASP4 |
| MUDENG | F2R | CUL4B | PTENP1 |
| ANAPC11 | FGD4 | RBBP6 | CLCN7 |
| ASB8 | ABCF2 | 232478_PM_at | DOCK11 |
| TPCN2 | DDX28 | SFXN3 | PECAM1 |
| SNX27 | ATG2B | GATAD2A | FLOT1 |
| 238733_PM_at | PTPMT1 | MLYCD | 243787_PM_at |
| ALDH9A1 | PSME3 | BAT4 | TPM4 |
| TBL1XR1 | RASSF4 | PLA2G12A | OLAH |
| FAM126B | ZNF598 | C7orf28B /// CCZ1 | 233270_PM_x_at |
| ATF6B | NEDD9 | TK2 | CHAF1A |
| CHCHD10 | 230123_PM_at | UHMK1 | MRFAP1 |
| MYLIP | ARIH2 | NCRNA00094 | GATM |
| NENF | NDUFB9 | WNK2 | TXNIP |
| UQCR10 | SMAD4 | TAOK3 | IL28RA |
| TGIF2 | PIK3AP1 | ALMS1 | AVIL |
| BCL7B | MRPL14 | HBA1 /// HBA2 | ACTG1 |
| EP400 | GFER | CASP2 | LOC645166 |
| RFX3 | TELO2 | PFKFB2 | MRPS10 |
| NCR3 | C9orf23 | ENTPD1 | ANKZF1 |
| CHCHD8 | RFTN1 | SRSF5 | PDGFA |
| RAB5C | 215392_PM_at | SMARCA4 | 217521_PM_at |
| 244772_PM_at | GUCY1A3 | LOC401320 | PHAX |
| 222303_PM_at | CCDC123 | 238619_PM_at | TTLL3 |
| SART3 | PFDN1 | PHTF2 | PPIL4 /// ZC3H12D |
| WWC3 | 235716_PM_at | MKLN1 | URM1 |
| 240231_PM_at | FAM173A | DHX40 | TSFM |
| AKAP17A | PTGDS | GADD45GIP1 | ST7L |
| ZFP91 | 229249_PM_at | 233808_PM_at | 235917_PM_at |
| 239809_PM_at | TET3 | KIF3B | SAAL1 |
| 235841_PM_at | PON2 | 1562669_PM_at | PDE6D |
| ATP5G3 | 242362_PM_at | STX7 | HNRNPD |
| CCDC107 | COX5A | LYRM4 | ASCL2 |
| GPX1 | C20orf30 | NUDT4 /// NUDT4P1 | KREMEN1 |
| RHOC | C19orf53 | P2RY10 | CD163 |
| VPS13B | GTF3C5 | TES | TMEM43 |
| TNPO1 | DEF8 | PRDX1 | TRGV5 |
| IL1R2 | SPTLC2 | ITCH | C11orf31 |
| DNMT3A | KLF12 | CX3CR1 | 243229_PM_at |
| C17orf90 | TROVE2 | MOBKL2A | KIAA0748 |
| C19orf52 | RABGAP1L | NUCKS1 | C8orf33 |
| CYTH2 | EMB /// EMBP1 | C8orf42 | FBXO9 |
| MYLIP | CCNK | FBXL12 | CMTM6 |
| CORO1B | 237330_PM_at | PID1 | KLRB1 |
| JMJD4 | UBTF | TNFSF8 | ANXA4 |
| UGGT1 | 239474_PM_at | NOL7 | TMEM64 |

TABLE 1d-continued

The gene list of all 4132 genes analyzed in the 3-Way AR, ADNR TX ANOVA Analysis (using the HT HG-U133 + PM Array Plates)

| | | | |
|---|---|---|---|
| YIF1A | ELF2 | SLC29A3 | HNRNPUL2 |
| 233010_PM_at | LOC550643 | PIGP | 241145_PM_at |
| CHD7 | PDE4A | C5orf41 | 238672_PM_at |
| MBNL1 | CUTA | HLA-E | PHF21A |
| TXNIP | NSFL1C | MDM2 | 232205_PM_at |
| DPP3 | 1569238_PM_a_at | IRAK3 | MDM4 |
| GLE1 | DNAJC30 | ELK1 | TFAP2E |
| NCRNA00094 | PLA2G12A | IDH3A | 243236_PM_at |
| 232307_PM_at | RPS15A | GMPPB | DUSP5 |
| ELOVL5 | CTSC | TFCP2 | CD36 |
| CNO | 229548_PM_at | 1557238_PM_s_at | DGCR14 |
| CDV3 | ABHD6 | ZDHHC19 | INF2 |
| MDH2 | RBMS1 | 232726_PM_at | ITGB2 |
| RHOF | PSMB6 | 244356_PM_at | RIOK3 |
| STK17B | SCFD2 | HECW2 | RALBP1 |
| 240271_PM_at | SMARCC2 | 1557633_PM_at | TBRG1 |
| KLF9 | CISH | 243578_PM_at | CYHR1 |
| 237881_PM_at | ADAM10 | DLEU2 | BMP1 |
| ANKHD1 | GPBP1L1 | LOC285830 | PLBD1 |
| DENND1B | UBE2D2 | RPAIN | NOL3 |
| NSFL1C | HIATL2 | SP1 | SFRS18 |
| RAB6A | 232963_PM_at | SLC2A4RG | BID |
| N4BP2L2-IT | 233867_PM_at | 242865_PM_at | MRI1 |
| 240867_PM_at | PRR14 | DDX51 | STS |
| COMMD5 | 1568903_PM_at | 242232_PM_at | 234578_PM_at |
| PSMD6 | PPP1R7 | 233264_PM_at | SNX3 |
| AKAP10 | ARL2BP | ECE1 | ARNTL |
| NCKAP1L | IKBKB | SF3A3 | UTP20 |
| IQGAP1 | CYC1 | NUP50 | GPCPD1 |
| BTF3 | ZNF644 | RSRC1 | PRKAB2 |
| C5orf22 | NUDT4 | CR1 | 1556518_PM_at |
| MAPRE2 | AES | ALG14 | 233406_PM_at |
| 236772_PM_s_at | ZC3H7B | TRBC1 | PITRM1 |
| 240326_PM_at | LHFPL5 | MAP3K2 | TMEM64 |
| LOC100128439 | REPS1 | RNF24 | TRIOBP |
| 7-Mar | EWSR1 /// FLI1 | 238902_PM_at | LFNG |
| RSBN1L | LOC100271836 /// LOC641298 | AGAP2 | PAM |
| ARRB1 | DDX28 | BAZ1A | MON1B |
| PAOX | N4BP2L2 | 236901_PM_at | NDUFB8 /// SEC31B |
| ZDHHC17 | RASSF7 | TCTN3 | HIST1H4C |
| ZNF394 | 242461_PM_at | ACRBP | STX11 |
| C22orf32 | YWHAB | WDR61 | 235466_PM_s_at |
| PELI1 | KIAA1267 | UBA7 | MRPL9 |
| 236558_PM_at | PABPC1 /// RLIM | SH2D2A | 1562982_PM_at |
| TMED9 | 233315_PM_at | CSF2RA | ATF2 |
| 238320_PM_at | SMAP1 | PRPF31 | TIMM17A |
| NLRP1 | LOC100190939 | NF1 | ZNF641 |
| GPR137B | MED13 | 229668_PM_at | DNAJC4 |
| NDUFA8 | LOC100127983 | CHCHD1 | ASXL2 |
| POLR2C | PREX1 | TAOK2 | FBXO16 /// ZNF395 |
| FAM118B | PAIP2 | MGMT | DPY19L4 |
| ASAH1 | 232952_PM_at | 1566201_PM_at | NBR1 |
| MRPL10 | STS | ATPBD4 | 237588_PM_at |
| TTYH2 | UBE2D3 | MFNG | NUDT16 |
| HECA | MRPS25 | HIPK3 | FAM65B |
| COX3 | LOC100133321 | SPAG9 | XIRP1 |
| REST | PUSL1 | 243888_PM_at | BECN1 |
| 242126_PM_at | ZDHHC24 | C10orf58 | RNF126 |
| ARRB1 | 234326_PM_at | RSRC2 | ZNF207 |
| RBBP9 | WWC3 | FAM86B2 /// FAM86C /// LOC645332 /// LOC729375 | DNAH1 |
| STX16 | 216756_PM_at | CD160 | C10orf78 |
| 232095_PM_at | 229670_PM_at | AK2 | YY1 |
| C19orf33 | RAB30 | LOC100128590 | 223860_PM_at |
| CISD3 | CNOT2 | PABPC3 | CRADD |
| PFAS | MAPK7 | UPF1 | 229264_PM_at |
| FLJ31306 | WDR48 | LAMA3 | 1568449_PM_at |
| TBC1D7 | 241692_PM_at | RASSF5 | LARP1B |
| MDM2 | PSMC2 | 1570165_PM_at | LSG1 |
| GSTZ1 | 243178_PM_at | SAP30L | 1563092_PM_at |
| 222378_PM_at | C6orf129 | FDX1 | ADO |
| KLHDC10 | 1562289_PM_at | UBE2J1 | NFATC1 |
| PPFIA1 | CALM1 | PRSS33 | PHPT1 |
| C1orf122 | MYO1C | MBD3 | POP4 |
| 244026_PM_at | HSBP1 | COX4NB | 244536_PM_at |

TABLE 1d-continued

The gene list of all 4132 genes analyzed in the 3-Way AR, ADNR TX ANOVA Analysis (using the HT HG-U133 + PM Array Plates)

| | | | |
|---|---|---|---|
| RANBP9 | EFEMP2 | DYRK1B | STOML1 |
| 241688_PM_at | UBE2E2 | TUFM | SSH2 |
| NDUFB10 | 233810_PM_x_at | PDLIM2 | ZDHHC16 |
| LIMS1 | PDIA3 | PSMD9 | OAT |
| C17orf106 | 241595_PM_at | BCL7A | RAB34 |
| 242403_PM_at | 229841_PM_at | PSMA5 | SEC61G |
| GSK3B | RWDD2B | RAD52 | LOC221442 |
| KBTBD2 | NDST2 | VAV3 | GNL2 |
| ARF5 | TFAM | TAAR8 | PACS1 |
| LCOR | 235592_PM_at | 227501_PM_at | CACNB1 |
| 238954_PM_at | C1orf50 | ADAM22 | MAP4K4 |
| 1565975_PM_at | MIA3 | MCL1 | LRRC14 |
| WIBG | RPS4X /// RPS4XP6 | BCL2L11 | C11orf31 |
| OPRL1 | ZBTB7A | TRPM6 | BCKDHB |
| C11orf31 | 237396_PM_at | 215147_PM_at | LOC728903 /// MGC21881 |
| 241658_PM_at | USP8 | NANP | NUMB |
| ZC3HAV1 | E2F3 | ONECUT2 | PPP1R15A |
| SLC9A3R1 | CYTH3 | RHOH | MALAT1 |
| YLPM1 | EXOC6 | PIK3R2 | INO80D |
| LRRFIP1 | MDM2 | R3HDM1 | SNX24 |
| PRDX6 | 239775_PM_at | TMEM107 | RBMX2 |
| FOXO3 /// FOXO3B | C15orf63 /// SERF2 | ZNF395 | 244022_PM_at |
| 230970_PM_at | LCP2 | ITM2A | TOMM22 |
| ACAA2 | CRY2 | PHYH | FLJ12334 |
| FXR2 | GGA2 | XPA | 232113_PM_at |
| ILF3 | CCL5 | DDR2 | VPS13B |
| ANKLE2 | HOPX | SEC11A | CSHL1 |
| 1560271_PM_at | CPEB4 | DVL1 | MLL3 |
| GNS | AGER | PREB | PSMA1 |
| SRSF9 | C1orf151 | SUB1 | MED21 |
| AP1S1 | FRYL | TSEN15 | C20orf11 |
| SPCS1 | CMTM5 | ECHDC1 | CRYZL1 |
| PADI4 | C7orf30 | 227384_PM_s_at | ORC5 |
| MEF2A | HIST1H4J | KCNE3 | SLC16A3 |
| IL21R | LOC100129195 | ACTG1 | MRAS |
| EDEM3 | NAT6 | SNORA28 | N4BP2L2 |
| C7orf30 | 216683_PM_at | WTAP | TSN |
| CHMP4A | SERPINB5 | MED31 | NUDC |
| MRPL52 | TRD@ | COMTD1 | OCEL1 |
| SRSF1 | RBM43 | JMJD4 | LOC441461 |
| ARFGEF1 | FLOT2 | SFRP1 | 223409_PM_at |
| MAN1A1 | BOLA3 | PPP3R1 /// WDR92 | 1557796_PM_at |
| VAPA | 237442_PM_at | QDPR | LOC284009 |
| TGFBR2 | HLA-E | RPL23 | MLANA |
| 232472_PM_at | LOC648987 | HMOX1 | PTP4A3 |
| GNB5 | RICTOR | NINJ1 | CX3CR1 |
| MYLIP | ARID4B | C9orf19 | TMEM53 |
| GTF2A2 | ANKRD57 | PSMF1 | PWP1 |
| ZNF688 | DNAJB6 /// TMEM135 | RNF17 | MRPL18 |
| ATP6 | PPTC7 | CATSPERG | PTAR1 |
| RNF14 | MRPL16 | 222315_PM_at | DPY30 /// MEMO1 |
| NCRNA00116 | LSM2 | KCNE3 | SPATA2L |
| PIK3R5 | COX5B | FNIP1 | FAM82B |
| ARFGEF1 | COX5B | ZNF80 | BTF3 |
| C1orf63 | HSD17B10 | ANKS1A | ZNF638 |
| ATP2A3 | COX19 | ATP5SL | 216782_PM_at |
| EIF4A2 | CRK | 239574_PM_at | SUGT1 |
| ND2 | NOP16 | 1555977_PM_at | MBP |
| PITPNC1 | ZBTB40 | RNF5 | LOC100507192 |
| SFSWAP | HIGD2A /// LOC100506614 | 236679_PM_x_at | KCTD20 |
| FKBP15 | CRIPAK | BLVRB | SCAMP1 |
| ZNF238 | C1orf128 | 232406_PM_at | B3GALT6 |
| MAZ | QRSL1 | LOC100134822 /// LOC100288069 | TRAPPC4 |
| NUPL1 | TMEM107 | RTN4IP1 | SBF2 |
| 220691_PM_at | MTMR11 | HIBADH | FANCF |
| CDKN1C | GLUL | C14orf167 | GRPEL1 |
| C9orf69 | COPB1 | CYP19A1 | ATP8B1 |
| SMAP2 | RASA4 /// RASA4B /// RASA4P | 239570_PM_at | ZNF24 |
| ACSL1 | FBXL21 | VAPB | SPECC1 |
| MBD4 | RALGDS | SDHAF2 | CHD1L |
| FCER1A | PTPRCAP | 1556462_PM_a_at | POP5 |
| 241413_PM_at | NSUN4 | 242995_PM_at | 1564154_PM_at |
| 240094_PM_at | UROD | ACVR1B | LOC728392 /// NLRP1 |

TABLE 1d-continued

The gene list of all 4132 genes analyzed in the 3-Way AR, ADNR TX ANOVA Analysis (using the HT HG-U133 + PM Array Plates)

| | | | |
|---|---|---|---|
| DPM3 | 1560230_PM_at | C12orf57 | SSNA1 |
| 236572_PM_at | FCAR | 231111_PM_at | FRG1 |
| ATP11A | 1564733_PM_at | C1orf58 | DCAF7 |
| SASH3 | NRD1 | TPM4 | 237586_PM_at |
| MRPS18B | FAM110A | CPEB3 | 240123_PM_at |
| 231258_PM_at | NUDT16 | 241936_PM_x_at | NUP37 |
| PIAS2 | MTMR10 | QDPR | AIF1 |
| LGALS3 | XRCC5 | CPD | PRKAR1A |
| 2-Sep | DAB2 | RSRC1 | 238064_PM_at |
| 239557_PM_at | GTF3C6 | CHCHD2 | TEX264 |
| IVD | DHX30 | HBB | TMEM41A |
| 236495_PM_at | SENP5 | LPAR1 | RAB4A |
| RBKS | SAMHD1 | SHMT2 | TAF9B |
| DPP3 | SSR2 | NID1 | RBMS1 |
| ABHD6 | 1556007_PM_s_at | 239331_PM_at | 239721_PM_at |
| SLC12A9 | DYNLRB1 | 241106_PM_at | MBD4 |
| 1565889_PM_at | CCDC93 | WDR61 | RAB6A |
| OTUB1 | C1orf77 | ACACB | KIAA0319L |
| 243663_PM_at | ZNF70 | MRP63 | MKKS |
| FAM96B | TNFAIP8L1 | TNFRSF10A | PMVK |
| LOC100130175 | EML2 | SERBP1 | STK36 |
| LOC401320 | MCTP2 | CYB5R3 | VNN2 |
| CHD4 | 227505_PM_at | ZNF384 | RBBP4 |
| 242612_PM_at | TSPAN32 | 1563075_PM_s_at | FAM192A |
| RPS26 | 214964_PM_at | EVL | IKBKE |
| PDCD2 | 236139_PM_at | LPIN2 | 216813_PM_at |
| NCRNA00275 | QKI | ZNRD1 | MRPL24 |
| SLC2A8 | WBP11 | FLJ38717 | ZNF75D |
| RLIM | EXOSC6 | DND1 | 1566680_PM_at |
| MRPL20 | DNAJC10 | ACLY | 242306_PM_at |
| STK38 | PLCL2 | CSN1S2AP | CSGALNACT1 |
| 242542_PM_at | BOLA2 /// BOLA2B | 236528_PM_at | 242457_PM_at |
| PIK3C3 | 236338_PM_at | ARHGAP26 | SNW1 |
| 1560342_PM_at | MAPK1 | SPG20 | PPARA |
| TRA2A | 243423_PM_at | C10orf93 | RUFY3 |
| UBE2B | 240137_PM_at | 236005_PM_at | SEC61A1 |
| UBE2D3 | 244433_PM_at | COQ4 | SUMO2 |
| SRSF4 | FBXO9 | GTPBP8 | 242857_PM_at |
| PPP6R3 | IL13RA1 | LOC148413 | NCOA2 |
| TIGIT | FBXO38 | 1565913_PM_at | CANX |
| ASB2 | IMMP2L | RIN3 | ZNF561 |
| RHOT1 | 242125_PM_at | C15orf28 | ISYNA1 |
| LAMP1 | SEMA4D | 239859_PM_x_at | VHL |
| ATP2A3 | RTN4 | 242958_PM_x_at | KRI1 |
| FAM13AOS | GDI2 | FLJ44342 | PDCD6IP |
| ZBTB4 | ATXN7L1 | 240547_PM_at | DNAJC17 |
| SELPLG | STK35 | C9orf16 | GDAP1L1 |
| 233369_PM_at | SRGAP2 | GAS7 | EIF4EBP1 |
| FLJ39582 | 1557637_PM_at | ZNF148 | 215369_PM_at |
| 233876_PM_at | FAM174B | TMEM5 | GPRIN3 |
| NSMAF | 238888_PM_at | FAM126B | C17orf63 |
| PPP1R2 | ALG13 | CSNK2B /// LY6G5B | STAU1 |
| BTF3 | USF2 | ASAP2 | ZNF439 |
| 1560706_PM_at | ADAMTS2 | ZNF407 | CSTB |
| 236883_PM_at | CABIN1 | GLI4 | RBM47 |
| FAM98B | TCP11L2 | AKAP13 | 240497_PM_at |
| HP1BP3 | RBM25 | ZBTB16 | TADA2B |
| CELF2 | 233473_PM_x_at | 1557993_PM_at | MRPS6 |
| COPG2 | HIST1H1T | TTF1 | HEATR6 |
| ZNF148 | SNCA | NUDT10 | MLL3 |
| DNAJC3 | 229879_PM_at | COQ4 | MDH1 |
| C17orf59 | SLC24A6 | GLT25D1 | SELENBP1 |
| POLR2I | PXK | IKZF2 | SLC7A6OS |
| UBE2H | TAGAP | GCNT7 | MTMR11 |
| LPAR2 | ATP5G1 | GPATCH2 | NFATC2 |
| TNPO1 | AKT2 | NMT2 | 244373_PM_at |
| CCDC97 | SLC8A1 | ADHFE1 | NOLC1 |
| KCTD5 | DIP2B | ZNF784 | C3orf21 |
| 238563_PM_at | MKRN1 | CYBASC3 | SIPA1L2 |
| RNF4 | MAL | BAT2 | HDDC3 |
| HBB | ZKSCAN1 | APP | SBK1 |
| TMCO3 | ATF7IP | 241630_PM_at | PFDN2 |
| 239245_PM_at | C1orf174 | MRPL45 | DPY19L1 |
| CDK5RAP1 | TAGAP | TMEM161A | MYL6 |
| FAM43A | LSS | 240008_PM_at | ZNF703 |
| ATP5S | 1565701_PM_at | AGTRAP | RBM47 |
| LRCH4 | 1560332_PM_at | 234164_PM_at | CD226 |

TABLE 1d-continued

The gene list of all 4132 genes analyzed in the 3-Way AR, ADNR
TX ANOVA Analysis (using the HT HG-U133 + PM Array Plates)

| | | | |
|---|---|---|---|
| ANKFY1 | CAPZA2 | 241152_PM_at | ORM1 |
| STK32C | COX6A1 | HBA1 /// HBA2 | 1560246_PM_at |
| TMCO3 | SNORA37 | TMX4 | 242233_PM_at |
| IL21R | CSTF1 | TNFSF4 | ZNF398 |
| LOC100506902 /// ZNF717 | EXPH5 | 243395_PM_at | PIKFYVE |
| NDUFB11 | CD74 | NOL7 | LRP6 |
| FAM193B | NPY2R | 236683_PM_at | C9orf86 |
| BCL6 | ATP13A3 | TNRC6B | SHISA5 |
| C6orf106 | GIGYF2 | UFM1 | MCTP2 |
| C14orf138 | MAP4K4 | FH | LOC100128071 |
| FAM65B | THAP7 | ESYT1 | PRSS23 |
| 1569237_PM_at | ACP1 | LGALS1 | C1orf212 |
| 231351_PM_at | SLC22A17 | 238652_PM_at | NDN |
| GATAD2B | DLEU2 /// DLEU2L | DIMT1L | TBC1D22A |
| NDUFS6 | BBX | TRIM66 | 242471_PM_at |
| GRAP | ESD | MTPN | LOC146880 |
| KLF6 | FAM49B | SNRNP27 | MYOC |
| SLC6A6 | CARS | FAIM3 | SMOX |
| GHITM | PLEC | TTC39C | MBD2 |
| FLT3 | ENTPD1 | RBL2 | JMJD6 |
| 1566257_PM_at | LOC285370 | CHMP1A | ACTR2 |
| FKBP2 | PRDX6 | UQCRB | 1562383_PM_at |
| HPS1 | CBX6 | ERCC8 | GPM6A |
| 229673_PM_at | C1orf21 | CCNB1IP1 | LOC284751 |
| SGCB | ORMDL3 | CC2D1B | 239045_PM_at |
| HGD | RHBDD2 | 241444_PM_at | TFCP2 |
| 229571_PM_at | LSG1 | NRG1 | 237377_PM_at |
| KIF5B | DNAJC30 | JAGN1 | COPZ1 |
| CSAD | ENTPD4 | RAF1 | ATP8B4 |
| MBP | PCMT1 | FAM181B | AMZ2P1 |
| HBB | COX2 | 1561915_PM_at | PARL |
| CTSZ | TIMM13 | SH3GLB1 | PROSC |
| AFF4 | CAPRIN1 | TMF1 | C1orf85 |
| RBM6 | TASP1 | SSRP1 | CISD1 |
| PGLS | 1558588_PM_at | IGF2R | COPA |
| FKBP5 | ZCRB1 | EPRS | ZBTB4 |
| 244048_PM_x_at | SNAP23 | IGLON5 | 1558299_PM_at |
| 2-Sep | FLJ33630 | UQCRB | ZNF333 |
| P4HB | ACPP | HUS1 | SPOPL |
| PFDN6 | CNST | STX16 | DUSP28 |
| ARL16 | SLC8A1 | LOC100287227 | PDZD8 |
| ABHD5 | CDK3 | 237710_PM_at | GPR27 |
| SCFD2 | A1BG | RBM22 | TMEM30A |
| ITPA | 243217_PM_at | LOC100286909 | RPL23A |
| 236889_PM_at | 1557688_PM_at | UBIAD1 | C20orf196 |
| 236168_PM_at | SLC8A1 | SNTB2 | 238243_PM_at |
| TMED3 | ARHGEF40 | CTBP1 | NOP16 |
| RARS2 | TMEM134 | EIF2B1 | SNAP23 |
| PALLD | PLA2G7 | C12orf75 | ZNF542 |
| RALGAPA2 | 216614_PM_at | 243222_PM_at | SSR1 |
| RP2 | SERINC3 | CASC4 | 5-Mar |
| FAM162A | PRPF18 | CTSO | C1orf151 |
| PTGER4 | RNF144B | ETFB | DDX10 |
| ASPH | ZCCHC6 | SOCS2 | RBM3 |
| SPTLC1 | 1564568_PM_at | 220711_PM_at | NUDT3 |
| MAP3K3 | SAFB | TTC12 | 234227_PM_at |
| 234151_PM_at | CD163 | TRAPPC2 /// TRAPPC2P1 | UBL5 |
| PSMB10 | CCNL2 | ALS2 | GUSBP1 |
| INSIG1 | DLEU2 | COX17 | 1559452_PM_a_at |
| ASPH | FLJ14107 | ABHD15 | MSH6 |
| 1565598_PM_at | EML2 | ZFYVE27 | BAGE2 /// BAGE4 |
| PEBP1 | 244474_PM_at | TNRC6B | MIDN |
| CXorf40A | NOP16 | ADPRH | LONP2 |
| 239383_PM_at | CLPTM1 | ANKRD36 | PPM1L |
| AKIRIN2 | LOC285949 | IDH2 | ZNF608 |
| 240146_PM_at | 1563076_PM_x_at | TP53TG1 | HAX1 |
| BMP2K | CXorf40A /// CXorf40B | FCGR2C | GIMAP1 |
| 240417_PM_at | THAP11 | FAM13A | ISCA1 |
| SH2D1B | 1565888_PM_at | 1565852_PM_at | 215204_PM_at |
| FBXO25 | BNC2 | JMJD8 | C1orf25 |
| GRB10 | RNF214 | TRIM46 | RNASEH2B |
| 1558877_PM_at | 235493_PM_at | PDE8A | TCP1 |
| KIAA1609 | MUSTN1 | MTMR3 | RAP1GDS1 |
| C2orf18 | SRPK2 | DNAJC8 | GP5 |
| CMTM8 | COMMD7 | CCNL1 | 228734_PM_at |

TABLE 1d-continued

The gene list of all 4132 genes analyzed in the 3-Way AR, ADNR TX ANOVA Analysis (using the HT HG-U133 + PM Array Plates)

| | | | |
|---|---|---|---|
| RNPEPL1 | CLCN3 | TMEM204 | UBB |
| TMEM160 | C11orf48 | WDR1 | SMARCB1 |
| GRB10 | RBM15B | GPER | 236592_PM_at |
| LOC100129907 | 227479_PM_at | C11orf31 | NCRNA00202 |
| DGCR6 /// DGCR6L | BMPR1B | TMEM191A | C5orf30 |
| MRPS18A | CD163 | APOOL | ARF1 |
| PCGF3 | CHN2 | 242235_PM_x_at | SLC41A3 |
| DCTPP1 | 243338_PM_at | SBK1 | FGFBP2 |
| 244732_PM_at | EPS15L1 | 240839_PM_at | ITCH |
| 2-Sep | CHCHD5 | 231513_PM_at | PACSIN1 |
| SERBP1 | ZNF689 | C1orf144 | DUSP1 |
| C19orf56 | ARL6IP4 | C22orf30 | HAVCR1 |
| ING4 | ETFA | HMGN3 | 242527_PM_at |
| LSMD1 | WDR61 | TEX10 | ATF6B |
| ADPRH | MRO | C1orf27 | TRAF3IP3 |
| C7orf68 | ZNF169 | FKBP1A | TGFBR3 |
| CACNA2D4 | MYST3 | ATP6V1C1 | ICAM4 |
| EXOSC7 | GATAD1 | DLEU2 | 242075_PM_at |
| CCND3 | RAB9A | 1564077_PM_at | C5orf4 |
| TLR2 | FAM120C | PRNP | AMBRA1 |
| TRABD | C7orf53 | RPL15 | AHCY |
| AKR7A2 | RGS10 | HCFC1R1 | RNF14 |
| 231644_PM_at | RYBP | SERPINE2 | UEVLD |
| ACP5 | CD247 | NFKBIA | RGS10 |
| 239845_PM_at | TRADD | 232580_PM_x_at | ENO1 |
| ARHGAP26 | 239274_PM_at | ME2 | SLC16A6 |
| MCAT | CBX5 | TNF | GTPBP6 /// LOC100508214 /// LOC100510565 |
| NUCKS1 | STAT6 | H2AFY | APOOL |
| LRCH4 /// SAP25 | HEATR2 | PSME1 | KLF4 |
| LOC100131015 | GUSBP3 | WHAMML2 | MS4A7 |
| CFLAR | 243992_PM_at | FLJ38109 | DRAP1 |
| MIF4GD | UCKL1 | TAP2 | 244607_PM_at |
| RBCK1 | DYRK4 | C6orf89 | 232615_PM_at |
| PTPRO | NGLRAP1 | PSMA3 | 236961_PM_at |
| 227082_PM_at | PPP2R5E | 1557456_PM_a_at | 1563487_PM_at |
| 241974_PM_at | SNCA | 1559133_PM_at | EGLN3 |
| TMEM102 | 1555261_PM_at | IFNGR1 | 239793_PM_at |
| IL13RA1 | PPP1R16B | ZNF397 | RBBP7 |
| LOC100506295 | SPATA7 | FAHD2A | PLDN |
| LOC100510649 | HEXB | MPZL1 | PSMG4 |
| MRPS34 | 240145_PM_at | MOBKL2C | WIPF2 |
| RPP21 /// TRIM39 /// TRIM39R | ABCB7 | DPY19L1 | ALG3 |
| KIL22 | NAT8B | SRD5A1 | ZSWIM1 |
| 241114_PM_s_at | AKAP10 | SEMA4C | SSX2IP |
| STAT6 | 243625_PM_at | DCTN6 | BSG |
| RNF113A | CRYL1 | E2F2 | 242968_PM_at |
| RPP38 | CDADC1 | CDC42SE1 | DNAJB4 |
| 1559362_PM_at | PBX2 | 240019_PM_at | PWP2 |
| INO80B /// WBP1 | SERINC3 | 244580_PM_at | 243350_PM_at |
| NLRP1 | TP53 | 227333_PM_at | SCP2 |
| 239804_PM_at | 240984_PM_at | MEAF6 | TOX2 |
| CDKN1C | 1556769_PM_a_at | FCF1 /// LOC100507758 /// MAPK1IP1L | QKI |
| C19orf70 | ADCK2 | PNN | AIF1L |
| INSIG1 | IMPACT | ZNL395 | 242901_PM_at |
| COG1 | GLTP | 243107_PM_at | 240990_PM_at |
| EIF5 | CMTM4 | 242117_PM_at | RPL14 |
| XCL1 /// XCL2 | 1563303_PM_at | GNL1 | GTF3C1 |
| ARHGAP27 | LOC100509088 | C2orf88 | NCKAP1 |
| SNHG7 | TMEM189-UBE2V1 /// UBE2V1 | HIST1H4J /// HIST1H4K | PPAPDC1B |
| LIMK1 | HMGB3 | TDRD3 | ATXN10 |
| BOLA1 | ZFAND2B | TRIP12 | SORT1 |
| 235028_PM_at | PTPRS | ANXA4 | NCAPH2 |
| SH3BP1 | CLCN5 | SNHG11 | TANK |
| PSMB4 | CHCHD3 | C17orf58 | SNRPA1 |
| PHTF1 | UQCRFS1 | PTEN | OSBPL3 |
| REM2 | MED8 | HRASLS5 | BPGM |
| EXOC6 | RPP30 | KRT10 | TNS1 |
| CELF2 | 1558048_PM_x_at | SLC46A2 | MRAS |
| FBXO38 | CXXC5 | 1562314_PM_at | IVD |
| TIMM23 /// TIMM23B | SETBP1 | SAC3D1 | PRTG |
| DNAJA4 | DNAJC10 | TRD@ | KLHL6 |
| 240638_PM_at | BZW1 | SRP72 | TTLL3 |

TABLE 1d-continued

The gene list of all 4132 genes analyzed in the 3-Way AR, ADNR
TX ANOVA Analysis (using the HT HG-U133 + PM Array Plates)

| | | | |
|---|---|---|---|
| HIGD2A | ZDHHC2 | 215252_PM_at | RHOBTB2 |
| 228151_PM_at | 237733_PM_at | ARHGDIA | MARK3 |
| FBXO33 | MBOAT2 | 224254_PM_x_at | C19orf60 |
| 1560386_PM_at | ETV3 | 215981_PM_at | CTSB |
| TMEM59 | FASLG | SLC43A3 | PRDM4 |
| MADD | SEPT7P2 | 1570281_PM_at | 1563210_PM_at |
| MDH2 | CHAF1A | DCAF7 | HNRNPUL2 |
| 1566959_PM_at | GSTK1 | 237341_PM_at | ARHGEF2 |
| NBR1 | RAB27B | ATP5O | DCPS |
| PHB | CXXC5 | TSPYL1 | DNAJA4 |
| RC3H2 | HCFC1R1 | DIS3L | ADCK2 |
| GTF2H2B | ZCCHC6 | 239780_PM_at | RPA1 |
| PIGU | KCTD6 | PPP1R15A | 216342_PM_x_at |
| C16orf58 | CSRP1 | NAALADL1 | DGKZ |
| IL21R | 234218_PM_at | ITGAM | 244688_PM_at |
| MRPL55 | JTB | CYTH4 | C1orf21 |
| NPFF | FARS2 | POLG | FASTKD3 |
| 6-Sep | 237018_PM_at | DCAF12 | 241762_PM_at |
| 237118_PM_at | PRKAR1A | RNF34 | TWIST2 |
| CXCL5 | HLA-DPA1 | C14orf128 | TPI1 |
| SLC25A26 | HBA1 /// HBA2 | A2LD1 | 239842_PM_x_at |
| 1555303_PM_at | 1556107_PM_at | LOC100505935 | FCHSD1 |
| 234604_PM_at | SYF2 | JMJD1C | 243064_PM_at |
| SLC2A6 | 238552_PM_at | SH3GLB1 | 239358_PM_at |
| TRA2A | NFIC | NDUFB2 | LANCL2 |
| SSSCA1 | 215846_PM_at | DNAJC8 | MDM2 |
| IFNGR1 | LEPROTL1 | ZNL792 | CD3D |
| HBG1 /// HBG2 | COX1 | DCAKD | TMPO |
| FAM162A | ZDHHC4 | RPL23A | SDHC |
| SORL1 | UXS1 | ALPK1 | SCD5 |
| HERC4 | NDUFB5 | MLAP3L | SLC4A11 |
| LPAR5 | 1558802_PM_at | RBM14 | YWHAB |
| POP4 | CCDC147 | ZNL330 | RPL28 |
| C14orf179 | 6-Sep | 238883_PM_at | DCXR |
| 232527_PM_at | CLC | RAB6A /// RAB6C | 6-Mar |
| PHF3 | 227571_PM_at | RAB8B | MAP3K7 |
| COX5A | CFLAR | RQCD1 | KPNA6 |
| 243858_PM_at | SDF2L1 | ABR | RFC3 |
| CLEC10A | CD3E | PLEK2 | SNRPD3 |
| 234807_PM_x_at | UBN2 | UFC1 | 242997_PM_at |
| CTBP1 | MRPS9 | TMX1 | PPIE |
| 9-Sep | 216871_PM_at | 241913_PM_at | HLA-DPA1 |
| GZMB | MPZL1 | 233931_PM_at | GLT8D1 |
| VPS24 | MTMR4 | 232700_PM_at | GPR56 |
| C1orf43 | NUP98 | ZNL638 | C12orf29 |
| IRS2 | TRRAP | ZBTB20 | HLA-G |
| PEX26 | USE1 | GUCY1A3 | ITPR2 |
| TP53RK | FKBP1A | VAMP3 | METTL6 |
| ZZEF1 | 238842_PM_at | MBP | MCL1 |
| XPNPEP1 | MAN2A2 | WWOX | 229569_PM_at |
| ATP6AP1 | PTMA | AFFX-M27830_M_at | GTF2H5 |
| TMED9 | CDK10 | 1557878_PM_at | DNAJC3 |
| PHF19 | SAMSN1 | NUB1 | C3orf78 |
| EIF5 | SNX5 | CBX3 | HLA-A /// HLA-F /// HLA-J |
| TRAPPC3 | AKAP8 | 233219_PM_at | ILF2 |
| 244633_PM_at | SERGEF | SLBP | TMED2 |
| RIPK1 | IGFL2 | COX15 | EPS8L2 |
| 243904_PM_at | NOB1 | PSPC1 | PLA2G6 |
| 1566166_PM_at | NME7 | LRRC8C | ERLIN1 |
| C2orf28 | CELF1 | 1566001_PM_at | JTB |
| CD84 | MRPL9 | PXK | CCND2 |
| MTA2 | CD3G | 1558401_PM_at | C11orf73 |
| NEAT1 | DHX35 | CHRAC1 | SSBP1 |
| TSTD1 | PDS5B | MGC16275 | LRRFIP1 |
| 236752_PM_at | FBXL17 | 1557224_PM_at | 241597_PM_at |
| MRPL49 | SLC39A4 /// SLC39A7 | 242059_PM_at | LUC7L |
| PLAGL2 | 223964_PM_x_at | MTIF2 | MRPL34 |
| VIPAR | NDUFB7 | PDHB | GUF1 |
| GSTK1 | LIMD1 | ACSL3 | 217379_PM_at |
| 241191_PM_at | THUMPD3 | ICAM2 | PRPSAP2 |
| THRAP3 | GNLY | EBLN2 | COPS6 |
| PTGDS | C12orf66 | LSS | YSK4 |
| SLC38A7 | HSD17B1 | 1563629_PM_a_at | BCL2L1 |
| RHOBTB3 | JTB | TARSL2 | CIRBP |
| LOC100507255 | 240217_PM_s_at | MBD6 | 1561644_PM_x_at |
| SRRM2 | PDLIM4 | QARS | SIPA1L3 |

TABLE 1d-continued

The gene list of all 4132 genes analyzed in the 3-Way AR, ADNR
TX ANOVA Analysis (using the HT HG-U133 + PM Array Plates)

| | | | |
|---|---|---|---|
| TANK | 237239_PM_at | 240665_PM_at | 1556492_PM_a_at |
| ZNF511 | FASTK | LOC400099 | 239023_PM_at |
| REPS2 | SRD5A1 | OPA1 | TMEM147 |
| ND6 | 1558695_PM_at | IFT81 | DKFZp667F0711 |
| 237456_PM_at | RICTOR | GATAD2A | ZNPHT2 |
| PI4KB | IFI27L2 | OLAH | CMTM3 |
| KLF6 | 1559156_PM_at | RAI1 | ELOVL5 |
| SNX3 | RASA2 | MAGED2 | GPSM3 |
| FXC1 | CYTH1 | C12orf5 | MOGS |
| 244010_PM_at | RBP4 | ARHGAP24 | MGC16384 |
| 1562505_PM_at | 215397_PM_x_at | RAB4A /// SPHAR | 1558783_PM_at |
| 237544_PM_at | 232047_PM_at | ICT1 | CDK11A /// CDK11B |
| C7orf26 | 1563277_PM_at | MED29 | C14orf64 |
| AP1S1 | MTCH2 | SLC25A38 | CPT1A |
| SRPK1 | TP53TG1 | SPTLC2 | COPS8 |
| RNF216 | HEXIM2 | CCNDBP1 | EPB41L5 |
| CFLAR | SSH2 | USP48 | KPNA2 |
| HBG1 /// HBG2 | C12orf62 | 242380_PM_at | APLP2 |
| 233239_PM_at | KRT81 | MRPL54 | ARHGEF40 |
| RAP2B | BAT4 | 225906_PM_at | PABPC1 |
| 1563958_PM_at | C19orf40 | HELQ | RALGPS1 |
| BCL6 | GNLY | NOTCH4 | DNAJB14 |
| NAA10 | CEP152 | HBA1 /// HBA2 | PSMA1 |
| LSM12 | 242875_PM_at | IL1RAP | COTL1 |
| 240636_PM_at | 239716_PM_at | SLC6A6 | RPS19 |
| NSMCE1 | 1559037_PM_a_at | CPT1A | TRIM41 |
| HADH | PHF21A | USP25 | 243469_PM_at |
| PPTC7 | PSMC5 | 216890_PM_at | INSR |
| 242167_PM_at | IL13RA1 | 236417_PM_at | TCEB2 |
| PHB2 | GPA33 | 239923_PM_at | NCOA2 |
| LPP | TMEM203 | PODN | ETFDH |
| PEMT | BTBD6 | N6AMT2 | GAS7 |
| MRPS12 | PDE1C | 242374_PM_at | 227897_PM_at |
| NECAP2 | UBN2 | NDUFS3 | 222626_PM_at |
| GRB10 | BAK1 | FAM120A | FRMD8 |
| ATP5G3 | PTK7 | LOC441454 /// LOC728026 /// PTMA /// PTMAP5 | PPP1R3B |
| KPNB1 | C12orf65 | COX4I1 | 1565862_PM_a_at |
| CTNNB1 | 238712_PM_at | GGCX | 243682_PM_at |
| ALKBH3 | SPNS1 | TTC39C | RECK |
| STAG2 | DHX37 | ZNF625 | TCTN3 |
| PNKD | 236370_PM_at | C20orf103 | CAST |
| FAM113A | 240038_PM_at | VDAC3 | TAB2 |
| RAMP1 | ZNF638 | SLC25A12 | METRN |
| 236322_PM_at | IRS2 | MRP63 | TCEAL8 |
| UBE2H | ANAPC5 | BAT2L2 | 239479_PM_x_at |
| 236944_PM_at | PDSS2 | 230868_PM_at | GLS2 |
| CHD2 | 240103_PM_at | PPP2R2B | 238812_PM_at |
| SPTLC2 | LMO7 | NEDD8 | ZNF33A |
| PRRG3 | MYST3 | RANGRF | MPP5 |
| FAR1 | C7orf53 | 1561202_PM_at | FOXP1 |
| MRPS11 | ZNF207 | TOMM40L | CDC14A |
| 237072_PM_at | NOC4L | CBX6 | MAPKAPK5 |
| PAPD4 | PTPLB | MVP | LOC100506245 |
| CC2D1A | 1556332_PM_at | LASS5 | EIF2AK3 |
| GIPC1 | MYCL1 | 229255_PM_x_at | ACSL3 |
| SELPLG | EXOSC7 | LYPLAL1 | HSCB |
| PICALM | ATP5F1 | CDV3 | MLKL |
| ZNF581 | LOC100272228 | LOC100505592 | TBC1D9 |
| NDUFA11 | PRKCB | LDOC1L | LOC728825 /// SUMO2 |
| ATXN10 | TAX1BP3 | GBF1 | LOC100130522 |
| SIT1 | LSM12 | 240176_PM_at | RSU1 |
| GSTM1 | STXBP3 | TRADD | RNF24 |
| ZNF207 | RPS19BP1 | 220912_PM_at | 242868_PM_at |
| RASGRP2 | PLEKHJ1 | RPL36 | 1558154_PM_at |
| ST20 | SELK | HSD17B8 | SUGP1 |
| 1557551_PM_at | 243305_PM_at | SEL1L | 220809_PM_at |
| CANX | MXD1 | FCGR2C | PSMA1 |
| PRPF4B | CDYL | PHF15 | ZNRF1 |
| NCRNA00152 | ASAP1 | 234150_PM_at | RRS1 |
| LRCH4 /// SAP25 | RABGGTB | COBLL1 | PDE5A |
| IL2RA | ESR2 | STYXL1 | GZF1 |
| SUDS3 | C14orf109 | SRSF6 | TIMM9 |
| TFB1M | EPC1 | 1556944_PM_at | 213979_PM_s_at |
| MIAT | PDCD7 | DDX24 | TTC27 |
| STX16 | SSTR2 | AVIL | BHLHE40 |

TABLE 1d-continued

The gene list of all 4132 genes analyzed in the 3-Way AR, ADNR TX ANOVA Analysis (using the HT HG-U133 + PM Array Plates)

| | | | |
|---|---|---|---|
| PRKAB1 | 1569477_PM_at | SEC14L2 | FGD4 |
| UFSP2 | CNPY2 | PRO0471 | RPL15 |
| SAMD4B | DDX42 | LOC553103 | NLRP1 |
| 1566825_PM_at | PDHB | CHD4 | 240761_PM_at |
| APC | COX4I1 | KCNJ2 | BZW2 |
| GDPD3 | EEF1D | C7orf41 | 1556195_PM_a_at |
| HBG1 /// HBG2 | LOC339352 | PTPN2 | BCAS2 |
| CD300A | 226252_PM_at | 239048_PM_at | SOS2 |
| SCUBE3 | PARK7 | 232595_PM_at | NCRNA00107 |
| PALLD | CPT2 | RFK | GAS7 |
| SIPA1L2 | USP40 | ACAP2 | DTHD1 |
| ZNF615 | SNRNP25 | PGGT1B | CDK2AP1 |
| PICALM | TSC22D1 | IAH1 | ARPP19 |
| HBB | GGNBP2 | TTC12 | ABCA5 |
| 241613_PM_at | LONP2 | ABHD5 | TROVE2 |
| LOC729013 | WDYHV1 | ROD1 | PSMB4 |
| PRKCD | TCP11L1 | CHFR | PGS1 |
| UGCG | IL13RA1 | 1556646_PM_at | C16orf13 |
| 213048_PM_s_at | 243931_PM_at | 230599_PM_at | C4orf45 |
| 1560474_PM_at | FLJ38717 | PEX11A | NUDT19 |
| NOTCH2 | 229370_PM_at | TRBC2 | 241445_PM_at |
| LOC100128439 | KIAA0141 | SEMA4F | LOC115110 |
| SRGAP2P1 | SLC6A13 | ARPP21 | 1560738_PM_at |
| ROCK1 | ACP1 | NFATC2 | CDC16 |
| GDE1 | SYNGR2 | RNPC3 | RHOB |
| DOCK8 | ZNF207 | POC1B | ERGIC1 |
| CEP72 | CUL2 | GORASP2 | OR2W3 |
| WHAMML1 /// WHAMML2 | RASGRP2 | 239603_PM_x_at | C1orf220 |
| TMSB4X /// TMSL3 | ATG13 | DHX37 | 235680_PM_at |
| NFYA | C3orf37 | TWF1 | UBE3C |
| 239709_PM_at | PHAX | 232685_PM_at | NACA |
| 237626_PM_at | KDELR1 | LOC100507596 | SLC6A6 |
| SH3BP2 | 243089_PM_at | 239597_PM_at | RIOK2 |
| 235894_PM_at | 243482_PM_at | BCL10 | 241860_PM_at |
| SSBP4 | CCDC50 | WIPF2 | C10orf76 |
| PRELID1 | CD68 | 230324_PM_at | 1561128_PM_at |
| MDM2 | HYLS1 | 232330_PM_at | LIG3 |
| RNF181 | CACNA2D3 | TBC1D8 | MRPS31 |
| CUL4B | ZNF43 | MGAT2 | 243249_PM_at |
| DOLK | LOC91548 | NXT1 | ZFAND5 |
| TOR1AIP2 | 1566501_PM_at | TNRC6B | DERA |
| CNIH4 | SNRPA1 | PER1 | TMEM159 |
| MAX | PNPO | TMEM43 | SCGB1C1 |
| 244592_PM_at | IL6ST | 224989_PM_at | ANO6 |
| SMARCAL1 | C15orf63 | TM6SF2 | 233506_PM_at |
| 237554_PM_at | DNAJB11 | FNTA | UNKL |
| NDUFB4 | MESDC1 | AP4M1 | GAB2 |
| ACBD6 | PPP1R14B | MRC2 | 1570621_PM_at |
| 238743_PM_at | WTAP | FNDC3B | SRGAP2 |
| RQCD1 | HSPC157 | ADAMTS1 | LOC151657 |
| RBBP6 | TRA2A | DSC2 | PTPRE |
| C17orf77 | C14orf119 | 234753_PM_x_at | MPV17 |
| TRIB3 | PPP1R16B | 1558418_PM_at | C17orf108 |
| 236781_PM_at | SLC25A5 | YY1 | 240154_PM_at |
| C15orf63 /// SERF2 | MEX3D | VEGFB | PRMT1 |
| C6orf226 | DDOST | AMBRA1 | 216490_PM_x_at |
| COX6B1 | KLHL22 | CCT6A | CSNK1A1 |
| ARID2 | 232344_PM_at | C4orf21 | HDDC2 |
| CD97 | VNN3 | MGA | MRPL33 |
| LRCH4 | CLEC4E | SAP30 | ORMDL2 |
| APBA3 | ANKRD57 | C20orf72 | TNFSF12-TNFSF13 /// TNFSF13 |
| FBXO41 | ERICH1 /// FLJ00290 | IQCK | RFX7 |
| 242772_PM_x_at | SRSF2IP | VIL1 | ZNF397 |
| C10orf76 | DPYSL5 | 244502_PM_at | PTPRC |
| IK /// TMCO6 | ANPEP | ATF6B /// TNXB | PARP8 |
| ATP6AP2 | ADAM17 | 214848_PM_at | C18orf21 |
| LOC727820 | SRD5A3 | PREX1 | ZEB2 |
| PIK3CD | CCDC12 | LSM14B | STK35 |
| AIP | SRC | NIP7 | 244548_PM_at |
| UBAC2 | 242440_PM_at | PPA2 | ASAH1 |
| MED23 | USP42 | PLIN5 | ZNF552 |
| EI24 | MIB2 | NAMPT | CAND1 |
| NME3 | GDF10 | RAPGEF2 | LOC647979 |
| 1559663_PM_at | RNPC3 | SNX2 | KIAA2026 |
| 237264_PM_at | CCDC154 | WIBG | SLC12A6 |

TABLE 1d-continued

The gene list of all 4132 genes analyzed in the 3-Way AR, ADNR TX ANOVA Analysis (using the HT HG-U133 + PM Array Plates)

| | | | |
|---|---|---|---|
| WAC | DPH2 | ZBED1 | C11orf10 |
| C17orf37 | P4HB | TRO | GRIN2B |
| 1560622_PM_at | CSNK1G2 | TPSAB1 | HNRNPA3 /// HNRNPA3P1 |
| 232876_PM_at | ATXN7 | SNX20 | BAZ2A |
| 1566966_PM_at | PITPNM1 | KRTAP9-2 | CISH |
| ZNF362 | PDLIM1 | C17orf63 | NSMAF |
| 239555_PM_at | KIAA1143 | SUPT4H1 | LETM1 |
| RASSF7 | KLF6 | PRKAA1 | 235596_PM_at |
| C17orf81 | 235685_PM_at | TRIM23 | ADORA3 |
| 224082_PM_at | SORD | ATP11B | RSBN1 |
| PALB2 | MALAT1 | ACTG1 | 233354_PM_at |
| 239819_PM_at | TMEM107 | PIGC | STAG2 |
| LOC200772 | PER1 | GRAMD1A | CD300LB |
| PCBP2 | NBR1 | SNUPN | 1564996_PM_at |
| BTF3 | RIBC1 | FLJ44342 | PHF1 |
| LOC221442 | 234255_PM_at | SMU1 | SEMA7A |
| 239893_PM_at | IFT27 | LOC100134822 | 1557772_PM_at |
| WDR1 | IMPAD1 | 229206_PM_at | WDFY3 |
| SMYD3 | IL17RA /// LOC150166 | IDH3A | 242016_PM_at |
| 242384_PM_at | LOC100190986 | FCHO2 | 231039_PM_at |
| MGEA5 | SNRK | GHITM | RNF213 |
| CTDNEP1 | ASTE1 | ELP3 | EML4 |
| 210598_PM_at | KIAA1659 | SUSD1 | HIPK3 |
| 1562898_PM_at | 231471_PM_at | STYXL1 | C14orf1 |
| ALKBH7 | RAC2 | URB1 | 242688_PM_at |
| XAB2 | C9orf89 | 1556645_PM_s_at | CD44 |
| DUSP23 | ZNF416 | EXOSC3 | WBSCR16 |
| PRKAR1A | ZNF599 | TRD@ | 237683_PM_s_at |
| PDSS1 | CCNH | CDYL | SLC14A1 |
| SAP18 | FAM190B | ITPKC | GNAS |
| CIRBP | SLC16A3 | NUDT2 | C4orf23 |
| MED19 | 229968_PM_at | XRCC6BP1 | DUSP10 |
| LOC644613 | RPRD1A | 241501_PM_at | 1564886_PM_at |
| PDK3 | WSB1 | C5orf20 | MBD1 |
| RBM5 | USP15 | RNMTL1 | KLHDC7B |

TABLE 2

| | Inclusion/Exclusion criteria |
|---|---|
| General Inclusion Criteria | 1) Adult kidney transplant (age >18 years): first or multiple transplants, high or low risk, cadaver or living donor organ recipients.<br>2) Any cause of end-stage renal disease except as described in Exclusions.<br>3) Consent to allow gene expression and proteomic studies to be done on samples.<br>4) Meeting clinical and biopsy criteria specified below for Groups 1-3. |
| General Exclusion Criteria | 1) Combined organ recipients: kidney/pancreas, kidney/islet, heart/kidney and liver/kidney.<br>2) A recipient of two kidneys simultaneously unless the organs are both adult and considered normal organs (rationale is to avoid inclusion of pediatric en bloc or dual adult transplants with borderline organs).<br>3) Any technical situation or medical problem such as a known bleeding disorder in which protocol biopsies would not be acceptable for safety reasons in the best judgment of the clinical investigators.<br>4) Patients with active immune-related disorders such as rheumatoid arthritis, SLE, scleroderma and multiple sclerosis.<br>5) Patients with acute viral or bacterial infections at the time of biopsy.<br>6) Patients with chronic active hepatitis or HIV.<br>7) CAN, that at the time of identification are in the best judgment of the clinicians too far along in the process or progressing to rapidly to make it likely that they will still have a functioning transplant a year later.<br>8) Patients enrolled in another research study that in the best judgment of the clinical center investigator involves such a radical departure from standard therapy that the patient would not be representative of the groups under study in the Program Project. |
| Acute Rejection (AR) Specific Inclusion Criteria | 1) Clinical presentation with acute kidney transplant dysfunction at any time post transplant<br>a. Biopsy-proven AR with tubulointerstitial cellular rejection with or without acute vascular rejection |
| Acute Rejection (AR) Specific Exclusion Criteria | 1) Evidence of concomitant acute infection<br>a. CMV<br>b. BK nephritis<br>c. Bacterial pyelonephritis<br>d. Other |

TABLE 2-continued

| | Inclusion/Exclusion criteria |
|---|---|
| | 2) Evidence of anatomical obstruction or vascular compromise |
| | 3) If the best judgment of the clinical team prior to the biopsy is that the acute decrease in kidney function is due to dehydration, drug effect (i.e. ACE inhibitor) or calcineurin inhibitor excess |
| | 4) If the biopsy is read as drug hypersensitivity (i.e. sulfa-mediated interstitial nephritis) |
| | 5) Evidence of hemolytic uremic syndrome |
| Well-functioning Transplant/No Rejection (TX) Specific Inclusion Criteria | 1) Patient between 12 and 24 months post transplant |
| | 2) Stable renal function defined as at least three creatinine levels over a three month period that do not change more than 20% and without any pattern of a gradual increasing creatinine. |
| | 3) No history of rejection or acute transplant dysfunction by clinical criteria or previous biopsy |
| | 4) Serum creatinines <1.5 mg/dL for women, <1.6 mg/dL for men |
| | 5) They must also have a calculated or measured creatinine clearance >45 ml/minute |
| | 6) They must have well controlled blood pressure defined according to the JNC 7 guidelines of <140/90 (JNC7 Express, The Seventh Report of the Noint National Committee on Prevention, Detection, Evaluation and Treatment of High Blood Pressure, NIH Publication No. 03-5233, December 2003) |
| Well-functioning Transplant/No Rejection (TX) Specific Exclusion Criteria | 1) Patient less than one month after steroid withdrawal |
| | 2) Patients with diabetes (Type I or II, poorly controlled) |
| | 3) Evidence of concomitant acute infection |
| | a. CMV |
| | b. BK nephritis |
| | c. Bacterial pyelonephritis |

*A special note regarding why noncompliance is not an exclusion criterion is important to emphasize. Noncompliance is not a primary issue in determining gene expression and proteomics profiles associated with molecular pathways of transplant immunity and tissue injury/repair.

TABLE 3

Clinical characteristics for the 148 study samples.

| | All Study Samples | | | | Multivariate Analysis¶ Significance | Multivariate Analysis¶ Significance (Phenotypes/ |
|---|---|---|---|---|---|---|
| | TX | AR | ADNR | Significance* | (Phenotypes) | Cohorts) |
| Subject Numbers | 45 | 64 | 39 | — | — | — |
| Recipient Age ± SD§ (Years) | 50.1 ± 14.5 | 44.9 ± 14.3 | 49.7 ± 14.6 | NS^ | NS | NS |
| % Female Recipients | 34.8 | 23.8 | 20.5 | NS | NS | NS |
| % Recipient African American | 6.8 | 12.7 | 12.8 | NS | NS | NS |
| % Pre-tx Type II Diabetes | 25.0 | 17.5 | 21.6 | NS | NS | NS |
| % PRA >20 | 29.4 | 11.3 | 11.5 | NS | NS | NS |
| HU Mismatch ± SD | 4.2 ± 2.1 | 4.3 ± 1.6 | 3.7 ± 2.1 | NS | NS | NS |
| % Deceased Donor | 43.5 | 65.1 | 53.8 | NS | NS | NS |
| Donor Age ± SD (Years) | 40.3 ± 14.5 | 38.0 ± 14.3 | 46.5 ± 14.6 | NS | NS | NS |
| % Female Donors | 37.0 | 50.8 | 46.2 | NS | NS | NS |
| % Donor African American | 3.2 | 4.9 | 13.3 | NS | NS | NS |
| % Delayed Graft Function | 19.0 | 34.4 | 29.0 | NS | NS | NS |
| % Induction | 63.0 | 84.1 | 82.1 | NS | NS | NS |
| Serum Creatinine ± SD (mg/dL) | 1.5 ± 0.5 | 3.2 ± 2.8 | 2.7 ± 1.8 | TX vs. AR = 0.00001 TX vs. ADNR = 0.0002 AR vs. ADNR = NS | TX vs. AR = 0.04 TX vs. ADNR = 0.01 | TX vs. AR vs. ADNR = 0.00002 AR vs. ADNR = NS |
| Time to Biopsy ± SD (Days) | 512 ± 1359 | 751 ± 1127 | 760 ± 972 | NS | NS | NS |
| Biopsy ≤365 days (%) | 27 (54.2%) | 38 (49.0%) | 23 (52.4%) | NS | NS | NS |
| Biopsy >366 days (%) | 19 (45.8%) | 32 (51.0%) | 18 (47.6%) | NS | NS | NS |
| % Calcineurin Inhibitors | 89.7 | 94.0 | 81.1 | NS | NS | NS |
| % Mycophenolic Acid Derivatives | 78.3 | 85.7 | 84.6 | NS | NS | NS |

TABLE 3-continued

Clinical characteristics for the 148 study samples.

| | All Study Samples | | | | Multivariate Analysis¶ Significance (Phenotypes) | Multivariate Analysis¶ Significance (Phenotypes/ Cohorts) |
|---|---|---|---|---|---|---|
| | TX | AR | ADNR | Significance* | | |
| % Oral Steroids | 26.1 | 65.1 | 74A | TX vs. AR = 0.001 TX vs. ADNR = 0.001 | TX vs. ADNR = 0.04 | NS |
| C4d Positive Staining (%)§ | 0/13 (0%) | 12/36 (33.3%) | 1/20 (5%) | NS | NS | NS |

*Significance for at comparisons were determined with paired Students t-test for pair-wise comparisons of data with Standard Deviations and for dichotomous data comparisons by Chi-Square.
¶A multivariate logistic regression model was used with a Wald test correction. In the first analysis (Phenotypes) we used all 148 samples and in the second analysis (Phenotypes/Cohorts) we did the analysis for each randomized set of 2 cohorts (Discovery and Validation).
⌐NS = not significant (p ≥ 0.05)
§Subjects with biopsy-positive staining for C4d and total number of subjects whose biopsies were stained for C4d with (%).

TABLE 4

Diagnostic metrics for the 3-way Nearest Centroid classifiers for AR, ADNR and TX in Discovery and Validation Cohorts

| Method | Classifies | % Predictive Accuracy (Discovery Cohort) | % Predictive Accuracy (Validation Cohort) | Sensitivity (%) | Specificity (X) | Positive Predictive Value (%) | Negative Predictive Value (%) | AUC | Sensitivity (%) | Specificity (%) | Positive Predictive Value (%) | Negative Predictive Value (%) | AUC |
|---|---|---|---|---|---|---|---|---|---|---|---|---|---|
| 200 Classifiers | TX vs. AR | 92% | 83% | 87% | 96% | 95% | 89% | 0.917 | 73% | 92% | 89% | 79% | 0.837 |
| | TX vs. ADNR | 91% | 82% | 95% | 90% | 91% | 95% | 0.913 | 89% | 76% | 76% | 89% | 0.817 |
| | AR vs. ADNR | 92% | 90% | 87% | 100% | 100% | 86% | 0.933 | 89% | 92% | 89% | 92% | 0.893 |
| 100 Classifiers | TX vs. AR | 91% | 83% | 87% | 93% | 91% | 90% | 0.903 | 76% | 88% | 84% | 82% | 0.825 |
| | TX vs. ADNR | 98% | 81% | 95% | 100% | 100% | 95% | 0.975 | 84% | 79% | 80% | 83% | 0.814 |
| | AR vs. ADNR | 98% | 90% | 95% | 100% | 100% | 97% | 0.980 | 88% | 92% | 88% | 92% | 0.900 |
| 50 Classifiers | TX vs. AR | 92% | 94% | 88% | 96% | 95% | 90% | 0.923 | 88% | 91% | 89% | 89% | 0.891 |
| | TX vs. ADNR | 94% | 95% | 92% | 98% | 98% | 90% | 0.944 | 92% | 90% | 88% | 89% | 0.897 |
| | AR vs. ADNR | 97% | 93% | 95% | 97% | 100% | 97% | 0.969 | 89% | 91% | 89% | 89% | 0.893 |
| 25 Classifiers | TX vs. AR | 89% | 92% | 81% | 96% | 95% | 84% | 0.890 | 88% | 90% | 90% | 89% | 0.894 |
| | TX vs. ADNR | 95% | 95% | 95% | 95% | 95% | 95% | 0.948 | 92% | 92% | 89% | 89% | 0.898 |
| | AR vs. ADNR | 96% | 91% | 95% | 96% | 95% | 96% | 0.955 | 85% | 90% | 89% | 88% | 0.882 |

TABLE 5

Diagnostic metrics for the 3-way DLDA and SVM classifiers for AR, ADNR and TX in Discovery and Validation Cohorts

| Method | Classifies | % Predictive Accuracy (Discovery Cohort) | % Predictive Accuracy (Validation Cohort) | Sensitivity (%) | Specificity (%) | Positive Predictive Value (%) | Negative Predictive Value (%) | AUC | Sensitivity (%) | Specificity (%) | Positive Predictive Value (%) | Negative Predictive Value (%) | AUC |
|---|---|---|---|---|---|---|---|---|---|---|---|---|---|
| 200 Classifiers DLDA | TX vs. AR | 90% | 84% | 87% | 93% | 91% | 89% | 0.896 | 76% | 92% | 89% | 81% | 0.845 |
| | TX vs. ADNR | 95% | 82% | 95% | 94% | 95% | 95% | 0.945 | 89% | 76% | 76% | 89% | 0.825 |
| | AR vs. ADNR | 92% | 84% | 83% | 100% | 100% | 86% | 0.923 | 84% | 92% | 89% | 88% | 0.880 |
| SVM | TX vs. AR | 100% | 83% | 100% | 100% | 100% | 100% | 1.000 | 82% | 86% | 81% | 86% | 0.833 |
| | TX vs. ADNR | 100% | 96% | 100% | 100% | 100% | 100% | 1.000 | 100% | 95% | 95% | 100% | 0.954 |

TABLE 5-continued

Diagnostic metrics for the 3-way DLDA and SVM classifiers for AR, ADNR and TX in Discovery and Validation Cohorts

| Method | Classifies | % Predictive Accuracy (Discovery Cohort) | % Predictive Accuracy (Validation Cohort) | Sensitivity (%) | Specificity (%) | Positive Predictive Value (%) | Negative Predictive Value (%) | AUC | Sensitivity (%) | Specificity (%) | Positive Predictive Value (%) | Negative Predictive Value (%) | AUC |
|---|---|---|---|---|---|---|---|---|---|---|---|---|---|
| | AR vs. ADNR | 100% | 95% | 100% | 100% | 100% | 100% | 1.000 | 95% | 96% | 95% | 96% | 0.954 |
| 100 Classifiers | | | | | | | | | | | 84% | 82% | 0.825 |
| DLDA | TX vs. AR | 91% | 83% | 88% | 93% | 91% | 90% | 0.905 | 76% | 88% | 80% | 83% | 0.815 |
| | TX vs. ADNR | 97% | 82% | 95% | 100% | 100% | 95% | 0.970 | 84% | 79% | | | |
| | AR vs. ADNR | 98% | 90% | 95% | 100% | 100% | 97% | 0.980 | 88% | 92% | 88% | 92% | 0.900 |
| SVM | TX vs. AR | 97% | 87% | 88% | 100% | 100% | 91% | 0.971 | 83% | 92% | 90% | 85% | 0.874 |
| | TX vs. ADNR | 98% | 86% | 96% | 100% | 100% | 95% | 0.988 | 86% | 88% | 90% | 83% | 0.867 |
| | AR vs. ADNR | 100% | 87% | 100% | 100% | 100% | 100% | 1.000 | 83% | 92% | 88% | 88% | 0.875 |
| 50 Classifiers | | | | | | | | | | | | | |
| DLDA | TX vs. AR | 93% | 83% | 88% | 97% | 96% | 90% | 0.927 | 78% | 88% | 86% | 81% | 0.832 |
| | TX vs. ADNR | 96% | 84% | 92% | 100% | 100% | 90% | 0.955 | 82% | 87% | 90% | 76% | 0.836 |
| | AR vs. ADNR | 98% | 85% | 95% | 100% | 100% | 97% | 0.979 | 81% | 88% | 81% | 88% | 0.845 |
| SVM | TX vs. AR | 95% | 83% | 88% | 100% | 100% | 91% | 0.946 | 77% | 88% | 87% | 79% | 0.827 |
| | TX vs. ADNR | 98% | 92% | 96% | 100% | 100% | 95% | 0.976 | 87% | 100% | 100% | 81% | 0.921 |
| | AR vs. ADNR | 100% | 85% | 100% | 100% | 100% | 100% | 1.000 | 87% | 85% | 77% | 92% | 0.852 |
| 25 Classifiers | | | | | | | | | | | | | |
| DLDA | TX vs. AR | 88% | 92% | 83% | 93% | 90% | 88% | 0.884 | 88% | 85% | 78% | 90% | 0.852 |
| | TX vs. ADNR | 92% | 93% | 95% | 90% | 90% | 95% | 0.924 | 92% | 88% | 85% | 81% | 0.864 |
| | AR vs. ADNR | 100% | 91% | 100% | 100% | 100% | 100% | 1.000 | 85% | 87% | 88% | 76% | 0.841 |
| SVM | TX vs. AR | 95% | 92% | 92% | 97% | 96% | 94% | 0.945 | 84% | 87% | 88% | 84% | 0.857 |
| | TX vs. ADNR | 96% | 100% | 96% | 95% | 96% | 95% | 0.955 | 100% | 85% | 83% | 81% | 0.874 |
| | AR vs. ADNR | 100% | 100% | 100% | 100% | 100% | 100% | 1.000 | 100% | 86% | 82% | 81% | 0.873 |

DLDA—Diagonal linear Discriminant Analysis
SVM—Support Vector Machines

TABLE 6

Optimism-corrected Area Under the Curves (AUC's) comparing two methods for creating and validating 3-Way classifiers for AR vs. ADNR vs. TX that demonstrates they provide equivalent results.

Discovery Cohort-based 200 probeset classifier*

| Method | Classifies | Original AUC | Optimism | Optimism Corrected AUC |
|---|---|---|---|---|
| Nearest Centroid | AR, TX, ADNR | 0.8500 | 0.0262 | 0.8238 |
| Diagonal Linear Discriminant Analysis | AR, TX, ADNR | 0.8441 | 0.0110 | 0.8331 |
| Support Vector Machines | AR, TX, ADNR | 0.8603 | 0.0172 | 0.8431 |

Full study sample-based 200 probeset classifier*

| Method | Classifies | Original AUC (Bootstrapping) | Optimism | Optimism Corrected AUC |
|---|---|---|---|---|
| Nearest Centroid | AR, TX, ADNR | 0.8641 | 0.0122 | 0.8519 |
| Diagonal Linear Discriminant Analysis | AR, TX, ADNR | 0.8590 | 0.0036 | 0.8554 |
| Support Vector Machines | AR, TX, ADNR | 0.8669 | 0.0005 | 0.8664 |

*153/200 (77%) of the discovery cohort-based classifier probesets were in the Top 500 of the full study sample-based 200 probeset classifier. Similarly, 141/200 (71%) of the full study sample-based 200 probeset classifier was in the top 500 probesets of the discovery cohort-based classifier.

Example 2

Materials and Methods

This Example describes some of the materials and methods employed in identification of differentially expressed genes in SCAR.

The discovery set of samples consisted of the following biopsy-documented peripheral blood samples. 69 PAXgene whole blood samples were collected from kidney transplant patients. The samples that were analyzed comprised 3 different phenotypes: (1) Acute Rejection (AR; n=21); (2) Sub-Clinical Acute Rejection (SCAR; n=23); and (3) Transplant Excellent (TX; n=25). Specifically, SCAR was defined by a protocol biopsy done on a patient with totally stable kidney function and the light histology revealed unexpected evidence of acute rejection (16 "Borderline", 7 Banff 1A). The SCAR samples consisted of 3 month and 1 year protocol biopsies, whereas the TXs were predominantly 3 month protocol biopsies. All the AR biopsies were "for cause" where clinical indications like a rise in serum creatinine prompted the need for a biopsy. All patients were induced with Thymoglobulin.

All samples were processed on the Affymetrix HG-U133 PM only peg microarrays. To eliminate low expressed signals we used a signal filter cut-off that was data dependent, and therefore expression signals $<\log_2 3.74$ (median signals on all arrays) in all samples were eliminated leaving us with 48734 probe sets from a total of 54721 probe sets. We performed a 3-way ANOVA analysis of AR vs. ADNR vs. TX. This yielded over 6000 differentially expressed probesets at a p-value <0.001. Even when a False Discovery rate cut-off of (FDR <10%), was used it gave us over 2700 probesets. Therefore for the purpose of a diagnostic signature we used the top 200 differentially expressed probe sets (Table 8) to build predictive models that could differentiate the three classes. We used three different predictive algorithms, namely Diagonal Linear Discriminant Analysis (DLDA), Nearest Centroid (NC) and Support Vector Machines (SVM) to build the predictive models. We ran the predictive models using two different methodologies and calculated the Area Under the Curve (AUC). SVM, DLDA and NC picked classifier sets of 200, 192 and 188 probesets as the best classifiers. Since there was very little difference in the AUC's we decided to use all 200 probesets as classifiers for all methods. We also demonstrated that these results were not the consequence of statistical over-fitting by using the replacement method of Harrell to perform a version of 1000-test cross-validation. Table 7 shows the performance of these classifier sets using both one-level cross validation as well as the Optimism Corrected Bootstrapping (1000 data sets).

An important point here is that in real clinical practice the challenge is actually not to distinguish SCAR from AR because by definition only AR presents with a significant increase in baseline serum creatinine. The real challenge is to take a patient with normal and stable creatinine and diagnose the hidden SCAR without having to depend on invasive and expensive protocol biopsies that cannot be done frequently in any case. Though we have already successfully done this using our 3-way analysis, we also tested a 2-way prediction of SCAR vs. TX. The point was to further validate that a phenotype as potentially subtle clinically as SCAR can be truly distinguished from TX. At a p-value <0.001, there were 33 probesets whose expression signals highly differentiated SCAR and TX, a result in marked contrast with the >2500 probesets differentially expressed between AR vs. TX at that same p-value. However, when these 33 probesets (Table 9) were used in NC to predict SCAR and TX creating a 2-way classifier, the predictive accuracies with a one-level cross-validation was 96% and with the Harrell 1000 test optimism correction it was 94%. Thus, we are confident that we can distinguish SCAR, TX and AR by peripheral blood gene expression profiling using this proof of principle data set.

TABLE 7

Blood Expression Profiling of Kidney Transplants: 3-Way Classifier AR vs. SCAR vs. TX.

| Algorithm | Predictors | Comparison | AUC after Thresholding | Predictive Accuracy (%) | Sensitivity (%) | Specificity (%) | Postive Predictive Value (%) | Negative Predictive Value (%) |
|---|---|---|---|---|---|---|---|---|
| Nearest Centroid | 200 | SCAR vs. TX | 1.000 | 100 | 100 | 100 | 100 | 100 |
| Nearest Centroid | 200 | SCAR vs. AR | 0.953 | 95 | 92 | 100 | 100 | 90 |
| Nearest Centroid | 200 | AR vs. TX | 0.932 | 93 | 96 | 90 | 92 | 95 |

It is understood that the examples and embodiments described herein are for illustrative purposes only and that various modifications or changes in light thereof will be suggested to persons skilled in the art and are to be included within the spirit and purview of this application and scope of the appended claims. Although any methods and materials similar or equivalent to those described herein can be used in the practice or testing of the present invention, the preferred methods and materials are described.

All publications, GenBank sequences, ATCC deposits, patents and patent applications cited herein are hereby expressly incorporated by reference in their entirety and for all purposes as if each is individually so denoted. Improvements in kidney transplantation have resulted in significant reductions in clinical acute rejection (AR) (8-14%) (Meier-Kriesche et al. 2004, Am J Transplant, 4(3): 378-383). However, histological AR without evidence of kidney dysfunction (i.e. subclinical AR) occurs in >15% of protocol biopsies done within the first year. Without a protocol biopsy, patients with subclinical AR would be treated as excellent functioning transplants (TX). Biopsy studies also document significant rates of progressive interstitial fibrosis and tubular atrophy in >50% of protocol biopsies starting as early as one year post transplant.

TABLE 8

200 Probeset classifer for distinguishing AR, SCAR and TX based on a 3-way ANOVA

| # | Probeset ID | Gene Symbol | Gene Title | p-value (Phenotype) | stepup p-value (Phenotype) | AR-Mean Signal | SCAR-Mean Signal | TX-Mean Signal |
|---|---|---|---|---|---|---|---|---|
| 1 | 238108_PM_at | — | — | 1.70E−10 | 8.27E−06 | 73.3 | 45.4 | 44.4 |
| 2 | 243524_PM_at | — | — | 3.98E−10 | 9.70E−06 | 72.3 | 41.3 | 37.7 |
| 3 | 1558831_PM_x_at | — | — | 5.11E−09 | 8.30E−05 | 48.1 | 30.8 | 31.4 |
| 4 | 229858_PM_at | — | — | 7.49E−09 | 8.31E−05 | 576.2 | 359.3 | 348.4 |
| 5 | 236685_PM_at | — | — | 8.53E−09 | 8.31E−05 | 409.1 | 213.3 | 211.0 |
| 6 | 213546_PM_at | DKFZP586l1420 | hypothetical protein DKFZp586l1420 | 3.52E−08 | 2.60E−04 | 619.2 | 453.7 | 446.0 |
| 7 | 231958_PM_at | C3orf31 | Chromosome 3 open reading frame 31 | 4.35E−08 | 2.60E−04 | 22.8 | 20.1 | 16.4 |
| 8 | 210275_PM_s_at | ZFAND5 | zinc finger, AN1-type domain 5 | 4.96E−08 | 2.60E−04 | 1045.9 | 1513.6 | 1553.8 |
| 9 | 244341_PM_at | — | — | 5.75E−08 | 2.60E−04 | 398.3 | 270.7 | 262.8 |
| 10 | 1558822_PM_at | — | — | 5.84E−08 | 2.60E−04 | 108.6 | 62.9 | 56.8 |
| 11 | 242175_PM_at | — | — | 5.87E−08 | 2.60E−04 | 69.1 | 37.2 | 40.0 |
| 12 | 222357_PM_at | ZBTB20 | zinc finger and BTB domain containing 20 | 6.97E−08 | 2.83E−04 | 237.4 | 127.4 | 109.8 |
| 13 | 206288_PM_at | PGGT1B | protein geranylgeranyltransferase type I, beta subunit | 9.42E−08 | 3.53E−04 | 20.8 | 34.7 | 34.2 |
| 14 | 222306_PM_at | — | — | 1.03E−07 | 3.59E−04 | 23.3 | 15.8 | 16.0 |
| 15 | 1569601_PM_at | — | — | 1.67E−07 | 4.80E−04 | 49.5 | 34.1 | 29.7 |
| 16 | 235138_PM_at | — | — | 1.69E−07 | 4.80E−04 | 1169.9 | 780.0 | 829.7 |
| 17 | 240452_PM_at | GSPT1 | G1 to S phase transition 1 | 1.74E−07 | 4.80E−04 | 97.7 | 54.4 | 48.6 |
| 18 | 243003_PM_at | — | — | 1.77E−07 | 4.80E−04 | 92.8 | 52.5 | 51.3 |
| 19 | 218109_PM_s_at | MFSD1 | major facilitator superfamily domain containing 1 | 1.90E−07 | 4.87E−04 | 1464.0 | 1881.0 | 1886.4 |
| 20 | 241681_PM_at | — | — | 2.00E−07 | 4.87E−04 | 1565.7 | 845.7 | 794.6 |
| 21 | 243878_PM_at | — | — | 2.19E−07 | 5.08E−04 | 76.1 | 39.7 | 39.5 |
| 22 | 233296_PM_x_at | — | — | 2.33E−07 | 5.17E−04 | 347.7 | 251.5 | 244.7 |
| 23 | 243318_PM_at | DCAF8 | DDB1 and CUL4 associated factor 8 | 2.52E−07 | 5.34E−04 | 326.2 | 229.5 | 230.2 |
| 24 | 236354_PM_at | — | — | 3.23E−07 | 6.39E−04 | 47.1 | 31.2 | 27.8 |
| 25 | 243768_PM_at | — | — | 3.35E−07 | 6.39E−04 | 1142.0 | 730.6 | 768.5 |
| 26 | 238558_PM_at | — | — | 3.65E−07 | 6.39E−04 | 728.5 | 409.4 | 358.4 |
| 27 | 237825_PM_x_at | — | — | 3.66E−07 | 6.39E−04 | 34.2 | 20.9 | 19.9 |
| 28 | 244414_PM_at | — | — | 3.67E−07 | 6.39E−04 | 548.7 | 275.2 | 284.0 |
| 29 | 215221_PM_at | — | — | 4.06E−07 | 6.83E−04 | 327.2 | 176.7 | 171.9 |
| 30 | 235912_PM_at | — | — | 4.46E−07 | 7.25E−04 | 114.1 | 71.4 | 59.5 |
| 31 | 239348_PM_at | — | — | 4.87E−07 | 7.54E−04 | 20.1 | 14.5 | 13.4 |
| 32 | 240499_PM_at | — | — | 5.06E−07 | 7.54E−04 | 271.4 | 180.1 | 150.2 |
| 33 | 208054_PM_at | HERC4 | hect domain and RLD 4 | 5.11E−07 | 7.54E−04 | 114.9 | 57.6 | 60.0 |
| 34 | 240263_PM_at | — | — | 5.46E−07 | 7.81E−04 | 120.9 | 78.7 | 66.6 |
| 35 | 241303_PM_x_at | — | — | 5.78E−07 | 7.81E−04 | 334.5 | 250.3 | 261.5 |
| 36 | 233692_PM_at | — | — | 5.92E−07 | 7.81E−04 | 22.4 | 15.5 | 15.0 |
| 37 | 243561_PM_at | — | — | 5.93E−07 | 7.81E−04 | 341.1 | 215.1 | 207.3 |
| 38 | 232778_PM_at | — | — | 6.91E−07 | 8.86E−04 | 46.5 | 31.0 | 28.5 |
| 39 | 237632_PM_at | — | — | 7.09E−07 | 8.86E−04 | 108.8 | 61.0 | 57.6 |
| 40 | 233690_PM_at | — | — | 7.30E−07 | 8.89E−04 | 351.1 | 222.7 | 178.1 |
| 41 | 220221_PM_at | VPS13D | vacuolar protein sorting 13 homolog D (S. cerevisiae) | 7.50E−07 | 8.89E−04 | 93.5 | 60.0 | 59.9 |
| 42 | 242877_PM_at | — | — | 7.72E−07 | 8.89E−04 | 173.8 | 108.1 | 104.0 |
| 43 | 218155_PM_x_at | TSR1 | TSR1, 20S rRNA accumulation, homolog (S. cerevisiae) | 7.86E−07 | 8.89E−04 | 217.2 | 165.6 | 164.7 |
| 44 | 239603_PM_x_at | — | — | 8.24E−07 | 8.89E−04 | 120.9 | 75.5 | 81.1 |
| 45 | 242859_PM_at | — | — | 8.48E−07 | 8.89E−04 | 221.1 | 135.4 | 138.3 |
| 46 | 240866_PM_at | — | — | 8.54E−07 | 8.89E−04 | 65.7 | 33.8 | 35.2 |
| 47 | 239661_PM_at | — | — | 8.72E−07 | 8.89E−04 | 100.5 | 48.3 | 45.2 |
| 48 | 224493_PM_x_at | C18orf45 | chromosome 18 open reading frame 45 | 8.77E−07 | 8.89E−04 | 101.8 | 78.0 | 89.7 |
| 49 | 1569202_PM_x_at | — | — | 8.98E−07 | 8.89E−04 | 23.3 | 18.5 | 16.6 |
| 50 | 1560474_PM_at | — | — | 9.12E−07 | 8.89E−04 | 25.2 | 17.8 | 18.5 |
| 51 | 232511_PM_at | — | — | 9.48E−07 | 9.06E−04 | 77.2 | 46.1 | 49.9 |
| 52 | 228119_PM_at | LRCH3 | leucine-rich repeats and calponin homology (CH) domain containing 3 | 1.01E−06 | 9.51E−04 | 117.2 | 84.2 | 76.1 |
| 53 | 228545_PM_at | ZNF148 | zinc finger protein 148 | 1.17E−06 | 9.99E−04 | 789.9 | 571.1 | 579.7 |
| 54 | 232779_PM_at | — | — | 1.17E−06 | 9.99E−04 | 36.7 | 26.0 | 20.7 |

TABLE 8-continued

200 Probeset classifer for distinguishing AR, SCAR and TX based on a 3-way ANOVA

| # | Probeset ID | Gene Symbol | Gene Title | p-value (Phenotype) | stepup p-value (Phenotype) | AR-Mean Signal | SCAR-Mean Signal | TX-Mean Signal |
|---|---|---|---|---|---|---|---|---|
| 55 | 239005_PM_at | FLJ39739 | Hypothetical FLJ39739 | 1.18E−06 | 9.99E−04 | 339.1 | 203.7 | 177.7 |
| 56 | 244478_PM_at | LRRC37A3 | leucine rich repeat containing 37, member A3 | 1.20E−06 | 9.99E−04 | 15.7 | 12.6 | 12.7 |
| 57 | 244535_PM_at | — | — | 1.28E−06 | 9.99E−04 | 261.5 | 139.5 | 137.8 |
| 58 | 1562673_PM_at | — | — | 1.28E−06 | 9.99E−04 | 77.4 | 46.5 | 51.8 |
| 59 | 240601_PM_at | — | — | 1.29E−06 | 9.99E−04 | 212.6 | 107.7 | 97.7 |
| 60 | 239533_PM_at | GPR155 | G protein-coupled receptor 155 | 1.30E−06 | 9.99E−04 | 656.3 | 396.7 | 500.1 |
| 61 | 222358_PM_x_at | — | — | 1.32E−06 | 9.99E−04 | 355.2 | 263.1 | 273.7 |
| 62 | 214707_PM_x_at | ALMS1 | Alstrom syndrome 1 | 1.32E−06 | 9.99E−04 | 340.2 | 255.9 | 266.0 |
| 63 | 236435_PM_at | — | — | 1.32E−06 | 9.99E−04 | 144.0 | 92.6 | 91.1 |
| 64 | 232333_PM_at | — | — | 1.33E−06 | 9.99E−04 | 487.7 | 243.7 | 244.3 |
| 65 | 222366_PM_at | — | — | 1.33E−06 | 9.99E−04 | 289.1 | 186.1 | 192.8 |
| 66 | 215611_PM_at | TCF12 | transcription factor 12 | 1.38E−06 | 1.02E−03 | 45.5 | 32.4 | 30.8 |
| 67 | 1558002_PM_at | STRAP | Serine/threonine kinase receptor associated protein | 1.40E−06 | 1.02E−03 | 199.6 | 146.7 | 139.7 |
| 68 | 239716_PM_at | — | — | 1.43E−06 | 1.02E−03 | 77.6 | 49.5 | 45.5 |
| 69 | 239091_PM_at | — | — | 1.45E−06 | 1.02E−03 | 76.9 | 44.0 | 45.0 |
| 70 | 238883_PM_at | — | — | 1.68E−06 | 1.15E−03 | 857.1 | 475.5 | 495.1 |
| 71 | 235615_PM_at | PGGT1B | protein geranylgeranyltransferase type I, beta subunit | 1.72E−06 | 1.15E−03 | 127.0 | 235.0 | 245.6 |
| 72 | 204055_PM_s_at | CTAGE5 | CTAGE family, member 5 | 1.77E−06 | 1.15E−03 | 178.8 | 115.2 | 105.9 |
| 73 | 239757_PM_at | ZFAND6 | Zinc finger, AN1-type domain 6 | 1.81E−06 | 1.15E−03 | 769.6 | 483.3 | 481.9 |
| 74 | 1558409_PM_at | — | — | 1.82E−06 | 1.15E−03 | 14.8 | 10.9 | 11.8 |
| 75 | 242688_PM_at | — | — | 1.85E−06 | 1.15E−03 | 610.5 | 338.4 | 363.4 |
| 76 | 242377_PM_x_at | THUMPD3 | THUMP domain containing 3 | 1.87E−06 | 1.15E−03 | 95.5 | 79.0 | 81.3 |
| 77 | 242650_PM_at | — | — | 1.88E−06 | 1.15E−03 | 86.0 | 55.5 | 47.4 |
| 78 | 243589_PM_at | KIAA1267 /// LOC100294337 | KIAA1267 /// hypothetical LOC100294337 | 1.89E−06 | 1.15E−03 | 377.8 | 220.3 | 210.4 |
| 79 | 227384_PM_s_at | — | — | 1.90E−06 | 1.15E−03 | 3257.0 | 2255.5 | 2139.7 |
| 80 | 237864_PM_at | — | — | 1.91E−06 | 1.15E−03 | 121.0 | 69.2 | 73.4 |
| 81 | 243490_PM_at | — | — | 1.92E−06 | 1.15E−03 | 24.6 | 17.5 | 16.5 |
| 82 | 244383_PM_at | — | — | 1.96E−06 | 1.17E−03 | 141.7 | 93.0 | 77.5 |
| 83 | 215908_PM_at | — | — | 2.06E−06 | 1.19E−03 | 98.5 | 67.9 | 67.5 |
| 84 | 230651_PM_at | — | — | 2.09E−06 | 1.19E−03 | 125.9 | 74.3 | 71.5 |
| 85 | 1561195_PM_at | — | — | 2.14E−06 | 1.19E−03 | 86.6 | 45.1 | 43.9 |
| 86 | 239268_PM_at | NDUFS1 | NADH dehydrogenase (ubiquinone) Fe—S protein 1, 75 kDa (NADH-coenzyme Q reductase) | 2.14E−06 | 1.19E−03 | 14.0 | 12.0 | 11.3 |
| 87 | 236431_PM_at | SR140 | U2-associated SR140 protein | 2.16E−06 | 1.19E−03 | 69.4 | 47.9 | 43.9 |
| 88 | 236978_PM_at | — | — | 2.19E−06 | 1.19E−03 | 142.4 | 88.6 | 88.1 |
| 89 | 1562957_PM_at | — | — | 2.21E−06 | 1.19E−03 | 268.3 | 181.8 | 165.4 |
| 90 | 238913_PM_at | — | — | 2.21E−06 | 1.19E−03 | 30.9 | 20.2 | 20.1 |
| 91 | 239646_PM_at | — | — | 2.23E−06 | 1.19E−03 | 100.3 | 63.1 | 60.8 |
| 92 | 235701_PM_at | — | — | 2.34E−06 | 1.24E−03 | 133.2 | 66.1 | 60.0 |
| 93 | 235601_PM_at | — | — | 2.37E−06 | 1.24E−03 | 121.9 | 75.5 | 79.0 |
| 94 | 230918_PM_at | — | — | 2.42E−06 | 1.25E−03 | 170.4 | 114.5 | 94.4 |
| 95 | 219112_PM_at | FNIP1 /// RAPGEF6 | folliculin interacting protein 1 /// Rap guanine nucleotide exchange factor (GEF) 6 | 2.49E−06 | 1.28E−03 | 568.2 | 400.2 | 393.4 |
| 96 | 202228_PM_s_at | NPTN | neuroplastin | 2.52E−06 | 1.28E−03 | 1017.7 | 1331.5 | 1366.4 |
| 97 | 242839_PM_at | — | — | 2.78E−06 | 1.39E−03 | 17.9 | 14.0 | 13.6 |
| 98 | 244778_PM_x_at | — | — | 2.85E−06 | 1.42E−03 | 105.1 | 68.0 | 65.9 |
| 99 | 237388_PM_at | — | — | 2.91E−06 | 1.42E−03 | 59.3 | 38.0 | 33.0 |
| 100 | 202770_PM_s_at | CCNG2 | cyclin G2 | 2.92E−06 | 1.42E−03 | 142.2 | 269.0 | 270.0 |
| 101 | 240008_PM_at | — | — | 2.96E−06 | 1.42E−03 | 96.2 | 65.6 | 56.2 |
| 102 | 1557718_PM_at | PPP2R5C | protein phosphatase 2, regulatory subunit B', gamma | 2.97E−06 | 1.42E−03 | 615.2 | 399.8 | 399.7 |

TABLE 8-continued

200 Probeset classifer for distinguishing AR, SCAR and TX based on a 3-way ANOVA

| # | Probeset ID | Gene Symbol | Gene Title | p-value (Phenotype) | stepup p-value (Phenotype) | AR-Mean Signal | SCAR-Mean Signal | TX-Mean Signal |
|---|---|---|---|---|---|---|---|---|
| 103 | 215528_PM_at | — | — | 3.01E−06 | 1.42E−03 | 126.8 | 62.6 | 69.0 |
| 104 | 204689_PM_at | HHEX | hematopoietically expressed homeobox | 3.08E−06 | 1.44E−03 | 381.0 | 499.9 | 567.9 |
| 105 | 213718_PM_at | RBM4 | RNA binding motif protein 4 | 3.21E−06 | 1.46E−03 | 199.3 | 140.6 | 132.2 |
| 106 | 243233_PM_at | — | — | 3.22E−06 | 1.46E−03 | 582.3 | 343.0 | 337.1 |
| 107 | 239597_PM_at | — | — | 3.23E−06 | 1.46E−03 | 1142.9 | 706.6 | 720.8 |
| 108 | 232890_PM_at | — | — | 3.24E−06 | 1.46E−03 | 218.0 | 148.7 | 139.9 |
| 109 | 232883_PM_at | — | — | 3.42E−06 | 1.53E−03 | 127.5 | 79.0 | 73.1 |
| 110 | 241391_PM_at | — | — | 3.67E−06 | 1.62E−03 | 103.8 | 51.9 | 48.3 |
| 111 | 244197_PM_x_at | — | — | 3.71E−06 | 1.62E−03 | 558.0 | 397.3 | 418.8 |
| 112 | 205434_PM_s_at | AAK1 | AP2 associated kinase 1 | 3.75E−06 | 1.62E−03 | 495.2 | 339.9 | 301.2 |
| 113 | 235725_PM_at | SMAD4 | SMAD family member 4 | 3.75E−06 | 1.62E−03 | 147.1 | 102.1 | 112.0 |
| 114 | 203137_PM_at | WTAP | Wilms tumor 1 associated protein | 3.89E−06 | 1.66E−03 | 424.1 | 609.4 | 555.8 |
| 115 | 231075_PM_x_at | RAPH1 | Ras association (RalGDS/AF-6) and pleckstrin homology domains 1 | 3.91E−06 | 1.66E−03 | 30.4 | 19.3 | 18.2 |
| 116 | 236043_PM_at | LOC100130175 | hypothetical protein LOC100130175 | 3.98E−06 | 1.67E−03 | 220.6 | 146.2 | 146.5 |
| 117 | 238299_PM_at | — | — | 4.09E−06 | 1.70E−03 | 217.1 | 130.4 | 130.3 |
| 118 | 243667_PM_at | — | — | 4.12E−06 | 1.70E−03 | 314.5 | 225.3 | 232.8 |
| 119 | 223937_PM_at | FOXP1 | forkhead box P1 | 4.20E−06 | 1.72E−03 | 147.7 | 85.5 | 90.9 |
| 120 | 238666_PM_at | — | — | 4.25E−06 | 1.72E−03 | 219.1 | 148.3 | 145.5 |
| 121 | 1554771_PM_at | — | — | 4.28E−06 | 1.72E−03 | 67.2 | 41.5 | 40.8 |
| 122 | 202379_PM_s_at | NKTR | natural killer-tumor recognition sequence | 4.34E−06 | 1.73E−03 | 1498.2 | 1170.6 | 1042.6 |
| 123 | 244695_PM_at | GHRLOS | ghrelin opposite strand (non-protein coding) | 4.56E−06 | 1.79E−03 | 78.0 | 53.0 | 52.5 |
| 124 | 239393_PM_at | — | — | 4.58E−06 | 1.79E−03 | 852.0 | 554.2 | 591.7 |
| 125 | 242920_PM_at | — | — | 4.60E−06 | 1.79E−03 | 392.8 | 220.9 | 251.8 |
| 126 | 242405_PM_at | — | — | 4.66E−06 | 1.80E−03 | 415.8 | 193.8 | 207.4 |
| 127 | 1556432_PM_at | — | — | 4.69E−06 | 1.80E−03 | 61.5 | 43.1 | 38.1 |
| 128 | 1570299_PM_at | — | — | 4.77E−06 | 1.81E−03 | 27.0 | 18.0 | 19.8 |
| 129 | 225198_PM_at | VAPA | VAMP (vesicle-associated membrane protein)-associated protein A, 33 kDa | 4.85E−06 | 1.83E−03 | 192.0 | 258.3 | 273.9 |
| 130 | 230702_PM_at | — | — | 4.94E−06 | 1.85E−03 | 28.2 | 18.4 | 17.5 |
| 131 | 240262_PM_at | — | — | 5.07E−06 | 1.88E−03 | 46.9 | 22.8 | 28.0 |
| 132 | 232216_PM_at | YME1L1 | YME1-like 1 (S. cerevisiae) | 5.14E−06 | 1.89E−03 | 208.6 | 146.6 | 130.1 |
| 133 | 225171_PM_at | ARHGAP18 | Rho GTPase activating protein 18 | 5.16E−06 | 1.89E−03 | 65.9 | 109.1 | 121.5 |
| 134 | 243992_PM_at | — | — | 5.28E−06 | 1.92E−03 | 187.1 | 116.0 | 125.6 |
| 135 | 227082_PM_at | — | — | 5.45E−06 | 1.96E−03 | 203.8 | 140.4 | 123.0 |
| 136 | 239948_PM_at | NUP153 | nucleoporin 153 kDa | 5.50E−06 | 1.96E−03 | 39.6 | 26.5 | 27.8 |
| 137 | 221905_PM_at | CYLD | cylindromatosis (turban tumor syndrome) | 5.51E−06 | 1.96E−03 | 433.0 | 316.8 | 315.1 |
| 138 | 242578_PM_x_at | SLC22A3 | Solute carrier family 22 (extraneuronal monoamine transporter), member 3 | 5.56E−06 | 1.96E−03 | 148.4 | 109.2 | 120.1 |
| 139 | 1569238_PM_a_at | — | — | 5.73E−06 | 1.99E−03 | 71.0 | 33.0 | 36.1 |
| 140 | 201453_PM_x_at | RHEB | Ras homolog enriched in brain | 5.76E−06 | 1.99E−03 | 453.3 | 600.0 | 599.0 |
| 141 | 236802_PM_at | — | — | 5.76E−06 | 1.99E−03 | 47.9 | 29.1 | 29.6 |
| 142 | 232615_PM_at | — | — | 5.82E−06 | 1.99E−03 | 4068.5 | 3073.4 | 2907.4 |
| 143 | 237179_PM_at | PCMTD2 | protein-L-isoaspartate (D-aspartate) O—methyltransferase domain containing 2 | 5.84E−06 | 1.99E−03 | 48.7 | 30.2 | 26.8 |
| 144 | 203255_PM_at | FBX011 | F-box protein 11 | 5.98E−06 | 2.02E−03 | 748.3 | 529.4 | 539.6 |
| 145 | 212989_PM_at | SGMS1 | sphingomyelin synthase 1 | 6.04E−06 | 2.03E−03 | 57.2 | 93.1 | 107.9 |

TABLE 8-continued

200 Probeset classifer for distinguishing AR, SCAR and TX based on a 3-way ANOVA

| # | Probeset ID | Gene Symbol | Gene Title | p-value (Phenotype) | stepup p-value (Phenotype) | AR-Mean Signal | SCAR-Mean Signal | TX-Mean Signal |
|---|---|---|---|---|---|---|---|---|
| 146 | 236754_PM_at | PPP1R2 | protein phosphatase 1, regulatory (inhibitor) subunit 2 | 6.17E−06 | 2.05E−03 | 505.3 | 380.7 | 370.1 |
| 147 | 1559496_PM_at | PPA2 | pyrophosphatase (inorganic) 2 | 6.24E−06 | 2.05E−03 | 68.8 | 39.7 | 39.3 |
| 148 | 236494_PM_x_at | — | — | 6.26E−06 | 2.05E−03 | 135.0 | 91.1 | 82.9 |
| 149 | 237554_PM_at | — | — | 6.30E−06 | 2.05E−03 | 53.4 | 31.5 | 30.1 |
| 150 | 243469_PM_at | — | — | 6.37E−06 | 2.05E−03 | 635.2 | 308.1 | 341.5 |
| 151 | 240155_PM_x_at | ZNF493 /// ZNF738 | zinc finger protein 493 /// zinc finger protein 738 | 6.45E−06 | 2.05E−03 | 483.9 | 299.9 | 316.6 |
| 152 | 222442_PM_s_at | ARL8B | ADP-ribosylation factor-like 8B | 6.47E−06 | 2.05E−03 | 201.5 | 292.6 | 268.3 |
| 153 | 240307_PM_at | — | — | 6.48E−06 | 2.05E−03 | 55.4 | 36.8 | 33.1 |
| 154 | 200864_PM_s_at | RAB11A | RAB11A, member RAS oncogene family | 6.50E−06 | 2.05E−03 | 142.1 | 210.9 | 233.0 |
| 155 | 235757_PM_at | — | — | 6.53E−06 | 2.05E−03 | 261.4 | 185.2 | 158.9 |
| 156 | 222351_PM_at | PPP2R1B | protein phosphatase 2, regulatory subunit A, beta | 6.58E−06 | 2.06E−03 | 75.8 | 51.1 | 45.4 |
| 157 | 222788_PM_s_at | RSBN1 | round spermatid basic protein 1 | 6.63E−06 | 2.06E−03 | 389.9 | 302.7 | 288.2 |
| 158 | 239815_PM_at | — | — | 6.70E−06 | 2.06E−03 | 216.9 | 171.4 | 159.5 |
| 159 | 219392_PM_x_at | PRR11 | proline rich 11 | 6.77E−06 | 2.07E−03 | 1065.3 | 827.5 | 913.2 |
| 160 | 240458_PM_at | — | — | 6.80E−06 | 2.07E−03 | 414.3 | 244.6 | 242.0 |
| 161 | 235879_PM_at | MBNL1 | Muscleblind-like (Drosophila) | 6.88E−06 | 2.08E−03 | 1709.2 | 1165.5 | 1098.0 |
| 162 | 230529_PM_at | HECA | headcase homolog (Drosophila) | 7.08E−06 | 2.13E−03 | 585.1 | 364.3 | 418.4 |
| 163 | 1562063_PM_x_at | KIAA1245 /// NBPF1 /// NBPF10 /// NBPF11 /// NBPF12 /// NBPF24 /// NBPF8 /// NBPF9 | KIAA1245 /// neuroblastoma breakpoint family, member 1 /// neuroblastoma breakpoint fam | 7.35E−06 | 2.20E−03 | 350.4 | 238.8 | 260.8 |
| 164 | 202769_PM_at | CCNG2 | cyclin G2 | 7.42E−06 | 2.20E−03 | 697.1 | 1164.0 | 1264.6 |
| 165 | 1556493_PM_a_at | KDM4C | lysine (K)-specific demethylase 4C | 7.64E−06 | 2.24E−03 | 81.4 | 49.0 | 44.5 |
| 166 | 216509_PM_x_at | MLLT10 | myeloid/lymphoid or mixed-lineage leukemia (trithorax homolog, Drosophila); translocate | 7.64E−06 | 2.24E−03 | 22.4 | 17.9 | 19.3 |
| 167 | 223697_PM_x_at | C9orf64 | chromosome 9 open reading frame 64 | 7.70E−06 | 2.25E−03 | 1013.6 | 771.2 | 836.8 |
| 168 | 235999_PM_at | — | — | 7.77E−06 | 2.25E−03 | 227.6 | 174.1 | 182.1 |
| 169 | 244766_PM_at | LOC100271836 /// LOC440354 /// LOC595101 /// LOC641298 /// SMG1 | SMG1 homolog, phosphatidylinositol 3-kinase-related kinase pseudogene /// PI-3-kinase-r | 8.03E−06 | 2.31E−03 | 133.4 | 99.4 | 87.5 |
| 170 | 230332_PM_at | ZCCHC7 | Zinc finger, CCHC domain containing 7 | 8.07E−06 | 2.31E−03 | 467.4 | 265.1 | 263.2 |
| 171 | 235308_PM_at | ZBTB20 | zinc finger and BTB domain containing 20 | 8.17E−06 | 2.32E−03 | 256.7 | 184.2 | 167.3 |
| 172 | 242492_PM_at | CLNS1A | Chloride channel, nucleotide-sensitive, 1A | 8.19E−06 | 2.32E−03 | 128.5 | 82.8 | 79.2 |
| 173 | 215898_PM_at | TTLL5 | tubulin tyrosine ligase-like family, member 5 | 8.24E−06 | 2.32E−03 | 20.9 | 14.0 | 13.8 |
| 174 | 244840_PM_x_at | DOCK4 | dedicator of cytokinesis 4 | 8.65E−06 | 2.42E−03 | 43.1 | 16.5 | 21.5 |
| 175 | 220235_PM_s_at | C1orf103 | chromosome 1 open reading frame 103 | 8.72E−06 | 2.43E−03 | 88.4 | 130.5 | 143.3 |
| 176 | 229467_PM_at | PCBP2 | Poly(rC) binding protein 2 | 8.80E−06 | 2.44E−03 | 186.5 | 125.4 | 135.8 |
| 177 | 232527_PM_at | — | — | 8.99E−06 | 2.48E−03 | 667.4 | 453.9 | 461.3 |
| 178 | 243286_PM_at | — | — | 9.24E−06 | 2.53E−03 | 142.6 | 98.2 | 87.2 |
| 179 | 215628_PM_x_at | — | — | 9.28E−06 | 2.53E−03 | 49.6 | 36.3 | 39.4 |

TABLE 8-continued

200 Probeset classifer for distinguishing AR, SCAR and TX based on a 3-way ANOVA

| # | Probeset ID | Gene Symbol | Gene Title | p-value (Phenotype) | stepup p-value (Phenotype) | AR-Mean Signal | SCAR-Mean Signal | TX-Mean Signal |
|---|---|---|---|---|---|---|---|---|
| 180 | 1556412_PM_at | — | — | 9.45E−06 | 2.56E−03 | 34.9 | 24.7 | 23.8 |
| 181 | 204786_PM_s_at | IFNAR2 | interferon (alpha, beta and omega) receptor 2 | 9.64E−06 | 2.59E−03 | 795.6 | 573.0 | 639.2 |
| 182 | 234258_PM_at | — | — | 9.73E−06 | 2.60E−03 | 27.4 | 17.8 | 20.3 |
| 183 | 233274_PM_at | — | — | 9.76E−06 | 2.60E−03 | 109.9 | 77.5 | 79.4 |
| 184 | 239784_PM_at | — | — | 9.82E−06 | 2.60E−03 | 137.0 | 80.1 | 70.1 |
| 185 | 242498_PM_x_at | — | — | 1.01E−05 | 2.65E−03 | 59.2 | 40.4 | 38.9 |
| 186 | 231351_PM_at | — | — | 1.02E−05 | 2.67E−03 | 124.8 | 70.8 | 60.6 |
| 187 | 222368_PM_at | — | — | 1.03E−05 | 2.67E−03 | 89.9 | 54.5 | 44.3 |
| 188 | 236524_PM_at | — | — | 1.03E−05 | 2.67E−03 | 313.2 | 234.7 | 214.2 |
| 189 | 243834_PM_at | TNRC6A | trinucleotide repeat containing 6A | 1.04E−05 | 2.67E−03 | 211.8 | 145.1 | 146.9 |
| 190 | 239167_PM_at | — | — | 1.04E−05 | 2.67E−03 | 287.4 | 150.2 | 160.3 |
| 191 | 239238_PM_at | — | — | 1.05E−05 | 2.67E−03 | 136.0 | 81.6 | 92.0 |
| 192 | 237194_PM_at | — | — | 1.05E−05 | 2.67E−03 | 57.2 | 34.4 | 27.9 |
| 193 | 242772_PM_x_at | — | — | 1.06E−05 | 2.67E−03 | 299.2 | 185.2 | 189.4 |
| 194 | 243827_PM_at | — | — | 1.06E−05 | 2.67E−03 | 115.9 | 50.1 | 56.4 |
| 195 | 1552536_PM_at | VTI1A | vesicle transport through interaction with t-SNAREs homolog 1A (yeast) | 1.10E−05 | 2.75E−03 | 61.7 | 35.1 | 34.6 |
| 196 | 243696_PM_at | KIAA0562 | KIAA0562 | 1.12E−05 | 2.77E−03 | 19.0 | 14.8 | 15.0 |
| 197 | 233648_PM_at | — | — | 1.12E−05 | 2.77E−03 | 33.9 | 21.0 | 24.1 |
| 198 | 225858_PM_s_at | XIAP | X-linked inhibitor of apoptosis | 1.16E−05 | 2.85E−03 | 1020.7 | 760.3 | 772.6 |
| 199 | 238736_PM_at | REV3L | REV3-like, catalytic subunit of DNA polymerase zeta (yeast) | 1.19E−05 | 2.91E−03 | 214.2 | 135.8 | 151.6 |
| 200 | 221192_PM_x_at | MFSD11 | major facilitator superfamily domain containing 11 | 1.20E−05 | 2.92E−03 | 100.4 | 74.5 | 81.2 |

TABLE 9

33 probesets that differentiate SCAR and TX at p-value <0.001 in PAXGene blood tubes

| Probeset ID | Gene Symbol | Gene Title | p-value (Phenotype) | FFold-Change (SCAR vs. TX) | ID | SCAR-Mean | TX-Mean |
|---|---|---|---|---|---|---|---|
| 1553094_PM_at | TAC4 | tachykinin 4 (hemokinin) | 0.000375027 | −1.1 | 1553094_PM_at | 8.7 | 9.6 |
| 1553352_PM_x_at | ERVWE1 | endogenous retroviral family W, env(C7), member 1 | 0.000494742 | −1.26 | 1553352_PM_x_at | 15.5 | 19.6 |
| 1553644_PM_at | C14orf49 | chromosome 14 open reading frame 49 | 0.000868817 | −1.16 | 1553644_PM_at | 10.1 | 11.7 |
| 1556178_PM_x_at | TAF8 | TAF8 RNA polymerase II, TATA box binding protein (TBP)-associated factor, 43 kDa | 0.000431074 | 1.24 | 1556178_PM_x_at | 39.2 | 31.7 |
| 1559687_PM_at | TMEM221 | transmembrane protein 221 | 8.09E−05 | −1.16 | 1559687_PM_at | 13.0 | 15.1 |
| 1562492_PM_at | LOC340090 | hypothetical LOC340090 | 0.00081096 | −1.1 | 1562492_PM_at | 8.8 | 9.7 |
| 1563204_PM_at | ZNF627 | Zinc finger protein 627 | 0.000784254 | −1.15 | 1563204_PM_at | 10.6 | 12.2 |
| 1570124_PM_at | — | | 0.000824814 | −1.14 | 1570124_PM_at | 10.6 | 12.2 |
| 204681_PM_s_at | RAPGEF5 | Rap guanine nucleotide exchange factor (GEF) 5 | 0.000717727 | −1.18 | 204681_PM_s_at | 9.6 | 11.3 |
| 206154_PM_at | RLBP1 | retinaldehyde binding protein 1 | 0.000211941 | −1.13 | 206154_PM_at | 11.0 | 12.4 |
| 209053_PM_s_at | WHSC1 | Wolf-Hirschhorn syndrome candidate 1 | 0.000772412 | 1.23 | 209053_PM_s_at | 15.1 | 12.3 |
| 209228_PM_x_at | TUSC3 | tumor suppressor candidate 3 | 0.000954529 | −1.13 | 209228_PM_x_at | 8.9 | 10.1 |

TABLE 9-continued 33 probesets that differentiate SCAR and TX at p-value <0.001 in PAXGene blood tubes

| Probeset ID | Gene Symbol | Gene Title | p-value (Phenotype) | FFold-Change (SCAR vs. TX) | ID | SCAR-Mean | TX-Mean |
|---|---|---|---|---|---|---|---|
| 211701_PM_s_at | TRO | trophinin | 0.000684486 | −1.13 | 211701_PM_s_at | 10.0 | 11.3 |
| 213369_PM_at | CDHR1 | cadherin-related family member 1 | 0.000556648 | −1.14 | 213369_PM_at | 10.8 | 12.3 |
| 215110_PM_at | MBL1P | mannose-binding lectin (protein A) 1, pseudogene | 0.000989176 | −1.13 | 215110_PM_at | 9.2 | 10.4 |
| 215232_PM_at | ARHGAP44 | Rho GTPase activating protein 44 | 0.000332776 | −1.18 | 215232_PM_at | 11.1 | 13.1 |
| 217158_PM_at | LOC442421 | hypothetical LOC442421 /// prostaglandin E2 receptor EP4 subtype-like | 2.98E−05 | 1.18 | 217158_PM_at | 14.2 | 12.0 |
| 218365_PM_s_at | DARS2 | aspartyl-tRNA synthetase 2, mitochondrial | 0.000716035 | 1.18 | 218365_PM_s_at | 17.2 | 14.5 |
| 219695_PM_at | SMPD3 | sphingomyelin phosphodiesterase 3, neutral membrane (neutral sphingomyelinase II) | 0.000377151 | −1.47 | 219695_PM_at | 12.0 | 17.6 |
| 220603_PM_s_at | MCTP2 | multiple C2 domains, transmembrane 2 | 0.000933412 | −1.38 | 220603_PM_s_at | 338.5 | 465.8 |
| 224963_PM_at | SLC26A2 | solute carrier family 26 (sulfate transporter), member 2 | 0.000961242 | 1.47 | 224963_PM_at | 94.3 | 64.0 |
| 226729_PM_at | USP37 | ubiquitin specific peptidase 37 | 0.000891038 | 1.24 | 226729_PM_at | 32.9 | 26.6 |
| 228226_PM_s_at | ZNF775 | zinc finger protein 775 | 0.000589512 | 1.2 | 228226_PM_s_at | 20.5 | 17.1 |
| 230608_PM_at | C1orf182 | chromosome 1 open reading frame 182 | 0.000153478 | −1.18 | 230608_PM_at | 15.9 | 18.8 |
| 230756_PM_at | ZNF683 | zinc finger protein 683 | 0.00044751 | 1.52 | 230756_PM_at | 26.7 | 17.6 |
| 231757_PM_at | TAS2R5 | taste receptor, type 2, member 5 | 0.000869775 | −1.12 | 231757_PM_at | 9.3 | 10.4 |
| 231958_PM_at | C3orf31 | Chromosome 3 open reading frame 31 | 4.09E−05 | 1.22 | 231958_PM_at | 20.1 | 16.4 |
| 237290_PM_at | — | — | 0.000948318 | −1.22 | 237290_PM_at | 10.3 | 12.5 |
| 237806_PM_s_at | LOC729296 | hypothetical LOC729296 | 0.00092234 | −1.18 | 237806_PM_s_at | 10.2 | 12.0 |
| 238459_PM_x_at | SPATA6 | spermatogenesis associated 6 | 0.000116525 | −1.15 | 238459_PM_x_at | 9.2 | 10.5 |
| 241331_PM_at | SKAP2 | Src kinase associated phosphoprotein 2 | 0.000821476 | −1.39 | 241331_PM_at | 16.4 | 22.9 |
| 241368_PM_at | PLIN5 | perilipin 5 | 0.000406066 | −1.61 | 241368_PM_at | 84.5 | 136.3 |
| 241543_PM_at | — | — | 0.000478221 | −1.17 | 241543_PM_at | 9.4 | 11.0 |

Example 3

Differentially Expressed Genes Associated with Kidney Transplant Rejections

This Example describes global analysis of gene expressions in kidney transplant patients with different types of rejections or injuries.

A total of biopsy-documented 274 kidney biopsy samples from the Transplant Genomics Collaborative Group (TGCG) were processed on the Affymetrix HG-U133 PM only peg microarrays. The 274 samples that were analyzed comprised of 4 different phenotypes: Acute Rejection (AR; n=75); Acute Dysfunction No Rejection (ADNR; n=39); Chronic Allograft Nephropathy (CAN; n=61); and Transplant Excellent (TX; n=99).

Signal Filters: To eliminate low expressed signals we used a signal filter cut-off that was data driven, and expression signals <Log 2 4.23 in all samples were eliminated leaving us with 48882 probe sets from a total of 54721 probe sets.

4-Way AR/ADNR/CAN/TX Classifier:

We first did a 4 way comparison of the AR, ADNR, CAN and TX samples. The samples comprised of four different classes a 4-way ANOVA analysis yielded more than 10,000 differentially expressed genes even at a stringent p value cut-off of <0.001. Since we were trying to discover a signature that could differentiate these four classes we used only the top 200 differentially expressed probe sets to build predictive models. We ran the Nearest Centroid (NC) algorithm to build the predictive models. When we used the top 200 differentially expressed probe sets between all four phenotypes, the best predictor model was based on 199 probe sets.

Nearest Centroid (NC) classification takes the gene expression profile of a new sample, and compares it to each of the existing class centroids. The class whose centroid that it is closest to, in squared distance, is the predicted class for that new sample. It also provides the centroid distances for each sample to each of the possible phenotypes being tested. In other words, in a 2-way classifier like AR vs. TX, the tool provides the "best" classification and provides the centroid distances to the two possible outcomes: TX and AR.

We observed in multiple datasets that there are 4 classes of predictions made. First, are correctly classified as TX by both biopsy and NC. Second, are correctly classified as AR by both biopsy and NC. Third, are truly misclassified samples. In other words, the biopsy says one thing and the molecular profile another. In these cases, the centroid distances for the given classifications are dramatically different, making the molecular classification very straightforward and simply not consistent with the biopsy phenotype assigned. Whether this is because the gold standard biopsy classification is wrong or the molecular classification is wrong is impossible to know at this point.

However, there is a fourth class that we call "mixed" classifications. In these cases supposedly "misclassified" samples by molecular profile show a nearest centroid distance that is not very different when compared to that of the "correct" classification based on the biopsy. In other words, the nearest centroid distances of most of these misclassified "mixed" samples are actually very close to the correct biopsy classification. However, because NC has no rules set to deal with the mixed situation it simply calls the sample by the nominally higher centroid distance.

The fact is that most standard implementations of class prediction algorithms currently available treat all classes as dichotomous variables (yes/no diagnostically). They are not designed to deal with the reality of medicine that molecular phenotypes of clinical samples can actually represent a continuous range of molecular scores based on the expression signal intensities with complex implications for the diagnoses. Thus, "mixed" cases where the centroid distances are only slightly higher for TX than AR is still classified as a TX, even if the AR distances are only slightly less. In this case, where there is a mixture of TX and AR by expression, it is obvious that the case is actually an AR for a transplant clinician, not a TX. Perhaps just a milder form of AR and this is the reason for using thresholding.

Thus, we set a threshold for the centroid distances. The threshold is driven by the data. The threshold equals the mean difference NC provides in centroid distances for the two possible classifications (i.e. AR vs. TX) for all correctly classified samples in the data set (e.g. classes 1 and 2 of the 4 possible outcomes of classification). This means that for the "mixed" class of samples, if a biopsy-documented sample was misclassified by molecular profiling, but the misclassification was within the range of the mean calculated centroid distances of the true classifications in the rest of the data, then that sample would not be considered as a misclassified sample.

Table 10a shows the performance of the 4 way AR, ADNR, CAN, TX NC classifier using such a data driven threshold. Table 10b shows the top 200 probeset used for the 4 way AR, ADNR, CAN, TX NC classifier. So, using the top 200 differentially expressed probesets from a 4-way AR, ADNR, CAN and TX ANOVA with a Nearest Centroid classifier, we are able to molecularly classify the 4 phenotypes at 97% accuracy. Smaller classifier sets did not afford any significant increase in the predictive accuracies. To validate this data we applied this classification to an externally collected data set. These were samples collected at the University of Sao Paolo in Brazil. A total of 80 biopsy-documented kidney biopsy samples were processed on the same Affymetrix HG-U133 PM only peg microarrays. These 80 samples that were analyzed comprised of the same 4 different phenotypes: AR (n=23); ADNR (n=11); CAN (n=29); and TX (n=17).

We performed the classification based on the "locked" NC predictor (meaning that none of the thresholding parameters were changed. Table 11 shows the performance of our locked 4 way AR, ADNR, CAN, TX NC classifier in the Brazilian cohort. So, using the top 200 differentially expressed probesets from a 4-way AR, ADNR, CAN and TX ANOVA with a "locked" Nearest Centroid classifier we are able to molecularly classify the 4 phenotypes with similar accuracy in an independently and externally collected validation set. This validates our molecular classifier of the biopsy on an independent external data set. It also demonstrates that the classifier is not subject to influence based on significant racial differences represented in the Brazilian population.

3-Way AR/ADNR/TX Classifier:

Similarly, we did a 3 way comparison of the AR, ADNR and TX samples since these are the most common phenotypes encountered during the early post-transplant period with CAN usually being a late manifestation of graft injury which is progressive. The samples comprised of these 3 different classes, and a 4-way ANOVA analysis again yielded more than 10,000 differentially expressed genes, so we used only the top 200 differentially expressed probe sets to build predictive models. We ran the Nearest Centroid (NC) algorithm to build the predictive models. When we used the top 200 differentially expressed probe sets between all four phenotypes the best predictor model was based on 197 probe sets.

Table 12a shows the performance of the 3 way AR, ADNR, TX NC classifier with which we are able to molecularly classify the 3 phenotypes at 98% accuracy in the TGCG cohort. Table 12b shows the top 200 probeset used for the 3 way AR, ADNR, TX NC classifier in the TGCG cohort. Similarly the locked 3 way classifier performs equally well on the Brazilian cohort with 98% accuracy (Table 13). Therefore, our 3 way classifier also validates on the external data set.

2-Way CAN/TX Classifier:

Finally we also did a 2 way comparison of the CAN and TX samples. The samples comprised of these 2 classes with an ANOVA analysis again yielded ~11,000 differentially expressed genes, so we used only the top 200 differentially expressed probe sets to build predictive models. We ran the Nearest Centroid (NC) algorithm to build the predictive models. When we used the top 200 differentially expressed probe sets the best predictor model was based on all 200 probe sets. Table 14a shows the performance of the 2 way CAN, TX NC classifier with which we are able to molecularly classify the 4 phenotypes at 97% accuracy in the TGCG cohort. Table 14b shows the top 200 probeset used for the 2 way CAN, TX NC classifier in the TGCG cohort. This locked classifier performs equally well on the Brazilian cohort with 95% accuracy (Table 15). Again we show that our 2 way CAN, TX classifier also validates on the external data set.

It is understood that the examples and embodiments described herein are for illustrative purposes only and that various modifications or changes in light thereof will be suggested to persons skilled in the art and are to be included within the spirit and purview of this application and scope of the appended claims. Although any methods and materials similar or equivalent to those described herein can be used in the practice or testing of the present invention, the preferred methods and materials are described.

All publications, GenBank sequences, ATCC deposits, patents and patent applications cited herein are hereby expressly incorporated by reference in their entirety and for all purposes as if each is individually so denoted.

TABLE 10a

Biopsy Expression Profiling of Kidney Transplants: 4-Way Classifier AR vs. ADNR vs. CAN vs. TX (TGCG Samples)

| Algorithm | Predictors | Comparison | Validation Cohort | | | | | |
|---|---|---|---|---|---|---|---|---|
| | | | AUC | Predictive Accuracy (%) | Sensitivity (%) | Specificity (%) | Postive Predictive Value (%) | Negative Predictive Value (%) |
| Nearest Centroid | 199 | AR vs. TX | 0.957 | 95 | 96 | 96 | 94 | 97 |
| Nearest Centroid | 199 | ADNR vs. TX | 0.977 | 97 | 94 | 100 | 100 | 97 |
| Nearest Centroid | 199 | CAN vs. TX | 0.992 | 99 | 98 | 100 | 100 | 99 |

TABLE 10b

Biopsy Expression Profiling of Kidney Transplants: 4-Way Classifier AR vs. ADNR vs. CAN vs. TX (TGCG Samples)

| # | Probeset ID | Entrez Gene | Gene Symbol | Gene Title | p-value (Final Phenotype) | ADNR-Mean | AR-Mean | CAN-Mean | TX-Mean |
|---|---|---|---|---|---|---|---|---|---|
| 1 | 204446_PM_s_at | 240 | ALOX5 | arachidonate 5-lipoxygenase | 2.82E−34 | 91.9 | 323.9 | 216.7 | 54.7 |
| 2 | 202207_PM_at | 10123 | ARL4C | ADP-ribosylation factor-like 4C | 1.31E−32 | 106.9 | 258.6 | 190.4 | 57.2 |
| 3 | 204698_PM_at | 3669 | ISG20 | interferon stimulated exonuclease gene 20 kDa | 1.50E−31 | 41.5 | 165.1 | 96.1 | 27.6 |
| 4 | 225701_PM_at | 80709 | AKNA | AT-hook transcription factor | 1.75E−31 | 37.7 | 102.8 | 73.2 | 29.0 |
| 5 | 207651_PM_at | 29909 | GPR171 | G protein-coupled receptor 171 | 6.30E−31 | 25.8 | 89.9 | 57.0 | 20.9 |
| 6 | 204205_PM_at | 60489 | APOBEC3G | apolipoprotein B mRNA editing enzyme, catalytic polypeptide-like 3G | 1.27E−30 | 95.4 | 289.4 | 192.0 | 78.7 |
| 7 | 208948_PM_s_at | 6780 | STAU1 | staufen, RNA binding protein, homolog 1 (Drosophila) | 1.37E−30 | 1807.9 | 1531.8 | 1766.0 | 2467.4 |
| 8 | 217733_PM_s_at | 9168 | TMSB10 | thymosin beta 10 | 2.38E−30 | 4414.7 | 6331.3 | 5555.2 | 3529.0 |
| 9 | 205831_PM_at | 914 | CD2 | CD2 molecule | 2.73E−30 | 40.4 | 162.5 | 100.9 | 33.9 |
| 10 | 209083_PM_at | 11151 | CORO1A | coronin, actin binding protein, 1A | 5.57E−30 | 46.9 | 163.8 | 107.1 | 34.3 |
| 11 | 210915_PM_x_at | 28638 | TRBC2 | T cell receptor beta constant 2 | 5.60E−30 | 39.7 | 230.7 | 129.7 | 37.5 |
| 12 | 211368_PM_s_at | 834 | CASP1 | caspase 1, apoptosis-related cysteine peptidase (interleukin 1, beta, convertase) | 6.21E−30 | 102.6 | 274.3 | 191.4 | 81.8 |
| 13 | 201042_PM_at | 7052 | TGM2 | transglutaminase 2 (C polypeptide, protein-glutamine-gamma-glutamyltransferase) | 6.28E−30 | 131.8 | 236.5 | 172.6 | 80.1 |
| 14 | 227353_PM_at | 147138 | TMC8 | transmembrane channel-like 8 | 7.76E−30 | 19.8 | 64.2 | 42.7 | 16.6 |
| 15 | 1555852_PM_at | 100507463 | LOC100507463 | hypothetical LOC100507463 | 8.29E−30 | 78.9 | 202.6 | 154.2 | 70.9 |
| 16 | 226878_PM_at | 3111 | HLA-DOA | major histocompatibility complex, class II, DO alpha | 1.63E−29 | 102.0 | 288.9 | 201.4 | 94.3 |
| 17 | 238327_PM_at | 440836 | ODF3B | outer dense fiber of sperm tails 3B | 1.74E−29 | 32.8 | 81.4 | 58.5 | 26.1 |
| 18 | 229437_PM_at | 114614 | MIR155HG | MIR155 host gene (non-protein coding) | 1.78E−29 | 15.4 | 50.4 | 28.5 | 12.9 |
| 19 | 33304_PM_at | 3669 | ISG20 | interferon stimulated exonuclease gene 20 kDa | 2.40E−29 | 33.2 | 101.3 | 63.4 | 22.1 |
| 20 | 226621_PM_at | 9180 | OSMR | oncostatin M receptor | 2.42E−29 | 545.6 | 804.5 | 682.9 | 312.1 |
| 21 | 1553906_PM_s_at | 221472 | FGD2 | FYVE, RhoGEF and PH domain containing 2 | 2.43E−29 | 104.6 | 321.0 | 219.3 | 71.9 |
| 22 | 1405_PM_i_at | 6352 | CCL5 | chemokine (C—C motif) ligand 5 | 2.54E−29 | 68.0 | 295.7 | 195.6 | 54.6 |
| 23 | 226219_PM_at | 257106 | ARHGAP30 | Rho GTPase activating protein 30 | 2.92E−29 | 46.4 | 127.9 | 91.8 | 37.5 |
| 24 | 204891_PM_s_at | 3932 | LCK | lymphocyte-specific protein tyrosine kinase | 3.79E−29 | 19.3 | 74.2 | 43.4 | 17.8 |
| 25 | 210538_PM_s_at | 330 | BIRC3 | baculoviral IAP repeat-containing 3 | 5.06E−29 | 106.7 | 276.7 | 199.1 | 84.6 |
| 26 | 202644_PM_s_at | 7128 | TNFAIP3 | tumor necrosis factor, alpha-induced protein 3 | 5.47E−29 | 169.8 | 380.4 | 278.2 | 136.6 |
| 27 | 227346_PM_at | 10320 | IKZF1 | IKAROS family zinc finger 1 (Ikaros) | 7.07E−29 | 24.9 | 79.7 | 53.3 | 19.8 |

TABLE 10b-continued

Biopsy Expression Profiling of Kidney Transplants: 4-Way Classifier AR vs. ADNR vs. CAN vs. TX (TGCG Samples)

| # | Probeset ID | Entrez Gene | Gene Symbol | Gene Title | p-value (Final Phenotype) | ADNR-Mean | AR-Mean | CAN-Mean | TX-Mean |
|---|---|---|---|---|---|---|---|---|---|
| 28 | 202957_PM_at | 3059 | HCLS1 | hematopoietic cell-specific Lyn substrate 1 | 8.26E-29 | 119.2 | 299.5 | 229.9 | 82.2 |
| 29 | 202307_PM_s_at | 6890 | TAP1 | transporter 1, ATP-binding cassette, sub-family B (MDR/TAP) | 1.01E-28 | 172.4 | 420.6 | 280.0 | 141.0 |
| 30 | 202748_PM_at | 2634 | GBP2 | guanylate binding protein 2, interferon-inducible | 1.10E-28 | 196.7 | 473.0 | 306.7 | 141.0 |
| 31 | 211796_PM_s_at | 28638 /// 28639 | TRBC1 /// TRBC2 | T cell receptor beta constant 1 /// T cell receptor beta constant 2 | 1.31E-28 | 69.2 | 431.5 | 250.2 | 63.6 |
| 32 | 213160_PM_at | 1794 | DOCK2 | dedicator of cytokinesis 2 | 1.36E-28 | 33.7 | 92.6 | 66.0 | 27.8 |
| 33 | 211656_PM_x_at | 100133583 /// 3119 | HLA-DQB1 /// LOC100133583 | major histocompatibility complex, class II, DQ beta 1 /// HLA class II histocompatibili | 1.63E-28 | 211.3 | 630.2 | 459.8 | 208.2 |
| 34 | 223322_PM_at | 83593 | RASSF5 | Ras association (RalGDS/AF-6) domain family member 5 | 1.68E-28 | 41.5 | 114.4 | 79.3 | 39.2 |
| 35 | 205488_PM_at | 3001 | GZMA | granzyme A (granzyme 1, cytotoxic T-lymphocyte-associated serine esterase 3) | 1.72E-28 | 37.3 | 164.8 | 102.3 | 33.4 |
| 36 | 213603_PM_s_at | 5880 | RAC2 | ras-related C3 botulinum toxin substrate 2 (rho family, small GTP binding protein Rac2) | 1.87E-28 | 113.9 | 366.5 | 250.3 | 86.5 |
| 37 | 229390_PM_at | 441168 | FAM26F | family with sequence | 1.94E-28 | 103.8 | 520.0 | 272.4 | 75.9 |
| 38 | 206804_PM_at | 917 | CD3G | CD3g molecule, gamma (CD3-TCR complex) | 1.99E-28 | 19.7 | 60.6 | 36.4 | 17.3 |
| 39 | 209795_PM_at | 969 | CD69 | CD69 molecule | 2.06E-28 | 17.6 | 57.6 | 40.6 | 15.2 |
| 40 | 219574_PM_at | 55016 | 1-Mar | membrane-associated ring finger (C3HC4) 1 | 2.07E-28 | 51.5 | 126.0 | 87.5 | 36.2 |
| 41 | 207320_PM_x_at | 6780 | STAU1 | staufen, RNA binding protein, homolog 1 (Drosophila) | 2.21E-28 | 1425.1 | 1194.6 | 1383.2 | 1945.3 |
| 42 | 218983_PM_at | 51279 | C1RL | complement component 1, r subcomponent-like | 2.97E-28 | 167.1 | 244.5 | 206.9 | 99.4 |
| 43 | 206011_PM_at | 834 | CASP1 | caspase 1, apoptosis-related cysteine peptidase (interleukin 1, beta, convertase) | 3.23E-28 | 74.5 | 198.0 | 146.2 | 60.7 |
| 44 | 213539_PM_at | 915 | CD3D | CD3d molecule, delta (CD3-TCR complex) | 5.42E-28 | 70.8 | 335.1 | 168.1 | 60.0 |
| 45 | 213193_PM_x_at | 28639 | TRBC1 | T cell receptor beta constant 1 | 5.69E-28 | 95.3 | 490.9 | 286.5 | 92.1 |
| 46 | 232543_PM_x_at | 64333 | ARHGAP9 | Rho GTPase activating protein 9 | 6.79E-28 | 31.7 | 99.1 | 62.3 | 25.8 |
| 47 | 200986_PM_at | 710 | SERPING1 | serpin peptidase inhibitor, clade G (C1 inhibitor), member 1 | 7.42E-28 | 442.7 | 731.5 | 590.2 | 305.3 |
| 48 | 213037_PM_x_at | 6780 | STAU1 | staufen, RNA binding protein, homolog 1 (Drosophila) | 9.35E-28 | 1699.0 | 1466.8 | 1670.1 | 2264.9 |
| 49 | 204670_PM_x_at | 3123 /// 3126 | HLA-DRB1 /// HLA-DRB4 | major histocompatibility complex, class II, DR beta 1 /// major histocompatibility comp | 1.03E-27 | 2461.9 | 4344.6 | 3694.9 | 2262.0 |
| 50 | 217028_PM_at | 7852 | CXCR4 | chemokine (C—X—C motif) receptor 4 | 1.52E-27 | 100.8 | 304.4 | 208.4 | 75.3 |
| 51 | 203761_PM_at | 6503 | SLA | Src-like-adaptor | 1.61E-27 | 69.6 | 179.2 | 138.4 | 51.4 |
| 52 | 201137_PM_s_at | 3115 | HLA-DPB1 | major histocompatibility complex, class II, DP beta 1 | 1.95E-27 | 1579.1 | 3863.7 | 3151.7 | 1475.9 |
| 53 | 205269_PM_at | 3937 | LCP2 | lymphocyte cytosolic protein 2 (SH2 domain containing leukocyte protein of 76 kDa) | 2.16E-27 | 30.2 | 92.2 | 58.9 | 22.9 |
| 54 | 205821_PM_at | 22914 | KLRK1 | killer cell lectin-like receptor subfamily K, member 1 | 2.56E-27 | 30.3 | 111.5 | 72.5 | 31.3 |
| 55 | 204655_PM_at | 6352 | CCL5 | chemokine (C—C motif) ligand 5 | 3.28E-27 | 77.5 | 339.4 | 223.4 | 66.8 |
| 56 | 226474_PM_at | 84166 | NLRC5 | NLR family, CARD domain containing 5 | 3.54E-27 | 64.4 | 173.5 | 129.8 | 55.1 |
| 57 | 212503_PM_s_at | 22982 | DIP2C | DIP2 disco-interacting protein 2 homolog C (Drosophila) | 3.69E-27 | 559.7 | 389.2 | 502.0 | 755.0 |

TABLE 10b-continued

Biopsy Expression Profiling of Kidney Transplants: 4-Way Classifier AR vs. ADNR vs. CAN vs. TX (TGCG Samples)

| # | Probeset ID | Entrez Gene | Gene Symbol | Gene Title | p-value (Final Phenotype) | ADNR-Mean | AR-Mean | CAN-Mean | TX-Mean |
|---|---|---|---|---|---|---|---|---|---|
| 58 | 213857_PM_s_at | 961 | CD47 | CD47 molecule | 4.33E-27 | 589.6 | 858.0 | 703.2 | 481.2 |
| 59 | 206118_PM_at | 6775 | STAT4 | signal transducer and activator of transcription 4 | 4.58E-27 | 21.0 | 49.5 | 37.7 | 18.1 |
| 60 | 227344_PM_at | 10320 | IKZF1 | IKAROS family zinc finger 1 (Ikaros) | 5.87E-27 | 17.8 | 40.0 | 28.5 | 14.9 |
| 61 | 230550_PM_at | 64231 | MS4A6A | membrane-spanning 4-domains, subfamily A, member 6A | 5.98E-27 | 44.8 | 124.3 | 88.0 | 30.9 |
| 62 | 235529_PM_x_at | 25939 | SAMHD1 | SAM domain and HD domain 1 | 6.56E-27 | 189.3 | 379.9 | 289.1 | 128.0 |
| 63 | 205758_PM_at | 925 | CD8A | CD8a molecule | 7.28E-27 | 24.2 | 105.8 | 60.3 | 22.2 |
| 64 | 211366_PM_x_at | 834 | CASP1 | caspase 1, apoptosis-related cysteine peptidase (interleukin 1, beta, convertase) | 7.37E-27 | 115.3 | 261.0 | 186.0 | 87.1 |
| 65 | 209606_PM_at | 9595 | CYTIP | cytohesin 1 interacting protein | 7.48E-27 | 41.4 | 114.3 | 79.0 | 32.9 |
| 66 | 201721_PM_s_at | 7805 | LAPTM5 | lysosomal protein transmembrane 5 | 8.04E-27 | 396.5 | 934.6 | 661.3 | 249.4 |
| 67 | 204774_PM_at | 2123 | EVI2A | ecotropic viral integration site 2A | 8.14E-27 | 63.6 | 168.5 | 114.7 | 44.9 |
| 68 | 215005_PM_at | 54550 | NECAB2 | N-terminal EF-hand calcium binding protein 2 | 8.32E-27 | 36.7 | 23.4 | 30.9 | 65.7 |
| 69 | 229937_PM_x_at | 10859 | LILRB1 | Leukocyte immunoglobulin-like receptor, subfamily B (with TM and ITIM domains), member | 8.33E-27 | 23.5 | 79.9 | 50.0 | 18.5 |
| 70 | 209515_PM_s_at | 5873 | RAB27A | RAB27A, member RAS oncogene family | 8.93E-27 | 127.3 | 192.2 | 160.5 | 85.2 |
| 71 | 242916_PM_at | 11064 | CEP110 | centrosomal protein 110 kDa | 8.98E-27 | 30.8 | 68.1 | 51.2 | 26.2 |
| 72 | 205270_PM_s_at | 3937 | LCP2 | lymphocyte cytosolic protein 2 (SH2 domain containing leukocyte protein of 76 kDa) | 9.04E-27 | 56.8 | 162.6 | 104.4 | 44.6 |
| 73 | 214022_PM_s_at | 8519 | IFITM1 | interferon induced transmembrane protein 1 (9-27) | 9.31E-27 | 799.1 | 1514.7 | 1236.6 | 683.3 |
| 74 | 1552703_PM_s_at | 114769 /// 834 | CARD16 /// CASP1 | caspase recruitment domain family, member 16 /// caspase 1, apoptosis-related cysteine | 1.01E-26 | 64.6 | 167.8 | 120.6 | 54.9 |
| 75 | 202720_PM_at | 26136 | TES | testis derived transcript (3 LIM doma ins) | 1.05E-26 | 285.4 | 379.0 | 357.9 | 204.2 |
| 76 | 202659_PM_at | 5699 | PSMB10 | proteasome (prosome, macropain) subunit, beta type, 10 | 1.10E-26 | 180.7 | 355.6 | 250.3 | 151.5 |
| 77 | 236295_PM_s_at | 197358 | NLRC3 | NLR family, CARD domain containing 3 | 1.19E-26 | 19.0 | 52.5 | 37.0 | 18.6 |
| 78 | 229041_PM_s_at | — | — | — | 1.31E-26 | 36.5 | 132.1 | 84.7 | 32.4 |
| 79 | 205798_PM_at | 3575 | IL7R | interleukin 7 receptor | 1.32E-26 | 44.1 | 136.8 | 106.3 | 33.4 |
| 80 | 209970_PM_x_at | 834 | CASP1 | caspase 1, apoptosis-related cysteine peptidase (interleukin 1, beta, convertase) | 1.36E-26 | 116.0 | 266.6 | 181.6 | 88.7 |
| 81 | 204336_PM_s_at | 10287 | RGS19 | regulator of G-protein signaling 19 | 1.54E-26 | 95.2 | 187.7 | 135.7 | 67.0 |
| 82 | 204912_PM_at | 3587 | IL10RA | interleukin 10 receptor, alpha | 1.61E-26 | 57.0 | 178.7 | 117.2 | 46.1 |
| 83 | 227184_PM_at | 5724 | PTAFR | platelet-activating factor receptor | 1.70E-26 | 89.8 | 191.4 | 134.4 | 62.7 |
| 84 | 209969_PM_s_at | 6772 | STAT1 | signal transducer and activator of transcription 1, 91 kDa | 1.82E-26 | 395.8 | 1114.5 | 664.6 | 320.8 |
| 85 | 232617_PM_at | 1520 | CTSS | cathepsin S | 1.88E-26 | 209.6 | 537.9 | 392.2 | 154.8 |
| 86 | 224451_PM_x_at | 64333 | ARHGAP9 | Rho GTPase activating protein 9 | 1.94E-26 | 34.2 | 103.4 | 71.8 | 29.4 |
| 87 | 209670_PM_at | 28755 | TRAC | T cell receptor alpha constant | 2.06E-26 | 37.9 | 149.9 | 96.2 | 38.5 |
| 88 | 1559584_PM_a_at | 283897 | C16orf54 | chromosome 16 open reading frame 54 | 2.22E-26 | 31.3 | 95.8 | 71.5 | 26.1 |
| 89 | 208306_PM_x_at | 3123 | HLA-DRB1 | Major histocompatibility complex, class II, DR beta 1 | 2.29E-26 | 2417.5 | 4278.5 | 3695.8 | 2255.0 |
| 90 | 229383_PM_at | 55016 | 1-Mar | membrane-associated ring finger (C3HC4) 1 | 2.36E-26 | 33.8 | 88.0 | 52.1 | 22.9 |
| 91 | 235735_PM_at | — | — | — | 2.46E-26 | 13.0 | 34.9 | 24.5 | 11.2 |

TABLE 10b-continued

Biopsy Expression Profiling of Kidney Transplants: 4-Way Classifier AR vs. ADNR vs. CAN vs. TX (TGCG Samples)

| # | Probeset ID | Entrez Gene | Gene Symbol | Gene Title | p-value (Final Phenotype) | ADNR-Mean | AR-Mean | CAN-Mean | TX-Mean |
|---|---|---|---|---|---|---|---|---|---|
| 92 | 203416_PM_at | 963 | CD53 | CD53 molecule | 2.56E-26 | 215.9 | 603.0 | 422.7 | 157.8 |
| 93 | 212504_PM_at | 22982 | DIP2C | DIP2 disco-interacting protein 2 homolog C (Drosophila) | 3.21E-26 | 334.5 | 227.2 | 289.4 | 452.5 |
| 94 | 204279_PM_at | 5698 | PSMB9 | proteasome (prosome, macropain) subunit, beta type, 9 (large multifunctional peptidase | 3.45E-26 | 241.6 | 637.4 | 419.4 | 211.3 |
| 95 | 235964_PM_x_at | 25939 | SAMHD1 | SAM domain and HID domain 1 | 3.60E-26 | 172.9 | 345.9 | 270.1 | 117.5 |
| 96 | 213566_PM_at | 6039 | RNASE6 | ribonuclease, RNase A family, k6 | 3.84E-26 | 180.9 | 482.0 | 341.1 | 134.3 |
| 97 | 221698_PM_s_at | 64581 | CLEC7A | C-type lectin domain family 7, member A | 4.00E-26 | 61.5 | 164.6 | 112.8 | 49.7 |
| 98 | 227125_PM_at | 3455 | IFNAR2 | interferon (alpha, beta and omega) receptor 2 | 4.03E-26 | 70.0 | 126.2 | 96.7 | 55.8 |
| 99 | 226525_PM_at | 9262 | STK17B | serine/threonine kinase 17b | 4.14E-26 | 146.8 | 338.7 | 259.1 | 107.6 |
| 100 | 221666_PM_s_at | 29108 | PYCARD | PYD and CARD domain containing | 4.95E-26 | 60.7 | 132.8 | 95.5 | 44.7 |
| 101 | 209774_PM_x_at | 2920 | CXCL2 | chemokine (C—X—C motif) ligand 2 | 5.73E-26 | 24.9 | 52.9 | 38.2 | 15.5 |
| 102 | 206082_PM_at | 10866 | HCP5 | HLA complex P5 | 5.98E-26 | 76.2 | 185.1 | 129.0 | 66.6 |
| 103 | 229391_PM_s_at | 441168 | FAM26F | family with sequence similarity 26, member F | 6.03E-26 | 98.6 | 379.7 | 212.1 | 73.7 |
| 104 | 229295_PM_at | 150166 /// 23765 | IL17RA /// LOC150166 | interleukin 17 receptor A /// hypothetical protein LOC150166 | 6.13E-26 | 76.4 | 131.8 | 98.4 | 50.0 |
| 105 | 202901_PM_x_at | 1520 | CTSS | cathepsin S | 6.32E-26 | 67.8 | 180.5 | 130.9 | 45.1 |
| 106 | 226991_PM_at | 4773 | NFATC2 | nuclear factor of activated T-cells, cytoplasmic, calcineurin-dependent 2 | 6.49E-26 | 37.9 | 87.0 | 66.7 | 30.3 |
| 107 | 223280_PM_x_at | 64231 | M54A6A | membrane-spanning 4-domains, subfamily A, member 6A | 6.72E-26 | 269.0 | 711.8 | 451.2 | 199.5 |
| 108 | 201601_PM_x_at | 8519 | IFITM1 | interferon induced transmembrane protein 1 (9-27) | 7.27E-26 | 1471.3 | 2543.5 | 2202.5 | 1251.1 |
| 109 | 1552701_PM_a_at | 114769 | CARD16 | caspase recruitment domain family, member 16 | 7.33E-26 | 143.8 | 413.6 | 273.3 | 119.8 |
| 110 | 229625_PM_at | 115362 | GBP5 | guanylate binding protein 5 | 7.80E-26 | 29.3 | 133.3 | 68.6 | 24.0 |
| 111 | 38149_PM_at | 9938 | ARHGAP25 | Rho GTPase activating protein 25 | 9.83E-26 | 51.3 | 108.9 | 83.2 | 43.2 |
| 112 | 203932_PM_at | 3109 | HLA-DMB | major histocompatibility complex, class II, DM beta | 1.03E-25 | 422.4 | 853.9 | 633.5 | 376.0 |
| 113 | 228964_PM_at | 639 | PRDM1 | PR domain containing 1, with ZNF domain | 1.15E-25 | 21.2 | 52.1 | 41.5 | 17.0 |
| 114 | 225799_PM_at | 112597 /// 541471 | LOC541471 /// NCRNA00152 | hypothetical LOC541471 /// non-protein coding RNA 152 | 1.23E-25 | 230.5 | 444.3 | 339.2 | 172.0 |
| 115 | 204118_PM_at | 962 | CD48 | CD48 molecule | 1.34E-25 | 82.9 | 341.5 | 212.4 | 65.2 |
| 116 | 211742_PM_s_at | 2124 | EVI2B | ecotropic viral integration site 2B | 1.36E-25 | 73.9 | 236.5 | 166.2 | 53.2 |
| 117 | 213416_PM_at | 3676 | ITGA4 | integrin, alpha 4 (antigen CD49D, alpha 4 subunit of VLA-4 receptor) | 1.47E-25 | 26.3 | 78.1 | 50.8 | 22.8 |
| 118 | 211991_PM_s_at | 3113 | HLA-DPA1 | major histocompatibility complex, class II, DP alpha 1 | 1.50E-25 | 1455.0 | 3605.4 | 2837.2 | 1462.9 |
| 119 | 232024_PM_at | 26157 | GIMAP2 | GTPase, IMAP family member 2 | 1.57E-25 | 90.2 | 197.7 | 146.7 | 72.5 |
| 120 | 205159_PM_at | 1439 | CSF2RB | colony stimulating factor 2 receptor, beta, low-affinity (granulocyte-macrophage) | 1.73E-25 | 33.7 | 107.5 | 70.4 | 26.3 |
| 121 | 228471_PM_at | 91526 | ANKRD44 | ankyrin repeat domain 44 | 1.79E-25 | 106.1 | 230.3 | 184.6 | 86.5 |
| 122 | 203332_PM_s_at | 3635 | INPP5D | inositol polyphosphate-5-phosphatase, 145 kDa | 1.88E-25 | 27.9 | 60.5 | 42.6 | 24.0 |
| 123 | 223502_PM_s_at | 10673 | TNFSF13B | tumor necrosis factor (ligand) superfamily, member 13b | 2.02E-25 | 73.0 | 244.3 | 145.5 | 60.0 |
| 124 | 229723_PM_at | 117289 | TAGAP | T-cell activation RhoGTPase activating protein | 2.07E-25 | 29.2 | 82.9 | 55.9 | 26.2 |
| 125 | 206978_PM_at | 729230 | CCR2 | chemokine (C—C motif) receptor 2 | 2.17E-25 | 32.1 | 100.7 | 68.6 | 27.3 |
| 126 | 1555832_PM_s_at | 1316 | KLF6 | Kruppel-like factor 6 | 2.31E-25 | 899.4 | 1076.8 | 1003.3 | 575.1 |
| 127 | 211990_PM_at | 3113 | HLA-DPA1 | major histocompatibility complex, class II, DP alpha | 2.53E-25 | 2990.7 | 5949.1 | 5139.9 | 3176.3 |

TABLE 10b-continued

Biopsy Expression Profiling of Kidney Transplants: 4-Way Classifier AR vs. ADNR vs. CAN vs. TX (TGCG Samples)

| # | Probeset ID | Entrez Gene | Gene Symbol | Gene Title | p-value (Final Phenotype) | ADNR-Mean | AR-Mean | CAN-Mean | TX-Mean |
|---|---|---|---|---|---|---|---|---|---|
| 128 | 202018_PM_s_at | 4057 | LTF | lactotransferrin | 2.90E-25 | 392.3 | 1332.4 | 624.5 | 117.7 |
| 129 | 210644_PM_s_at | 3903 | LAIR1 | leukocyte-associated immunoglobulin-like receptor 1 | 2.90E-25 | 29.7 | 74.6 | 45.3 | 21.2 |
| 130 | 222294_PM_s_at | 5873 | RAB27A | RAB27A, member RAS oncogene family | 3.13E-25 | 198.7 | 309.1 | 263.0 | 146.4 |
| 131 | 238668_PM_at | — | — | — | 3.29E-25 | 18.2 | 49.2 | 33.6 | 14.5 |
| 132 | 213975_PM_s_at | 4069 | LYZ | lysozyme | 3.31E-25 | 458.4 | 1626.0 | 1089.7 | 338.1 |
| 133 | 204220_PM_at | 9535 | GMFG | glia maturation factor, gamma | 3.46E-25 | 147.0 | 339.3 | 241.4 | 128.9 |
| 134 | 243366_PM_s_at | — | — | — | 3.46E-25 | 24.7 | 72.1 | 52.5 | 22.0 |
| 135 | 221932_PM_s_at | 51218 | GLRX5 | glutaredoxin 5 | 3.64E-25 | 1351.5 | 1145.8 | 1218.1 | 1599.3 |
| 136 | 225415_PM_at | 151636 | DTX3L | deltex 3-like (Drosophila) | 3.77E-25 | 230.2 | 376.4 | 290.8 | 166.9 |
| 137 | 205466_PM_s_at | 9957 | HS3ST1 | heparan sulfate (glucosamine) 3-O—sulfotransferase 1 | 4.15E-25 | 73.6 | 123.8 | 96.0 | 42.1 |
| 138 | 200904_PM_at | 3133 | HLA-E | major histocompatibility complex, class I, E | 4.20E-25 | 1142.5 | 1795.2 | 1607.7 | 994.7 |
| 139 | 228442_PM_at | 4773 | NFATC2 | nuclear factor of activated T-cells, cytoplasmic, calcineurin-dependent 2 | 4.48E-25 | 39.0 | 84.8 | 62.8 | 32.0 |
| 140 | 204923_PM_at | 54440 | SASH3 | SAM and SH3 domain containing 3 | 4.49E-25 | 25.4 | 68.2 | 47.6 | 21.7 |
| 141 | 223640_PM_at | 10870 | HCST | hematopoietic cell signal transducer | 4.52E-25 | 91.0 | 234.0 | 158.3 | 72.7 |
| 142 | 211582_PM_x_at | 7940 | LST1 | leukocyte specific transcript 1 | 4.53E-25 | 57.5 | 183.8 | 121.2 | 49.4 |
| 143 | 219014_PM_at | 51316 | PLAC8 | placenta-specific 8 | 5.94E-25 | 38.8 | 164.1 | 88.6 | 30.7 |
| 144 | 210895_PM_s_at | 942 | CD86 | CD86 molecule | 6.21E-25 | 32.3 | 85.0 | 52.6 | 21.6 |
| 145 | AFFX-HUMISGF3A/M97935_3_at | 6772 | STAT1 | signal transducer and activator of transcription 1, 91 kDa | 6.81E-25 | 642.1 | 1295.1 | 907.8 | 539.6 |
| 146 | 201315_PM_x_at | 10581 | IFITM2 | interferon induced transmembrane protein 2 (1-8D) | 6.87E-25 | 2690.9 | 3712.1 | 3303.7 | 2175.3 |
| 147 | 228532_PM_at | 128346 | C1orf162 | chromosome 1 open reading frame 162 | 7.07E-25 | 82.6 | 217.7 | 140.2 | 60.0 |
| 148 | 202376_PM_at | 12 | SERPINA3 | serpin peptidase inhibitor, clade A (alpha-1 antiproteinase, antitrypsin), member 3 | 7.13E-25 | 186.2 | 387.1 | 210.2 | 51.7 |
| 149 | 212587_PM_s_at | 5788 | PTPRC | protein tyrosine phosphatase, receptor type, C | 7.18E-25 | 114.8 | 398.6 | 265.7 | 90.3 |
| 150 | 223218_PM_s_at | 64332 | NFKBIZ | nuclear factor of kappa light polypeptide gene enhancer in B-cells inhibitor, zeta | 7.26E-25 | 222.6 | 497.9 | 399.9 | 159.1 |
| 151 | 224356_PM_x_at | 64231 | MS4A6A | membrane-spanning 4-domains, subfamily A, member 6A | 7.33E-25 | 150.6 | 399.6 | 249.6 | 111.2 |
| 152 | 206420_PM_at | 10261 | IGSF6 | immunoglobulin superfamily, member 6 | 7.58E-25 | 45.1 | 131.5 | 74.3 | 32.7 |
| 153 | 225764_PM_at | 2120 | ETV6 | ets variant 6 | 7.66E-25 | 92.6 | 133.0 | 112.8 | 77.0 |
| 154 | 1555756_PM_a_at_ | 64581 | CLEC7A | C-type lectin domain family 7, member A | 7.74E-25 | 16.6 | 45.4 | 28.9 | 13.2 |
| 155 | 226218_PM_at | 3575 | IL7R | interleukin 7 receptor | 8.14E-25 | 55.6 | 197.0 | 147.1 | 41.4 |
| 156 | 209198_PM_s_at | 23208 | SYT11 | synaptotagmin XI | 8.28E-25 | 30.0 | 45.3 | 41.8 | 22.8 |
| 157 | 202803_PM_s_at | 3689 | ITGB2 | integrin, beta 2 (complement component 3 receptor 3 and 4 subunit) | 9.57E-25 | 100.5 | 253.0 | 182.6 | 65.2 |
| 158 | 215049_PM_x_at | 9332 | CD163 | CD163 molecule | 9.85E-25 | 232.8 | 481.3 | 344.5 | 112.9 |
| 159 | 202953_PM_at | 713 | C1QB | complement component 1, q subcomponent, B chain | 9.99E-25 | 215.8 | 638.4 | 401.1 | 142.5 |
| 160 | 208091_PM_s_at | 81552 | VOPP1 | vesicular, overexpressed in cancer, prosurvival protein 1 | 1.02E-24 | 495.5 | 713.9 | 578.1 | 409.7 |
| 161 | 201288_PM_at | 397 | ARHGDIB | Rho GDP dissociation inhibitor (GDI) beta | 1.13E-24 | 354.9 | 686.8 | 542.2 | 308.1 |
| 162 | 213733_PM_at | 4542 | MYO1F | myosin IF | 1.27E-24 | 26.8 | 52.7 | 39.4 | 20.9 |
| 163 | 212588_PM_at | 5788 | PTPRC | protein tyrosine phosphatase, receptor type, C | 1.41E-24 | 94.4 | 321.0 | 217.7 | 76.4 |
| 164 | 242907_PM_at | — | — | — | 1.49E-24 | 59.3 | 165.1 | 99.7 | 39.8 |
| 165 | 209619_PM_at | 972 | CD74 | CD74 molecule, major histocompatibility complex, class II invariant chain | 1.55E-24 | 989.0 | 1864.7 | 1502.3 | 864.9 |
| 166 | 239237_PM_at | — | — | — | 1.75E-24 | 15.9 | 34.9 | 25.3 | 14.5 |

TABLE 10b-continued

Biopsy Expression Profiling of Kidney Transplants: 4-Way Classifier AR vs. ADNR vs. CAN vs. TX (TGCG Samples)

| # | Probeset ID | Entrez Gene | Gene Symbol | Gene Title | p-value (Final Phenotype) | ADNR-Mean | AR-Mean | CAN-Mean | TX-Mean |
|---|---|---|---|---|---|---|---|---|---|
| 167 | 217022_PM_s_at | 100126583 /// 3493 /// 3494 | IGHA1 /// IGHA2 /// LOC100126583 | immunoglobulin heavy constant alpha 1 /// immunoglobulin heavy constant alpha 2 (A2m ma | 1.80E-24 | 77.7 | 592.5 | 494.6 | 49.4 |
| 168 | 201859_PM_at | 5552 | SRGN | serglycin | 1.82E-24 | 1237.9 | 2171.99 | 1747.0 | 981.8 |
| 169 | 243418_PM_at | — | — | — | 1.88E-24 | 56.3 | 31.1 | 49.8 | 104.8 |
| 170 | 202531_PM_at | 3659 | IRF1 | interferon regulatory factor 1 | 1.93E-24 | 92.9 | 226.0 | 154.5 | 77.0 |
| 171 | 208966_PM_x_at | 3428 | IFI16 | interferon, gamma-inducible protein 16 | 1.98E-24 | 406.7 | 760.4 | 644.9 | 312.6 |
| 172 | 1555759_PM_a_at | 6352 | CCL5 | chemokine (C—C motif) ligand 5 | 2.02E-24 | 81.4 | 350.8 | 233.2 | 68.3 |
| 173 | 202643_PM_s_at | 7128 | TNFAIP3 | tumor necrosis factor, alpha-induced protein 3 | 2.11E-24 | 43.7 | 92.8 | 68.1 | 34.8 |
| 174 | 223922_PM_x_at | 64231 | MS4A6A | membrane-spanning 4-domains, subfamily A, member 6A | 2.22E-24 | 289.2 | 656.8 | 424.1 | 214.5 |
| 175 | 209374_PM_s_at | 3507 | IGHM | immunoglobulin heavy constant mu | 2.26E-24 | 61.8 | 437.0 | 301.0 | 45.0 |
| 176 | 227677_PM_at | 3718 | JAK3 | Janus kinase 3 | 2.29E-24 | 18.6 | 51.7 | 32.0 | 15.5 |
| 177 | 221840_PM_at | 5791 | PTPRE | protein tyrosine phosphatase, receptor type, E | 2.38E-24 | 71.0 | 133.2 | 102.5 | 51.8 |
| 178 | 200887_PM_s_at | 6772 | STAT1 | signal transducer and activator of transcription 1, 91 kDa | 2.47E-24 | 1141.7 | 2278.6 | 1602.9 | 972.9 |
| 179 | 221875_PM_x_at | 3134 | HLA-F | major histocompatibility complex, class I, F | 2.72E-24 | 1365.3 | 2400.6 | 1971.8 | 1213.0 |
| 180 | 206513_PM_at | 9447 | AIM2 | absent in melanoma 2 | 2.87E-24 | 17.2 | 50.7 | 30.5 | 13.9 |
| 181 | 214574_PM_x_at | 7940 | LST1 | leukocyte specific transcript 1 | 2.95E-24 | 74.1 | 222.8 | 142.0 | 61.7 |
| 182 | 231776_PM_at | 8320 | EOMES | eomesodermin | 3.07E-24 | 24.0 | 63.9 | 43.5 | 22.4 |
| 183 | 205639_PM_at | 313 | AOAH | acyloxyacyl hydrolase (neutrophil) | 4.03E-24 | 30.3 | 72.6 | 45.3 | 25.2 |
| 184 | 201762_PM_s_at | 5721 | PSME2 | proteasome (prosome, macropain) activator subunit 2 (PA28 beta) | 4.45E-24 | 1251.6 | 1825.1 | 1423.4 | 1091.0 |
| 185 | 217986_PM_s_at | 11177 | BAZ1A | bromodom ainadjacent to zinc finger domain, 1A | 4.79E-24 | 87.5 | 145.2 | 116.4 | 62.5 |
| 186 | 235229_PM_at | — | — | — | 4.84E-24 | 50.9 | 210.6 | 135.0 | 41.9 |
| 187 | 204924_PM_at | 7097 | TLR2 | toll-like receptor 2 | 4.84E-24 | 96.8 | 162.0 | 116.6 | 66.6 |
| 188 | 202208_PM_s_at | 10123 | ARL4C | ADP-ribosylation factor-like 4C | 4.89E-24 | 54.0 | 99.6 | 77.0 | 42.2 |
| 189 | 227072_PM_at | 25914 | RTTN | rotatin | 5.01E-24 | 101.1 | 74.5 | 83.6 | 132.9 |
| 190 | 202206_PM_at | 10123 | ARL4C | ADP-ribosylation factor-like 4C | 5.08E-24 | 60.8 | 128.5 | 96.1 | 36.0 |
| 191 | 204563_PM_at | 6402 | SELL | selectin L | 5.11E-24 | 40.7 | 134.7 | 76.1 | 31.7 |
| 192 | 219386_PM_s_at | 56833 | SLAMF8 | SLAM family member 8 | 5.17E-24 | 28.2 | 92.1 | 52.2 | 19.4 |
| 193 | 218232_PM_at | 712 | C1QA | complement component 1, q subcomponent, A chain | 5.88E-24 | 128.8 | 287.1 | 197.0 | 85.8 |
| 194 | 232311_PM_at | 567 | B2M | Beta-2-microglobulin | 6.06E-24 | 42.3 | 118.6 | 83.7 | 35.2 |
| 195 | 219684_PM_at | 64108 | RTP4 | receptor (chemosensory) transporter protein 4 | 6.09E-24 | 63.1 | 129.3 | 93.7 | 50.4 |
| 196 | 204057_PM_at | 3394 | IRF8 | interferon regulatory factor 8 | 6.59E-24 | 89.8 | 184.8 | 134.9 | 71.4 |
| 197 | 208296_PM_x_at | 25816 | TNFAIP8 | tumor necrosis factor, alpha-induced protein 8 | 6.65E-24 | 136.9 | 242.5 | 195.1 | 109.6 |
| 198 | 204122_PM_at | 7305 | TYROBP | TYRO protein tyrosine kinase binding protein | 6.73E-24 | 190.5 | 473.4 | 332.8 | 143.3 |
| 199 | 224927_PM_at | 170954 | KIAA1949 | KIAA1949 | 6.87E-24 | 98.8 | 213.6 | 160.2 | 74.7 |

TABLE 11

Biopsy Expression Profiling of Kidney Transplants: 4-Way Classifier AR vs. ADNR vs. CAN vs. TX (Brazilian Samples)

| | | | Validation Cohort | | | | | |
|---|---|---|---|---|---|---|---|---|
| Algorithm | Predictors | Comparison | AUC | Predictive Accuracy (%) | Sensitivity (%) | Specificity (%) | Postive Predictive Value (%) | Negative Predictive Value (%) |
| Nearest Centroid | 199 | AR vs. TX | 0.976 | 98 | 100 | 95 | 95 | 100 |
| Nearest Centroid | 199 | ADNR vs. TX | 1.000 | 100 | 100 | 100 | 100 | 100 |
| Nearest Centroid | 199 | CAN vs. TX | 1.000 | 100 | 100 | 100 | 100 | 100 |

TABLE 12a

Biopsy Expression Profiling of Kidney Transplants: 3-Way Classifier AR vs. ADNR vs. TX (TGCG Samples)

| Algorithm | Predictors | Comparison | AUC | Validation Cohort Predictive Accuracy (%) | Sensitivity (%) | Specificity (%) | Postive Predictive Value (%) | Negative Predictive Value (%) |
|---|---|---|---|---|---|---|---|---|
| Nearest Centroid | 197 | AR vs. TX | 0.979 | 98 | 96 | 100 | 100 | 96 |
| Nearest Centroid | 197 | ADNR vs. TX | 0.987 | 99 | 97 | 100 | 100 | 98 |
| Nearest Centroid | 197 | AR vs. ADNR | 0.968 | 97 | 100 | 93 | 95 | 100 |

TABLE 12b

Biopsy Expression Profiling of Kidney Transplants: 3-Way Classifier AR vs. ADNR vs. TX (TGCG Samples)

| # | Probeset ID | Entrez Gene | Gene Symbol | Gene Title | p-value (Final Phenotype) | ADNR-Mean | AR-Mean | TX-Mean |
|---|---|---|---|---|---|---|---|---|
| 1 | 242956_PM_at | 3417 | IDH1 | Isocitrate dehydrogenase 1 (NADP+), soluble | 2.95E−22 | 32.7 | 29.9 | 53.6 |
| 2 | 208948_PM_s_at | 6780 | STAU1 | staufen, RNA binding protein, homolog 1 (Drosophila) | 1.56E−29 | 1807.9 | 1531.8 | 2467.4 |
| 3 | 213037_PM_x_at | 6780 | STAU1 | staufen, RNA binding protein, homolog 1 (Drosophila) | 4.77E−27 | 1699.0 | 1466.8 | 2264.9 |
| 4 | 207320_PM_x_at | 6780 | STAU1 | staufen, RNA binding protein, homolog 1 (Drosophila) | 6.17E−28 | 1425.1 | 1194.6 | 1945.3 |
| 5 | 1555832_PM_s_at | 1316 | KLF6 | Kruppel-like factor 6 | 5.82E−23 | 899.4 | 1076.8 | 575.1 |
| 6 | 202376_PM_at | 12 | SERPINA3 | serpin peptidase inhibitor, clade A (alpha-1 antiproteinase, antitrypsin), member 3 | 1.05E−25 | 186.2 | 387.1 | 51.7 |
| 7 | 226621_PM_at | 9180 | OSMR | oncostatin M receptor | 1.28E−27 | 545.6 | 804.5 | 312.1 |
| 8 | 218983_PM_at | 51279 | C1RL | complement component 1, r subcomponent-like | 9.46E−25 | 167.1 | 244.5 | 99.4 |
| 9 | 215005_PM_at | 54550 | NECAB2 | N-terminal EF-hand calcium binding protein 2 | 1.95E−25 | 36.7 | 23.4 | 65.7 |
| 10 | 202720_PM_at | 26136 | TES | testis derived transcript (3 LIM domains) | 4.32E−24 | 285.4 | 379.0 | 204.2 |
| 11 | 240320_PM_at | 100131781 | C14orf164 | chromosome 14 open reading frame 164 | 1.64E−23 | 204.9 | 84.2 | 550.0 |
| 12 | 243418_PM_at | — | — | — | 1.81E−24 | 56.3 | 31.1 | 104.8 |
| 13 | 205466_PM_s_at | 9957 | HS3ST1 | heparan sulfate (glucosamine) 3-O-sulfotransferase 1 | 5.64E−24 | 73.6 | 123.8 | 42.1 |
| 14 | 201042_PM_at | 7052 | TGM2 | transglutaminase 2 (C polypeptide, protein-glutamine-gamma-glutamyltransferase) | 3.87E−28 | 131.8 | 236.5 | 80.1 |
| 15 | 202018_PM_s_at | 4057 | LTF | lactotransferrin | 4.00E−25 | 392.3 | 1332.4 | 117.7 |
| 16 | 212503_PM_s_at | 22982 | DIP2C | DIP2 disco-interacting protein 2 homolog C (Drosophila) | 6.62E−27 | 559.7 | 389.2 | 755.0 |
| 17 | 215049_PM_x_at | 9332 | CD163 | CD163 molecule | 4.65E−23 | 232.8 | 481.3 | 112.9 |
| 18 | 209515_PM_s_at | 5873 | RAB27A | RAB27A, member RAS oncogene family | 2.11E−23 | 127.3 | 192.2 | 85.2 |
| 19 | 221932_PM_s_at | 51218 | GLRX5 | glutaredoxin 5 | 2.08E−22 | 1351.5 | 1145.8 | 1599.3 |
| 20 | 202207_PM_at | 10123 | ARL4C | ADP-ribosylation factor-like 4 C | 1.83E−29 | 106.9 | 258.6 | 57.2 |
| 21 | 227697_PM_at | 9021 | SOCS3 | suppressor of cytokine signaling 3 | 2.93E−23 | 35.9 | 69.1 | 19.9 |
| 22 | 227072_PM_at | 25914 | RTTN | rotatin | 4.26E−23 | 101.1 | 74.5 | 132.9 |
| 23 | 201136_PM_at | 5355 | PLP2 | proteolipid protein 2 (colonic epithelium-enriched) | 2.71E−22 | 187.7 | 274.0 | 131.7 |
| 24 | 212504_PM_at | 22982 | DIP2C | DIP2 disco-interacting protein 2 homolog C (Drosophila) | 2.57E−25 | 334.5 | 227.2 | 452.5 |
| 25 | 200986_PM_at | 710 | SERPING1 | serpin peptidase inhibitor, clade G (C1 inhibitor), member 1 | 2.88E−26 | 442.7 | 731.5 | 305.3 |

TABLE 12b-continued

Biopsy Expression Profiling of Kidney Transplants: 3-Way Classifier AR vs. ADNR vs. TX (TGCG Samples)

| # | Probeset ID | Entrez Gene | Gene Symbol | Gene Title | p-value (Final Phenotype) | ADNR-Mean | AR-Mean | TX-Mean |
|---|---|---|---|---|---|---|---|---|
| 26 | 203233_PM_at | 3566 | IL4R | interleukin 4 receptor | 6.30E−23 | 97.6 | 138.5 | 72.0 |
| 27 | 229295_PM_at | 150166 /// 23765 | IL17RA /// LOC150166 | interleukin 17 receptor A /// hypothetical protein LOC150166 | 6.40E−25 | 76.4 | 131.8 | 50.0 |
| 28 | 231358_PM_at | 83876 | MRO | maestro | 1.11E−22 | 199.7 | 81.2 | 422.1 |
| 29 | 201666_PM_at | 7076 | TIMP1 | TIMP metallopeptidase inhibitor 1 | 1.54E−22 | 1035.3 | 1879.4 | 648.0 |
| 30 | 209774_PM_x_at | 2920 | CXCL2 | chemokine (C-X-C motif) ligand 2 | 1.50E−26 | 24.9 | 52.9 | 15.5 |
| 31 | 217733_PM_s_at | 9168 | TMSB10 | thymosin beta 10 | 9.34E−27 | 4414.7 | 6331.3 | 3529.0 |
| 32 | 222939_PM_s_at | 117247 | SLC16A10 | solute carrier family 16, member 10 (aromatic amino acid transporter) | 2.55E−22 | 156.6 | 93.7 | 229.6 |
| 33 | 204924_PM_at | 7097 | TLR2 | toll-like receptor 2 | 2.11E−22 | 96.8 | 162.0 | 66.6 |
| 34 | 225415_PM_at | 151636 | DTX3L | deltex 3-like (Drosophila) | 3.04E−24 | 230.2 | 376.4 | 166.9 |
| 35 | 202206_PM_at | 10123 | ARL4C | ADP-ribosylation factor-like 4 C | 1.16E−22 | 60.8 | 128.5 | 36.0 |
| 36 | 213857_PM_s_at | 961 | CD47 | CD47 molecule | 2.56E−27 | 589.6 | 858.0 | 481.2 |
| 37 | 235529_PM_x_at | 25939 | SAMHD1 | SAM domain and HD domain 1 | 4.49E−24 | 189.3 | 379.9 | 128.0 |
| 38 | 206693_PM_at | 3574 | IL7 | interleukin 7 | 3.12E−22 | 37.3 | 57.0 | 28.9 |
| 39 | 219033_PM_at | 79668 | PARP8 | poly (ADP-ribose) polymerase family, member 8 | 1.88E−22 | 47.9 | 79.2 | 35.7 |
| 40 | 201721_PM_s_at | 7805 | LAPTM5 | lysosomal protein transmembrane 5 | 3.72E−24 | 396.5 | 934.6 | 249.4 |
| 41 | 204336_PM_s_at | 10287 | RGS19 | regulator of G-protein signaling 19 | 3.52E−25 | 95.2 | 187.7 | 67.0 |
| 42 | 235964_PM_x_at | 25939 | SAMHD1 | SAM domain and HD domain 1 | 2.45E−23 | 172.9 | 345.9 | 117.5 |
| 43 | 208091_PM_s_at | 81552 | VOPP1 | vesicular, overexpressed in cancer, prosurvival protein 1 | 9.47E−25 | 495.5 | 713.9 | 409.7 |
| 44 | 204446_PM_s_at | 240 | ALOX5 | arachidonate 5-lipoxygenase | 6.25E−31 | 91.9 | 323.9 | 54.7 |
| 45 | 212703_PM_at | 83660 | TLN2 | talin 2 | 6.13E−23 | 270.8 | 159.7 | 357.5 |
| 46 | 213414_PM_s_at | 6223 | RPS19 | ribosomal protein S19 | 1.57E−22 | 4508.2 | 5432.1 | 4081.7 |
| 47 | 1565681_PM_s_at | 22982 | DIP2C | DIP2 disco-interacting protein 2 homolog C (Drosophila) | 2.57E−22 | 66.4 | 35.7 | 92.5 |
| 48 | 225764_PM_at | 2120 | ETV6 | ets variant 6 | 2.63E−23 | 92.6 | 133.0 | 77.0 |
| 49 | 227184_PM_at | 5724 | PTAFR | platelet-activating factor receptor | 1.73E−24 | 89.8 | 191.4 | 62.7 |
| 50 | 221840_PM_at | 5791 | PTPRE | protein tyrosine phosphatase, receptor type, E | 8.52E−23 | 71.0 | 133.2 | 51.8 |
| 51 | 225799_PM_at | 112597 /// 541471 | LOC541471 /// NCRNA00152 | hypothetical LOC541471 /// non-protein coding RNA 152 | 1.18E−23 | 230.5 | 444.3 | 172.0 |
| 52 | 202957_PM_at | 3059 | HCLS1 | hematopoietic cell-specific Lyn substrate 1 | 1.94E−25 | 119.2 | 299.5 | 82.2 |
| 53 | 229383_PM_at | 55016 | 1-Mar | membrane-associated ring finger (C3HC4) 1 | 8.09E−25 | 33.8 | 88.0 | 22.9 |
| 54 | 33304_PM_at | 3669 | ISG20 | interferon stimulated exonuclease gene 20 kDa | 2.83E−27 | 33.2 | 101.3 | 22.1 |
| 55 | 222062_PM_at | 9466 | IL27RA | interleukin 27 receptor, alpha | 1.79E−22 | 34.9 | 65.8 | 26.4 |
| 56 | 219574_PM_at | 55016 | 1-Mar | membrane-associated ring finger (C3HC4) 1 | 6.65E−25 | 51.5 | 126.0 | 36.2 |
| 57 | 202748_PM_at | 2634 | GBP2 | guanylate binding protein 2, interferon-inducible | 7.51E−26 | 196.7 | 473.0 | 141.0 |
| 58 | 210895_PM_s_at | 942 | CD86 | CD86 molecule | 3.80E−23 | 32.3 | 85.0 | 21.6 |
| 59 | 202208_PM_s_at | 10123 | ARL4C | ADP-ribosylation factor-like 4 C | 1.24E−23 | 54.0 | 99.6 | 42.2 |
| 60 | 221666_PM_s_at | 29108 | PYCARD | PYD and CARD domain containing | 5.55E−24 | 60.7 | 132.8 | 44.7 |
| 61 | 227125_PM_at | 3455 | IFNAR2 | interferon (alpha, beta and omega) receptor 2 | 3.57E−24 | 70.0 | 126.2 | 55.8 |
| 62 | 226525_PM_at | 9262 | STK17B | serine/threonine kinase 17 b | 3.43E−24 | 146.8 | 338.7 | 107.6 |
| 63 | 210644_PM_s_at | 3903 | LAIR1 | leukocyte-associated immunoglobulin-like receptor 1 | 2.96E−24 | 29.7 | 74.6 | 21.2 |

TABLE 12b-continued

Biopsy Expression Profiling of Kidney Transplants: 3-Way Classifier AR vs. ADNR vs. TX (TGCG Samples)

| # | Probeset ID | Entrez Gene | Gene Symbol | Gene Title | p-value (Final Phenotype) | ADNR-Mean | AR-Mean | TX-Mean |
|---|---|---|---|---|---|---|---|---|
| 64 | 230391_PM_at | 8832 | CD84 | CD84 molecule | 1.89E−22 | 47.9 | 130.1 | 32.5 |
| 65 | 242907_PM_at | — | — | — | 2.54E−22 | 59.3 | 165.1 | 39.8 |
| 66 | 1553906_PM_s_at | 221472 | FGD2 | FYVE, RhoGEF and PH domain containing 2 | 1.67E−26 | 104.6 | 321.0 | 71.9 |
| 67 | 223922_PM_x_at | 64231 | MS4A6A | membrane-spanning 4-domains, subfamily A, member 6 A | 8.68E−24 | 289.2 | 656.8 | 214.5 |
| 68 | 230550_PM_at | 64231 | MS4A6A | membrane-spanning 4-domains, subfamily A, member 6 A | 7.63E−24 | 44.8 | 124.3 | 30.9 |
| 69 | 202953_PM_at | 713 | C1QB | complement component 1, q subcomponent, B chain | 2.79E−22 | 215.8 | 638.4 | 142.5 |
| 70 | 213733_PM_at | 4542 | MYO1F | myosin IF | 2.25E−23 | 26.8 | 52.7 | 20.9 |
| 71 | 204774_PM_at | 2123 | EVI2A | ecotropic viral integration site 2 A | 5.10E−24 | 63.6 | 168.5 | 44.9 |
| 72 | 211366_PM_x_at | 834 | CASP1 | caspase 1, apoptosis-related cysteine peptidase (interleukin 1, beta, convertase) | 3.40E−24 | 115.3 | 261.0 | 87.1 |
| 73 | 204698_PM_at | 3669 | ISG20 | interferon stimulated exonuclease gene 20 kDa | 1.27E−28 | 41.5 | 165.1 | 27.6 |
| 74 | 201762_PM_s_at | 5721 | PSME2 | proteasome (prosome, macropain) activator subunit 2 (PA28 beta) | 2.31E−22 | 1251.6 | 1825.1 | 1091.0 |
| 75 | 204470_PM_at | 2919 | CXCL1 | chemokine (C-X-C motif) ligand 1 (melanoma growth stimulating activity, alpha) | 2.81E−24 | 22.9 | 63.7 | 16.2 |
| 76 | 242827_PM_x_at | — | — | — | 9.00E−23 | 22.1 | 52.3 | 16.3 |
| 77 | 209970_PM_x_at | 834 | CASP1 | caspase 1, apoptosis-related cysteine peptidase (interleukin 1, beta, convertase) | 4.40E−25 | 116.0 | 266.6 | 88.7 |
| 78 | 228532_PM_at | 128346 | C1orf162 | chromosome 1 open reading frame 162 | 1.57E−22 | 82.6 | 217.7 | 60.0 |
| 79 | 232617_PM_at | 1520 | CTSS | cathepsin S | 2.83E−23 | 209.6 | 537.9 | 154.8 |
| 80 | 203761_PM_at | 6503 | SLA | Src-like-adaptor | 3.80E−23 | 69.6 | 179.2 | 51.4 |
| 81 | 219666_PM_at | 64231 | MS4A6A | membrane-spanning 4-domains, subfamily A, member 6 A | 4.29E−23 | 159.2 | 397.6 | 118.7 |
| 82 | 223280_PM_x_at | 64231 | MS4A6A | membrane-spanning 4-domains, subfamily A, member 6 A | 2.53E−24 | 269.0 | 711.8 | 199.5 |
| 83 | 225701_PM_at | 80709 | AKNA | AT-hook transcription factor | 2.87E−29 | 37.7 | 102.8 | 29.0 |
| 84 | 224356_PM_x_at | 64231 | MS4A6A | membrane-spanning 4-domains, subfamily A, member 6 A | 1.56E−23 | 150.6 | 399.6 | 111.2 |
| 85 | 202643_PM_s_at | 7128 | TNFAIP3 | tumor necrosis factor, alpha-induced protein 3 | 9.92E−24 | 43.7 | 92.8 | 34.8 |
| 86 | 202644_PM_s_at | 7128 | TNFAIP3 | tumor necrosis factor, alpha-induced protein 3 | 2.12E−27 | 169.8 | 380.4 | 136.6 |
| 87 | 213566_PM_at | 6039 | RNASE6 | ribonuclease, RNase A family, k6 | 1.55E−23 | 180.9 | 482.0 | 134.3 |
| 88 | 219386_PM_s_at | 56833 | SLAMF8 | SLAM family member 8 | 1.22E−22 | 28.2 | 92.1 | 19.4 |
| 89 | 203416_PM_at | 963 | CD53 | CD53 molecule | 3.13E−23 | 215.9 | 603.0 | 157.8 |
| 90 | 200003_PM_s_at | 6158 | RPL28 | ribosomal protein L28 | 1.73E−22 | 4375.2 | 5531.2 | 4069.9 |
| 91 | 206420_PM_at | 10261 | IGSF6 | immunoglobulin superfamily, member 6 | 5.65E−23 | 45.1 | 131.5 | 32.7 |
| 92 | 217028_PM_at | 7852 | CXCR4 | chemokine (C-X-C motif) receptor 4 | 6.84E−27 | 100.8 | 304.4 | 75.3 |
| 93 | 232024_PM_at | 26157 | GIMAP2 | GTPase, IMAP family member 2 | 2.94E−24 | 90.2 | 197.7 | 72.5 |
| 94 | 238327_PM_at | 440836 | ODF3B | outer dense fiber of sperm tails 3 B | 1.75E−27 | 32.8 | 81.4 | 26.1 |
| 95 | 209083_PM_at | 11151 | CORO1A | coronin, actin binding protein, 1 A | 2.78E−27 | 46.9 | 163.8 | 34.3 |
| 96 | 232724_PM_at | 64231 | MS4A6A | membrane-spanning 4-domains, subfamily A, member 6 A | 6.28E−23 | 24.8 | 47.6 | 20.7 |
| 97 | 211742_PM_s_at | 2124 | EVI2B | ecotropic viral integration site 2 B | 1.56E−22 | 73.9 | 236.5 | 53.2 |

TABLE 12b-continued

Biopsy Expression Profiling of Kidney Transplants: 3-Way Classifier AR vs. ADNR vs. TX (TGCG Samples)

| # | Probeset ID | Entrez Gene | Gene Symbol | Gene Title | p-value (Final Phenotype) | ADNR-Mean | AR-Mean | TX-Mean |
|---|---|---|---|---|---|---|---|---|
| 98 | 202659_PM_at | 5699 | PSMB10 | proteasome (prosome, macropain) subunit, beta type, 10 | 2.29E−24 | 180.7 | 355.6 | 151.5 |
| 99 | 226991_PM_at | 4773 | NFATC2 | nuclear factor of activated T-cells, cytoplasmic, calcineurin-dependent 2 | 2.42E−23 | 37.9 | 87.0 | 30.3 |
| 100 | 210538_PM_s_at | 330 | BIRC3 | baculoviral IAP repeat-containing 3 | 5.40E−26 | 106.7 | 276.7 | 84.6 |
| 101 | 205269_PM_at | 3937 | LCP2 | lymphocyte cytosolic protein 2 (SH2 domain containing leukocyte protein of 76 kDa) | 7.35E−25 | 30.2 | 92.2 | 22.9 |
| 102 | 211368_PM_s_at | 834 | CASP1 | caspase 1, apoptosis-related cysteine peptidase (interleukin 1, beta, convertase) | 9.43E−27 | 102.6 | 274.3 | 81.8 |
| 103 | 205798_PM_at | 3575 | IL7R | interleukin 7 receptor | 1.57E−24 | 44.1 | 136.8 | 33.4 |
| 104 | 228442_PM_at | 4773 | NFATC2 | nuclear factor of activated T-cells, cytoplasmic, calcineurin-dependent 2 | 5.58E−23 | 39.0 | 84.8 | 32.0 |
| 105 | 213603_PM_s_at | 5880 | RAC2 | ras-related C3 botulinum toxin substrate 2 (rho family, small GTP binding protein Rac2) | 3.38E−25 | 113.9 | 366.5 | 86.5 |
| 106 | 228964_PM_at | 639 | PRDM1 | PR domain containing 1, with ZNF domain | 1.42E−23 | 21.2 | 52.1 | 17.0 |
| 107 | 209606_PM_at | 9595 | CYTIP | cytohesin 1 interacting protein | 1.66E−26 | 41.4 | 114.3 | 32.9 |
| 108 | 214022_PM_s_at | 8519 | IFITM1 | interferon induced transmembrane protein 1 (9-27) | 1.61E−23 | 799.1 | 1514.7 | 683.3 |
| 109 | 202307_PM_s_at | 6890 | TAP1 | transporter 1, ATP-binding cassette, sub-family B (MDR/TAP) | 8.61E−26 | 172.4 | 420.6 | 141.0 |
| 110 | 204882_PM_at | 9938 | ARHGAP25 | Rho GTPase activating protein 25 | 8.14E−23 | 51.5 | 107.3 | 43.0 |
| 111 | 227344_PM_at | 10320 | IKZF1 | IKAROS family zinc finger 1 (Ikaros) | 5.30E−26 | 17.8 | 40.0 | 14.9 |
| 112 | 205270_PM_s_at | 3937 | LCP2 | lymphocyte cytosolic protein 2 (SH2 domain containing leukocyte protein of 76 kDa) | 3.75E−24 | 56.8 | 162.6 | 44.6 |
| 113 | 223640_PM_at | 10870 | HCST | hematopoietic cell signal transducer | 5.55E−23 | 91.0 | 234.0 | 72.7 |
| 114 | 226218_PM_at | 3575 | IL7R | interleukin 7 receptor | 2.15E−23 | 55.6 | 197.0 | 41.4 |
| 115 | 226219_PM_at | 257106 | ARHGAP30 | Rho GTPase activating protein 30 | 1.87E−26 | 46.4 | 127.9 | 37.5 |
| 116 | 38149_PM_at | 9938 | ARHGAP25 | Rho GTPase activating protein 25 | 1.20E−23 | 51.3 | 108.9 | 43.2 |
| 117 | 213975_PM_s_at | 4069 | LYZ | lysozyme | 2.70E−22 | 458.4 | 1626.0 | 338.1 |
| 118 | 238668_PM_at | — | — | — | 1.35E−23 | 18.2 | 49.2 | 14.5 |
| 119 | 200887_PM_s_at | 6772 | STAT1 | signal transducer and activator of transcription 1.91 kDa | 1.27E−22 | 1141.7 | 2278.6 | 972.9 |
| 120 | 1555756_PM_a_at | 64581 | CLEC7A | C-type lectin domain family 7, member A | 2.11E−22 | 16.6 | 45.4 | 13.2 |
| 121 | 205039_PM_s_at | 10320 | IKZF1 | IKAROS family zinc finger 1 (Ikaros) | 6.73E−23 | 29.1 | 65.9 | 24.2 |
| 122 | 206011_PM_at | 834 | CASP1 | caspase 1, apoptosis-related cysteine peptidase (interleukin 1, beta, convertase) | 6.34E−25 | 74.5 | 198.0 | 60.7 |
| 123 | 221698_PM_s_at | 64581 | CLEC7A | C-type lectin domain family 7, memberA | 9.79E−24 | 61.5 | 164.6 | 49.7 |
| 124 | 227346_PM_at | 10320 | IKZF1 | IKAROS family zinc finger 1 (Ikaros) | 1.51E−26 | 24.9 | 79.7 | 19.8 |
| 125 | 230499_PM_at | — | — | — | 8.55E−23 | 29.7 | 68.7 | 24.7 |
| 126 | 229391_PM_s_at | 441168 | FAM26F | family with sequence similarity 26, member F | 2.74E−23 | 98.6 | 379.7 | 73.7 |
| 127 | 205159_PM_at | 1439 | CSF2RB | colony stimulating factor 2 receptor, beta, low-affinity (granulocyte-macrophage) | 1.74E−23 | 33.7 | 107.5 | 26.3 |

TABLE 12b-continued

Biopsy Expression Profiling of Kidney Transplants: 3-Way
Classifier AR vs. ADNR vs. TX (TGCG Samples)

| # | Probeset ID | Entrez Gene | Gene Symbol | Gene Title | p-value (Final Phenotype) | ADNR-Mean | AR-Mean | TX-Mean |
|---|---|---|---|---|---|---|---|---|
| 128 | 205639_PM_at | 313 | AOAH | acyloxyacyl hydrolase (neutrophil) | 4.43E−23 | 30.3 | 72.6 | 25.2 |
| 129 | 204563_PM_at | 6402 | SELL | selectin L | 1.00E−23 | 40.7 | 134.7 | 31.7 |
| 130 | 201288_PM_at | 397 | ARHGDIB | Rho GDP dissociation inhibitor (GDI) beta | 1.92E−22 | 354.9 | 686.8 | 308.1 |
| 131 | 209969_PM_s_at | 6772 | STAT1 | signal transducer and activator of transcription 1.91 kDa | 5.49E−24 | 395.8 | 1114.5 | 320.8 |
| 132 | 229390_PM_at | 441168 | FAM26F | family with sequence similarity 26, member F | 3.91E−25 | 103.8 | 520.0 | 75.9 |
| 133 | 242916_PM_at | 11064 | CEP110 | centrosomal protein 110 kDa | 1.99E−23 | 30.8 | 68.1 | 26.2 |
| 134 | 207651_PM_at | 29909 | GPR171 | G protein-coupled receptor 171 | 1.90E−29 | 25.8 | 89.9 | 20.9 |
| 135 | 229937_PM_x_at | 10859 | LILRB1 | Leukocyte immunoglobulin-like receptor, subfamily B (with TM and ITIM domains), member | 1.67E−24 | 23.5 | 79.9 | 18.5 |
| 136 | 232543_PM_x_at | 64333 | ARHGAP9 | RhoGTPase activating protein 9 | 3.66E−26 | 31.7 | 99.1 | 25.8 |
| 137 | 203332_PM_s_at | 3635 | INPP5D | inositol polyphosphate-5-phosphatase, 145 kDa | 3.66E−24 | 27.9 | 60.5 | 24.0 |
| 138 | 213160_PM_at | 1794 | DOCK2 | dedicator of cytokinesis 2 | 1.03E−24 | 33.7 | 92.6 | 27.8 |
| 139 | 204912_PM_at | 3587 | IL10RA | interleukin 10 receptor, alpha | 1.28E−24 | 57.0 | 178.7 | 46.1 |
| 140 | 204205_PM_at | 60489 | APOBEC3G | apolipoprotein B mRNA editing enzyme, catalytic polypeptide-like 3 G | 6.40E−27 | 95.4 | 289.4 | 78.7 |
| 141 | 206513_PM_at | 9447 | AIM2 | absent in melanoma 2 | 9.67E−23 | 17.2 | 50.7 | 13.9 |
| 142 | 203741_PM_s_at | 113 | ADCY7 | adenylate cyclase 7 | 2.34E−22 | 23.6 | 59.3 | 19.7 |
| 143 | 206118_PM_at | 6775 | STAT4 | signal transducer and activator of transcription 4 | 8.28E−26 | 21.0 | 49.5 | 18.1 |
| 144 | 227677_PM_at | 3718 | JAK3 | Janus kinase 3 | 6.48E−24 | 18.6 | 51.7 | 15.5 |
| 145 | 227353_PM_at | 147138 | TMC8 | transmembrane channel-like 8 | 6.49E−29 | 19.8 | 64.2 | 16.6 |
| 146 | 1552701_PM_a_at | 114769 | CARD16 | caspase recruitment domain family, member 16 | 2.52E−23 | 143.8 | 413.6 | 119.8 |
| 147 | 1552703_PM_s_at | 114769 /// 834 | CARD16 /// CASP1 | caspase recruitment domain family, member 16 /// caspase 1, apoptosis-related cysteine | 7.57E−24 | 64.6 | 167.8 | 54.9 |
| 148 | 229437_PM_at | 114614 | MIR155HG | MIR155 host gene (non-protein coding) | 3.90E−27 | 15.4 | 50.4 | 12.9 |
| 149 | 204319_PM_s_at | 6001 | RGS10 | regulator of G-protein signaling 10 | 6.54E−24 | 159.7 | 360.4 | 139.4 |
| 150 | 204118_PM_at | 962 | CD48 | CD48 molecule | 3.85E−23 | 82.9 | 341.5 | 65.2 |
| 151 | 1559584_PM_a_at | 283897 | C16orf54 | chromosome 16 open reading frame 54 | 2.86E−24 | 31.3 | 95.8 | 26.1 |
| 152 | 212588_PM_at | 5788 | PTPRC | protein tyrosine phosphatase, receptor type, C | 2.46E−22 | 94.4 | 321.0 | 76.4 |
| 153 | 219014_PM_at | 51316 | PLAC8 | placenta-specific 8 | 2.03E−23 | 38.8 | 164.1 | 30.7 |
| 154 | 235735_PM_at | — | — | — | 1.39E−25 | 13.0 | 34.9 | 11.2 |
| 155 | 203932_PM_at | 3109 | HLA-DMB | major histocompatibility complex, class II, DM beta | 6.25E−23 | 422.4 | 853.9 | 376.0 |
| 156 | 223502_PM_s_at | 10673 | TNFSF13B | tumor necrosis factor (ligand) superfamily, member 13 b | 2.62E−23 | 73.0 | 244.3 | 60.0 |
| 157 | 1405_PM_i_at | 6352 | CCL5 | chemokine (C-C motif) ligand 5 | 2.22E−25 | 68.0 | 295.7 | 54.6 |
| 158 | 226474_PM_at | 84166 | NLRC5 | NLR family, CARD domain containing 5 | 1.33E−23 | 64.4 | 173.5 | 55.1 |
| 159 | 204220_PM_at | 9535 | GMFG | glia maturation factor, gamma | 1.56E−23 | 147.0 | 339.3 | 128.9 |
| 160 | 204923_PM_at | 54440 | SASH3 | SAM and SH3 domain containing 3 | 4.56E−23 | 25.4 | 68.2 | 21.7 |

TABLE 12b-continued

Biopsy Expression Profiling of Kidney Transplants: 3-Way Classifier AR vs. ADNR vs. TX (TGCG Samples)

| # | Probeset ID | Entrez Gene | Gene Symbol | Gene Title | p-value (Final Phenotype) | ADNR-Mean | AR-Mean | TX-Mean |
|---|---|---|---|---|---|---|---|---|
| 161 | 206082_PM_at | 10866 | HCP5 | HLA complex P5 | 1.23E−23 | 76.2 | 185.1 | 66.6 |
| 162 | 204670_PM_x_at | 3123 /// 3126 | HLA-DRB1 /// HLA-DRB4 | major histocompatibility complex, class II, DR beta 1 /// major histocompatibility comp | 1.31E−23 | 2461.9 | 4344.6 | 2262.0 |
| 163 | 228869_PM_at | 124460 | SNX20 | sorting nexin 20 | 2.59E−22 | 25.7 | 67.3 | 22.2 |
| 164 | 205831_PM_at | 914 | CD2 | CD2 molecule | 2.30E−27 | 40.4 | 162.5 | 33.9 |
| 165 | 206978_PM_at | 729230 | CCR2 | chemokine (C-C motif) receptor 2 | 4.46E−23 | 32.1 | 100.7 | 27.3 |
| 166 | 224451_PM_x_at | 64333 | ARHGAP9 | Rho GTPase activating protein 9 | 4.23E−24 | 34.2 | 103.4 | 29.4 |
| 167 | 204279_PM_at | 5698 | PSMB9 | proteasome (prosome, macropain) subunit, beta type, 9 (large multifunctional peptidase | 2.81E−23 | 241.6 | 637.4 | 211.3 |
| 168 | 209795_PM_at | 969 | CD69 | CD69 molecule | 5.81E−27 | 17.6 | 57.6 | 15.2 |
| 169 | 229625_PM_at | 115362 | GBP5 | guanylate binding protein 5 | 5.85E−24 | 29.3 | 133.3 | 24.0 |
| 170 | 213416_PM_at | 3676 | ITGA4 | integrin, alpha 4 (antigen CD49D, alpha 4 subunit of VLA-4 receptor) | 1.19E−23 | 26.3 | 78.1 | 22.8 |
| 171 | 206804_PM_at | 917 | CD3G | CD3g molecule, gamma (CD3-TCR complex) | 1.50E−27 | 19.7 | 60.6 | 17.3 |
| 172 | 222895_PM_s_at | 64919 | BCL11B | B-cell CLL/lymphoma 11 B (zinc finger protein) | 7.01E−23 | 22.0 | 64.5 | 19.1 |
| 173 | 211582_PM_x_at | 7940 | LST1 | leukocyte specific transcript 1 | 2.13E−22 | 57.5 | 183.8 | 49.4 |
| 174 | 1555852_PM_at | 100507463 | LOC100507463 | hypothetical LOC100507463 | 8.92E−26 | 78.9 | 202.6 | 70.9 |
| 175 | 213539_PM_at | 915 | CD3D | CD3d molecule, delta (CD3-TCR complex) | 9.01E−27 | 70.8 | 335.1 | 60.0 |
| 176 | 239237_PM_at | — | — | — | 9.82E−24 | 15.9 | 34.9 | 14.5 |
| 177 | 229723_PM_at | 117289 | TAGAP | T-cell activation RhoGTPase activating protein | 5.21E−24 | 29.2 | 82.9 | 26.2 |
| 178 | 204655_PM_at | 6352 | CCL5 | chemokine (C-C motif) ligand 5 | 7.63E−24 | 77.5 | 339.4 | 66.8 |
| 179 | 229041_PM_s_at | — | — | — | 1.64E−24 | 36.5 | 132.1 | 32.4 |
| 180 | 205267_PM_at | 5450 | POU2AF1 | POU class 2 associating factor 1 | 4.47E−23 | 17.9 | 86.8 | 15.7 |
| 181 | 226878_PM_at | 3111 | HLA-DOA | major histocompatibility complex, class II, DO alpha | 2.59E−25 | 102.0 | 288.9 | 94.3 |
| 182 | 205488_PM_at | 3001 | GZMA | granzyme A (granzyme 1, cytotoxic T-lymphocyte-associated serine esterase 3) | 4.14E−25 | 37.3 | 164.8 | 33.4 |
| 183 | 201137_PM_s_at | 3115 | HLA-DPB1 | major histocompatibility complex, class II, DP beta 1 | 2.17E−22 | 1579.1 | 3863.7 | 1475.9 |
| 184 | 204891_PM_s_at | 3932 | LCK | lymphocyte-specific protein tyrosine kinase | 7.95E−28 | 19.3 | 74.2 | 17.8 |
| 185 | 231776_PM_at | 8320 | EOMES | eomesodermin | 1.71E−23 | 24.0 | 63.9 | 22.4 |
| 186 | 211339_PM_s_at | 3702 | ITK | IL2-inducible T-cell kinase | 7.40E−23 | 16.7 | 44.4 | 15.7 |
| 187 | 223322_PM_at | 83593 | RASSF5 | Ras association (RalGDS/AF-6) domain family member 5 | 5.21E−26 | 41.5 | 114.4 | 39.2 |
| 188 | 205758_PM_at | 925 | CD8A | CD8a molecule | 2.80E−25 | 24.2 | 105.8 | 22.2 |
| 189 | 231124_PM_x_at | 4063 | LY9 | lymphocyte antigen 9 | 2.81E−23 | 16.7 | 45.8 | 15.7 |
| 190 | 211796_PM_s_at | 28638 /// 28639 | TRBC1 /// TRBC2 | T cell receptor beta constant 1 /// T cell receptor beta constant 2 | 4.38E−25 | 69.2 | 431.5 | 63.6 |
| 191 | 210915_PM_x_at | 28638 | TRBC2 | T cell receptor beta constant 2 | 1.91E−27 | 39.7 | 230.7 | 37.5 |
| 192 | 205821_PM_at | 22914 | KLRK1 | killer cell lectin-like receptor subfamily K, member 1 | 1.18E−25 | 30.3 | 111.5 | 31.3 |
| 193 | 236295_PM_s_at | 197358 | NLRC3 | NLR family, CARD domain containing 3 | 6.22E−26 | 19.0 | 52.5 | 18.6 |
| 194 | 213193_PM_x_at | 28639 | TRBC1 | T cell receptor beta constant 1 | 4.22E−25 | 95.3 | 490.9 | 92.1 |

TABLE 12b-continued

Biopsy Expression Profiling of Kidney Transplants: 3-Way Classifier AR vs. ADNR vs. TX (TGCG Samples)

| # | Probeset ID | Entrez Gene | Gene Symbol | Gene Title | p-value (Final Phenotype) | ADNR-Mean | AR-Mean | TX-Mean |
|---|---|---|---|---|---|---|---|---|
| 195 | 211656_PM_x_at | 100133583 /// 3119 | HLA-DQB1 /// LOC100133583 | major histocompatibility complex, class II, DQ beta 1 /// HLA class II histocompatibili | 5.98E−25 | 211.3 | 630.2 | 208.2 |
| 196 | 209670_PM_at | 28755 | TRAC | T cell receptor alpha constant | 1.44E−24 | 37.9 | 149.9 | 38.5 |
| 197 | 213888_PM_s_at | 80342 | TRAF3IP3 | TRAF3 interacting protein 3 | 1.66E−22 | 30.8 | 101.9 | 30.5 |

TABLE 13

Biopsy Expression Profiling of Kidney Transplants: 3-Way Classifier AR vs. ADNR vs. TX (Brazilian Samples)

| | | | Validation Cohort | | | | |
|---|---|---|---|---|---|---|---|
| Algorithm | Predictors | Comparison | AUC | Predictive Accuracy (%) | Sensitivity (%) | Specificity (%) | Postive Predictive Value (%) | Negative Predictive Value (%) |
|---|---|---|---|---|---|---|---|---|
| Nearest Centroid | 197 | AR vs. TX | 0.976 | 98 | 100 | 95 | 95 | 100 |
| Nearest Centroid | 197 | ADNR vs. TX | 1.000 | 100 | 100 | 100 | 100 | 100 |
| Nearest Centroid | 197 | AR vs. ADNR | 0.962 | 97 | 100 | 91 | 95 | 100 |

TABLE 14a

Biopsy Expression Profiling of Kidney Transplants: 2-Way Classifier CAN vs. TX (TGCG Samples)

| Algorithm | Predictors | Comparison | AUC | Predictive Accuracy (%) | Sensitivity (%) | Specificity (%) | Postive Predictive Value (%) | Negative Predictive Value (%) |
|---|---|---|---|---|---|---|---|---|
| Nearest Centroid | 200 | AR vs. TX | 0.965 | 97 | 96 | 97 | 96 | 97 |

TABLE 14b

Biopsy Expression Profiling of Kidney Transplants. 2-Way Classifier CAN vs. TX

| # | Probeset ID | Entrez Gene | Gene Symbol | Gene Title | p-value (Final Phenotype) | CAN-Mean | TX-Mean |
|---|---|---|---|---|---|---|---|
| 1 | 204698_PM_at | 3669 | ISG20 | interferon stimulated exonuclease gene 20 kDa | 1.93E−19 | 96.1 | 27.6 |
| 2 | 33304_PM_at | 3669 | ISG20 | interferon stimulated exonuclease gene 20 kDa | 2.02E−19 | 63.4 | 22.1 |
| 3 | 217022_PM_s_at | 100126583 /// 3493 /// 3494 | IGHA1 /// IGHA2 /// LOC100126583 | immunoglobulin heavy constant alpha 1 /// immunoglobulin heavy constant alpha 2 (A2m ma | 4.31E−19 | 494.6 | 49.4 |
| 4 | 202957_PM_at | 3059 | HCLS1 | hematopoietic cell-specific Lyn substrate 1 | 5.13E−19 | 229.9 | 82.2 |
| 5 | 203761_PM_at | 6503 | SLA | Src-like-adaptor | 1.10E−18 | 138.4 | 51.4 |
| 6 | 204446_PM_s_at | 240 | ALOX5 | arachidonate 5-lipoxygen ase | 1.36E−18 | 216.7 | 54.7 |
| 7 | 209198_PM_s_at | 23208 | SYT11 | synaptotagmin XI | 1.93E−18 | 41.8 | 22.8 |
| 8 | 228964_PM_at | 639 | PRDM1 | PR domain containing 1, with ZNF domain | 2.37E−18 | 41.5 | 17.0 |
| 9 | 201042_PM_at | 7052 | TGM2 | transglutaminase 2 (C polypeptide, protein-glutamine-gamma-glutamyltransferase) | 3.13E−18 | 172.6 | 80.1 |
| 10 | 226219_PM_at | 257106 | ARHGAP30 | Rho GTPase activating protein 30 | 7.21E−18 | 91.8 | 37.5 |

TABLE 14b-continued

Biopsy Expression Profiling of Kidney Transplants. 2-Way Classifier CAN vs. TX

| # | Probeset ID | Entrez Gene | Gene Symbol | Gene Title | p-value (Final Phenotype) | CAN-Mean | TX-Mean |
|---|---|---|---|---|---|---|---|
| 11 | 225701_PM_at | 80709 | AKNA | AT-hook transcription factor | 7.27E−18 | 73.2 | 29.0 |
| 12 | 202207_PM_at | 10123 | ARL4C | ADP-ribosylation factor-like 4 C | 7.98E−18 | 190.4 | 57.2 |
| 13 | 219574_PM_at | 55016 | MAR1 | membrane-associated ring finger (C3HC4) 1 | 8.98E−18 | 87.5 | 36.2 |
| 14 | 209083_PM_at | 12-Jul | CORO1A | coronin, actin binding protein, 1 A | 1.06E−17 | 107.1 | 34.3 |
| 15 | 226621_PM_at | 9180 | OSMR | oncostatin M receptor | 1.85E−17 | 682.9 | 312.1 |
| 16 | 1405_PM_i_at | 6352 | CCL5 | chemokine (C-C motif) ligand 5 | 2.19E−17 | 195.6 | 54.6 |
| 17 | 213160_PM_at | 1794 | DOCK2 | dedicator of cytokinesis 2 | 2.75E−17 | 66.0 | 27.8 |
| 18 | 227346_PM_at | 10320 | IKZF1 | IKAROS family zinc finger 1 (Ikaros) | 2.92E−17 | 53.3 | 19.8 |
| 19 | 204205_PM_at | 60489 | APOBEC3G | apolipoprotein B mRNA editing enzyme, catalytic polypeptide-like 3 G | 2.92E−17 | 192.0 | 78.7 |
| 20 | 218322_PM_s_at | 51703 | ACSL5 | acyl-CoA synthetase long-chain family member | 3.15E−17 | 84.5 | 48.1 |
| 21 | 238327_PM_at | 440836 | ODF3B | outer dense fiber of sperm tails 3 B | 3.42E−17 | 58.5 | 26.1 |
| 22 | 218983_PM_at | 51279 | C1RL | complement component 1, r subcomponent-like | 4.33E−17 | 206.9 | 99.4 |
| 23 | 210538_PM_s_at | 330 | BIRC3 | baculoviral IAP repeat-containing 3 | 4.49E−17 | 199.1 | 84.6 |
| 24 | 207651_PM_at | 29909 | GPR171 | G protein-coupled receptor 171 | 5.48E−17 | 57.0 | 20.9 |
| 25 | 201601_PM_x_at | 8519 | IFITM1 | interferon induced transmembrane protein 1 (9-27) | 6.07E−17 | 2202.5 | 1251.1 |
| 26 | 226878_PM_at | 3111 | HLA-DOA | major histocompatibility complex, class II, DO alpha | 6.12E−17 | 201.4 | 94.3 |
| 27 | 1555756_PM_a_at | 64581 | CLEC7A | C-type lectin domain family 7, member A | 6.22E−17 | 28.9 | 13.2 |
| 28 | 1559584_PM_a_at | 283897 | C16orf54 | chromosome 16 open reading frame 54 | 6.73E−17 | 71.5 | 26.1 |
| 29 | 209795_PM_at | 969 | CD69 | CD69 molecule | 9.46E−17 | 40.6 | 15.2 |
| 30 | 230550_PM_at | 64231 | MS4A6A | membrane-spanning 4-domains, subfamily A, member 6 A | 1.20E−16 | 88.0 | 30.9 |
| 31 | 1553906_PM_s_at | 221472 | FGD2 | FYVE, RhoGEF and PH domain containing 2 | 1.34E−16 | 219.3 | 71.9 |
| 32 | 205798_PM_at | 3575 | IL7R | interleukin 7 receptor | 1.55E−16 | 106.3 | 33.4 |
| 33 | 1555852_PM_at | 100507463 | LOC100507463 | hypothetical LOC100507463 | 1.81E−16 | 154.2 | 70.9 |
| 34 | 224916_PM_at | 340061 | TMEM173 | transmembrane protein 173 | 1.84E−16 | 67.8 | 40.0 |
| 35 | 211368_PM_s_at | 834 | CASP1 | caspase 1, apoptosis-related cysteine peptidase (interleukin 1, beta, convertase) | 1.85E−16 | 191.4 | 81.8 |
| 36 | 226474_PM_at | 84166 | NLRC5 | NLRC5 family, CARD domain containing 5 | 1.85E−16 | 129.8 | 55.1 |
| 37 | 201137_PM_s_at | 3115 | HLA-DPB1 | major histocompatibility complex, class II, DP beta 1 | 1.90E−16 | 3151.7 | 1475.9 |
| 38 | 210785_PM_s_at | 9473 | C1orf38 | chromosome 1 open reading frame 38 | 2.07E−16 | 39.9 | 16.4 |
| 39 | 215121_PM_x_at | 100290481 /// 28823 /// 28834 | IGLC7 /// IGLV1-44 /// LOC100290481 | immunoglobulin lambda constant 7 /// immunoglobulin lambda variable 1-44 /// immunoglob | 2.13E−16 | 1546.8 | 250.4 |
| 40 | 1555832_PM_s_at | 1316 | KLF6 | Kruppel-like factor 6 | 2.35E−16 | 1003.3 | 575.1 |
| 41 | 221932_PM_s_at | 51218 | GLRX5 | glutaredoxin 5 | 2.49E−16 | 1218.1 | 1599.3 |
| 42 | 207677_PM_s_at | 4689 | NCF4 | neutrophil cytosolic factor 4.40 kDa | 2.65E−16 | 39.5 | 19.2 |
| 43 | 202720_PM_at | 26136 | TES | testis derived transcript (3 LIM domains) | 2.68E−16 | 357.9 | 204.2 |
| 44 | 220005_PM_at | 53829 | P2RY13 | purinergic receptor P2Y, G-protein coupled, 13 | 2.72E−16 | 29.6 | 14.8 |
| 45 | 200904_PM_at | 3133 | HLA-E | major histocompatibility complex, class I, E | 2.73E−16 | 1607.7 | 994.7 |
| 46 | 222294_PM_s_at | 5873 | RAB27A | RAB27A, member RAS oncogene family | 2.91E−16 | 263.0 | 146.4 |

TABLE 14b-continued

Biopsy Expression Profiling of Kidney Transplants. 2-Way Classifier CAN vs. TX

| # | Probeset ID | Entrez Gene | Gene Symbol | Gene Title | p-value (Final Phenotype) | CAN-Mean | TX-Mean |
|---|---|---|---|---|---|---|---|
| 47 | 205831_PM_at | 914 | CD2 | CD2 molecule | 3.32E−16 | 100.9 | 33.9 |
| 48 | 227344_PM_at | 10320 | IKZF1 | IKAROS family zinc finger 1 (Ikaros) | 3.39E−16 | 28.5 | 14.9 |
| 49 | 209374_PM_s_at | 3507 | IGHM | immunoglobulin heavy constant mu | 3.73E−16 | 301.0 | 45.0 |
| 50 | 202307_PM_s_at | 6890 | TAP1 | transporter 1, ATP-binding cassette, sub-family B (MDR/TAP) | 4.84E−16 | 280.0 | 141.0 |
| 51 | 223218_PM_s_at | 64332 | NFKBIZ | nuclear factor of kappa light polypeptide gene enhancer in B-cells inhibitor, zeta | 5.05E−16 | 399.9 | 159.1 |
| 52 | 229437_PM_at | 114614 | MIR155HG | MIR155 host gene (non-protein coding) | 5.85E−16 | 28.5 | 12.9 |
| 53 | 213603_PM_s_at | 5880 | RAC2 | ras-related C3 botulinum toxin substrate 2 (rho family, small GTP binding protein Rac2) | 5.98E−16 | 250.3 | 86.5 |
| 54 | 214669_PM_x_at | 3514 /// 50802 | IGK@ /// IGKC | immunoglobulin kappa locus /// immunoglobulin kappa constant | 6.32E−16 | 3449.1 | 587.1 |
| 55 | 211430_PM_s_at | 28396 /// 3500 /// 3507 | IGHG1 /// IGHM /// IGHV4-31 | immunoglobulin heavy constant gamma 1 (G1m marker) /// immunoglobulin heavy constant mu | 6.39E−16 | 2177.7 | 266.9 |
| 56 | 228471_PM_at | 91526 | ANKRD44 | ankyrin repeat domain 44 | 6.42E−16 | 184.6 | 86.5 |
| 57 | 209138_PM_x_at | 3535 | IGL@ | Immunoglobulin lambda locus | 7.54E−16 | 2387.0 | 343.2 |
| 58 | 227353_PM_at | 147138 | TMC8 | transmembrane channel-like 8 | 8.01E−16 | 42.7 | 16.6 |
| 59 | 200986_PM_at | 710 | SERPING1 | serpin peptidase inhibitor, clade G (C1 inhibitor), member 1 | 8.10E−16 | 590.2 | 305.3 |
| 60 | 212203_PM_x_at | 10410 | IFITM3 | interferon induced transmembrane protein 3 (1-8U) | 8.17E−16 | 4050.1 | 2773.8 |
| 61 | 221651_PM_x_at | 3514 //// 50802 | IGK@ /// IGKC | immunoglobulin kappa locus /// immunoglobulin kappa constant | 9.60E−16 | 3750.2 | 621.2 |
| 62 | 214836_PM_x_at | 28299 /// 3514 /// 50802 | IGK@ /// IGKC /// IGKV1-5 | immunoglobulin kappa locus /// immunoglobulin kappa constant /// immunoglobulin kappa v | 9.72E−16 | 544.2 | 109.1 |
| 63 | 1552703_PM_s_at | 114769 /// 834 | CARD16 /// CASP1 | caspase recruitment domain family, member 16 /// caspase 1, apoptosis-related cysteine | 1.12E−15 | 120.6 | 54.9 |
| 64 | 202901_PM_x_at | 1520 | CTSS | cathepsin S | 1.13E−15 | 130.9 | 45.1 |
| 65 | 215379_PM_x_at | 28823 /// 28834 | IGLC7 /// IGLV1-44 | immunoglobulin lambda constant 7 /// immunoglobulin lambda variable 1-44 | 1.16E−15 | 1453.0 | 248.1 |
| 66 | 222939_PM_s_at | 117247 | SLC16A10 | solute carrier family 16, member 10 (aromatic amino acid transporter) | 1.22E−15 | 115.1 | 229.6 |
| 67 | 232617_PM_at | 1520 | CTSS | cathepsin S | 1.22E−15 | 392.2 | 154.8 |
| 68 | 235964_PM_x_at | 25939 | SAMHD1 | SAM domain and HD domain 1 | 1.26E−15 | 270.1 | 117.5 |
| 69 | 205159_PM_at | 1439 | CSF2RB | colony stimulating factor 2 receptor, beta, low-affinity (granulocyte-macrophage) | 1.28E−15 | 70.4 | 26.3 |
| 70 | 224451_PM_x_at | 64333 | ARHGAP9 | Rho GTPase activating protein 9 | 1.34E−15 | 71.8 | 29.4 |
| 71 | 214677_PM_x_at | 100287927 /// 3535 | IGL@ /// LOC100287927 | Immunoglobulin lambda locus /// Hypothetical protein LOC100287927 | 1.35E−15 | 2903.1 | 433.7 |
| 72 | 217733_PM_s_at | 9168 | TMSB10 | thymosin beta 10 | 1.37E−15 | 5555.2 | 3529.0 |
| 73 | 38149_PM_at | 9938 | ARHGAP25 | Rho GTPase activating protein 25 | 1.46E−15 | 83.2 | 43.2 |
| 74 | 221671_PM_x_at | 3514 /// 50802 | IGK@ /// IGKC | immunoglobulin kappa locus /// immunoglobulin kappa constant | 1.57E−15 | 3722.5 | 642.9 |

TABLE 14b-continued

Biopsy Expression Profiling of Kidney Transplants. 2-Way Classifier CAN vs. TX

| # | Probeset ID | Entrez Gene | Gene Symbol | Gene Title | p-value (Final Pheno-type) | CAN-Mean | TX-Mean |
|---|---|---|---|---|---|---|---|
| 75 | 214022_PM_s_at | 8519 | IFITM1 | interferon induced transmembrane protein 1 (9-27) | 1.59E-15 | 1236.6 | 683.3 |
| 76 | 223217_PM_s_at | 64332 | NFKBIZ | nuclear factor of kappa light polypeptide gene enhancer in B-cells inhibitor, zeta | 1.61E-15 | 196.6 | 79.7 |
| 77 | 206118_PM_at | 6775 | STAT4 | signal transducer and activator of transcription 4 | 1.67E-15 | 37.7 | 18.1 |
| 78 | 221666_PM_s_at | 29108 | PYCARD | PYD and CARD domain containing | 1.82E-15 | 95.5 | 44.7 |
| 79 | 207375_PM_s_at | 3601 | IL15RA | interleukin 15 receptor, alpha | 1.94E-15 | 51.2 | 28.2 |
| 80 | 209197_PM_at | 23208 | SYT11 | synaptotagmin XI | 2.02E-15 | 38.2 | 24.9 |
| 81 | 243366_PM_s_at | — | — | | 2.05E-15 | 52.5 | 22.0 |
| 82 | 224795_PM_x_at | 3514 /// 50802 | IGK@ /// IGKC | immunoglobulin kappa locus /// immunoglobulin kappa constant | 2.18E-15 | 3866.2 | 670.5 |
| 83 | 36711_PM_at | 23764 | MAFF | v-maf musculoaponeurotic fibrosarcoma oncogene homolog F (avian) | 2.26E-15 | 113.0 | 40.7 |
| 84 | 227125_PM_at | 3455 | IFNAR2 | interferon (alpha, beta and omega) receptor 2 | 2.27E-15 | 96.7 | 55.8 |
| 85 | 235735_PM_at | — | — | | 2.58E-15 | 24.5 | 11.2 |
| 86 | 209515_PM_s_at | 5873 | RAB27A | RAB27A, member RAS oncogene family | 2.61E-15 | 160.5 | 85.2 |
| 87 | 204670_PM_x_at | 3123 /// 3126 | HLA-DRB1 /// HLA-DRB4 | major histocompatibility complex, class II, DR beta 1 /// major histocompatibility comp | 2.61E-15 | 3694.9 | 2262.0 |
| 88 | 205269_PM_at | 3937 | LCP2 | lymphocyte cytosolic protein 2 (SH2 domain containing leukocyte protein of 76 kDa) | 2.85E-15 | 58.9 | 22.9 |
| 89 | 226525_PM_at | 9262 | STK17B | serine/threonine kinase 17 b | 3.00E-15 | 259.1 | 107.6 |
| 90 | 229295_PM_at | 150166 /// 23765 | IL17RA /// LOC150166 | interleukin 17 receptor A /// hypothetical protein LOC150166 | 3.02E-15 | 98.4 | 50.0 |
| 91 | 206513_PM_at | 9447 | AIM2 | absent in melanoma 2 | 3.18E-15 | 30.5 | 13.9 |
| 92 | 209774_PM_x_at | 2920 | CXCL2 | chemokine (C-X-C motif) ligand 2 | 3.45E-15 | 38.2 | 15.5 |
| 93 | 211656_PM_x_at | 100133583 /// 3119 | HLA-DQB1 /// LOC100133583 | major histocompatibility complex, class II, DQ beta 1 /// HLA class II histocompatibili | 3.51E-15 | 459.8 | 208.2 |
| 94 | 206011_PM_at | 834 | CASP1 | caspase 1, apoptosis-related cysteine peptidase (interleukin 1, beta, convertase) | 3.56E-15 | 146.2 | 60.7 |
| 95 | 202803_PM_s_at | 3689 | ITGB2 | integrin, beta 2 (complement component 3 receptor 3 and 4 subunit) | 3.68E-15 | 182.6 | 65.2 |
| 96 | 221698_PM_s_at | 64581 | CLEC7A | C-type lectin domain family 7, member A | 3.69E-15 | 112.8 | 49.7 |
| 97 | 229937_PM_x_at | 10859 | LILRB1 | Leukocyte immunoglobulin-like receptor, subfamily B (with TM and ITIM domains), member | 3.75E-15 | 50.0 | 18.5 |
| 98 | 235529_PM_x_at | 25939 | SAMHD1 | SAM domain and HD domain 1 | 3.99E-15 | 289.1 | 128.0 |
| 99 | 223322_PM_at | 83593 | RASSF5 | Ras association (RalGDS/AF-6) domain family member 5 | 4.03E-15 | 79.3 | 39.2 |
| 100 | 211980_PM_at | 1282 | COL4A1 | collagen, type IV, alpha 1 | 4.75E-15 | 1295.8 | 774.7 |
| 101 | 201721_PM_s_at | 7805 | LAPTM5 | lysosomal protein transmembrane 5 | 4.83E-15 | 661.3 | 249.4 |
| 102 | 242916_PM_at | 11064 | CEP110 | centrosomal protein 110 kDa | 4.89E-15 | 51.2 | 26.2 |
| 103 | 206978_PM_at | 729230 | CCR2 | chemokine (C-C motif) receptor 2 | 5.01E-15 | 68.6 | 27.3 |
| 104 | 244353_PM_s_at | 154091 | SLC2A12 | solute carrier family 2 (facilitated glucose transporter), member 12 | 5.72E-15 | 51.6 | 100.5 |

TABLE 14b-continued

Biopsy Expression Profiling of Kidney Transplants. 2-Way Classifier CAN vs. TX

| # | Probeset ID | Entrez Gene | Gene Symbol | Gene Title | p-value (Final Phenotype) | CAN-Mean | TX-Mean |
|---|---|---|---|---|---|---|---|
| 105 | 215049_PM_x_at | 9332 | CD163 | CD163 molecule | 6.21E-15 | 344.5 | 112.9 |
| 106 | 1552510_PM_at | 142680 | SLC34A3 | solute carrier family 34 (sodium phosphate), member 3 | 6.40E-15 | 95.6 | 206.6 |
| 107 | 225636_PM_at | 6773 | STAT2 | signal transducer and activator of transcription 2, 113 kDa | 6.63E-15 | 711.5 | 485.3 |
| 108 | 229390_PM_at | 441168 | FAM26F | family with sequence similarity 26, member F | 6.73E-15 | 272.4 | 75.9 |
| 109 | 235229_PM_at | — | — |  | 6.90E-15 | 135.0 | 41.9 |
| 110 | 226218_PM_at | 3575 | IL7R | interleukin 7 receptor | 7.22E-15 | 147.1 | 41.4 |
| 111 | 217028_PM_at | 7852 | CXCR4 | chemokine (C-X-C motif) receptor 4 | 7.40E-15 | 208.4 | 75.3 |
| 112 | 204655_PM_at | 6352 | CCL5 | chemokine (C-C motif) ligand 5 | 8.57E-15 | 223.4 | 66.8 |
| 113 | 227184_PM_at | 5724 | PTAFR | platelet-activating factor receptor | 8.78E-15 | 134.4 | 62.7 |
| 114 | 202748_PM_at | 2634 | GBP2 | guanylate binding protein 2, interferon-inducible | 8.91E-15 | 306.7 | 141.0 |
| 115 | 226991_PM_at | 4773 | NFATC2 | nuclear factor of activated T-cells, cytoplasmic, calcineurin-dependent 2 | 9.05E-15 | 66.7 | 30.3 |
| 116 | 216565_PM_x_at | — | — |  | 9.49E-15 | 1224.6 | 779.1 |
| 117 | 203104_PM_at | 1436 | CSF1R | colony stimulating factor 1 receptor | 9.57E-15 | 42.7 | 22.1 |
| 118 | 238668_PM_at | — | — |  | 9.84E-15 | 33.6 | 14.5 |
| 119 | 204923_PM_at | 54440 | SASH3 | SAM and SH3 domain containing 3 | 9.93E-15 | 47.6 | 21.7 |
| 120 | 230036_PM_at | 219285 | SAMD9L | sterile alpha motif domain containing 9-like | 1.02E-14 | 128.0 | 72.7 |
| 121 | 211742_PM_s_at | 2124 | EVI2B | ecotropic viral integration site 2 B | 1.03E-14 | 166.2 | 53.2 |
| 122 | 236782_PM_at | 154075 | SAMD3 | sterile alpha motif domain containing 3 | 1.11E-14 | 23.3 | 13.3 |
| 123 | 232543_PM_x_at | 64333 | ARHGAP9 | Rho GTPase activating protein 9 | 1.13E-14 | 62.3 | 25.8 |
| 124 | 231124_PM_x_at | 4063 | LY9 | lymphocyte antigen 9 | 1.18E-14 | 33.7 | 15.7 |
| 125 | 215946_PM_x_at | 3543 /// 91316 /// 91353 | IGLL1 /// IGLL3P /// LOC91316 | immunoglobulin lambda-like polypeptide 1 /// immunoglobulin lambda-like polypeptide 3, | 1.22E-14 | 187.5 | 52.1 |
| 126 | 208306_PM_x_at | 3123 | HLA-DRB1 | Major histocompatibility complex, class II, DR beta 1 | 1.25E-14 | 3695.8 | 2255.0 |
| 127 | 217235_PM_x_at | 28816 | IGLV2-11 | immunoglobulin lambda variable 2-11 | 1.29E-14 | 196.8 | 37.8 |
| 128 | 209546_PM_s_at | 8542 | APOL1 | apolipoprotein L, 1 | 1.33E-14 | 206.8 | 114.1 |
| 129 | 203416_PM_at | 963 | CD53 | CD53 molecule | 1.34E-14 | 422.7 | 157.8 |
| 130 | 211366_PM_x_at | 834 | CASP1 | caspase 1, apoptosis-related cysteine peptidase (interleukin 1, beta, convertase) | 1.35E-14 | 186.0 | 87.1 |
| 131 | 200797_PM_s_at | 4170 | MCL1 | myeloid cell leukemia sequence 1 (BCL2-related) | 1.38E-14 | 793.7 | 575.9 |
| 132 | 31845_PM_at | 2000 | ELF4 | E74-like factor 4 (ets domain transcription factor) | 1.40E-14 | 60.7 | 34.3 |
| 133 | 221841_PM_s_at | 9314 | KLF4 | Kruppel-like factor 4 (gut) | 1.48E-14 | 132.3 | 65.2 |
| 134 | 229391_PM_s_at | 441168 | FAM26F | family with sequence similarity 26, member F | 1.49E-14 | 212.1 | 73.7 |
| 135 | 203645_PM_s_at | 9332 | CD163 | CD163 molecule | 1.51E-14 | 274.9 | 85.0 |
| 136 | 211643_PM_x_at | 100510044 /// 28875 /// 3514 /// 50802 | IGK@ /// IGKC /// IGKV3D-15 /// LOC100510044 | immunoglobulin kappa locus /// immunoglobulin kappa constant /// immunoglobulin kappa v | 1.61E-14 | 131.1 | 32.6 |
| 137 | 205488_PM_at | 3001 | GZMA | granzyme A (granzyme 1, cytotoxic T-lymphocyte-associated serine esterase 3) | 1.82E-14 | 102.3 | 33.4 |
| 138 | 201464_PM_x_at | 3725 | JUN | jun proto-oncogene | 1.90E-14 | 424.7 | 244.5 |
| 139 | 204774_PM_at | 2123 | EVI2A | ecotropic viral integration site 2 A | 1.95E-14 | 114.7 | 44.9 |
| 140 | 204336_PM_s_at | 10287 | RGS19 | regulator of G-protein signaling 19 | 2.01E-14 | 135.7 | 67.0 |

TABLE 14b-continued

Biopsy Expression Profiling of Kidney Transplants. 2-Way Classifier CAN vs. TX

| # | Probeset ID | Entrez Gene | Gene Symbol | Gene Title | p-value (Final Phenotype) | CAN-Mean | TX-Mean |
|---|---|---|---|---|---|---|---|
| 141 | 244654_PM_at | 64005 | MYO1G | myosin IG | 2.03E-14 | 26.8 | 14.9 |
| 142 | 228442_PM_at | 4773 | NFATC2 | nuclear factor of activated T-cells, cytoplasmic, calcineurin-dependent 2 | 2.06E-14 | 62.8 | 32.0 |
| 143 | 206804_PM_at | 917 | CD3G | CD3g molecule, gamma (CD3-TCR complex) | 2.18E-14 | 36.4 | 17.3 |
| 144 | 201315_PM_x_at | 10581 | IFITM2 | interferon induced transmembrane protein 2 (1-8 D) | 2.21E-14 | 3303.7 | 2175.3 |
| 145 | 203561_PM_at | 2212 | FCGR2A | Fc fragment of IgG, low affinity IIa, receptor (CD32) | 2.22E-14 | 66.4 | 29.2 |
| 146 | 219117_PM_s_at | 51303 | FKBP11 | FK506 binding protein 11, 19 kDa | 2.31E-14 | 341.3 | 192.9 |
| 147 | 242827_PM_x_at | — | — | — | 2.37E-14 | 38.9 | 16.3 |
| 148 | 214768_PM_x_at | 28299 /// 3514 /// 50802 | IGK@ /// IGKC /// IGKV1-5 | immunoglobulin kappa locus /// immunoglobulin kappa constant /// immunoglobulin kappa v | 2.38E-14 | 116.7 | 21.1 |
| 149 | 227253_PM_at | 1356 | CP | ceruloplasmin (ferroxidase) | 2.49E-14 | 44.7 | 22.0 |
| 150 | 209619_PM_at | 972 | CD74 | CD74 molecule, major histocompatibility complex, class II invariant chain | 2.51E-14 | 1502.3 | 864.9 |
| 151 | 208966_PM_x_at | 3428 | IFI16 | interferon, gamma-inducible protein 16 | 2.65E-14 | 644.9 | 312.6 |
| 152 | 239237_PM_at | — | — | — | 2.79E-14 | 25.3 | 14.5 |
| 153 | 213566_PM_at | 6039 | RNASE6 | ribonuclease, RNase A family, k6 | 2.82E-14 | 341.1 | 134.3 |
| 154 | 201288_PM_at | 397 | ARHGDIB | Rho GDP dissociation inhibitor (GDI) beta | 2.86E-14 | 542.2 | 308.1 |
| 155 | 209606_PM_at | 9595 | CYTIP | cytohesin 1 interacting protein | 2.90E-14 | 79.0 | 32.9 |
| 156 | 205758_PM_at | 925 | CD8A | CD8a molecule | 2.91E-14 | 60.3 | 22.2 |
| 157 | 202953_PM_at | 713 | C1QB | complement component 1, q subcomponent, B chain | 3.00E-14 | 401.1 | 142.5 |
| 158 | 203233_PM_at | 3566 | IL4R | interleukin 4 receptor | 3.06E-14 | 116.7 | 72.0 |
| 159 | 205270_PM_s_at | 3937 | LCP2 | lymphocyte cytosolic protein 2 (SH2 domain containing leukocyte protein of 76 kDa) | 3.12E-14 | 104.4 | 44.6 |
| 160 | 223658_PM_at | 9424 | KCNK6 | potassium channel, subfamily K, member 6 | 3.18E-14 | 35.9 | 22.0 |
| 161 | 202637_PM_s_at | 3383 | ICAM1 | intercellular adhesion molecule 1 | 3.18E-14 | 89.1 | 45.7 |
| 162 | 202935_PM_s_at | 6662 | SOX9 | SRY (sex determining region Y)-box 9 | 3.18E-14 | 117.0 | 46.1 |
| 163 | 217986_PM_s_at | 11177 | BAZ1A | bromodomain adjacent to zinc finger domain, 1 A | 3.21E-14 | 116.4 | 62.5 |
| 164 | 210915_PM_x_at | 28638 | TRBC2 | T cell receptor beta constant 2 | 3.27E-14 | 129.7 | 37.5 |
| 165 | 223343_PM_at | 58475 | MS4A7 | membrane-spanning 4-domains, subfamily A, member 7 | 3.38E-14 | 346.0 | 128.3 |
| 166 | 1552701_PM_a_at | 114769 | CARD16 | caspase recruitment domain family, member 16 | 3.60E-14 | 273.3 | 119.8 |
| 167 | 226659_PM_at | 50619 | DEF6 | differentially expressed in FDCP 6 homolog (mouse) | 3.63E-14 | 35.2 | 22.2 |
| 168 | 213502_PM_x_at | 91316 | LOC91316 | glucuronidase, beta/immunoglobulin lambda-like polypeptide 1 pseudogene | 3.63E-14 | 1214.7 | 419.3 |
| 169 | 219332_PM_at | 79778 | MICALL2 | MICAL-like 2 | 3.71E-14 | 68.7 | 44.4 |
| 170 | 204891_PM_s_at | 3932 | LCK | lymphocyte-specific protein tyrosine kinase | 3.74E-14 | 43.4 | 17.8 |
| 171 | 224252_PM_s_at | 53827 | FXYD5 | FXYD domain containing ion transport regulator 5 | 3.76E-14 | 73.8 | 32.5 |
| 172 | 242878_PM_at | — | — | — | 3.90E-14 | 53.2 | 30.1 |
| 173 | 224709_PM_s_at | 56990 | CDC42SE2 | CDC42 small effector 2 | 4.07E-14 | 1266.2 | 935.7 |
| 174 | 40420_PM_at | 6793 | STK10 | serine/threonine kinase 10 | 4.32E-14 | 42.0 | 24.4 |
| 175 | 218084_PM_x_at | 53827 | FXYD5 | FXYD domain containing ion transport regulator 5 | 4.52E-14 | 89.2 | 39.1 |
| 176 | 218232_PM_at | 712 | C1QA | complement component 1, q subcomponent, A chain | 4.63E-14 | 197.0 | 85.8 |

TABLE 14b-continued

Biopsy Expression Profiling of Kidney Transplants. 2-Way Classifier CAN vs. TX

| # | Probeset ID | Entrez Gene | Gene Symbol | Gene Title | p-value (Final Phenotype) | CAN-Mean | TX-Mean |
|---|---|---|---|---|---|---|---|
| 177 | 202208_PM_s_at | 10123 | ARL4C | ADP-ribosylation factor-like 4 C | 4.63E−14 | 77.0 | 42.2 |
| 178 | 220146_PM_at | 51284 | TLR7 | toll-like receptor 7 | 4.93E−14 | 31.6 | 17.8 |
| 179 | 228752_PM_at | 84766 | EFCAB4B | EF-hand calcium binding domain 4 B | 5.05E−14 | 20.6 | 12.1 |
| 180 | 208948_PM_s_at | 6780 | STAU1 | staufen, RNA binding protein, homolog 1 (Drosophila) | 5.23E−14 | 1766.0 | 2467.4 |
| 181 | 211645_PM_x_at | — | — | | 5.24E−14 | 166.7 | 27.4 |
| 182 | 236295_PM_s_at | 197358 | NLRC3 | NLR family, CARD domain containing 3 | 5.28E−14 | 37.0 | 18.6 |
| 183 | 224927_PM_at | 170954 | KIAA1949 | KIAA1949 | 5.44E−14 | 160.2 | 74.7 |
| 184 | 225258_PM_at | 54751 | FBLIM1 | filamin binding LIM protein 1 | 6.03E−14 | 228.7 | 125.4 |
| 185 | 202898_PM_at | 9672 | SDC3 | syndecan 3 | 6.07E−14 | 64.8 | 32.0 |
| 186 | 218789_PM_s_at | 54494 | C11orf71 | chromosome 11 open reading frame 71 | 6.12E−14 | 175.8 | 280.8 |
| 187 | 204912_PM_at | 3587 | IL10RA | interleukin 10 receptor, alpha | 6.25E−14 | 117.2 | 46.1 |
| 188 | 211582_PM_x_at | 7940 | LST1 | leukocyte specific transcript 1 | 6.48E−14 | 121.2 | 49.4 |
| 189 | 214617_PM_at | 5551 | PRF1 | perforin 1 (pore forming protein) | 6.77E−14 | 85.6 | 40.8 |
| 190 | 231887_PM_s_at | 27143 | KIAA1274 | KIAA1274 | 7.00E−14 | 45.6 | 30.0 |
| 191 | 223773_PM_s_at | 85028 | SNHG12 | small nucleolar RNA host gene 12 (non-protein coding) | 7.00E−14 | 174.8 | 93.2 |
| 192 | 202644_PM_s_at | 7128 | TNFAIP3 | tumor necrosis factor, alpha-induced protein 3 | 7.11E−14 | 278.2 | 136.6 |
| 193 | 211796_PM_s_at | 28638 /// 28639 | TRBC1 /// TRBC2 | T cell receptor beta constant 1 /// T cell receptor beta constant 2 | 7.13E−14 | 250.2 | 63.6 |
| 194 | 206254_PM_at | 1950 | EGF | epidermal growth factor | 7.38E−14 | 176.6 | 551.3 |
| 195 | 216207_PM_x_at | 28299 /// 28904 /// 3514 /// 652493 /// 652694 | IGKC /// IGKV1-5 /// IGKV1D-8 /// LOC652493 /// LOC652694 | immunoglobulin kappa constant /// immunoglobulin kappa variable 1-5 /// immunoglobulin | 7.51E−14 | 266.3 | 50.9 |
| 196 | 232311_PM_at | 567 | B2M | Beta-2-microglobulin | 7.73E−14 | 83.7 | 35.2 |
| 197 | 205466_PM_s_at | 9957 | HS3ST1 | heparan sulfate (glucosamine) 3-O-sulfotransferase 1 | 7.84E−14 | 96.0 | 42.1 |
| 198 | 203332_PM_s_at | 3635 | INPP5D | inositol polyphosphate-5-phosphatase, 145 kDa | 7.89E−14 | 42.6 | 24.0 |
| 199 | 64064_PM_at | 55340 | GIMAP5 | GTPase, IMAP family member 5 | 7.98E−14 | 170.6 | 111.4 |
| 200 | 211644_PM_x_at | 3514 /// 50802 | IGK@ /// IGKC | immunoglobulin kappa locus /// immunoglobulin kappa constant | 8.04E−14 | 246.9 | 47.5 |

TABLE 15

Biopsy Expression Profiling of Kidney Transplants:
2-Way Classifier CAN vs. TX (Brazilian Samples)

| | | | Validation Cohort | | | | | |
|---|---|---|---|---|---|---|---|---|
| Algorithm | Predictors | Comparison | AUC | Predictive Accuracy (%) | Sensitivity (%) | Specificity (%) | Postive Predictive Value (%) | Negative Predictive Value (%) |
| Nearest Centroid | 200 | AR vs. TX | 0.954 | 95 | 95 | 96 | 95 | 96 |

Example 4

Expression Signatures to Distinguish Liver Transplant Injuries

Biomarker profiles diagnostic of specific types of graft injury post-liver transplantation (LT), such as acute rejection (AR), hepatitis C virus recurrence (HCV-R), and other causes (acute dysfunction no rejection/recurrence; ADNR) could enhance the diagnosis and management of recipients. Our aim was to identify diagnostic genomic (mRNA) signatures of these clinical phenotypes in the peripheral blood and allograft tissue.

Patient Populations: The study population consisted of 114 biopsy-documented Liver PAXgene whole blood samples comprised of 5 different phenotypes: AR (n=25), ADNR (n=16), HCV(n=36), HCV+AR (n=13), and TX (n=24).

Gene Expression Profiling and Analysis: All samples were processed on the Affymetrix HG-U133 PM only peg microarrays. To eliminate low expressed signals we used a signal filter cut-off that was data dependent, and therefore expression signals <Log 2 4.23 (median signals on all arrays) in all samples were eliminated leaving us with 48882 probe sets from a total of 54721 probe sets. The first comparison performed was a 3-way ANOVA analysis of AR vs. ADNR vs. TX. This yielded 263 differentially expressed probesets at a False Discovery rate (FDR <10%). We used these 263 probesets to build predictive models that could differentiate the three classes. We used the Nearest Centroid (NC) algorithm to build the predictive models. We ran the predictive models using two different methodologies and calculated the Area Under the Curve (AUC). First we did a one-level cross validation, where the data is first divided into 10 random partitions. At each iteration, 1/10 of the data is held out for testing while the remaining 9/10 of the data is used to fit the parameters of the model. This can be used to obtain an estimate of prediction accuracy for a single model. Then we modeled an algorithm for estimating the optimism, or over-fitting, in predictive models based on using bootstrapped datasets to repeatedly quantify the degree of overfitting in the model building process using sampling with replacement. This optimism corrected AUC value is a nearly unbiased estimate of the expected values of the optimism that would be obtained in external validation (we used 1000 randomly created data sets). Table 16a shows the optimism corrected AUCs for the 263 probesets that were used to predict the accuracies for distinguishing between AR, ADNR and TX in Liver PAXgene samples. Table 16b shows the 263 probesets used for distinguishing between AR, ADNR and TX in Liver PAXgene samples.

It is clear from the above Table 16a that the 263 probeset classifier was able to distinguish the three phenotypes with very high predictive accuracy. The NC classifier had a sensitivity of 83%, specificity of 93%, and positive predictive value of 95% and a negative predictive value of 78% for the AR vs. ADNR comparison. It is important to note that these values did not change after the optimism correction where we simulated 1000 data sets showing that these are really robust signatures.

The next comparison we performed was a 3-way ANOVA of AR vs. HCV vs. HCV+AR which yielded 147 differentially expressed probesets at a p value <0.001. We chose to use this set of predictors because at an FDR <10% we had only 18 predictors, which could possibly be due to the smaller sample size of the HCV+AR (n=13) or a smaller set of differentially expressed genes in one of the phenotypes. However, since this was a discovery set to test the proof of principle whether there were signatures that could distinguish samples that had an admixture of HCV and AR from the pure AR and the pure HCV populations, we ran the predictive algorithms on the 147 predictors. Table 17a shows the AUCs for the 147 probesets that were used to predict the accuracies for distinguishing between AR, HCV and HCV+AR in Liver PAXgene samples. Table 17b shows the 147 probesets used for distinguishing between AR, HCV and HCV+AR in Liver PAXgene samples.

The NC classifier had a sensitivity of 87%, specificity of 97%, and positive predictive value of 95% and a negative predictive value of 92% for the AR vs HCV comparison using the optimism correction where we simulated 1000 data sets giving us confidence that the simulations that were done to mimic a real clinical situation did not alter the robustness of this set of predictors.

For the biopsies, again, we performed a 3-way ANOVA of AR vs. HCV vs. HCV+AR that yielded 320 differentially expressed probesets at an FDR <10%. We specifically did this because at a p-value <0.001 there were over 950 probesets. We ran the predictive models on this set of classifiers in the same way mentioned for the PAXgene samples. Table 18a shows the AUCs for the one-level cross validation and the optimism correction for the classifier set comprised of 320 probesets that were used to predict the accuracies for distinguishing between AR, HCV and HCV+AR in Liver biopsies. Table 18b shows the 320 probesets that used for distinguishing AR vs. HCV vs. HCV+AR in Liver biopsies.

In summary, for both the blood and the biopsy samples from liver transplant subjects we have classifier sets that can distinguish AR, HCV and HCV+AR with AUCs between 0.79-0.83 in blood and 0.69-0.83 in the biopsies. We also have a signature from whole blood that can distinguish AR, ADNR and TX samples with AUC's ranging from 0.87-0.92.

It is understood that the examples and embodiments described herein are for illustrative purposes only and that various modifications or changes in light thereof will be suggested to persons skilled in the art and are to be included within the spirit and purview of this application and scope of the appended claims. Although any methods and materials similar or equivalent to those described herein can be used in the practice or testing of the present invention, the preferred methods and materials are described.

All publications, GenBank sequences, ATCC deposits, patents and patent applications cited herein are hereby expressly incorporated by reference in their entirety and for all purposes as if each is individually so denoted.

TABLE 16a

AUCs for the 263 probes to predict AR, ADNR and TX in Liver whole blood samples.

| Algorithm | Predictors | Comparison | AUC | Predictive Accuracy (%) | Sensitivity (%) | Specificity (%) | Postive Predictive Value (%) | Negative Predictive Value (%) |
|---|---|---|---|---|---|---|---|---|
| Nearest Centroid | 263 | AR vs. ADNR | 0.882 | 88 | 83 | 93 | 95 | 78 |
| Nearest Centroid | 263 | AR vs. TX | 0.943 | 95 | 95 | 95 | 95 | 95 |
| Nearest Centroid | 263 | ADNR vs. TX | 0.883 | 88 | 93 | 83 | 78 | 95 |

TABLE 16b

The 263 probesets for distinguishing between AR, ADNR and TX in Liver PAXgene samples

| # | Probeset ID | Gene Symbol | Gene Title | p-value (Phenotype) | ADNR - Mean | AR - Mean | TX - Mean |
|---|---|---|---|---|---|---|---|
| 1 | 215415_PM_s_at | LYST | lysosomal trafficking regulator | 3.79E−07 | 32.3 | 25.8 | 43.6 |
| 2 | 241038_PM_at | — | — | 4.79E−07 | 16.1 | 21.0 | 16.4 |
| 3 | 230776_PM_at | — | — | 2.10E−06 | 10.4 | 13.7 | 10.2 |
| 4 | 212805_PM_at | PRUNE2 | prune homolog 2 (*Drosophila*) | 4.09E−06 | 15.8 | 15.2 | 33.9 |
| 5 | 215090_PM_x_at | LOC440434 | aminopeptidase puromycin sensitive pseudogene | 7.28E−06 | 164.6 | 141.0 | 208.0 |
| 6 | 243625_PM_at | — | — | 7.64E−06 | 31.2 | 20.8 | 29.9 |
| 7 | 232222_PM_at | C18orf49 | chromosome 18 open reading frame 49 | 8.85E−06 | 33.7 | 35.7 | 42.4 |
| 8 | 235341_PM_at | DNAJC3 | DnaJ (Hsp40) homolog, subfamily C, member 3 | 1.06E−05 | 21.8 | 22.1 | 35.0 |
| 9 | 1557733_PM_a_at | — | — | 1.21E−05 | 83.8 | 116.0 | 81.2 |
| 10 | 212906_PM_at | GRAMD1B | GRAM domain containing 1B | 1.26E−05 | 52.7 | 51.0 | 45.7 |
| 11 | 1555874_PM_x_at | MGC21881 | hypothetical locus MGC21881 | 1.53E−05 | 20.5 | 20.0 | 19.3 |
| 12 | 227645_PM_at | PIK3R5 | phosphoinositide-3-kinase, regulatory subunit 5 | 1.66E−05 | 948.4 | 824.5 | 1013.0 |
| 13 | 235744_PM_at | PPTC7 | PTC7 protein phosphatase homolog (*S. cerevisiae*) | 1.73E−05 | 21.3 | 18.0 | 25.7 |
| 14 | 1553873_PM_at | KLHL34 | kelch-like 34 (*Drosophila*) | 1.89E−05 | 11.1 | 12.1 | 9.9 |
| 15 | 218408_PM_at | TIMM10 | translocase of inner mitochondrial membrane 10 homolog (yeast) | 2.16E−05 | 125.9 | 137.7 | 99.4 |
| 16 | 227486_PM_at | NT5E | 5'-nucleotidase, ecto (CD73) | 2.46E−05 | 14.7 | 18.6 | 15.6 |
| 17 | 231798_PM_at | NOG | noggin | 2.49E−05 | 17.0 | 25.9 | 15.1 |
| 18 | 205920_PM_at | SLC6A6 | solute carrier family 6 (neurotransmitter transporter, taurine), member 6 | 2.53E−05 | 25.9 | 25.0 | 39.3 |
| 19 | 222435_PM_s_at | UBE2J1 | ubiquitin-conjugating enzyme E2, J1 (UBC6 homolog, yeast) | 2.63E−05 | 212.6 | 292.4 | 324.0 |
| 20 | 207737_PM_at | — | — | 2.89E−05 | 8.2 | 8.5 | 8.6 |
| 21 | 209644_PM_x_at | CDKN2A | cyclin-dependent kinase inhibitor 2A (melanoma, p16, inhibits CDK4) | 2.91E−05 | 13.7 | 13.9 | 11.5 |
| 22 | 241661_PM_at | JMJD1C | jumonji domain containing 1C | 2.99E−05 | 18.4 | 21.9 | 34.8 |
| 23 | 202086_PM_at | MX1 | myxovirus (influenza virus) resistance 1, interferon-inducible protein p78 (mouse) | 3.04E−05 | 562.6 | 496.4 | 643.9 |
| 24 | 243819_PM_at | — | — | 3.11E−05 | 766.7 | 495.1 | 661.8 |
| 25 | 210524_PM_x_at | — | — | 3.12E−05 | 154.5 | 209.2 | 138.6 |
| 26 | 217714_PM_x_at | STMN1 | stathmin 1 | 3.39E−05 | 22.3 | 28.5 | 20.4 |
| 27 | 219659_PM_at | ATP8A2 | ATPase, aminophospholipid transporter, class I, type 8A, member 2 | 3.65E−05 | 10.4 | 10.8 | 9.8 |
| 28 | 219915_PM_s_at | SLC16A10 | solute carrier family 16, member 10 (aromatic amino acid transporter) | 3.70E−05 | 19.4 | 21.8 | 15.8 |
| 29 | 214039_PM_s_at | LAPTM4B | lysosomal protein transmembrane 4 beta | 3.81E−05 | 70.4 | 104.0 | 74.2 |

TABLE 16b-continued

The 263 probesets for distinguishing between AR, ADNR and TX in Liver PAXgene samples

| # | Probeset ID | Gene Symbol | Gene Title | p-value (Phenotype) | ADNR - Mean | AR - Mean | TX - Mean |
|---|---|---|---|---|---|---|---|
| 30 | 214107_PM_x_at | LOC440434 | aminopeptidase puromycin sensitive pseudogene | 4.27E−05 | 182.8 | 155.0 | 224.7 |
| 31 | 225408_PM_at | MBP | myelin basic protein | 4.54E−05 | 34.1 | 32.6 | 47.9 |
| 32 | 1552623_PM_at | HSH2D | hematopoietic SH2 domain containing | 4.93E−05 | 373.7 | 323.9 | 401.3 |
| 33 | 206974_PM_at | CXCR6 | chemokine (C-X-C motif) receptor 6 | 5.33E−05 | 24.6 | 31.0 | 22.9 |
| 34 | 203764_PM_at | DLGAP5 | discs, large (*Drosophila*) homolog-associated protein 5 | 5.41E−05 | 9.3 | 10.9 | 8.6 |
| 35 | 213915_PM_at | NKG7 | natural killer cell group 7 sequence | 5.73E−05 | 2603.1 | 1807.7 | 1663.1 |
| 36 | 1570597_PM_at | — | — | 5.86E−05 | 8.3 | 7.8 | 7.5 |
| 37 | 228290_PM_at | PLK1S1 | Polo-like kinase 1 substrate 1 | 6.00E−05 | 47.2 | 35.6 | 45.8 |
| 38 | 230753_PM_at | PATL2 | protein associated with topoisomerase II homolog 2 (yeast) | 6.11E−05 | 169.0 | 123.0 | 131.6 |
| 39 | 202016_PM_at | MEST | mesoderm specific transcript homolog (mouse) | 6.25E−05 | 18.3 | 27.5 | 17.3 |
| 40 | 212730_PM_at | SYNM | synemin, intermediate filament protein | 6.30E−05 | 16.7 | 19.5 | 14.4 |
| 41 | 209203_PM_s_at | BICD2 | bicaudal D homolog 2 (*Drosophila*) | 6.50E−05 | 197.8 | 177.0 | 256.6 |
| 42 | 1554397_PM_s_at | UEVLD | UEV and lactate/malate dehydrogenase domains | 6.59E−05 | 20.8 | 17.7 | 25.2 |
| 43 | 217963_PM_s_at | NGFRAP1 | nerve growth factor receptor (TNFRSF16) associated protein 1 | 7.61E−05 | 505.9 | 713.1 | 555.7 |
| 44 | 201656_PM_at | ITGA6 | integrin, alpha 6 | 7.75E−05 | 87.4 | 112.6 | 84.1 |
| 45 | 1553685_PM_s_at | SP1 | Sp1 transcription factor | 7.83E−05 | 27.4 | 27.3 | 41.3 |
| 46 | 236717_PM_at | FAM179A | family with sequence similarity 179, member A | 8.00E−05 | 55.1 | 39.8 | 42.1 |
| 47 | 240913_PM_at | FGFR2 | fibroblast growth factor receptor 2 | 8.33E−05 | 9.2 | 9.6 | 10.2 |
| 48 | 243756_PM_at | — | — | 8.47E−05 | 7.9 | 8.5 | 7.4 |
| 49 | 222036_PM_s_at | MCM4 | minichromosome maintenance complex component 4 | 8.52E−05 | 29.5 | 35.1 | 25.4 |
| 50 | 202644_PM_s_at | TNFAIP3 | tumor necrosis factor, alpha-induced protein 3 | 8.57E−05 | 516.0 | 564.5 | 475.8 |
| 51 | 229625_PM_at | GBP5 | guanylate binding protein 5 | 9.23E−05 | 801.9 | 1014.7 | 680.8 |
| 52 | 235545_PM_at | DEPDC1 | DEP domain containing 1 | 9.83E−05 | 8.0 | 8.7 | 8.3 |
| 53 | 204641_PM_at | NEK2 | NIMA (never in mitosis gene a)-related kinase 2 | 0.000100269 | 10.2 | 12.5 | 10.0 |
| 54 | 213931_PM_at | ID2 /// ID2B | inhibitor of DNA binding 2, dominant negative helix-loop-helix protein /// inhibitor of | 0.000101645 | 562.9 | 504.9 | 384.6 |
| 55 | 216125_PM_s_at | RANBP9 | RAN binding protein 9 | 0.000102366 | 35.4 | 37.0 | 50.3 |
| 56 | 205660_PM_at | OASL | 2'-5'-oligoadenylate synthetase-like | 0.000102776 | 470.5 | 394.6 | 493.4 |
| 57 | 222816_PM_s_at | ZCCHC2 | zinc finger, CCHC domain containing 2 | 0.000105861 | 301.3 | 308.7 | 320.8 |
| 58 | 1554696_PM_s_at | TYMS | thymidylate synthetase | 0.000110478 | 11.1 | 16.2 | 11.2 |
| 59 | 232229_PM_at | SETX | senataxin | 0.000113076 | 44.2 | 34.5 | 48.7 |
| 60 | 204929_PM_s_at | VAMP5 | vesicle-associated membrane protein 5 (myobrevin) | 0.000113182 | 152.8 | 197.8 | 153.6 |
| 61 | 203819_PM_s_at | IGF2BP3 | insulin-like growth factor 2 mRNA binding protein 3 | 0.000113349 | 45.4 | 75.4 | 51.1 |
| 62 | 210164_PM_at | GZMB | granzyme B (granzyme 2, cytotoxic T-lymphocyte-associated serine esterase 1) | 0.000113466 | 955.2 | 749.5 | 797.1 |
| 63 | 202589_PM_at | TYMS | thymidylate synthetase | 0.000113758 | 50.0 | 85.8 | 44.4 |
| 64 | 240507_PM_at | — | — | 0.000116854 | 8.8 | 8.4 | 8.2 |
| 65 | 204475_PM_at | MMP1 | matrix metallopeptidase 1 (interstitial collagenase) | 0.000116902 | 9.2 | 15.4 | 9.6 |
| 66 | 222625_PM_s_at | NDE1 | nudE nuclear distribution gene E homolog 1 (*A. nidulans*) | 0.000119388 | 60.6 | 55.3 | 72.2 |
| 67 | 1562697_PM_at | LOC339988 | hypothetical LOC339988 | 0.000125343 | 145.2 | 97.8 | 105.4 |
| 68 | 218662_PM_s_at | NCAPG | non-SMC condensin I complex, subunit G | 0.000129807 | 11.5 | 14.8 | 10.7 |
| 69 | 201212_PM_at | LGMN | legumain | 0.000129933 | 15.4 | 18.9 | 14.2 |

TABLE 16b-continued

The 263 probesets for distinguishing between AR, ADNR and TX in Liver PAXgene samples

| # | Probeset ID | Gene Symbol | Gene Title | p-value (Phenotype) | ADNR - Mean | AR - Mean | TX - Mean |
|---|---|---|---|---|---|---|---|
| 70 | 236191_PM_at | — | — | 0.000133129 | 83.4 | 71.0 | 76.6 |
| 71 | 33736_PM_at | STOML1 | stomatin (EPB72)-like 1 | 0.000137232 | 44.9 | 47.9 | 37.4 |
| 72 | 221695_PM_s_at | MAP3K2 | mitogen-activated protein kinase kinase kinase 2 | 0.000139287 | 76.4 | 76.8 | 130.8 |
| 73 | 241692_PM_at | — | — | 0.000142595 | 57.5 | 44.8 | 61.8 |
| 74 | 218741_PM_at | CENPM | centromere protein M | 0.000142617 | 13.5 | 15.9 | 12.3 |
| 75 | 220684_PM_at | TBX21 | T-box 21 | 0.00014693 | 272.6 | 169.0 | 182.2 |
| 76 | 233700_PM_at | — | — | 0.000148072 | 125.7 | 74.1 | 156.3 |
| 77 | 217336_PM_at | RPS10 /// RPS10P7 | ribosomal protein S10 /// ribosomal protein S10 pseudogene 7 | 0.000149318 | 76.4 | 93.5 | 63.0 |
| 78 | 224391_PM_s_at | SIAE | sialic acid acetylesterase | 0.000152602 | 28.8 | 42.0 | 33.8 |
| 79 | 201220_PM_x_at | CTBP2 | C-terminal binding protein 2 | 0.000155512 | 1316.8 | 1225.6 | 1516.2 |
| 80 | 204589_PM_at | NUAK1 | NUAK family, SNF1-like kinase, 1 | 0.00015593 | 13.1 | 10.1 | 9.6 |
| 81 | 1565254_PM_s_at | ELL | elongation factor RNA polymerase II | 0.000157726 | 29.2 | 24.5 | 40.4 |
| 82 | 243362_PM_s_at | LOC641518 | hypothetical LOC641518 | 0.000159096 | 14.3 | 21.1 | 13.5 |
| 83 | 219288_PM_at | C3orf14 | chromosome 3 open reading frame 14 | 0.000162164 | 31.1 | 43.4 | 28.0 |
| 84 | 210797_PM_s_at | OASL | 2'-5'-oligoadenylate synthetase-like | 0.000167239 | 268.3 | 219.6 | 304.2 |
| 85 | 243917_PM_at | CLIC5 | chloride intracellular channel 5 | 0.00017077 | 10.9 | 9.6 | 10.5 |
| 86 | 237538_PM_at | — | — | 0.000176359 | 18.4 | 21.3 | 18.0 |
| 87 | 207926_PM_at | GP5 | glycoprotein V (platelet) | 0.000178057 | 17.3 | 19.3 | 15.7 |
| 88 | 204103_PM_at | CCL4 | chemokine (C-C motif) ligand 4 | 0.000178791 | 338.5 | 265.9 | 235.5 |
| 89 | 212843_PM_at | NCAM1 | neural cell adhesion molecule 1 | 0.000180762 | 28.7 | 25.8 | 33.5 |
| 90 | 213629_PM_x_at | MT1F | metallothionein 1F | 0.000186273 | 268.3 | 348.4 | 234.3 |
| 91 | 212687_PM_at | LIMS1 | LIM and senescent cell antigen-like domains 1 | 0.000188224 | 859.6 | 1115.2 | 837.3 |
| 92 | 242898_PM_at | EIF2AK2 | eukaryotic translation initiation factor 2-alpha kinase 2 | 0.000189906 | 82.5 | 66.4 | 81.2 |
| 93 | 208228_PM_s_at | FGFR2 | fibroblast growth factor receptor 2 | 0.000194281 | 8.9 | 11.1 | 8.7 |
| 94 | 219386_PM_s_at | SLAMF8 | SLAM family member 8 | 0.000195762 | 18.6 | 23.0 | 16.5 |
| 95 | 201470_PM_at | GSTO1 | glutathione S-transferase omega 1 | 0.000200503 | 1623.3 | 1902.3 | 1495.5 |
| 96 | 204326_PM_x_at | MT1X | metallothionein 1X | 0.000202494 | 370.5 | 471.8 | 313.0 |
| 97 | 213996_PM_at | YPEL1 | yippee-like 1 (Drosophila) | 0.00020959 | 48.9 | 37.9 | 40.4 |
| 98 | 203820_PM_s_at | IGF2BP3 | insulin-like growth factor 2 mRNA binding protein 3 | 0.000210022 | 21.8 | 35.5 | 23.2 |
| 99 | 218599_PM_at | REC8 | REC8 homolog (yeast) | 0.000216761 | 42.6 | 43.3 | 41.1 |
| 100 | 216836_PM_s_at | ERBB2 | v-erb-b2 erythroblastic leukemia viral oncogene homolog 2, neuro/glioblastoma derived o | 0.000217714 | 14.6 | 12.0 | 12.9 |
| 101 | 213258_PM_at | TFPI | tissue factor pathway inhibitor (lipoprotein-associated coagulation inhibitor) | 0.000218458 | 13.6 | 24.6 | 14.2 |
| 102 | 212859_PM_x_at | MT1E | metallothionein 1E | 0.000218994 | 166.9 | 238.1 | 134.5 |
| 103 | 214617_PM_at | PRF1 | perforin 1 (pore forming protein) | 0.000222846 | 1169.2 | 822.3 | 896.0 |
| 104 | 38918_PM_at | SOX13 | SRY (sex determining region Y)-box 13 | 0.000223958 | 14.1 | 10.9 | 11.8 |
| 105 | 209969_PM_s_at | STAT1 | signal transducer and activator of transcription 1, 91 kDa | 0.00022534 | 1707.4 | 1874.3 | 1574.4 |
| 106 | 205909_PM_at | POLE2 | polymerase (DNA directed), epsilon 2 (p59 subunit) | 0.000226803 | 14.0 | 16.0 | 12.7 |
| 107 | 205612_PM_at | MMRN1 | multimerin 1 | 0.000227425 | 10.3 | 15.5 | 11.1 |
| 108 | 218400_PM_at | OAS3 | 2'-5'-oligoadenylate synthetase 3, 100 kDa | 0.000231476 | 142.6 | 125.9 | 170.8 |
| 109 | 202503_PM_s_at | KIAA0101 | KIAA0101 | 0.00023183 | 34.4 | 65.8 | 25.5 |
| 110 | 225636_PM_at | STAT2 | signal transducer and activator of transcription 2, 113 kDa | 0.000234463 | 1425.0 | 1422.9 | 1335.1 |

TABLE 16b-continued

The 263 probesets for distinguishing between AR, ADNR and TX in Liver PAXgene samples

| # | Probeset ID | Gene Symbol | Gene Title | p-value (Phenotype) | ADNR - Mean | AR - Mean | TX - Mean |
|---|---|---|---|---|---|---|---|
| 111 | 226579_PM_at | — | — | 0.000234844 | 97.7 | 81.1 | 104.6 |
| 112 | 1555764_PM_s_at | TIMM10 | translocase of inner mitochondrial membrane 10 homolog (yeast) | 0.000235756 | 195.6 | 204.3 | 158.7 |
| 113 | 218429_PM_s_at | C19orf66 | chromosome 19 open reading frame 66 | 0.00024094 | 569.9 | 524.1 | 527.4 |
| 114 | 242155_PM_x_at | RFFL | ring finger and FYVE-like domain containing 1 | 0.000244391 | 62.8 | 46.7 | 72.0 |
| 115 | 1556643_PM_at | FAM125A | Family with sequence similarity 125, member A | 0.000244814 | 173.2 | 181.8 | 181.2 |
| 116 | 201957_PM_at | PPP1R12B | protein phosphatase 1, regulatory (inhibitor) subunit 12B | 0.000246874 | 93.3 | 63.9 | 107.9 |
| 117 | 219716_PM_at | APOL6 | apolipoprotein L, 6 | 0.000248621 | 86.0 | 95.2 | 79.1 |
| 118 | 1554206_PM_at | TMLHE | trimethyllysine hydroxylase, epsilon | 0.00026882 | 45.3 | 41.0 | 53.4 |
| 119 | 207795_PM_s_at | KLRD1 | killer cell lectin-like receptor subfamily D, member 1 | 0.000271145 | 294.6 | 201.8 | 192.5 |
| 120 | 210756_PM_s_at | NOTCH2 | notch 2 | 0.000271193 | 94.0 | 99.4 | 142.6 |
| 121 | 219815_PM_at | GAL3ST4 | galactose-3-O-sulfotransferase 4 | 0.00027183 | 17.3 | 19.9 | 16.4 |
| 122 | 230405_PM_at | C5orf56 | chromosome 5 open reading frame 56 | 0.000279441 | 569.5 | 563.2 | 521.9 |
| 123 | 228617_PM_at | XAF1 | XIAP associated factor 1 | 0.000279625 | 1098.8 | 1162.1 | 1043.0 |
| 124 | 240733_PM_at | — | — | 0.000281133 | 87.3 | 54.9 | 81.2 |
| 125 | 209773_PM_s_at | RRM2 | ribonucleotide reductase M2 | 0.000281144 | 48.7 | 88.2 | 40.4 |
| 126 | 215236_PM_s_at | PICALM | phosphatidylinositol binding clathrin assembly protein | 0.000284863 | 61.6 | 65.8 | 113.8 |
| 127 | 229534_PM_at | ACOT4 | acyl-CoA thioesterase 4 | 0.000286097 | 17.1 | 13.2 | 12.6 |
| 128 | 215177_PM_s_at | ITGA6 | integrin, alpha 6 | 0.000287492 | 35.2 | 44.2 | 34.0 |
| 129 | 210321_PM_at | GZMH | granzyme H (cathepsin G-like 2, protein h-CCPX) | 0.000293732 | 1168.2 | 616.6 | 532.0 |
| 130 | 206194_PM_at | HOXC4 | homeobox C4 | 0.000307767 | 20.0 | 17.1 | 15.1 |
| 131 | 214115_PM_at | VAMP5 | Vesicle-associated membrane protein 5 (myobrevin) | 0.000308837 | 11.8 | 13.2 | 12.2 |
| 132 | 211102_PM_s_at | LILRA2 | leukocyte immunoglobulin-like receptor, subfamily A (with TM domain), member 2 | 0.000310388 | 94.3 | 78.0 | 129.0 |
| 133 | 201818_PM_at | LPCAT1 | lysophosphatidylcholine acyltransferase 1 | 0.000311597 | 662.1 | 517.3 | 651.3 |
| 134 | 53720_PM_at | C19orf66 | chromosome 19 open reading frame 66 | 0.000311821 | 358.7 | 323.7 | 319.7 |
| 135 | 221648_PM_s_at | LOC100507192 | hypothetical LOC100507192 | 0.000312201 | 68.4 | 96.2 | 56.1 |
| 136 | 236899_PM_at | — | — | 0.000318309 | 9.8 | 10.5 | 8.8 |
| 137 | 220467_PM_at | — | — | 0.000319714 | 205.5 | 124.9 | 201.6 |
| 138 | 218638_PM_s_at | SPON2 | spondin 2, extracellular matrix protein | 0.000320682 | 168.2 | 109.2 | 137.0 |
| 139 | 211287_PM_x_at | CSF2RA | colony stimulating factor 2 receptor, alpha, low-affinity (granulocyte-macrophage) | 0.00032758 | 173.0 | 150.9 | 224.0 |
| 140 | 222058_PM_at | — | — | 0.000332098 | 82.7 | 61.0 | 101.6 |
| 141 | 224428_PM_s_at | CDCA7 | cell division cycle associated 7 | 0.000332781 | 22.9 | 31.5 | 19.6 |
| 142 | 228675_PM_at | LOC100131733 | hypothetical LOC100131733 | 0.000346627 | 15.2 | 17.6 | 14.5 |
| 143 | 221248_PM_s_at | WHSC1L1 | Wolf-Hirschhorn syndrome candidate 1-like 1 | 0.000354663 | 25.6 | 26.9 | 33.0 |
| 144 | 227697_PM_at | SOCS3 | suppressor of cytokine signaling 3 | 0.000354764 | 103.6 | 192.4 | 128.8 |
| 145 | 240661_PM_at | LOC284475 | hypothetical protein LOC284475 | 0.000355764 | 79.3 | 53.9 | 89.5 |
| 146 | 204886_PM_at | PLK4 | polo-like kinase 4 | 0.000357085 | 8.9 | 11.8 | 8.9 |
| 147 | 216834_PM_at | RGS1 | regulator of G-protein signaling 1 | 0.00035762 | 12.4 | 19.6 | 11.4 |
| 148 | 234089_PM_at | — | — | 0.000359586 | 10.5 | 10.1 | 11.2 |
| 149 | 236817_PM_at | ADAT2 | adenosine deaminase, tRNA-specific 2, TAD2 homolog (S. cerevisiae) | 0.000362076 | 15.6 | 14.3 | 12.0 |
| 150 | 225349_PM_at | ZNF496 | zinc finger protein 496 | 0.000363116 | 11.7 | 12.0 | 10.4 |
| 151 | 219863_PM_at | HERC5 | hect domain and RLD 5 | 0.000365254 | 621.1 | 630.8 | 687.7 |
| 152 | 221985_PM_at | KLHL24 | kelch-like 24 (Drosophila) | 0.000374117 | 183.6 | 184.7 | 216.9 |

TABLE 16b-continued

The 263 probesets for distinguishing between AR, ADNR and TX in Liver PAXgene samples

| # | Probeset ID | Gene Symbol | Gene Title | p-value (Phenotype) | ADNR - Mean | AR - Mean | TX - Mean |
|---|---|---|---|---|---|---|---|
| 153 | 1552977_PM_a_at | CNPY3 | canopy 3 homolog (zebrafish) | 0.000378983 | 351.3 | 319.3 | 381.7 |
| 154 | 1552667_PM_a_at | SH2D3C | SH2 domain containing 3C | 0.000380655 | 67.1 | 55.5 | 82.8 |
| 155 | 223502_PM_s_at | TNFSF13B | tumor necrosis factor (ligand) superfamily, member 13b | 0.000387301 | 2713.6 | 3366.3 | 2999.3 |
| 156 | 235139_PM_at | GNGT2 | guanine nucleotide binding protein (G protein), gamma transducing activity polypeptide | 0.000389019 | 41.8 | 35.8 | 38.6 |
| 157 | 239979_PM_at | — | — | 0.000389245 | 361.6 | 375.0 | 282.8 |
| 158 | 211882_PM_x_at | FUT6 | fucosyltransferase 6 (alpha (1,3) fucosyltransferase) | 0.000392613 | 11.1 | 11.6 | 10.6 |
| 159 | 1562698_PM_x_at | LOC339988 | hypothetical LOC339988 | 0.000394736 | 156.3 | 108.5 | 117.0 |
| 160 | 201890_PM_at | RRM2 | ribonucleotide reductase M2 | 0.000397796 | 23.6 | 42.5 | 21.7 |
| 161 | 243349_PM_at | KIAA1324 | KIAA1324 | 0.000399335 | 15.4 | 12.8 | 20.2 |
| 162 | 243947_PM_s_at | — | — | 0.000399873 | 8.4 | 9.6 | 8.9 |
| 163 | 205483_PM_s_at | ISG15 | ISG15 ubiquitin-like modifier | 0.000409282 | 1223.6 | 1139.6 | 1175.7 |
| 164 | 202705_PM_at | CCNB2 | cyclin B2 | 0.000409541 | 14.7 | 20.9 | 13.8 |
| 165 | 210835_PM_s_at | CTBP2 | C-terminal binding protein 2 | 0.000419387 | 992.3 | 926.1 | 1150.4 |
| 166 | 210554_PM_s_at | CTBP2 | C-terminal binding protein 2 | 0.000429433 | 1296.5 | 1198.0 | 1519.5 |
| 167 | 207085_PM_x_at | CSF2RA | colony stimulating factor 2 receptor, alpha, low-affinity (granulocyte-macrophage) | 0.000439275 | 204.5 | 190.0 | 290.3 |
| 168 | 204205_PM_at | APOBEC3G | apolipoprotein B mRNA editing enzyme, catalytic polypeptide-like 3G | 0.000443208 | 1115.8 | 988.8 | 941.4 |
| 169 | 227394_PM_at | NCAM1 | neural cell adhesion molecule 1 | 0.000443447 | 19.1 | 19.4 | 25.3 |
| 170 | 1568943_PM_at | INPP5D | inositol polyphosphate-5-phosphatase, 145 kDa | 0.000450045 | 127.3 | 87.7 | 114.0 |
| 171 | 213932_PM_x_at | HLA-A | major histocompatibility complex, class I, A | 0.00045661 | 9270.0 | 9080.1 | 9711.9 |
| 172 | 226202_PM_at | ZNF398 | zinc finger protein 398 | 0.000457538 | 84.5 | 78.4 | 98.3 |
| 173 | 233675_PM_s_at | LOC374491 | TPTE and PTEN homologous inositol lipid phosphatase pseudogene | 0.000457898 | 8.8 | 8.1 | 8.5 |
| 174 | 220711_PM_at | — | — | 0.000458552 | 197.6 | 162.7 | 209.0 |
| 175 | 1552646_PM_at | IL11RA | interleukin 11 receptor, alpha | 0.000463237 | 18.9 | 15.9 | 19.6 |
| 176 | 227055_PM_at | METTL7B | methyltransferase like 7B | 0.000464226 | 11.1 | 15.0 | 11.8 |
| 177 | 223980_PM_s_at | SP110 | SP110 nuclear body protein | 0.000471467 | 1330.9 | 1224.3 | 1367.3 |
| 178 | 242367_PM_at | — | — | 0.000471796 | 9.1 | 10.5 | 9.6 |
| 179 | 218543_PM_s_at | PARP12 | poly (ADP-ribose) polymerase family, member 12 | 0.000476879 | 513.8 | 485.7 | 475.7 |
| 180 | 204972_PM_at | OAS2 | 2'-5'-oligoadenylate synthetase 2, 69/71 kDa | 0.000480934 | 228.5 | 215.8 | 218.7 |
| 181 | 205746_PM_s_at | ADAM17 | ADAM metallopeptidase domain 17 | 0.000480965 | 39.0 | 47.0 | 60.4 |
| 182 | 1570645_PM_at | — | — | 0.000482948 | 9.3 | 9.1 | 8.4 |
| 183 | 211286_PM_x_at | CSF2RA | colony stimulating factor 2 receptor, alpha, low-affinity (granulocyte-macrophage) | 0.000484313 | 261.3 | 244.7 | 345.6 |
| 184 | 1557545_PM_s_at | RNF165 | ring finger protein 165 | 0.000489377 | 17.4 | 15.4 | 18.3 |
| 185 | 236545_PM_at | — | — | 0.000491065 | 479.3 | 367.8 | 526.2 |
| 186 | 228280_PM_at | ZC3HAV1L | zinc finger CCCH-type, antiviral 1-like | 0.000495768 | 25.3 | 36.4 | 23.7 |
| 187 | 239798_PM_at | — | — | 0.000505865 | 43.9 | 63.7 | 48.8 |
| 188 | 208055_PM_s_at | HERC4 | hect domain and RLD 4 | 0.000507283 | 37.6 | 34.8 | 45.8 |
| 189 | 225692_PM_at | CAMTA1 | calmodulin binding transcription activator 1 | 0.000515621 | 244.8 | 308.6 | 245.1 |
| 190 | 210986_PM_s_at | TPM1 | tropomyosin 1 (alpha) | 0.000532739 | 344.0 | 379.1 | 391.9 |
| 191 | 205929_PM_at | GPA33 | glycoprotein A33 (transmembrane) | 0.00053619 | 18.3 | 21.8 | 16.7 |
| 192 | 242234_PM_at | XAF1 | XIAP associated factor 1 | 0.000537429 | 123.1 | 133.1 | 114.9 |
| 193 | 206113_PM_s_at | RAB5A | RAB5A, member RAS oncogene family | 0.000543933 | 77.5 | 73.0 | 111.4 |
| 194 | 242520_PM_s_at | C1orf228 | chromosome 1 open reading frame 228 | 0.000547685 | 30.4 | 42.5 | 29.4 |
| 195 | 229203_PM_at | B4GALNT3 | beta-1,4-N-acetyl-galactosaminyl transferase 3 | 0.000549855 | 9.1 | 9.0 | 9.7 |

TABLE 16b-continued

The 263 probesets for distinguishing between AR, ADNR and TX in Liver PAXgene samples

| # | Probeset ID | Gene Symbol | Gene Title | p-value (Phenotype) | ADNR - Mean | AR - Mean | TX - Mean |
|---|---|---|---|---|---|---|---|
| 196 | 201601_PM_x_at | IFITM1 | interferon induced transmembrane protein 1 (9-27) | 0.000554665 | 6566.1 | 7035.7 | 7016.0 |
| 197 | 221024_PM_s_at | SLC2A10 | solute carrier family 2 (facilitated glucose transporter), member 10 | 0.000559418 | 8.3 | 9.7 | 8.6 |
| 198 | 204439_PM_at | IFI44L | interferon-induced protein 44-like | 0.000570113 | 343.5 | 312.4 | 337.1 |
| 199 | 215894_PM_at | PTGDR | prostaglandin D2 receptor (DP) | 0.000571076 | 343.8 | 191.2 | 233.7 |
| 200 | 230846_PM_at | AKAP5 | A kinase (PRKA) anchor protein 5 | 0.000572655 | 10.7 | 10.9 | 9.6 |
| 201 | 210340_PM_s_at | CSF2RA | colony stimulating factor 2 receptor, alpha, low-affinity (granulocyte-macrophage) | 0.000572912 | 154.2 | 146.3 | 200.8 |
| 202 | 237240_PM_at | — | — | 0.000573343 | 9.4 | 10.7 | 9.4 |
| 203 | 223836_PM_at | FGFBP2 | fibroblast growth factor binding protein 2 | 0.000574294 | 792.6 | 432.4 | 438.4 |
| 204 | 233743_PM_x_at | S1PR5 | sphingosine-1-phosphate receptor 5 | 0.000577598 | 9.3 | 8.6 | 9.6 |
| 205 | 229254_PM_at | MFSD4 | major facilitator superfamily domain containing 4 | 0.000581119 | 9.4 | 11.0 | 9.3 |
| 206 | 243674_PM_at | LOC100240735 /// LOC401522 | hypothetical LOC100240735 /// hypothetical LOC401522 | 0.00058123 | 14.5 | 12.9 | 12.1 |
| 207 | 208116_PM_s_at | MAN1A1 | mannosidase, alpha, class 1A, member 1 | 0.000581644 | 34.4 | 39.1 | 55.0 |
| 208 | 222246_PM_at | — | — | 0.000584363 | 15.9 | 13.9 | 17.9 |
| 209 | 212659_PM_s_at | IL1RN | interleukin 1 receptor antagonist | 0.000592065 | 87.2 | 94.5 | 116.3 |
| 210 | 204070_PM_at | RARRES3 | retinoic acid receptor responder (tazarotene induced) 3 | 0.000597748 | 771.6 | 780.7 | 613.7 |
| 211 | 219364_PM_at | DHX58 | DEXH (Asp-Glu-X-His) box polypeptide 58 | 0.000599299 | 92.7 | 85.2 | 85.3 |
| 212 | 204747_PM_at | IFIT3 | interferon-induced protein with tetratricopeptide repeats 3 | 0.000601375 | 603.1 | 576.7 | 586.2 |
| 213 | 240258_PM_at | ENO1 | enolase 1, (alpha) | 0.000601726 | 9.0 | 9.3 | 10.5 |
| 214 | 210724_PM_at | EMR3 | egf-like module containing, mucin-like, hormone receptor-like 3 | 0.000609884 | 622.3 | 437.3 | 795.3 |
| 215 | 204211_PM_x_at | EIF2AK2 | eukaryotic translation initiation factor 2-alpha kinase 2 | 0.000611116 | 168.3 | 139.2 | 179.6 |
| 216 | 234975_PM_at | GSPT1 | G1 to S phase transition 1 | 0.000615027 | 16.6 | 16.3 | 21.4 |
| 217 | 228145_PM_s_at | ZNF398 | zinc finger protein 398 | 0.000620533 | 373.0 | 329.5 | 374.3 |
| 218 | 201565_PM_s_at | ID2 | inhibitor of DNA binding 2, dominant negative helix-loop-helix protein | 0.000627734 | 1946.2 | 1798.1 | 1652.9 |
| 219 | 226906_PM_s_at | ARHGAP9 | Rho GTPase activating protein 9 | 0.000630617 | 636.2 | 516.2 | 741.5 |
| 220 | 228412_PM_at | LOC643072 | hypothetical LOC643072 | 0.00064178 | 213.5 | 186.6 | 282.7 |
| 221 | 233957_PM_at | — | — | 0.000644277 | 33.2 | 24.7 | 40.1 |
| 222 | 221277_PM_s_at | PUS3 | pseudouridylate synthase 3 | 0.000649375 | 86.6 | 99.3 | 77.8 |
| 223 | 203911_PM_at | RAP1GAP | RAP1 GTPase activating protein | 0.000658389 | 106.6 | 40.1 | 116.1 |
| 224 | 219352_PM_at | HERC6 | hect domain and RLD 6 | 0.000659313 | 94.6 | 87.2 | 81.8 |
| 225 | 204994_PM_at | MX2 | myxovirus (influenza virus) resistance 2 (mouse) | 0.000663904 | 1279.3 | 1147.0 | 1329.9 |
| 226 | 227499_PM_at | FZD3 | frizzled homolog 3 (Drosophila) | 0.00066528 | 11.7 | 11.0 | 9.8 |
| 227 | 222930_PM_s_at | AGMAT | agmatine ureohydrolase (agmatinase) | 0.000665618 | 12.9 | 14.9 | 11.4 |
| 228 | 204575_PM_s_at | MMP19 | matrix metallopeptidase 19 | 0.000668161 | 9.6 | 9.3 | 9.9 |
| 229 | 221038_PM_at | — | — | 0.000671518 | 8.7 | 8.2 | 9.3 |
| 230 | 233425_PM_at | — | — | 0.000676591 | 76.4 | 70.6 | 77.9 |
| 231 | 228972_PM_at | LOC100306951 | hypothetical LOC100306951 | 0.000679857 | 77.8 | 84.0 | 60.0 |
| 232 | 1560999_PM_a_at | — | — | 0.000680202 | 9.8 | 10.6 | 10.7 |
| 233 | 225931_PM_s_at | RNF213 | ring finger protein 213 | 0.000685818 | 339.7 | 313.2 | 333.3 |
| 234 | 1559110_PM_at | — | — | 0.000686358 | 11.7 | 11.5 | 13.4 |
| 235 | 207538_PM_at | IL4 | interleukin 4 | 0.000697306 | 8.3 | 9.5 | 8.7 |
| 236 | 210358_PM_x_at | GATA2 | GATA binding protein 2 | 0.000702179 | 22.8 | 30.8 | 16.8 |

TABLE 16b-continued

The 263 probesets for distinguishing between AR, ADNR and TX in Liver PAXgene samples

| # | Probeset ID | Gene Symbol | Gene Title | p-value (Phenotype) | ADNR - Mean | AR - Mean | TX - Mean |
|---|---|---|---|---|---|---|---|
| 237 | 236341_PM_at | CTLA4 | cytotoxic T-lymphocyte-associated protein 4 | 0.000706875 | 16.5 | 22.3 | 16.8 |
| 238 | 227416_PM_s_at | ZCRB1 | zinc finger CCHC-type and RNA binding motif 1 | 0.000708438 | 388.0 | 422.6 | 338.2 |
| 239 | 210788_PM_s_at | DHRS7 | dehydrogenase/reductase (SDR family) member 7 | 0.000719333 | 1649.6 | 1559.9 | 1912.3 |
| 240 | 213287_PM_s_at | KRT10 | keratin 10 | 0.000721676 | 557.8 | 585.1 | 439.3 |
| 241 | 204026_PM_s_at | ZWINT | ZW10 interactor | 0.000724993 | 23.3 | 31.1 | 19.9 |
| 242 | 239223_PM_s_at | FBXL20 | F-box and leucine-rich repeat protein 20 | 0.00073241 | 106.8 | 75.0 | 115.9 |
| 243 | 234196_PM_at | — | | 0.000742539 | 140.6 | 81.3 | 162.4 |
| 244 | 214931_PM_s_at | SRPK2 | SRSF protein kinase 2 | 0.00074767 | 30.0 | 30.9 | 45.3 |
| 245 | 216907_PM_x_at | KIR3DL1 /// KIR3DL2 /// LOC727787 | killer cell immunoglobulin-like receptor, three domains, long cytoplasmic tail, 1 /// k | 0.000748056 | 18.8 | 12.6 | 13.8 |
| 246 | 243802_PM_at | DNAH12 | dynein, axonemal, heavy chain 12 | 0.000751054 | 8.8 | 9.9 | 8.4 |
| 247 | 212070_PM_at | GPR56 | G protein-coupled receptor 56 | 0.000760168 | 338.8 | 177.5 | 198.1 |
| 248 | 239185_PM_at | ABCA9 | ATP-binding cassette, sub-family A (ABC1), member 9 | 0.000767347 | 8.3 | 9.0 | 9.8 |
| 249 | 229597_PM_s_at | WDFY4 | WDFY family member 4 | 0.000769378 | 128.9 | 96.6 | 148.4 |
| 250 | 216243_PM_s_at | IL1RN | interleukin 1 receptor antagonist | 0.000770819 | 131.4 | 134.1 | 180.7 |
| 251 | 206991_PM_s_at | CCR5 | chemokine (C-C motif) receptor 5 | 0.000771059 | 128.5 | 128.6 | 110.5 |
| 252 | 219385_PM_at | SLAMF8 | SLAM family member 8 | 0.000789607 | 13.8 | 13.2 | 11.3 |
| 253 | 240438_PM_at | — | | 0.000801737 | 10.8 | 10.4 | 11.4 |
| 254 | 226303_PM_at | PGM5 | phosphoglucomutase 5 | 0.000802853 | 11.9 | 12.6 | 24.2 |
| 255 | 205875_PM_s_at | TREX1 | three prime repair exonuclease 1 | 0.000804871 | 254.9 | 251.6 | 237.6 |
| 256 | 1566201_PM_at | — | | 0.000809569 | 10.4 | 9.0 | 10.2 |
| 257 | 211230_PM_s_at | PIK3CD | phosphoinositide-3-kinase, catalytic, delta polypeptide | 0.000812288 | 20.4 | 20.3 | 24.6 |
| 258 | 202566_PM_s_at | SVIL | supervillin | 0.000819718 | 43.9 | 41.0 | 67.5 |
| 259 | 244846_PM_at | — | | 0.000821386 | 75.0 | 55.1 | 84.9 |
| 260 | 208436_PM_s_at | IRF7 | interferon regulatory factor 7 | 0.000826426 | 264.0 | 262.4 | 281.2 |
| 261 | 242020_PM_s_at | ZBP1 | Z-DNA binding protein 1 | 0.000828174 | 87.9 | 83.1 | 102.5 |
| 262 | 203779_PM_s_at | MPZL2 | myelin protein zero-like 2 | 0.000830222 | 10.4 | 10.0 | 12.9 |
| 263 | 212458_PM_at | SPRED2 | sprouty-related, EVH1 domain containing 2 | 0.000833211 | 11.5 | 11.4 | 13.4 |

TABLE 17a

AUCs for the 147 probes to predict AR, HCV and AR + HCV in Liver whole blood samples.

| Algorithm | Predictors | Comparison | AUC | Predictive Accuracy (%) | Sensitivity (%) | Specificity (%) | Postive Predictive Value (%) | Negative Predictive Value (%) |
|---|---|---|---|---|---|---|---|---|
| Nearest Centroid | 147 | AR vs. HCV | 0.952 | 96 | 87 | 97 | 95 | 92 |
| Nearest Centroid | 147 | AR vs. HCV + AR | 0.821 | 82 | 91 | 92 | 95 | 85 |
| Nearest Centroid | 147 | HCV vs. HCV + AR | 0.944 | 94 | 92 | 97 | 92 | 97 |

TABLE 17b

The 147 probesets for distinguishing between AR, HCV and HCV + AR in Liver PAXgene samples

| # | Probeset ID | Gene Symbol | Gene Title | p-value (Phenotype) | AR - Mean | HCV - Mean | HCV + AR - Mean |
|---|---|---|---|---|---|---|---|
| 1 | 241038_PM_at | — | — | 4.76E−08 | 21.0 | 13.2 | 13.9 |
| 2 | 207737_PM_at | — | — | 5.33E−06 | 8.5 | 8.4 | 10.2 |

TABLE 17b-continued

The 147 probesets for distinguishing between AR, HCV and HCV + AR in Liver PAXgene samples

| # | Probeset ID | Gene Symbol | Gene Title | p-value (Phenotype) | AR - Mean | HCV - Mean | HCV + AR - Mean |
|---|---|---|---|---|---|---|---|
| 3 | 1557733_PM_a_at | — | — | 6.19E−06 | 116.0 | 50.8 | 64.5 |
| 4 | 228290_PM_at | PLK1S1 | Polo-like kinase 1 substrate 1 | 7.97E−06 | 35.6 | 48.1 | 48.5 |
| 5 | 231798_PM_at | NOG | noggin | 8.34E−06 | 25.9 | 12.6 | 9.4 |
| 6 | 214039_PM_s_at | LAPTM4B | lysosomal protein transmembrane 4 beta | 9.49E−06 | 104.0 | 58.3 | 68.5 |
| 7 | 241692_PM_at | — | — | 9.61E−06 | 44.8 | 65.1 | 78.4 |
| 8 | 230776_PM_at | — | — | 1.21E−05 | 13.7 | 10.4 | 9.5 |
| 9 | 217963_PM_s_at | NGFRAP1 | nerve growth factor receptor (TNFRSF16) associated protein 1 | 1.56E−05 | 713.1 | 461.2 | 506.6 |
| 10 | 243917_PM_at | CLIC5 | chloride intracellular channel 5 | 1.67E−05 | 9.6 | 10.9 | 11.6 |
| 11 | 219915_PM_s_at | SLC16A10 | solute carrier family 16, member 10 (aromatic amino acid transporter) | 1.77E−05 | 21.8 | 13.2 | 12.5 |
| 12 | 1553873_PM_at | KLHL34 | kelch-like 34 (*Drosophila*) | 1.85E−05 | 12.1 | 9.6 | 9.1 |
| 13 | 227645_PM_at | PIK3R5 | phosphoinositide-3-kinase, regulatory subunit 5 | 2.12E−05 | 824.5 | 1003.6 | 1021.4 |
| 14 | 1552623_PM_at | HSH2D | hematopoietic SH2 domain containing | 2.54E−05 | 323.9 | 497.5 | 445.4 |
| 15 | 227486_PM_at | NT5E | 5'-nucleotidase, ecto (CD73) | 2.66E−05 | 18.6 | 13.4 | 12.2 |
| 16 | 219659_PM_at | ATP8A2 | ATPase, aminophospholipid transporter, class I, type 8A, member 2 | 4.00E−05 | 10.8 | 9.0 | 8.9 |
| 17 | 1555874_PM_x_at | MGC21881 | hypothetical locus MGC21881 | 4.16E−05 | 20.0 | 21.0 | 31.4 |
| 18 | 202086_PM_at | MX1 | myxovirus (influenza virus) resistance 1, interferon-inducible protein p78 (mouse) | 4.52E−05 | 496.4 | 1253.1 | 1074.1 |
| 19 | 233675_PM_s_at | LOC374491 | TPTE and PTEN homologous inositol lipid phosphatase pseudogene | 4.85E−05 | 8.1 | 8.2 | 9.9 |
| 20 | 219815_PM_at | GAL3ST4 | galactose-3-O-sulfotransferase 4 | 5.37E−05 | 19.9 | 17.0 | 14.3 |
| 21 | 242898_PM_at | EIF2AK2 | eukaryotic translation initiation factor 2-alpha kinase 2 | 6.06E−05 | 66.4 | 116.6 | 108.7 |
| 22 | 215177_PM_s_at | ITGA6 | integrin, alpha 6 | 6.39E−05 | 44.2 | 26.9 | 23.9 |
| 23 | 236717_PM_at | FAM179A | family with sequence similarity 179, member A | 6.43E−05 | 39.8 | 51.3 | 73.3 |
| 24 | 242520_PM_s_at | C1orf228 | chromosome 1 open reading frame 228 | 6.67E−05 | 42.5 | 29.1 | 26.4 |
| 25 | 207926_PM_at | GP5 | glycoprotein V (platelet) | 7.03E−05 | 19.3 | 14.7 | 16.0 |
| 26 | 211882_PM_x_at | FUT6 | fucosyltransferase 6 (alpha (1,3) fucosyltransferase) | 8.11E−05 | 11.6 | 9.8 | 10.7 |
| 27 | 201656_PM_at | ITGA6 | integrin, alpha 6 | 8.91E−05 | 112.6 | 69.0 | 70.7 |
| 28 | 233743_PM_x_at | S1PR5 | sphingosine-1-phosphate receptor 5 | 9.26E−05 | 8.6 | 10.1 | 9.2 |
| 29 | 210797_PM_s_at | OASL | 2'-5'-oligoadenylate synthetase-like | 9.28E−05 | 219.6 | 497.2 | 446.0 |
| 30 | 243819_PM_at | — | — | 9.55E−05 | 495.1 | 699.2 | 769.8 |
| 31 | 209728_PM_at | HLA-DRB4 /// LOC100509582 | major histocompatibility complex, class II, DR beta 4 /// HLA class II histocompatibili | 0.000102206 | 33.8 | 403.5 | 55.2 |
| 32 | 218638_PM_s_at | SPON2 | spondin 2, extracellular matrix protein | 0.000103572 | 109.2 | 215.7 | 187.9 |
| 33 | 224293_PM_at | TTTY10 | testis-specific transcript, Y-linked 10 (non-protein coding) | 0.000103782 | 8.7 | 11.1 | 10.2 |
| 34 | 205660_PM_at | OASL | 2'-5'-oligoadenylate synthetase-like | 0.000105267 | 394.6 | 852.0 | 878.1 |
| 35 | 230753_PM_at | PATL2 | protein associated with topoisomerase II homolog 2 (yeast) | 0.00010873 | 123.0 | 168.6 | 225.2 |
| 36 | 243362_PM_s_at | LOC641518 | hypothetical LOC641518 | 0.000114355 | 21.1 | 13.1 | 11.2 |
| 37 | 213996_PM_at | YPEL1 | yippee-like 1 (*Drosophila*) | 0.00012688 | 37.9 | 55.8 | 59.5 |
| 38 | 232222_PM_at | C18orf49 | chromosome 18 open reading frame 49 | 0.000129064 | 35.7 | 65.1 | 53.0 |
| 39 | 205612_PM_at | MMRN1 | multimerin 1 | 0.000142028 | 15.5 | 9.9 | 11.2 |
| 40 | 214791_PM_at | SP140L | SP140 nuclear body protein-like | 0.000150108 | 223.4 | 278.8 | 285.8 |

TABLE 17b-continued

The 147 probesets for distinguishing between AR, HCV and HCV + AR in Liver PAXgene samples

| # | Probeset ID | Gene Symbol | Gene Title | p-value (Phenotype) | AR - Mean | HCV - Mean | HCV + AR - Mean |
|---|---|---|---|---|---|---|---|
| 41 | 240507_PM_at | — | — | 0.000152167 | 8.4 | 9.5 | 8.1 |
| 42 | 203819_PM_s_at | IGF2BP3 | insulin-like growth factor 2 mRNA binding protein 3 | 0.000174054 | 75.4 | 45.9 | 62.4 |
| 43 | 219288_PM_at | C3orf14 | chromosome 3 open reading frame 14 | 0.000204911 | 43.4 | 29.2 | 51.0 |
| 44 | 214376_PM_at | — | — | 0.000213039 | 8.9 | 9.6 | 8.1 |
| 45 | 1568609_PM_s_at | FAM91A2 /// FLJ39739 /// LOC100286793 /// LOC728855 /// LOC728875 | family with sequence similarity 91, member A2 /// hypothetical FLJ39739 /// hypothetica | 0.000218802 | 378.6 | 472.7 | 427.1 |
| 46 | 207538_PM_at | IL4 | interleukin 4 | 0.000226354 | 9.5 | 8.3 | 8.9 |
| 47 | 243947_PM_s_at | — | — | 0.000227289 | 9.6 | 8.4 | 8.6 |
| 48 | 204211_PM_x_at | EIF2AK2 | eukaryotic translation initiation factor 2-alpha kinase 2 | 0.000227971 | 139.2 | 222.0 | 225.5 |
| 49 | 221648_PM_s_at | LOC100507192 | hypothetical LOC100507192 | 0.000230544 | 96.2 | 62.4 | 62.1 |
| 50 | 202016_PM_at | MEST | mesoderm specific transcript homolog (mouse) | 0.000244181 | 27.5 | 17.0 | 19.3 |
| 51 | 220684_PM_at | TBX21 | T-box 21 | 0.000260563 | 169.0 | 279.9 | 309.1 |
| 52 | 219018_PM_s_at | CCDC85C | coiled-coil domain containing 85C | 0.000261452 | 14.9 | 17.1 | 17.1 |
| 53 | 204575_PM_s_at | MMP19 | matrix metallopeptidase 19 | 0.00026222 | 9.3 | 9.3 | 11.3 |
| 54 | 1568943_PM_at | INPP5D | inositol polyphosphate-5-phosphatase, 145 kDa | 0.000265939 | 87.7 | 143.4 | 133.5 |
| 55 | 220467_PM_at | — | — | 0.000269919 | 124.9 | 215.2 | 206.0 |
| 56 | 207324_PM_s_at | DSC1 | desmocollin 1 | 0.000280239 | 14.5 | 11.3 | 10.3 |
| 57 | 218400_PM_at | OAS3 | 2'-5'-oligoadenylate synthetase 3, 100 kDa | 0.000288454 | 125.9 | 316.7 | 299.6 |
| 58 | 214617_PM_at | PRF1 | perforin 1 (pore forming protein) | 0.000292417 | 822.3 | 1327.9 | 1415.4 |
| 59 | 239798_PM_at | — | — | 0.000294263 | 63.7 | 39.1 | 35.3 |
| 60 | 242020_PM_s_at | ZBP1 | Z-DNA binding protein 1 | 0.000303843 | 83.1 | 145.8 | 128.5 |
| 61 | 201786_PM_s_at | ADAR | adenosine deaminase, RNA-specific | 0.000305042 | 2680.0 | 3340.9 | 3194.2 |
| 62 | 234974_PM_at | GALM | galactose mutarotase (aldose 1-epimerase) | 0.000308107 | 63.1 | 88.8 | 93.7 |
| 63 | 233121_PM_at | — | — | 0.000308702 | 17.8 | 23.8 | 19.4 |
| 64 | 1557545_PM_s_at | RNF165 | ring finger protein 165 | 0.000308992 | 15.4 | 24.2 | 22.1 |
| 65 | 229203_PM_at | B4GALNT3 | beta-1,4-N-acetyl-galactosaminyl transferase 3 | 0.000309508 | 9.0 | 10.1 | 8.6 |
| 66 | 210164_PM_at | GZMB | granzyme B (granzyme 2, cytotoxic T-lymphocyte-associated serine esterase 1) | 0.000322925 | 749.5 | 1241.7 | 1374.7 |
| 67 | 222468_PM_at | KIAA0319L | KIAA0319-like | 0.000327428 | 286.7 | 396.3 | 401.1 |
| 68 | 223272_PM_s_at | C1orf57 | chromosome 1 open reading frame 57 | 0.000342477 | 69.0 | 54.6 | 77.4 |
| 69 | 240913_PM_at | FGFR2 | fibroblast growth factor receptor 2 | 0.00035107 | 9.6 | 10.6 | 11.7 |
| 70 | 230854_PM_at | BCAR4 | breast cancer anti-estrogen resistance 4 | 0.000352682 | 10.2 | 10.2 | 8.9 |
| 71 | 1562697_PM_at | LOC339988 | hypothetical LOC339988 | 0.000360155 | 97.8 | 151.3 | 142.0 |
| 72 | 222732_PM_at | TRIM39 | tripartite motif-containing 39 | 0.000372812 | 115.6 | 135.8 | 115.4 |
| 73 | 227917_PM_at | FAM85A /// FAM85B | family with sequence similarity 85, member A /// family with sequence similarity 85, me | 0.000373226 | 206.8 | 154.1 | 154.9 |
| 74 | 212687_PM_at | LIMS1 | LIM and senescent cell antigen-like domains 1 | 0.000383722 | 1115.2 | 824.0 | 913.2 |
| 75 | 216836_PM_s_at | ERBB2 | v-erb-b2 erythroblastic leukemia viral oncogene homolog 2, neuro/glioblastoma derived o | 0.000384613 | 12.0 | 16.3 | 14.3 |
| 76 | 236191_PM_at | — | — | 0.000389259 | 71.0 | 95.0 | 114.3 |
| 77 | 213932_PM_x_at | HLA-A | major histocompatibility complex, class I, A | 0.000391535 | 9080.1 | 10344.2 | 10116.9 |
| 78 | 229254_PM_at | MFSD4 | major facilitator superfamily domain containing 4 | 0.000393739 | 11.0 | 9.0 | 9.5 |
| 79 | 212843_PM_at | NCAM1 | neural cell adhesion molecule 1 | 0.000401596 | 25.8 | 50.2 | 37.7 |
| 80 | 235256_PM_s_at | GALM | galactose mutarotase (aldose 1-epimerase) | 0.000417617 | 58.0 | 79.8 | 90.2 |

TABLE 17b-continued

The 147 probesets for distinguishing between AR, HCV and HCV + AR in Liver PAXgene samples

| # | Probeset ID | Gene Symbol | Gene Title | p-value (Phenotype) | AR - Mean | HCV - Mean | HCV + AR - Mean |
|---|---|---|---|---|---|---|---|
| 81 | 1566201_PM_at | — | — | 0.000420058 | 9.0 | 10.3 | 8.8 |
| 82 | 204994_PM_at | MX2 | myxovirus (influenza virus) resistance 2 (mouse) | 0.000438751 | 1147.0 | 1669.1 | 1518.5 |
| 83 | 237240_PM_at | — | — | 0.000440008 | 10.7 | 9.2 | 9.1 |
| 84 | 232478_PM_at | — | — | 0.000447263 | 51.3 | 96.8 | 71.5 |
| 85 | 211410_PM_x_at | KIR2DL5A | killer cell immunoglobulin-like receptor, two domains, long cytoplasmic tail, 5A | 0.00045859 | 24.8 | 31.7 | 39.0 |
| 86 | 1569551_PM_at | — | — | 0.00045899 | 12.7 | 17.5 | 17.9 |
| 87 | 222816_PM_s_at | ZCCHC2 | zinc finger, CCHC domain containing 2 | 0.00046029 | 308.7 | 502.0 | 404.6 |
| 88 | 1557071_PM_s_at | NUB1 | negative regulator of ubiquitin-like proteins 1 | 0.000481473 | 108.5 | 144.0 | 155.3 |
| 89 | 219737_PM_s_at | PCDH9 | protocadherin 9 | 0.000485253 | 37.9 | 76.4 | 66.9 |
| 90 | 230563_PM_at | RASGEF1A | RasGEF domain family, member 1A | 0.000488148 | 86.8 | 121.7 | 139.4 |
| 91 | 1560080_PM_at | — | — | 0.000488309 | 9.9 | 11.0 | 12.2 |
| 92 | 243756_PM_at | — | — | 0.000488867 | 8.5 | 7.5 | 8.2 |
| 93 | 212730_PM_at | SYNM | synemin, intermediate filament protein | 0.000521028 | 19.5 | 15.7 | 27.7 |
| 94 | 1552977_PM_a_at | CNPY3 | canopy 3 homolog (zebrafish) | 0.000521239 | 319.3 | 395.2 | 261.4 |
| 95 | 218657_PM_at | RAPGEFL1 | Rap guanine nucleotide exchange factor (GEF)-like 1 | 0.000529963 | 10.4 | 11.9 | 11.5 |
| 96 | 228139_PM_at | RIPK3 | receptor-interacting serine-threonine kinase 3 | 0.000530418 | 87.8 | 107.4 | 102.7 |
| 97 | 38918_PM_at | SOX13 | SRY (sex determining region Y)-box 13 | 0.000534735 | 10.9 | 13.1 | 13.1 |
| 98 | 207795_PM_s_at | KLRD1 | killer cell lectin-like receptor subfamily D, member 1 | 0.000538523 | 201.8 | 309.8 | 336.1 |
| 99 | 212906_PM_at | GRAMD1B | GRAM domain containing 1B | 0.000540879 | 51.0 | 58.3 | 78.1 |
| 100 | 1561098_PM_at | LOC641365 | hypothetical LOC641365 | 0.000541122 | 8.7 | 8.5 | 10.1 |
| 101 | 209593_PM_s_at | TOR1B | torsin family 1, member B (torsin B) | 0.000542383 | 271.7 | 392.9 | 408.3 |
| 102 | 223980_PM_s_at | SP110 | SP110 nuclear body protein | 0.000543351 | 1224.3 | 1606.9 | 1561.2 |
| 103 | 1554206_PM_at | TMLHE | trimethyllysine hydroxylase, epsilon | 0.000545869 | 41.0 | 50.6 | 46.5 |
| 104 | 240438_PM_at | — | — | 0.000555441 | 10.4 | 12.0 | 13.1 |
| 105 | 212190_PM_at | SERPINE2 | serpin peptidase inhibitor, clade E (nexin, plasminogen activator inhibitor type 1), me | 0.00055869 | 25.8 | 18.3 | 21.4 |
| 106 | 202081_PM_at | IER2 | immediate early response 2 | 0.000568285 | 1831.1 | 2155.1 | 1935.4 |
| 107 | 234089_PM_at | — | — | 0.000585869 | 10.1 | 12.4 | 11.9 |
| 108 | 235139_PM_at | GNGT2 | guanine nucleotide binding protein (G protein), gamma transducing activity polypeptide | 0.000604705 | 35.8 | 50.6 | 51.5 |
| 109 | 235545_PM_at | DEPDC1 | DEP domain containing 1 | 0.00060962 | 8.7 | 8.4 | 10.0 |
| 110 | 242096_PM_at | — | — | 0.000618307 | 8.6 | 8.7 | 10.3 |
| 111 | 1553042_PM_a_at | NFKBID | nuclear factor of kappa light polypeptide gene enhancer in B-cells inhibitor, delta | 0.000619863 | 14.9 | 17.7 | 16.0 |
| 112 | 209368_PM_at | EPHX2 | epoxide hydrolase 2, cytoplasmic | 0.000625958 | 33.6 | 25.2 | 22.3 |
| 113 | 1553681_PM_a_at | PRF1 | perforin 1 (pore forming protein) | 0.000629562 | 181.7 | 312.5 | 312.3 |
| 114 | 223836_PM_at | FGFBP2 | fibroblast growth factor binding protein 2 | 0.000647084 | 432.4 | 739.7 | 788.9 |
| 115 | 210812_PM_at | XRCC4 | X-ray repair complementing defective repair in Chinese hamster cells 4 | 0.000674811 | 13.2 | 15.5 | 16.5 |
| 116 | 230846_PM_at | AKAP5 | A kinase (PRKA) anchor protein 5 | 0.000678814 | 10.9 | 9.3 | 11.2 |
| 117 | 214567_PM_s_at | XCL1 /// XCL2 | chemokine (C motif) ligand 1 /// chemokine (C motif) ligand 2 | 0.000680647 | 211.0 | 338.8 | 347.2 |
| 118 | 237221_PM_at | — | — | 0.00069712 | 9.9 | 8.7 | 9.5 |
| 119 | 232793_PM_at | — | — | 0.000698404 | 10.2 | 12.5 | 13.0 |
| 120 | 239479_PM_x_at | — | — | 0.000700142 | 28.1 | 18.0 | 20.6 |
| 121 | 1558836_PM_at | — | — | 0.000706412 | 33.2 | 53.1 | 45.7 |
| 122 | 1562698_PM_x_at | LOC339988 | hypothetical LOC339988 | 0.000710123 | 108.5 | 165.5 | 158.7 |
| 123 | 1552646_PM_at | IL11RA | interleukin 11 receptor, alpha | 0.000716149 | 15.9 | 19.4 | 16.3 |

TABLE 17b-continued

The 147 probesets for distinguishing between AR, HCV and HCV + AR in Liver PAXgene samples

| # | Probeset ID | Gene Symbol | Gene Title | p-value (Phenotype) | AR - Mean | HCV - Mean | HCV + AR - Mean |
|---|---|---|---|---|---|---|---|
| 124 | 236220_PM_at | — | — | 0.000735209 | 9.9 | 8.3 | 7.7 |
| 125 | 211379_PM_x_at | B3GALNT1 | beta-1,3-N-acetylgalactosaminyl-transferase 1 (globoside blood group) | 0.00074606 | 8.9 | 8.2 | 9.7 |
| 126 | 222830_PM_at | GRHL1 | grainyhead-like 1 (*Drosophila*) | 0.000766774 | 14.7 | 10.5 | 10.4 |
| 127 | 210948_PM_s_at | LEF1 | lymphoid enhancer-binding factor 1 | 0.000768363 | 54.2 | 36.2 | 33.1 |
| 128 | 244798_PM_at | LOC100507492 | hypothetical LOC100507492 | 0.000800826 | 48.3 | 32.0 | 26.6 |
| 129 | 226666_PM_at | DAAM1 | dishevelled associated activator of morphogenesis 1 | 0.000828238 | 64.3 | 50.3 | 47.8 |
| 130 | 229378_PM_at | STOX1 | storkhead box 1 | 0.000836722 | 10.2 | 8.5 | 9.6 |
| 131 | 206366_PM_x_at | XCL1 | chemokine (C motif) ligand 1 | 0.000839844 | 194.1 | 306.8 | 324.9 |
| 132 | 214115_PM_at | VAMP5 | Vesicle-associated membrane protein 5 (myobrevin) | 0.000866755 | 13.2 | 12.1 | 16.6 |
| 133 | 201212_PM_at | LGMN | legumain | 0.00087505 | 18.9 | 15.9 | 13.1 |
| 134 | 204863_PM_s_at | IL6ST | interleukin 6 signal transducer (gp130, oncostatin M receptor) | 0.000897042 | 147.6 | 107.1 | 111.1 |
| 135 | 232229_PM_at | SETX | senataxin | 0.000906105 | 34.5 | 45.3 | 36.9 |
| 136 | 1555407_PM_s_at | FGD3 | FYVE, RhoGEF and PH domain containing 3 | 0.00091116 | 88.7 | 103.2 | 67.0 |
| 137 | 223127_PM_s_at | C1orf21 | chromosome 1 open reading frame 21 | 0.000923068 | 9.1 | 10.3 | 11.0 |
| 138 | 202458_PM_at | PRSS23 | protease, serine, 23 | 0.000924141 | 38.8 | 74.1 | 79.3 |
| 139 | 210606_PM_x_at | KLRD1 | killer cell lectin-like receptor subfamily D, member 1 | 0.000931313 | 289.8 | 421.9 | 473.0 |
| 140 | 212444_PM_at | — | — | 0.000935909 | 10.2 | 11.6 | 10.2 |
| 141 | 240893_PM_at | — | — | 0.000940973 | 8.6 | 9.7 | 10.3 |
| 142 | 219474_PM_at | C3orf52 | chromosome 3 open reading frame 52 | 0.000948853 | 8.9 | 10.0 | 10.2 |
| 143 | 235087_PM_at | UNKL | unkempt homolog (*Drosophila*)-like | 0.000967141 | 10.3 | 9.8 | 8.3 |
| 144 | 216907_PM_x_at | KIR3DL1 /// KIR3DL2 /// LOC727787 | killer cell immunoglobulin-like receptor, three domains, long cytoplasmic tail, 1 /// k | 0.000987803 | 12.6 | 16.1 | 19.1 |
| 145 | 238402_PM_s_at | FLJ35220 | hypothetical protein FLJ35220 | 0.000990348 | 17.2 | 19.9 | 15.3 |
| 146 | 239273_PM_s_at | MMP28 | matrix metallopeptidase 28 | 0.000993809 | 11.7 | 9.0 | 8.7 |
| 147 | 215894_PM_at | PTGDR | prostaglandin D2 receptor (DP) | 0.000994157 | 191.2 | 329.4 | 283.2 |

TABLE 18a

AUCs for the 320 probes to predict AR, ADNR and TX in Liver biopsy samples.

| Algorithm | Predictors | Comparison | AUC | Predictive Accuracy (%) | Sensitivity (%) | Specificity (%) | Postive Predictive Value (%) | Negative Predictive Value (%) |
|---|---|---|---|---|---|---|---|---|
| Nearest Centroid | 320 | AR vs. HCV | 0.937 | 94 | 84 | 100 | 100 | 89 |
| Nearest Centroid | 320 | AR vs. HCV + AR | 1.000 | 100 | 100 | 100 | 100 | 100 |
| Nearest Centroid | 320 | HCV vs. HCV + AR | 0.829 | 82 | 82 | 89 | 75 | 92 |

TABLE 18b

The 320 probesets that distinguish AR vs. HCV vs. HCV + AR in Liver Biopsies

| # | Probeset ID | Gene Symbol | Gene Title | p-value (Phenotype) | AR - Mean | HCV - Mean | HCV + AR - Mean |
|---|---|---|---|---|---|---|---|
| 1 | 219863_PM_at | HERC5 | hect domain and RLD 5 | 1.53E−14 | 250.4 | 1254.7 | 1620.1 |
| 2 | 205660_PM_at | OASL | 2'-5'-oligoadenylate synthetase-like | 3.30E−14 | 128.1 | 1273.7 | 1760.9 |

TABLE 18b-continued

The 320 probesets that distinguish AR vs. HCV vs. HCV + AR in Liver Biopsies

| # | Probeset ID | Gene Symbol | Gene Title | p-value (Phenotype) | AR - Mean | HCV - Mean | HCV + AR - Mean |
|---|---|---|---|---|---|---|---|
| 3 | 210797_PM_s_at | OASL | 2'-5'-oligoadenylate synthetase-like | 4.03E−14 | 62.0 | 719.3 | 915.2 |
| 4 | 214453_PM_s_at | IFI44 | interferon-induced protein 44 | 3.98E−13 | 342.2 | 1646.7 | 1979.2 |
| 5 | 218986_PM_s_at | DDX60 | DEAD (Asp-Glu-Ala-Asp) box polypeptide 60 | 5.09E−12 | 352.2 | 1253.2 | 1403.0 |
| 6 | 202869_PM_at | OAS1 | 2',5'-oligoadenylate synthetase 1, 40/46 kDa | 4.47E−11 | 508.0 | 1648.7 | 1582.5 |
| 7 | 226702_PM_at | CMPK2 | cytidine monophosphate (UMP-CMP) kinase 2, mitochondrial | 5.23E−11 | 257.3 | 1119.1 | 1522.6 |
| 8 | 203153_PM_at | IFIT1 | interferon-induced protein with tetratricopeptide repeats 1 | 5.31E−11 | 704.0 | 2803.7 | 3292.9 |
| 9 | 202086_PM_at | MX1 | myxovirus (influenza virus) resistance 1, interferon-inducible protein p78 (mouse) | 5.53E−11 | 272.4 | 1420.9 | 1836.8 |
| 10 | 242625_PM_at | RSAD2 | radical S-adenosyl methionine domain containing 2 | 9.62E−11 | 56.2 | 389.2 | 478.2 |
| 11 | 213797_PM_at | RSAD2 | radical S-adenosyl methionine domain containing 2 | 1.43E−10 | 91.4 | 619.3 | 744.7 |
| 12 | 204972_PM_at | OAS2 | 2'-5'-oligoadenylate synthetase 2, 69/71 kDa | 2.07E−10 | 88.7 | 402.1 | 536.1 |
| 13 | 219352_PM_at | HERC6 | hect domain and RLD 6 | 2.52E−10 | 49.5 | 206.7 | 272.8 |
| 14 | 205483_PM_s_at | ISG15 | ISG15 ubiquitin-like modifier | 3.68E−10 | 629.9 | 3181.1 | 4608.0 |
| 15 | 205552_PM_s_at | OAS1 | 2',5'-oligoadenylate synthetase 1, 40/46 kDa | 4.08E−10 | 224.7 | 868.7 | 921.2 |
| 16 | 204415_PM_at | IFI6 | interferon, alpha-inducible protein 6 | 5.83E−10 | 787.8 | 4291.7 | 5465.6 |
| 17 | 205569_PM_at | LAMP3 | lysosomal-associated membrane protein 3 | 6.80E−10 | 21.8 | 91.3 | 126.2 |
| 18 | 219209_PM_at | IFIH1 | interferon induced with helicase C domain 1 | 8.15E−10 | 562.3 | 1246.9 | 1352.7 |
| 19 | 218400_PM_at | OAS3 | 2'-5'-oligoadenylate synthetase 3, 100 kDa | 2.85E−09 | 87.9 | 265.2 | 364.5 |
| 20 | 229450_PM_at | IFIT3 | interferon-induced protein with tetratricopeptide repeats 3 | 4.69E−09 | 1236.3 | 2855.3 | 3291.7 |
| 21 | 226757_PM_at | IFIT2 | interferon-induced protein with tetratricopeptide repeats 2 | 5.35E−09 | 442.3 | 1083.2 | 1461.9 |
| 22 | 204439_PM_at | IFI44L | interferon-induced protein 44-like | 5.77E−09 | 146.3 | 794.4 | 1053.5 |
| 23 | 227609_PM_at | EPSTI1 | epithelial stromal interaction 1 (breast) | 1.03E−08 | 396.9 | 1079.8 | 1370.3 |
| 24 | 204747_PM_at | IFIT3 | interferon-induced protein with tetratricopeptide repeats 3 | 1.59E−08 | 228.3 | 698.1 | 892.7 |
| 25 | 217502_PM_at | IFIT2 | interferon-induced protein with tetratricopeptide repeats 2 | 1.85E−08 | 222.9 | 575.1 | 745.9 |
| 26 | 228607_PM_at | OAS2 | 2'-5'-oligoadenylate synthetase 2, 69/71 kDa | 2.16E−08 | 60.9 | 182.0 | 225.6 |
| 27 | 224870_PM_at | KIAA0114 | KIAA0114 | 2.48E−08 | 156.5 | 81.8 | 66.0 |
| 28 | 202411_PM_at | IFI27 | interferon, alpha-inducible protein 27 | 4.25E−08 | 1259.4 | 5620.8 | 5634.1 |
| 29 | 223220_PM_s_at | PARP9 | poly (ADP-ribose) polymerase family, member 9 | 4.48E−08 | 561.7 | 1084.4 | 1143.1 |
| 30 | 208436_PM_s_at | IRF7 | interferon regulatory factor 7 | 4.57E−08 | 58.9 | 102.9 | 126.9 |
| 31 | 219211_PM_at | USP18 | ubiquitin specific peptidase 18 | 6.39E−08 | 51.0 | 183.6 | 196.1 |
| 32 | 206133_PM_at | XAF1 | XIAP associated factor 1 | 7.00E−08 | 463.9 | 1129.2 | 1327.1 |
| 33 | 202446_PM_s_at | PLSCR1 | phospholipid scramblase 1 | 1.12E−07 | 737.8 | 1317.7 | 1419.8 |
| 34 | 235276_PM_at | EPSTI1 | epithelial stromal interaction 1 (breast) | 1.58E−07 | 93.5 | 244.2 | 279.9 |
| 35 | 219684_PM_at | RTP4 | receptor (chemosensory) transporter protein 4 | 1.64E−07 | 189.5 | 416.3 | 541.7 |
| 36 | 222986_PM_s_at | SPHISA5 | shisa homolog 5 (*Xenopus laevis*) | 1.68E−07 | 415.0 | 586.9 | 681.4 |
| 37 | 223298_PM_s_at | NT5C3 | 5'-nucleotidase, cytosolic III | 2.06E−07 | 247.6 | 443.4 | 474.7 |
| 38 | 228275_PM_at | — | — | 2.24E−07 | 71.6 | 159.3 | 138.9 |
| 39 | 228617_PM_at | XAF1 | XIAP associated factor 1 | 2.28E−07 | 678.3 | 1412.3 | 1728.5 |
| 40 | 214022_PM_s_at | IFITM1 | interferon induced transmembrane protein 1 (9-27) | 2.37E−07 | 1455.1 | 2809.3 | 3537.2 |
| 41 | 214059_PM_at | IFI44 | Interferon-induced protein 44 | 2.61E−07 | 37.1 | 158.8 | 182.5 |

TABLE 18b-continued

The 320 probesets that distinguish AR vs. HCV vs. HCV + AR in Liver Biopsies

| # | Probeset ID | Gene Symbol | Gene Title | p-value (Phenotype) | AR - Mean | HCV - Mean | HCV + AR - Mean |
|---|---|---|---|---|---|---|---|
| 42 | 206553_PM_at | OAS2 | 2'-5'-oligoadenylate synthetase 2, 69/71 kDa | 2.92E−07 | 18.9 | 45.6 | 53.1 |
| 43 | 214290_PM_s_at | HIST2H2AA3 /// HIST2H2AA4 | histone cluster 2, H2aa3 /// histone cluster 2, H2aa4 | 3.50E−07 | 563.4 | 1151.2 | 1224.7 |
| 44 | 1554079_PM_at | GALNTL4 | UDP-N-acetyl-alpha-D-galactosamine: polypeptide N-acetylgalactosaminyltransferase-like 4 | 3.58E−07 | 69.9 | 142.6 | 109.0 |
| 45 | 202430_PM_s_at | PLSCR1 | phospholipid scramblase 1 | 3.85E−07 | 665.7 | 1162.8 | 1214.5 |
| 46 | 218280_PM_x_at | HIST2H2AA3 /// HIST2H2AA4 | histone cluster 2, H2aa3 /// histone cluster 2, H2aa4 | 5.32E−07 | 299.7 | 635.3 | 721.7 |
| 47 | 202708_PM_s_at | HIST2H2BE | histone cluster 2, H2be | 7.04E−07 | 62.4 | 112.2 | 115.4 |
| 48 | 222134_PM_at | DDO | D-aspartate oxidase | 7.37E−07 | 76.0 | 134.9 | 118.4 |
| 49 | 215071_PM_s_at | HIST1H2AC | histone cluster 1, H2ac | 9.11E−07 | 502.4 | 1009.1 | 1019.0 |
| 50 | 209417_PM_s_at | IFI35 | interferon-induced protein 35 | 9.12E−07 | 145.5 | 258.9 | 323.5 |
| 51 | 218543_PM_s_at | PARP12 | poly (ADP-ribose) polymerase family, member 12 | 9.29E−07 | 172.3 | 280.3 | 366.3 |
| 52 | 202864_PM_s_at | SP100 | SP100 nuclear antigen | 1.09E−06 | 372.5 | 604.2 | 651.9 |
| 53 | 217719_PM_at | EIF3L | eukaryotic translation initiation factor 3, subunit L | 1.15E−06 | 4864.0 | 3779.0 | 3600.0 |
| 54 | 230314_PM_at | — | — | 1.29E−06 | 36.0 | 62.5 | 59.5 |
| 55 | 202863_PM_at | SP100 | SP100 nuclear antigen | 1.37E−06 | 500.1 | 751.3 | 815.8 |
| 56 | 236798_PM_at | — | — | 1.38E−06 | 143.1 | 307.0 | 276.8 |
| 57 | 233555_PM_s_at | SULF2 | sulfatase 2 | 1.38E−06 | 47.0 | 133.4 | 119.0 |
| 58 | 236717_PM_at | FAM179A | family with sequence similarity 179, member A | 1.44E−06 | 16.5 | 16.1 | 24.2 |
| 59 | 228531_PM_at | SAMD9 | sterile alpha motif domain containing 9 | 1.54E−06 | 143.0 | 280.3 | 351.7 |
| 60 | 209911_PM_x_at | HIST1H2BD | histone cluster 1, H2bd | 1.69E−06 | 543.7 | 999.9 | 1020.2 |
| 61 | 238039_PM_at | LOC728769 | hypothetical LOC728769 | 1.77E−06 | 62.8 | 95.5 | 97.2 |
| 62 | 222067_PM_x_at | HIST1H2BD | histone cluster 1, H2bd | 1.78E−06 | 378.1 | 651.6 | 661.4 |
| 63 | 201601_PM_x_at | IFITM1 | interferon induced transmembrane protein 1 (9-27) | 2.00E−06 | 1852.8 | 2956.0 | 3664.5 |
| 64 | 213361_PM_at | TDRD7 | tudor domain containing 7 | 2.09E−06 | 158.5 | 314.1 | 328.6 |
| 65 | 224998_PM_at | CMTM4 | CKLF-like MARVEL transmembrane domain containing 4 | 2.15E−06 | 42.6 | 30.0 | 22.3 |
| 66 | 222793_PM_at | DDX58 | DEAD (Asp-Glu-Ala-Asp) box polypeptide 58 | 2.41E−06 | 93.9 | 231.9 | 223.1 |
| 67 | 225076_PM_s_at | ZNFX1 | zinc finger, NFX1-type containing 1 | 2.55E−06 | 185.0 | 286.0 | 359.1 |
| 68 | 236381_PM_s_at | WDR8 | WD repeat domain 8 | 2.68E−06 | 41.6 | 61.5 | 64.8 |
| 69 | 202365_PM_at | UNC119B | unc-119 homolog B (C. elegans) | 2.72E−06 | 383.4 | 272.7 | 241.0 |
| 70 | 215690_PM_x_at | GPAA1 | glycosylphosphatidylinositol anchor attachment protein 1 homolog (yeast) | 2.75E−06 | 141.0 | 103.7 | 107.5 |
| 71 | 211799_PM_x_at | HLA-C | major histocompatibility complex, class I, C | 2.77E−06 | 912.3 | 1446.0 | 1649.4 |
| 72 | 218943_PM_s_at | DDX58 | DEAD (Asp-Glu-Ala-Asp) box polypeptide 58 | 2.87E−06 | 153.9 | 310.7 | 350.7 |
| 73 | 235686_PM_at | C2orf60 | chromosome 2 open reading frame 60 | 3.32E−06 | 17.2 | 23.2 | 20.1 |
| 74 | 236193_PM_at | LOC100506979 | hypothetical LOC100506979 | 3.96E−06 | 24.5 | 48.1 | 51.2 |
| 75 | 221767_PM_x_at | HDLBP | high density lipoprotein binding protein | 4.00E−06 | 1690.9 | 1301.2 | 1248.4 |
| 76 | 225796_PM_at | PXK | PX domain containing serine/threonine kinase | 4.08E−06 | 99.2 | 168.1 | 154.9 |
| 77 | 209762_PM_x_at | SP110 | SP110 nuclear body protein | 4.68E−06 | 150.5 | 242.3 | 282.0 |
| 78 | 211060_PM_x_at | GPAA1 | glycosylphosphatidylinositol anchor attachment protein 1 homolog (yeast) | 4.74E−06 | 153.1 | 113.3 | 116.8 |
| 79 | 218019_PM_s_at | PDXK | pyridoxal (pyridoxine, vitamin B6) kinase | 4.95E−06 | 304.5 | 210.8 | 198.6 |
| 80 | 219364_PM_at | DHX58 | DEXH (Asp-Glu-X-His) box polypeptide 58 | 5.46E−06 | 71.5 | 111.2 | 113.0 |
| 81 | 203281_PM_s_at | UBA7 | ubiquitin-like modifier activating enzyme 7 | 6.79E−06 | 80.2 | 108.2 | 131.0 |
| 82 | 200923_PM_at | LGALS3BP | lectin, galactoside-binding, soluble, 3 binding protein | 6.99E−06 | 193.1 | 401.5 | 427.4 |

TABLE 18b-continued

The 320 probesets that distinguish AR vs. HCV vs. HCV + AR in Liver Biopsies

| # | Probeset ID | Gene Symbol | Gene Title | p-value (Phenotype) | AR - Mean | HCV - Mean | HCV + AR - Mean |
|---|---|---|---|---|---|---|---|
| 83 | 208527_PM_x_at | HIST1H2BE | histone cluster 1, H2be | 7.54E−06 | 307.7 | 529.7 | 495.4 |
| 84 | 219479_PM_at | KDELC1 | KDEL (Lys-Asp-Glu-Leu) containing 1 | 7.81E−06 | 74.1 | 131.5 | 110.6 |
| 85 | 200950_PM_at | ARPC1A | actin related protein 2/3 complex, subunit 1A, 41 kDa | 1.00E−05 | 1015.8 | 862.8 | 782.0 |
| 86 | 213294_PM_at | EIF2AK2 | eukaryotic translation initiation factor 2-alpha kinase 2 | 1.02E−05 | 390.4 | 690.7 | 651.6 |
| 87 | 205943_PM_at | TDO2 | tryptophan 2,3-dioxygenase | 1.06E−05 | 7808.6 | 10534.7 | 10492.0 |
| 88 | 217969_PM_at | C11orf2 | chromosome 11 open reading frame 2 | 1.21E−05 | 302.6 | 235.0 | 214.8 |
| 89 | 1552370_PM_at | C4orf33 | chromosome 4 open reading frame 33 | 1.24E−05 | 58.4 | 124.5 | 97.2 |
| 90 | 211911_PM_x_at | HLA-B | major histocompatibility complex, class I, B | 1.34E−05 | 4602.1 | 6756.7 | 7737.3 |
| 91 | 232563_PM_at | ZNF684 | zinc finger protein 684 | 1.36E−05 | 131.9 | 236.2 | 231.8 |
| 92 | 203882_PM_at | IRF9 | interferon regulatory factor 9 | 1.43E−05 | 564.0 | 780.1 | 892.0 |
| 93 | 225991_PM_at | TMEM41A | transmembrane protein 41A | 1.45E−05 | 122.5 | 202.1 | 179.6 |
| 94 | 239988_PM_at | — | — | 1.53E−05 | 11.5 | 15.4 | 16.1 |
| 95 | 244434_PM_at | GPR82 | G protein-coupled receptor 82 | 1.55E−05 | 18.5 | 32.5 | 37.0 |
| 96 | 201489_PM_at | PPIF | peptidylprolyl isomerase F | 1.58E−05 | 541.7 | 899.5 | 672.9 |
| 97 | 221476_PM_s_at | RPL15 | ribosomal protein L15 | 1.58E−05 | 3438.3 | 2988.5 | 2742.8 |
| 98 | 244398_PM_x_at | ZNF684 | zinc finger protein 684 | 1.65E−05 | 57.2 | 96.9 | 108.5 |
| 99 | 208628_PM_s_at | YBX1 | Y box binding protein 1 | 1.66E−05 | 4555.5 | 3911.6 | 4365.0 |
| 100 | 211710_PM_x_at | RPL4 | ribosomal protein L4 | 1.73E−05 | 5893.1 | 4853.3 | 4955.4 |
| 101 | 229741_PM_at | MAVS | mitochondrial antiviral signaling protein | 1.78E−05 | 65.2 | 44.6 | 34.4 |
| 102 | 206386_PM_at | SERPINA7 | serpin peptidase inhibitor, clade A (alpha-1 antiproteinase, antitrypsin), member 7 | 1.90E−05 | 3080.8 | 4251.6 | 4377.2 |
| 103 | 213293_PM_s_at | TRIM22 | tripartite motif-containing 22 | 1.92E−05 | 1122.0 | 1829.6 | 2293.2 |
| 104 | 200089_PM_s_at | RPL4 | ribosomal protein L4 | 1.93E−05 | 3387.5 | 2736.6 | 2823.9 |
| 105 | 235037_PM_at | TMEM41A | transmembrane protein 41A | 1.96E−05 | 134.7 | 218.5 | 192.9 |
| 106 | 226459_PM_at | PIK3AP1 | phosphoinositide-3-kinase adaptor protein 1 | 2.10E−05 | 2152.4 | 2747.6 | 2929.7 |
| 107 | 200023_PM_s_at | EIF3F | eukaryotic translation initiation factor 3, subunit F | 2.16E−05 | 1764.9 | 1467.2 | 1365.3 |
| 108 | 205161_PM_s_at | PEX11A | peroxisomal biogenesis factor 11 alpha | 2.17E−05 | 51.9 | 87.3 | 76.9 |
| 109 | 225291_PM_at | PNPT1 | polyribonucleotide nucleotidyltransferase 1 | 2.18E−05 | 287.0 | 469.1 | 455.0 |
| 110 | 220445_PM_s_at | CSAG2 /// CSAG3 | CSAG family, member 2 /// CSAG family, member 3 | 2.24E−05 | 16.3 | 91.2 | 120.9 |
| 111 | 226229_PM_s_at | SSU72 | SSU72 RNA polymerase II CTD phosphatase homolog (S. cerevisiae) | 2.24E−05 | 50.4 | 36.7 | 32.3 |
| 112 | 207418_PM_s_at | DDO | D-aspartate oxidase | 2.48E−05 | 35.2 | 57.0 | 50.7 |
| 113 | 201786_PM_s_at | ADAR | adenosine deaminase, RNA-specific | 2.59E−05 | 1401.5 | 1867.9 | 1907.8 |
| 114 | 224724_PM_at | SULF2 | sulfatase 2 | 2.61E−05 | 303.6 | 540.1 | 553.9 |
| 115 | 201618_PM_x_at | GPAA1 | glycosylphosphatidylinositol anchor attachment protein 1 homolog (yeast) | 2.63E−05 | 131.2 | 98.1 | 97.5 |
| 116 | 201154_PM_x_at | RPL4 | ribosomal protein L4 | 2.78E−05 | 3580.5 | 2915.6 | 2996.2 |
| 117 | 200094_PM_s_at | EEF2 | eukaryotic translation elongation factor 2 | 3.08E−05 | 3991.6 | 3248.5 | 3061.1 |
| 118 | 208424_PM_s_at | CIAPIN1 | cytokine induced apoptosis inhibitor 1 | 3.17E−05 | 66.7 | 94.8 | 94.8 |
| 119 | 204102_PM_s_at | EEF2 | eukaryotic translation elongation factor 2 | 3.23E−05 | 3680.8 | 3102.7 | 2853.6 |
| 120 | 203595_PM_s_at | IFIT5 | interferon-induced protein with tetratricopeptide repeats 5 | 3.44E−05 | 266.9 | 445.8 | 450.9 |
| 121 | 228152_PM_s_at | DDX60L | DEAD (Asp-Glu-Ala-Asp) box polypeptide 60-like | 3.52E−05 | 136.1 | 280.8 | 304.5 |
| 122 | 201490_PM_s_at | PPIF | peptidylprolyl isomerase F | 3.64E−05 | 209.2 | 443.5 | 251.4 |
| 123 | 217933_PM_s_at | LAP3 | leucine aminopeptidase 3 | 3.81E−05 | 3145.6 | 3985.6 | 4629.9 |
| 124 | 203596_PM_s_at | IFIT5 | interferon-induced protein with tetratricopeptide repeats 5 | 3.93E−05 | 195.9 | 315.8 | 339.0 |
| 125 | 220104_PM_at | ZC3HAV1 | zinc finger CCCH-type, antiviral 1 | 4.25E−05 | 23.3 | 53.1 | 57.7 |
| 126 | 213080_PM_x_at | RPL5 | ribosomal protein L5 | 4.28E−05 | 6986.7 | 6018.3 | 5938.6 |

TABLE 18b-continued

The 320 probesets that distinguish AR vs. HCV vs. HCV + AR in Liver Biopsies

| # | Probeset ID | Gene Symbol | Gene Title | p-value (Phenotype) | AR - Mean | HCV - Mean | HCV + AR - Mean |
|---|---|---|---|---|---|---|---|
| 127 | 208729_PM_x_at | HLA-B | major histocompatibility complex, class I, B | 4.58E−05 | 4720.9 | 6572.7 | 7534.4 |
| 128 | 32541_PM_at | PPP3CC | protein phosphatase 3, catalytic subunit, gamma isozyme | 4.71E−05 | 63.3 | 79.7 | 81.3 |
| 129 | 216231_PM_s_at | B2M | beta-2-microglobulin | 4.79E−05 | 13087.7 | 14063.7 | 14511.1 |
| 130 | 206082_PM_at | HCP5 | HLA complex P5 | 4.91E−05 | 129.7 | 205.7 | 300.9 |
| 131 | 213275_PM_x_at | CTSB | cathepsin B | 4.93E−05 | 2626.4 | 2001.3 | 2331.0 |
| 132 | 200643_PM_at | HDLBP | high density lipoprotein binding protein | 5.04E−05 | 404.4 | 317.8 | 304.4 |
| 133 | 235309_PM_at | RPS15A | ribosomal protein S15a | 5.08E−05 | 98.5 | 77.4 | 55.3 |
| 134 | 209761_PM_s_at | SP110 | SP110 nuclear body protein | 5.33E−05 | 84.2 | 145.6 | 156.0 |
| 135 | 230753_PM_at | PATL2 | protein associated with topoisomerase II homolog 2 (yeast) | 5.55E−05 | 42.8 | 52.1 | 68.4 |
| 136 | 225369_PM_at | ESAM | endothelial cell adhesion molecule | 5.72E−05 | 14.9 | 13.1 | 11.9 |
| 137 | 219255_PM_x_at | IL17RB | interleukin 17 receptor B | 5.88E−05 | 334.9 | 607.9 | 568.7 |
| 138 | 208392_PM_x_at | SP110 | SP110 nuclear body protein | 6.05E−05 | 60.2 | 96.1 | 115.5 |
| 139 | 221044_PM_s_at | TRIM34 /// TRIM6-TRIM34 | tripartite motif-containing 34 /// TRIM6-TRIM34 readthrough | 6.07E−05 | 47.0 | 65.1 | 70.9 |
| 140 | 1554375_PM_a_at | NR1H4 | nuclear receptor subfamily 1, group H, member 4 | 6.23E−05 | 585.8 | 913.1 | 791.8 |
| 141 | 210218_PM_s_at | SP100 | SP100 nuclear antigen | 6.41E−05 | 129.0 | 207.4 | 222.0 |
| 142 | 206340_PM_at | NR1H4 | nuclear receptor subfamily 1, group H, member 4 | 6.67E−05 | 983.3 | 1344.6 | 1278.4 |
| 143 | 222868_PM_s_at | IL18BP | interleukin 18 binding protein | 7.04E−05 | 72.0 | 45.4 | 90.9 |
| 144 | 204211_PM_x_at | EIF2AK2 | eukaryotic translation initiation factor 2-alpha kinase 2 | 7.04E−05 | 144.8 | 215.9 | 229.8 |
| 145 | 231702_PM_at | TDO2 | Tryptophan 2,3-dioxygenase | 7.09E−05 | 57.9 | 101.7 | 83.6 |
| 146 | 204906_PM_at | RPS6KA2 | ribosomal protein S6 kinase, 90 kDa, polypeptide 2 | 7.10E−05 | 40.1 | 28.3 | 28.7 |
| 147 | 218192_PM_at | IP6K2 | inositol hexakisphosphate kinase 2 | 7.15E−05 | 84.0 | 112.5 | 112.7 |
| 148 | 211528_PM_x_at | HLA-G | major histocompatibility complex, class I, G | 7.45E−05 | 1608.7 | 2230.0 | 2613.2 |
| 149 | 208546_PM_x_at | HIST1H2BB /// HIST1H2BC /// HIST1H2BD /// HIST1H2BE /// HIST1H2BG /// HIST1H2BH /// HIST1H2BI | histone cluster 1, H2bb /// histone cluster 1, H2bc /// histone cluster 1, H2bd /// his | 7.82E−05 | 65.3 | 131.7 | 112.0 |
| 150 | 204483_PM_at | ENO3 | enolase 3 (beta, muscle) | 7.85E−05 | 547.8 | 1183.9 | 891.4 |
| 151 | 203148_PM_s_at | TRIM14 | tripartite motif-containing 14 | 7.97E−05 | 590.8 | 803.6 | 862.4 |
| 152 | 1557120_PM_at | EEF1A1 | Eukaryotic translation elongation factor 1 alpha 1 | 8.14E−05 | 20.5 | 17.4 | 17.4 |
| 153 | 203067_PM_at | PDHX | pyruvate dehydrogenase complex, component X | 8.21E−05 | 322.0 | 457.6 | 413.2 |
| 154 | 224156_PM_x_at | IL17RB | interleukin 17 receptor B | 8.48E−05 | 426.4 | 755.4 | 699.9 |
| 155 | 203073_PM_at | COG2 | component of oligomeric golgi complex 2 | 9.64E−05 | 73.6 | 100.2 | 96.2 |
| 156 | 211937_PM_at | EIF4B | eukaryotic translation initiation factor 4B | 9.68E−05 | 823.8 | 617.5 | 549.7 |
| 157 | 229804_PM_x_at | CBWD2 | COBW domain containing 2 | 9.69E−05 | 170.0 | 225.0 | 229.1 |
| 158 | 225009_PM_at | CMTM4 | CKLF-like MARVEL transmembrane domain containing 4 | 0.00010207 | 54.0 | 40.5 | 32.3 |
| 159 | 221305_PM_s_at | UGT1A8 /// UGT1A9 | UDP glucuronosyltransferase 1 family, polypeptide A8 /// UDP glucuronosyltransferase 1 | 0.000109701 | 214.3 | 526.8 | 346.9 |
| 160 | 1557820_PM_at | AFG3L2 | AFG3 ATPase family gene 3-like 2 (S. cerevisiae) | 0.000112458 | 1037.9 | 1315.0 | 1232.5 |
| 161 | 237627_PM_at | LOC100506318 | hypothetical LOC100506318 | 0.000115046 | 29.2 | 22.6 | 19.1 |
| 162 | 205819_PM_at | MARCO | macrophage receptor with collagenous structure | 0.000115755 | 625.3 | 467.4 | 904.8 |
| 163 | 215313_PM_x_at | HLA-A /// LOC100507703 | major histocompatibility complex, class I, A /// HLA class I histocompatibility antigen | 0.000116881 | 6193.5 | 8266.5 | 9636.7 |

TABLE 18b-continued

The 320 probesets that distinguish AR vs. HCV vs. HCV + AR in Liver Biopsies

| # | Probeset ID | Gene Symbol | Gene Title | p-value (Phenotype) | AR - Mean | HCV - Mean | HCV + AR - Mean |
|---|---|---|---|---|---|---|---|
| 164 | 226950_PM_at | ACVRL1 | activin A receptor type II-like 1 | 0.000118584 | 28.2 | 25.1 | 35.5 |
| 165 | 213716_PM_s_at | SECTM1 | secreted and transmembrane 1 | 0.000118874 | 44.7 | 32.0 | 50.6 |
| 166 | 207468_PM_s_at | SFRP5 | secreted frizzled-related protein 5 | 0.000121583 | 19.6 | 25.5 | 20.2 |
| 167 | 218674_PM_at | C5orf44 | chromosome 5 open reading frame 44 | 0.000124195 | 60.4 | 97.9 | 77.7 |
| 168 | 219691_PM_at | SAMD9 | sterile alpha motif domain containing 9 | 0.000126093 | 29.6 | 49.5 | 53.9 |
| 169 | 230795_PM_at | — | — | 0.00012691 | 115.4 | 188.1 | 164.2 |
| 170 | 200941_PM_at | HSBP1 | heat shock factor binding protein 1 | 0.000127149 | 559.2 | 643.2 | 623.6 |
| 171 | 230174_PM_at | LYPLAL1 | lysophospholipase-like 1 | 0.000127616 | 476.3 | 597.5 | 471.3 |
| 172 | 214459_PM_x_at | HLA-C | major histocompatibility complex, class I, C | 0.000131095 | 4931.4 | 6208.3 | 6855.4 |
| 173 | 228971_PM_at | LOC100505759 | hypothetical LOC100505759 | 0.000131603 | 210.7 | 139.7 | 91.6 |
| 174 | 217073_PM_x_at | APOA1 | apolipoprotein A-I | 0.000135801 | 12423.8 | 13707.0 | 13369.3 |
| 175 | 203964_PM_at | NMI | N-myc (and STAT) interactor | 0.000138824 | 641.8 | 820.4 | 930.9 |
| 176 | 1556988_PM_s_at | CHD1L | chromodomain helicase DNA binding protein 1-like | 0.000142541 | 164.4 | 241.1 | 226.9 |
| 177 | 214890_PM_s_at | FAM149A | family with sequence similarity 149, member A | 0.000144828 | 534.0 | 444.9 | 342.4 |
| 178 | 209115_PM_at | UBA3 | ubiquitin-like modifier activating enzyme 3 | 0.000144924 | 456.2 | 532.0 | 555.8 |
| 179 | 212284_PM_x_at | TPT1 | tumor protein, translationally-controlled 1 | 0.000146465 | 15764.0 | 14965.0 | 14750.6 |
| 180 | 1552274_PM_at | PXK | PX domain containing serine/threonine kinase | 0.000150376 | 24.9 | 37.1 | 43.1 |
| 181 | 214889_PM_at | FAM149A | family with sequence similarity 149, member A | 0.00015075 | 295.1 | 236.6 | 152.6 |
| 182 | 213287_PM_s_at | KRT10 | keratin 10 | 0.000151197 | 644.2 | 551.6 | 509.4 |
| 183 | 213051_PM_at | ZC3HAV1 | zinc finger CCCH-type, antiviral 1 | 0.000152213 | 635.3 | 963.0 | 917.5 |
| 184 | 219731_PM_at | CC2D2B | Coiled-coil and C2 domain containing 2B | 0.000152224 | 37.5 | 50.5 | 50.5 |
| 185 | 206211_PM_at | SELE | selectin E | 0.000156449 | 76.0 | 35.1 | 22.8 |
| 186 | 217436_PM_x_at | HLA-A /// HLA-F /// HLA-J | major histocompatibility complex, class I, A /// major histocompatibility complex, clas | 0.000159936 | 972.4 | 1408.3 | 1820.7 |
| 187 | 203970_PM_s_at | PEX3 | peroxisomal biogenesis factor 3 | 0.000164079 | 387.4 | 540.4 | 434.7 |
| 188 | 1556643_PM_at | FAM125A | Family with sequence similarity 125, member A | 0.000170998 | 68.0 | 107.1 | 95.8 |
| 189 | 211529_PM_x_at | HLA-G | major histocompatibility complex, class I, G | 0.000174559 | 2166.9 | 3107.2 | 3708.7 |
| 190 | 223187_PM_s_at | ORMDL1 | ORM1-like 1 (*S. cerevisiae*) | 0.000182187 | 784.3 | 918.4 | 945.5 |
| 191 | 1566249_PM_at | — | — | 0.000182326 | 15.1 | 12.7 | 12.3 |
| 192 | 218111_PM_s_at | CMAS | cytidine monophosphate N-acetylneuraminic acid synthetase | 0.000182338 | 242.6 | 418.6 | 310.9 |
| 193 | 224361_PM_s_at | IL17RB | interleukin 17 receptor B | 0.000183121 | 231.0 | 460.8 | 431.4 |
| 194 | 217807_PM_s_at | GLTSCR2 | glioma tumor suppressor candidate region gene 2 | 0.000185926 | 3262.6 | 2650.0 | 2523.4 |
| 195 | 222571_PM_at | ST6GALNAC6 | ST6 (alpha-N-acetyl-neuraminyl-2,3-beta-galactosyl-1,3)-N-acetylgalactosaminide alpha-2 | 0.00018814 | 31.7 | 24.2 | 25.0 |
| 196 | 208012_PM_x_at | SP110 | SP110 nuclear body protein | 0.000189717 | 245.7 | 344.1 | 397.9 |
| 197 | 208579_PM_x_at | H2BFS | H2B histone family, member S | 0.000192843 | 352.8 | 581.2 | 525.7 |
| 198 | 204309_PM_at | CYP11A1 | cytochrome P450, family 11, subfamily A, polypeptide 1 | 0.000193276 | 17.5 | 27.3 | 29.2 |
| 199 | 211956_PM_s_at | EIF1 | eukaryotic translation initiation factor 1 | 0.000193297 | 6954.0 | 6412.9 | 6189.5 |
| 200 | 214455_PM_at | HIST1H2BC | histone cluster 1, H2bc | 0.000196036 | 49.9 | 104.4 | 101.5 |
| 201 | 232140_PM_at | — | — | 0.00019705 | 25.3 | 32.7 | 30.9 |
| 202 | 214054_PM_at | DOK2 | docking protein 2, 56 kDa | 0.000197843 | 28.6 | 25.1 | 39.9 |
| 203 | 210606_PM_x_at | KLRD1 | killer cell lectin-like receptor subfamily D, member 1 | 0.000201652 | 59.7 | 46.6 | 94.1 |
| 204 | 211943_PM_x_at | TPT1 | tumor protein, translationally-controlled 1 | 0.000202842 | 12849.6 | 11913.9 | 11804.6 |

TABLE 18b-continued

The 320 probesets that distinguish AR vs. HCV vs. HCV + AR in Liver Biopsies

| # | Probeset ID | Gene Symbol | Gene Title | p-value (Phenotype) | AR - Mean | HCV - Mean | HCV + AR - Mean |
|---|---|---|---|---|---|---|---|
| 205 | 205506_PM_at | VIL1 | villin 1 | 0.000209043 | 67.1 | 28.6 | 21.7 |
| 206 | 210514_PM_x_at | HLA-G | major histocompatibility complex, class I, G | 0.000214822 | 715.2 | 976.4 | 1100.2 |
| 207 | 235885_PM_at | P2RY12 | purinergic receptor P2Y, G-protein coupled, 12 | 0.000216727 | 21.1 | 30.2 | 49.1 |
| 208 | 212997_PM_s_at | TLK2 | tousled-like kinase 2 | 0.000217726 | 86.1 | 108.5 | 119.7 |
| 209 | 211976_PM_at | — | — | 0.000218277 | 145.9 | 115.9 | 104.8 |
| 210 | 231718_PM_at | SLU7 | SLU7 splicing factor homolog (*S. cerevisiae*) | 0.000221207 | 185.0 | 205.3 | 234.8 |
| 211 | 225634_PM_at | ZC3HAV1 | zinc finger CCCH-type, antiviral 1 | 0.000224661 | 388.3 | 511.6 | 490.5 |
| 212 | 205936_PM_s_at | HK3 | hexokinase 3 (white cell) | 0.000231343 | 22.5 | 19.2 | 30.2 |
| 213 | 203912_PM_s_at | DNASE1L1 | deoxyribonuclease I-like 1 | 0.000231815 | 171.2 | 151.3 | 183.8 |
| 214 | 224603_PM_at | — | — | 0.000232518 | 562.4 | 449.5 | 405.8 |
| 215 | 218085_PM_at | CHMP5 | chromatin modifying protein 5 | 0.000232702 | 484.6 | 584.5 | 634.2 |
| 216 | 204821_PM_at | BTN3A3 | butyrophilin, subfamily 3, member A3 | 0.000235674 | 245.0 | 335.6 | 401.3 |
| 217 | 217819_PM_at | GOLGA7 | golgin A7 | 0.000242192 | 845.3 | 1004.2 | 967.8 |
| 218 | 200629_PM_at | WARS | tryptophanyl-tRNA synthetase | 0.000244656 | 423.1 | 279.6 | 508.5 |
| 219 | 206342_PM_x_at | IDS | iduronate 2-sulfatase | 0.000246177 | 122.3 | 88.8 | 95.0 |
| 220 | 1560023_PM_x_at | — | — | 0.000247892 | 14.4 | 12.5 | 12.6 |
| 221 | 213706_PM_at | GPD1 | glycerol-3-phosphate dehydrogenase 1 (soluble) | 0.000254153 | 124.3 | 227.8 | 162.9 |
| 222 | 204312_PM_x_at | CREB1 | cAMP responsive element binding protein 1 | 0.000257352 | 28.9 | 41.8 | 34.8 |
| 223 | 230036_PM_at | SAMD9L | sterile alpha motif domain containing 9-like | 0.000265574 | 54.8 | 75.0 | 115.7 |
| 224 | 222730_PM_s_at | ZDHHC2 | zinc finger, DHHC-type containing 2 | 0.000270517 | 96.7 | 66.7 | 58.1 |
| 225 | 224225_PM_s_at | ETV7 | ets variant 7 | 0.000274744 | 32.8 | 55.4 | 71.0 |
| 226 | 1294_PM_at | UBA7 | ubiquitin-like modifier activating enzyme 7 | 0.000290256 | 94.7 | 122.9 | 138.8 |
| 227 | 211075_PM_s_at | CD47 | CD47 molecule | 0.000296663 | 767.0 | 998.4 | 1061.6 |
| 228 | 228091_PM_at | STX17 | syntaxin 17 | 0.000298819 | 94.3 | 134.9 | 110.7 |
| 229 | 205821_PM_at | KLRK1 | killer cell lectin-like receptor subfamily K, member 1 | 0.000299152 | 95.2 | 73.8 | 156.4 |
| 230 | 1563075_PM_s_at | — | — | 0.000300425 | 41.4 | 63.6 | 82.2 |
| 231 | 224701_PM_at | PARP14 | poly (ADP-ribose) polymerase family, member 14 | 0.000301162 | 367.5 | 538.6 | 589.3 |
| 232 | 209300_PM_s_at | NECAP1 | NECAP endocytosis associated 1 | 0.000304084 | 184.5 | 246.0 | 246.0 |
| 233 | 200937_PM_s_at | RPL5 | ribosomal protein L5 | 0.00030872 | 3893.3 | 3346.0 | 3136.1 |
| 234 | 208523_PM_x_at | HIST1H2BI | histone cluster 1, H2bi | 0.000310294 | 79.8 | 114.5 | 115.8 |
| 235 | 210657_PM_s_at | 4-Sep | septin 4 | 0.000314978 | 122.1 | 78.4 | 61.6 |
| 236 | 239979_PM_at | — | — | 0.000315949 | 40.3 | 78.8 | 114.4 |
| 237 | 208941_PM_s_at | SEPHS1 | selenophosphate synthetase 1 | 0.000316337 | 291.7 | 228.3 | 213.0 |
| 238 | 201649_PM_at | UBE2L6 | ubiquitin-conjugating enzyme E2L 6 | 0.000320318 | 928.3 | 1228.3 | 1623.0 |
| 239 | 211927_PM_x_at | EEF1G | eukaryotic translation elongation factor 1 gamma | 0.000325197 | 5122.7 | 4241.7 | 4215.5 |
| 240 | 225458_PM_at | LOC25845 | hypothetical LOC25845 | 0.000337719 | 93.6 | 131.5 | 110.8 |
| 241 | 208490_PM_x_at | HIST1H2BF | histone cluster 1, H2bf | 0.000339692 | 61.0 | 96.3 | 97.7 |
| 242 | 201322_PM_at | ATP5B | ATP synthase, H+ transporting, mitochondrial F1 complex, beta polypeptide | 0.000342076 | 2068.5 | 2566.2 | 2543.7 |
| 243 | 221978_PM_at | HLA-F | major histocompatibility complex, class I, F | 0.00034635 | 49.8 | 69.5 | 100.6 |
| 244 | 204031_PM_s_at | PCBP2 | poly(rC) binding protein 2 | 0.000351625 | 2377.6 | 2049.5 | 1911.5 |
| 245 | 243624_PM_at | PIAS2 | Protein inhibitor of activated STAT, 2 | 0.000352892 | 17.7 | 15.4 | 14.1 |
| 246 | 212998_PM_x_at | HLA-DQB1 /// LOC100133583 | major histocompatibility complex, class II, DQ beta 1 /// HLA class II histocompatibili | 0.000359233 | 570.2 | 339.6 | 742.5 |
| 247 | 204875_PM_s_at | GMDS | GDP-mannose 4,6-dehydratase | 0.00035965 | 73.9 | 41.2 | 45.5 |
| 248 | 225721_PM_at | SYNPO2 | synaptopodin 2 | 0.000362084 | 69.1 | 43.3 | 32.1 |
| 249 | 229696_PM_at | FECH | ferrochelatase | 0.000362327 | 42.6 | 34.1 | 28.8 |
| 250 | 208812_PM_x_at | HLA-C | major histocompatibility complex, class I, C | 0.000365707 | 7906.3 | 9602.6 | 10311.7 |
| 251 | 211666_PM_x_at | RPL3 | ribosomal protein L3 | 0.000376419 | 4594.1 | 4006.1 | 3490.3 |

TABLE 18b-continued

The 320 probesets that distinguish AR vs. HCV vs. HCV + AR in Liver Biopsies

| # | Probeset ID | Gene Symbol | Gene Title | p-value (Phenotype) | AR - Mean | HCV - Mean | HCV + AR - Mean |
|---|---|---|---|---|---|---|---|
| 252 | 219948_PM_x_at | UGT2A3 | UDP glucuronosyltransferase 2 family, polypeptide A3 | 0.000376972 | 219.5 | 454.5 | 350.3 |
| 253 | 204158_PM_s_at | TCIRG1 | T-cell, immune regulator 1, ATPase, H+ transporting, lysosomal V0 subunit A3 | 0.000384367 | 217.8 | 197.5 | 311.3 |
| 254 | 209846_PM_s_at | BTN3A2 | butyrophilin, subfamily 3, member A2 | 0.000386605 | 424.5 | 612.5 | 703.0 |
| 255 | 243225_PM_at | LOC283481 | hypothetical LOC283481 | 0.000388527 | 62.6 | 42.2 | 39.2 |
| 256 | 1554676_PM_at | SRGN | serglycin | 0.000399135 | 11.6 | 12.7 | 15.0 |
| 257 | 202748_PM_at | GBP2 | guanylate binding protein 2, interferon-inducible | 0.000406447 | 393.4 | 258.6 | 446.1 |
| 258 | 238654_PM_at | VSIG10L | V-set and immunoglobulin domain containing 10 like | 0.000411449 | 15.7 | 19.5 | 19.7 |
| 259 | 218949_PM_s_at | QRSL1 | glutaminyl-tRNA synthase (glutamine-hydrolyzing)-like 1 | 0.000413577 | 154.7 | 217.8 | 188.1 |
| 260 | 230306_PM_at | VPS26B | vacuolar protein sorting 26 homolog B (S. pombe) | 0.000420436 | 80.8 | 66.4 | 59.0 |
| 261 | 204450_PM_x_at | APOA1 | apolipoprotein A-I | 0.000427479 | 11811.2 | 13302.5 | 13014.4 |
| 262 | 213932_PM_x_at | HLA-A | major histocompatibility complex, class I, A | 0.000435087 | 7218.3 | 9083.8 | 10346.9 |
| 263 | 201641_PM_at | BST2 | bone marrow stromal cell antigen 2 | 0.000438494 | 217.2 | 396.5 | 401.8 |
| 264 | 1552275_PM_s_at | PXK | PX domain containing serine/threonine kinase | 0.000438718 | 24.7 | 38.6 | 34.4 |
| 265 | 210633_PM_x_at | KRT10 | keratin 10 | 0.000438865 | 535.9 | 466.6 | 443.1 |
| 266 | 217874_PM_at | SUCLG1 | succinate-CoA ligase, alpha subunit | 0.000441648 | 2582.3 | 3199.8 | 3034.6 |
| 267 | 223192_PM_at | SLC25A28 | solute carrier family 25, member 28 | 0.000456748 | 157.1 | 178.0 | 220.5 |
| 268 | 204820_PM_s_at | BTN3A2 /// BTN3A3 | butyrophilin, subfamily 3, member A2 /// butyrophilin, subfamily 3, member A3 | 0.000457313 | 1264.5 | 1537.9 | 1932.9 |
| 269 | 32069_PM_at | N4BP1 | NEDD4 binding protein 1 | 0.00045791 | 320.7 | 400.4 | 402.0 |
| 270 | 208870_PM_x_at | ATP5C1 | ATP synthase, H+ transporting, mitochondrial F1 complex, gamma polypeptide 1 | 0.000464012 | 3210.8 | 3791.7 | 3616.3 |
| 271 | 207104_PM_x_at | LILRB1 | leukocyte immunoglobulin-like receptor, subfamily B (with TM and ITIM domains), member | 0.000468733 | 52.9 | 52.0 | 80.6 |
| 272 | 209035_PM_at | MDK | midkine (neurite growth-promoting factor 2) | 0.000469597 | 18.5 | 25.2 | 30.3 |
| 273 | 230307_PM_at | LOC100129794 | similar to hCG1804255 | 0.000471715 | 17.3 | 14.8 | 13.5 |
| 274 | 225255_PM_at | MRPL35 | mitochondrial ribosomal protein L35 | 0.000478299 | 44.4 | 59.0 | 49.3 |
| 275 | 229625_PM_at | GBP5 | guanylate binding protein 5 | 0.000478593 | 243.9 | 147.4 | 393.5 |
| 276 | 209140_PM_x_at | HLA-B | major histocompatibility complex, class I, B | 0.000478945 | 8305.0 | 10032.9 | 11493.8 |
| 277 | 210905_PM_x_at | POU5F1P4 | POU class 5 homeobox 1 pseudogene 4 | 0.000492713 | 11.9 | 13.7 | 13.9 |
| 278 | 218480_PM_at | AGBL5 | ATP/GTP binding protein-like 5 | 0.000494707 | 23.8 | 20.7 | 18.1 |
| 279 | 209253_PM_at | SORBS3 | sorbin and SH3 domain containing 3 | 0.000495796 | 97.5 | 86.2 | 78.2 |
| 280 | 207801_PM_s_at | RNF10 | ring finger protein 10 | 0.000508149 | 374.0 | 297.5 | 327.3 |
| 281 | 212539_PM_at | CHD1L | chromodomain helicase DNA binding protein 1-like | 0.000509089 | 482.2 | 677.2 | 613.0 |
| 282 | 224492_PM_s_at | ZNF627 | zinc finger protein 627 | 0.000513422 | 127.6 | 168.3 | 125.0 |
| 283 | 1557186_PM_s_at | TPCN1 | two pore segment channel 1 | 0.000513966 | 26.5 | 21.5 | 22.4 |
| 284 | 203610_PM_s_at | TRIM38 | tripartite motif-containing 38 | 0.000514783 | 100.5 | 139.2 | 156.0 |
| 285 | 211530_PM_x_at | HLA-G | major histocompatibility complex, class I, G | 0.000525417 | 1034.7 | 1429.2 | 1621.6 |
| 286 | 201421_PM_s_at | WDR77 | WD repeat domain 77 | 0.000527341 | 114.5 | 143.9 | 133.4 |
| 287 | 200617_PM_at | MLEC | malectin | 0.000529672 | 244.8 | 174.2 | 147.7 |
| 288 | 1555982_PM_at | ZFYVE16 | zinc finger, FYVE domain containing 16 | 0.000550743 | 27.5 | 35.4 | 27.8 |
| 289 | 211345_PM_x_at | EEF1G | eukaryotic translation elongation factor 1 gamma | 0.000555581 | 4011.7 | 3333.0 | 3247.8 |
| 290 | 1555202_PM_a_at | RPRD1A | regulation of nuclear pre-mRNA domain containing 1A | 0.000561763 | 14.0 | 17.2 | 14.3 |
| 291 | 218304_PM_s_at | OSBPL11 | oxysterol binding protein-like 11 | 0.000565559 | 230.5 | 347.9 | 328.7 |

TABLE 18b-continued

The 320 probesets that distinguish AR vs. HCV vs. HCV + AR in Liver Biopsies

| # | Probeset ID | Gene Symbol | Gene Title | p-value (Phenotype) | AR - Mean | HCV - Mean | HCV + AR - Mean |
|---|---|---|---|---|---|---|---|
| 292 | 219464_PM_at | CA14 | carbonic anhydrase XIV | 0.000570778 | 64.9 | 43.5 | 32.6 |
| 293 | 204278_PM_s_at | EBAG9 | estrogen receptor binding site associated, antigen, 9 | 0.000570888 | 482.5 | 591.0 | 510.6 |
| 294 | 218298_PM_s_at | C14orf159 | chromosome 14 open reading frame 159 | 0.000571869 | 411.1 | 515.6 | 573.0 |
| 295 | 213675_PM_at | — | — | 0.000576321 | 39.1 | 27.4 | 25.2 |
| 296 | 1555097_PM_a_at | PTGFR | prostaglandin F receptor (FP) | 0.000581257 | 11.0 | 12.8 | 14.0 |
| 297 | 209056_PM_s_at | CDC5L | CDC5 cell division cycle 5-like (*S. pombe*) | 0.000582594 | 552.0 | 682.3 | 659.9 |
| 298 | 208912_PM_s_at | CNP | 2',3'-cyclic nucleotide 3' phosphodiesterase | 0.00058579 | 308.8 | 415.8 | 392.9 |
| 299 | 227018_PM_at | DPP8 | dipeptidyl-peptidase 8 | 0.000587266 | 29.6 | 38.2 | 41.9 |
| 300 | 224650_PM_at | MAL2 | mal, T-cell differentiation protein 2 | 0.000592979 | 600.4 | 812.5 | 665.3 |
| 301 | 217492_PM_s_at | PTEN /// PTENP1 | phosphatase and tensin homolog /// phosphatase and tensin homolog pseudogene 1 | 0.000601775 | 545.5 | 511.2 | 426.0 |
| 302 | 211654_PM_x_at | HLA-DQB1 | major histocompatibility complex, class II, DQ beta 1 | 0.000608592 | 538.8 | 350.2 | 744.4 |
| 303 | 220312_PM_at | FAM83E | family with sequence similarity 83, member E | 0.000609835 | 16.0 | 13.9 | 13.7 |
| 304 | 228230_PM_at | PRIC285 | peroxisomal proliferator-activated receptor A interacting complex 285 | 0.00061118 | 42.0 | 55.4 | 57.6 |
| 305 | 215171_PM_s_at | TIMM17A | translocase of inner mitochondrial membrane 17 homolog A (yeast) | 0.000624663 | 1432.1 | 1905.5 | 1715.4 |
| 306 | 228912_PM_at | VIL1 | villin 1 | 0.000630544 | 53.0 | 29.5 | 27.6 |
| 307 | 203047_PM_at | STK10 | serine/threonine kinase 10 | 0.000638877 | 41.0 | 39.1 | 54.7 |
| 308 | 232617_PM_at | CTSS | cathepsin S | 0.000640978 | 1192.9 | 1083.0 | 1561.2 |
| 309 | 236219_PM_at | TMEM20 | transmembrane protein 20 | 0.000648505 | 20.5 | 38.9 | 36.1 |
| 310 | 240681_PM_at | — | — | 0.000649144 | 140.6 | 202.3 | 192.8 |
| 311 | 1553317_PM_s_at | GPR82 | G protein-coupled receptor 82 | 0.000667359 | 13.3 | 20.1 | 21.2 |
| 312 | 212869_PM_x_at | TPT1 | tumor protein, translationally-controlled 1 | 0.000669242 | 14240.7 | 13447.2 | 13475.2 |
| 313 | 219356_PM_s_at | CHMP5 | chromatin modifying protein 5 | 0.000670413 | 1104.5 | 1310.4 | 1322.9 |
| 314 | 1552555_PM_at | PRSS36 | protease, serine, 36 | 0.000676354 | 14.2 | 12.9 | 11.8 |
| 315 | 203147_PM_s_at | TRIM14 | tripartite motif-containing 14 | 0.000676359 | 334.8 | 419.3 | 475.4 |
| 316 | 43511_PM_s_at | — | — | 0.000678774 | 70.7 | 60.9 | 80.0 |
| 317 | 221821_PM_s_at | C12orf41 | chromosome 12 open reading frame 41 | 0.000683679 | 180.0 | 213.8 | 206.9 |
| 318 | 218909_PM_at | RPS6KC1 | ribosomal protein S6 kinase, 52 kDa, polypeptide 1 | 0.000686673 | 105.8 | 155.8 | 151.5 |
| 319 | 232724_PM_at | MS4A6A | membrane-spanning 4-domains, subfamily A, member 6A | 0.000686877 | 106.7 | 108.3 | 160.4 |
| 320 | 218164_PM_at | SPATA20 | spermatogenesis associated 20 | 0.000693114 | 181.5 | 130.4 | 156.0 |

What is claimed is:

1. A method of detecting gene expression products and treating acute rejection in a transplant recipient on an immunosuppressive drug, the method comprising:

(a) obtaining a blood sample, wherein the blood sample comprises mRNA from the transplant recipient on an immunosuppressive drug or DNA complements of mRNA from the transplant recipient on an immunosuppressive drug;

(b) performing a microarray assay or sequencing assay to determine an expression level of the mRNA from the transplant recipient on an immunosuppressive drug or DNA complements of mRNA from the transplant recipient on an immunosuppressive drug;

(c) detecting or predicting acute rejection in the transplant recipient by applying a trained algorithm to the expression level determined in step (b), wherein the trained algorithm comprises one or more classifiers, wherein the trained algorithm is trained on 25 or more genes selected from the group consisting of SMARCB1, STP6AP2, PLEKHA3, TP53, PRKAG2, ND2, YWHAE, SSR1, CCDC91, PRKAG2, ADPGK, CHFR, PRNP, CDYL, SPTLC1, CHMP1B, KBTBD2, MST4, CDC42EP3, UBXN4, PGGT1B, CCR2, ZNF426, SP1, MED18, FLI1, LUC7L2, CD46, CASKIN1, UGP2, ARNTL, PLEKHF2, ZNF117, ITGB1, MAP3K1, FBXW7, SRGAP2B, ZNF136, ARPC5, FBXL18, TMED2, YWHAZ, SNAP23, TMEM30A, CD46, INSIG1, SRSF2, API5, FLI1, SLC35E1, PAPOLA, MLLT10, SLC35B4, ARL2BP, CNOT8, SYPL1, BRWD3, RBBP4, GLCCI1, MBP, RAB8B, YTHDF3, TOR1AIP1, ATF1, TMEM230, LRCH3, ARID2, CNOT8, ZBTB20, PSMD10, RHOP, ATF71P, LOC100131541, STYX, CN1H4, EMC1, MACF1, NOP14-AS1, HHEX, DHX36, DAPP1, WTAP, PSEN1, MAP3K7, PPP2R5E, FAM108B1, TAB2, FAR1, METTL21A, FYTTD1, TMED2, TROVE2, LNPEP, CAB39, RC3H2, SLBP, SNAP23, VWA9, MGAT2, OCIAD1, SH2D1B, PEX7, CD4, BZW1, RNF125, GNL3L, TRMT10B, RHEB, TMF1, STAG3L1, WSB1, PDE4B, ARID2, ATXN3, CUL4B, PRMT2, CTSS, ANAPC2, GLUD1, SGPP1, FAM178A, 2-Sep, KCTD5, ZEB1, RAC1, UVSSA, RBM4, ALKBH7, 214405_PM_at_EST1, SIVA1, 214482_PM_at_EST2, CHD2, POLR2C, 1556865_PM_at_EST3, GTF2H4, RNF25, DICER1, C9orf86, C5orf24, KIDINS220, ADPGK, HNRNPA0, 236237_PM_at_EST4, BAX, MBNL1, RAB5A, POLR2G, CELF2, 1561909_PM_at_EST5, FNBP1, FOXO3 /// FOXO3B, 233303_PM_at_EST6, 244219_PM_at_EST7, R3HCC1, DLST, CALM3, U2AF1, ANTXR2, LILRA4, TLE4, SMARCC1, BET1L, VAMP2, MRPS18A, KLF7, 242726_PM_at_EST8, USP34, APPL2, 240991_PM_at_EST9, NCR3, TXN1P, SDHAF1, HECTD1, C6orf62, 243751_PM_at_EST10, ATAD2B, MLL3, ATF6, C1orf128, SERPINF1, PAFAH1B1, C2ORF7, FOXO3 /// FOXO3B, CHMP4A, ANXA11, TAF10, DLEU2, 15622_PM_at_EST11, SEPT9, RBM5, MGEA5, TRAF4, LOC100132707, OTUD4, KLHL12, MED1, 216112_PM_at_EST12, ACSL4, ATXN7L3b, DCTN3, MGEA4, MS4A6A, CCDC69, H2AFY, TMEM165, INO80D, PSEN1, C15orf17, RBM27, GZMM, ATP6, ZDHHC1, TLE4, SDHC, HNRNPUL1, SF3A2, 236545_PM_at_EST13, CDH23, LOC100506866, C4orf48, EMD, NEK1, HNRNPM, 241240_PM_at_EST15, LIMD2, THOC2, 243046_PM_at_EST16, BAT2L2, ZCCHC6, 228723_PM_at_EST17, 242695_PM_at_EST18, PLEC, U1MC1, LRRFIP1, 1556055_PM_at_EST19, AFFX-, M27830_5_at_EST20, GRB10, CD84, KLHDC3, BAX, NRD1, RASA2, 1559589_PM_a_at_EST21, MTPAP, ZFP36L2, AGPAT1, KIDINS220, ISOC2, KLF7, MED27, TLR4, ABHD14B, 244349_PM_at_EST22, 244418_PM_at_EST23, MLXIP, PPID, MRPL43, ND3 /// SH3KBP1, TNRC6B, KLHL28, SLC25A37, NELF, FARS2, ZCCHC6, TRIM25, TAF15, LTB, 221995_PM_s_at_EST24, IFNGR1, 228826_PM_at_EST25, C7orf16, NEDD9, NDUFA7, ZC3H11A, DNAJA4, ERICH1, RALB, MPZL1, EZR, RBKS, TMOD1 /// TSTD2, LOC729683, PTK2B, APBB11P, UBXN4, SETD5, 243032_PM_at_EST26, 216380_PM_x_at_EST27, TRAPPC4, CKB, CANX, 1558624_PM_at_EST28, SIVA1, 240652_PM_at_EST29, HOXA1, C11orf49, SLC11A1, C9orf86, IVNS1ABP, PDXP /// SH3BP1, CHTF8, FKBP5, FGFR1OP2, SECISBP2L, ARF1, B4GALT1, PHF19, C16orf5, C11orf59, PIP4K2A, GCLC, EMILIN2, NGLY1, ANKHD1 /// ANKHD1-EIF4EBP3, DLEU2, PBLS, RALGAPA2, 230733_PM_at_EST30, 1557804_PM_at_EST31, PKN2, and GGNBP2, wherein the trained algorithm is capable of distinguishing between acute rejection and acute dysfunction with no rejection, and wherein the trained algorithm has a negative predictive value of greater than 70%; and (d) administering a higher dosage of the immunosuppressive drug or administering a new immunosuppressive drug in order to treat or prevent the acute rejection detected or predicted in the transplant recipient in step (c).

2. The method of claim 1, wherein the trained algorithm comprises a linear classifier.

3. The method of claim 2, wherein the linear classifier comprises one or more of linear discriminant analysis, Fisher's linear discriminant, Nave Bayes classifier, Logistic regression, Perceptron, Support vector machine (SVM) or a combination thereof.

4. The method of claim 1, wherein the trained algorithm comprises a Diagonal Linear Discriminant Analysis (DLDA) algorithm.

5. The method of claim 1, wherein the trained algorithm comprises a Nearest Centroid algorithm.

6. The method of claim 1, wherein the trained algorithm comprises a Random Forest algorithm or statistical bootstrapping.

7. The method of claim 1, wherein the trained algorithm comprises a Prediction Analysis of Microarrays (PAM) algorithm.

8. The method of claim 1, wherein the trained algorithm is not validated by a cohort-based analysis of an entire cohort.

9. The method of claim 1, wherein the determining the expression level in step (b) comprises determining the expression level of 25 or more gene expression products with different sequences.

10. The method of claim 9, wherein the 25 or more gene expression products correspond to less than 200 genes listed selected from the group consisting of SMARCB1, STP6AP2, PLEKHA3, TP53, PRKAG2, ND2, YWHAE, SSR1, CCDC91, PRKAG2, ADPGK, CHFR, PRNP, CDYL, SPTLC1, CHMP1B, KBTBD2, MST4, CDC42EP3, UBXN4, PGGT1B, CCR2, ZNF426, SP1, MED18, FLI1, LUC7L2, CD46, CASKIN1, UGP2, ARNTL, PLEKHF2, ZNF117, ITGB1, MAP3K1, FBXW7, SRGAP2B, ZNF136, ARPC5, FBXL18, TMED2, YWHAZ, SNAP23, TMEM30A, CD46, INSIG1, SRSF2, API5, FLI1, SLC35E1, PAPOLA, MLLT10, SLC35B4, ARL2BP, CNOT8, SYPL1, BRWD3, RBBP4, GLCCI1, MBP, RAB8B, YTHDF3, TOR1AIP1, ATF1, TMEM230, LRCH3, ARID2, CNOT8, ZBTB20, PSMD10, RHOP, ATF71P, LOC100131541, STYX, CN1H4, EMC1, MACF1, NOP14-AS1, HHEX, DHX36, DAPP1, WTAP, PSEN1, MAP3K7, PPP2R5E, FAM108B1, TAB2, FAR1, METTL21A, FYTTD1, TMED2, TROVE2, LNPEP, CAB39, RC3H2, SLBP, SNAP23, VWA9, MGAT2, OCIAD1, SH2D1B, PEX7, CD4, BZW1, RNF125, GNL3L, TRMT10B, RHEB, TMF1, STAG3L1, WSB1, PDE4B, ARID2, ATXN3, CUL4B, PRMT2, CTSS, ANAPC2, GLUD1, SGPP1, FAM178A, 2-Sep, KCTD5, ZEB1, RAC1, UVSSA, RBM4, ALKBH7, 214405_PM_at_EST1, SIVA1, 214482_PM_at_EST2, CHD2, POLR2C, 1556865_PM_at_EST3, GTF2H4, RNF25, DICER1, C9orf86, C5orf24, KIDINS220, ADPGK, HNRNPA0, 236237_PM_at_EST4, BAX, MBNL1, RAB5A, POLR2G, CELF2, 1561909_PM_at_EST5, FNBP1, FOXO3 /// FOXO3B, 233303_PM_at_EST6, 244219_PM_at_EST7, R3HCC1, DLST, CALM3, U2AF1, ANTXR2, LILRA4, TLE4, SMARCC1, BET1L, VAMP2, MRPS18A, KLF7, 242726_PM_at_EST8, USP34, APPL2, 240991_PM_at_EST9, NCR3, TXN1P, SDHAF1, HECTD1, C6orf62, 243751_PM_at_EST10, ATAD2B, MLL3, ATF6, C1orf128, SERPINF1, PAFAH1B1, C2ORF7, FOXO3 /// FOXO3B, CHMP4A, ANXA11, TAF10, DLEU2, 15622_PM_at_EST11, SEPT9, RBM5, MGEA5, TRAF4, LOC100132707, OTUD4, KLHL12, MED1, 216112_PM_at_EST12, ACSL4, ATXN7L3b, DCTN3, MGEA4, MS4A6A, CCDC69, H2AFY, TMEM165, INO80D, PSEN1, C15orf17, RBM27, GZMM, ATP6, ZDHHC1, TLE4, SDHC, HNRNPUL1, SF3A2, 236545_PM_at_EST13, CDH23, LOC100506866, C4orf48, EMD, NEK1, HNRNPM, 241240_PM_at_EST15, LIMD2, THOC2, 243046_PM_at_EST16, BAT2L2, ZCCHC6, 228723_PM_at_EST17, 242695_PM_at_EST18, PLEC, U1MC1, LRRFIP1, 1556055_PM_at_EST19, AFFX-, M27830_5_at_EST20, GRB10, CD84, KLHDC3, BAX, NRD1, RASA2, 1559589_PM_a_at_EST21, MTPAP, ZFP36L2, AGPAT1, KIDINS220, ISOC2, KLF7, MED27, TLR4, ABHD14B, 244349_PM_at_EST22, 244418_PM_at_EST23, MLXIP, PPID, MRPL43, ND3 /// SH3KBP1, TNRC6B, KLHL28, SLC25A37, NELF, FARS2, ZCCHC6, TRIM25, TAF15, LTB, 221995_PM_s_at_EST24, IFNGR1, 228826_PM_at_EST25, C7orf16, NEDD9, NDUFA7, ZC3H11A, DNAJA4, ERICH1, RALB, MPZL1, EZR, RBKS, TMOD1 /// TSTD2, LOC729683, PTK2B, APBB11P, UBXN4, SETD5, 243032_PM_at_EST26, 216380_PM_x_at_EST27, TRAPPC4, CKB, CANX, 1558624_PM_at_EST28, SIVA1, 240652_PM_at_EST29, HOXA1, C11orf49, SLC11A1, C9orf86, IVNS1ABP, PDXP /// SH3BP1, CHTF8, FKBP5, FGFR1OP2, SECISBP2L, ARF1, B4GALT1, PHF19, C16orf5, C11orf59, PIP4K2A, GCLC, EMILIN2, NGLY1, ANKHD1 /// ANKHD1-EIF4EBP3, DLEU2, PBLS, RALGAPA2, 230733_PM_at_EST30, 1557804_PM_at_EST31, PKN2, and GGNBP2.

11. The method of claim 1, wherein the blood sample is a peripheral blood sample.

12. The method of claim 1, wherein the blood sample is a whole blood sample.

13. The method of claim 1, wherein the blood sample is not derived from tissue from a biopsy of a transplanted organ of the transplant recipient on an immunosuppressive drug.

14. The method of claim 1, wherein the performing a microarray assay or sequencing assay in step (b) comprises performing an RNA sequencing assay on the mRNA from the transplant recipient on an immunosuppressive drug.

15. The method of claim 1, wherein the performing a microarray assay or sequencing assay comprises performing a DNA sequencing assay on the DNA complements of mRNA from the transplant recipient on an immunosuppressive drug.

16. The method of claim 1, wherein the determining the expression level in step (b) comprises determining the expression level of 25 or more genes selected from the group consisting of SMARCB1, STP6AP2, PLEKHA3, TP53, PRKAG2, ND2, YWHAE, SSR1, CCDC91, PRKAG2, ADPGK, CHFR, PRNP, CDYL, SPTLC1, CHMP1B, KBTBD2, MST4, CDC42EP3, UBXN4, PGGT1B, CCR2, ZNF426, SP1, MED18, FLI1, LUC7L2, CD46, CASKIN1, UGP2, ARNTL, PLEKHF2, ZNF117, ITGB1, MAP3K1, FBXW7, SRGAP2B, ZNF136, ARPC5, FBXL18, TMED2, YWHAZ, SNAP23, TMEM30A, CD46, INSIG1, SRSF2, API5, FLI1, SLC35E1, PAPOLA, MLLT10, SLC35B4, ARL2BP, CNOT8, SYPL1, BRWD3, RBBP4, GLCCI1, MBP, RAB8B, YTHDF3, TOR1AIP1, ATF1, TMEM230, LRCH3, ARID2, CNOT8, ZBTB20, PSMD10, RHOP, ATF71P, LOC100131541, STYX, CN1H4, EMC1, MACF1, NOP14-AS1, HHEX, DHX36, DAPP1, WTAP, PSEN1, MAP3K7, PPP2R5E, FAM108B1, TAB2, FAR1, METTL21A, FYTTD1, TMED2, TROVE2, LNPEP, CAB39, RC3H2, SLBP, SNAP23, VWA9, MGAT2, OCIAD1, SH2D1B, PEX7, CD4, BZW1, RNF125, GNL3L, TRMT10B, RHEB, TMF1, STAG3L1, WSB1, PDE4B, ARID2, ATXN3, CUL4B, PRMT2, CTSS, ANAPC2, GLUD1, SGPP1, FAM178A, 2-Sep, KCTD5, ZEB1, RAC1, UVSSA, RBM4, ALKBH7, 214405_PM_at_EST1, SIVA1, 214482_PM_at_EST2, CHD2, POLR2C, 1556865_PM_at_EST3, GTF2H4, RNF25, DICER1, C9orf86, C5orf24, KIDINS220, ADPGK, HNRNPA0, 236237_PM_at_EST4, BAX, MBNL1, RAB5A, POLR2G, CELF2, 1561909_PM_at_EST5, FNBP1, FOXO3 /// FOXO3B, 233303_PM_at_EST6, 244219_PM_at_EST7, R3HCC1, DLST, CALM3, U2AF1, ANTXR2, LILRA4, TLE4, SMARCC1, BET1L, VAMP2, MRPS18A, KLF7, 242726_PM_at_EST8, USP34, APPL2, 240991_PM_at_EST9, NCR3, TXN1P, SDHAF1, HECTD1, C6orf62, 243751_PM_at_EST10, ATAD2B, MLL3, ATF6, C1orf128, SERPINF1, PAFAH1B1, C2ORF7, FOXO3 /// FOXO3B, CHMP4A, ANXA11, TAF10, DLEU2, 15622_PM_at_EST11, SEPT9, RBM5, MGEA5, TRAF4, LOC100132707, OTUD4, KLHL12, MED1, 216112_PM_at_EST12, ACSL4, ATXN7L3b, DCTN3, MGEA4, MS4A6A, CCDC69, H2AFY, TMEM165, INO80D, PSEN1, C15orf17, RBM27, GZMM, ATP6, ZDHHC1, TLE4, SDHC, HNRNPUL1, SF3A2, 236545_PM_at_EST13, CDH23, LOC100506866, C4orf48, EMD, NEK1, HNRNPM, 241240_PM_at_EST15, LIMD2, THOC2, 243046_PM_at_EST16, BAT2L2, ZCCHC6, 228723_PM_at_EST17, 242695_PM_at_EST18, PLEC, U1MC1, LRRFIP1, 1556055_PM_at_EST19, AFFX-, M27830_5_at_EST20, GRB10, CD84, KLHDC3, BAX, NRD1, RASA2, 1559589_PM_a_at_EST21, MTPAP, ZFP36L2, AGPAT1, KIDINS220, ISOC2, KLF7, MED27, TLR4, ABHD14B, 244349_PM_at_EST22, 244418_PM_at_EST23, MLXIP, PPID, MRPL43, ND3 /// SH3KBP1, TNRC6B, KLHL28, SLC25A37, NELF, FARS2, ZCCHC6, TRIM25, TAF15, LTB, 221995_PM_s_at_EST24, IFNGR1, 228826_PM_at_EST25, C7orf16, NEDD9, NDUFA7, ZC3H11A, DNAJA4, ERICH1, RALB, MPZL1, EZR, RBKS, TMOD1 /// TSTD2, LOC729683, PTK2B, APBB11P, UBXN4, SETD5, 243032_PM_at_EST26, 216380_PM_x_at_EST27, TRAPPC4, CKB, CANX, 1558624_PM_at_EST28, SIVA1, 240652_PM_at_EST29, HOXA1, C11orf49, SLC11A1, C9orf86, IVNS1ABP, PDXP /// SH3BP1, CHTF8, FKBP5, FGFR1OP2, SECISBP2L, ARF1, B4GALT1, PHF19, C16orf5, C11orf59, PIP4K2A, GCLC, EMILIN2, NGLY1, ANKHD1 /// ANKHD1-EIF4EBP3, DLEU2, PBLS, RALGAPA2, 230733_PM_at_EST30, 1557804_PM_at_EST31, PKN2, and GGNBP2.

17. The method of claim 1, wherein the method has a sensitivity of at least about 80%.

18. The method of claim 1, wherein the method has a specificity of at least about 80%.

19. The method of claim 1, wherein the transplant recipient on an immunosuppressive drug has a serum creatinine level of at least 1.5 mg/dL.

20. The method of claim 1, wherein the transplant recipient on an immunosuppressive drug has a serum creatinine level of at least 3 mg/dL.

21. The method of claim 1, wherein the transplant recipient is a kidney transplant recipient.

22. The method of claim 1, wherein the trained algorithm is further capable of distinguishing normal transplant functioning from acute rejection and from acute dysfunction with no rejection.

23. The method of claim 1, wherein the method comprises administering an increased dose of the immunosuppressive drug to the transplant recipient in order to treat or prevent the acute rejection detected or predicted in the transplant recipient in step (c).

24. The method of claim 1, wherein the method comprises administering a new immunosuppressive drug to the transplant recipient in order to treat or prevent the acute rejection detected or predicted in the transplant recipient in step (c).

25. The method of claim 1, wherein the immunosuppressive drug or new immunosuppressive drug is selected from the group consisting of a calcineurin inhibitor, an mTOR inhibitor, an anti-proliferative, a corticosteroid, and an anti-T-cell antibody.

26. The method of claim 1, wherein the immunosuppressive drug or new immunosuppressive drug is selected from the group consisting of cyclosporine, tacrolimus, azathioprine, mycophenolic acid, prednisolone, hydrocortisone, basiliximab, daclizumab, Orthoclone, anti-thymocyte globulin, and anti-lymphocyte globulin.

27. The method of claim 1, wherein the detecting or predicting comprises diagnosing the acute rejection in the transplant recipient.

28. The method of claim 1, wherein the detecting or predicting comprises detecting the acute rejection in the transplant recipient.

29. The method of claim 1, wherein the detecting or predicting comprises predicting a risk of acute rejection in the transplant recipient.

30. A method of detecting gene expression products and treating acute rejection in a transplant recipient on an immunosuppressive drug, the method comprising:
(a) obtaining a blood sample, wherein the blood sample comprises mRNA from the transplant recipient or DNA complements of mRNA from the transplant recipient;
(b) performing a microarray assay or sequencing assay to determine an expression level of mRNA from the transplant recipient or DNA complements of mRNA from the transplant recipient; and
(c) detecting or predicting acute rejection in the transplant recipient by applying a trained algorithm to the expression level determined in step (b), wherein the trained algorithm is trained on 25 or more genes selected from the group consisting of SMARCB1, STP6AP2, PLEKHA3, TP53, PRKAG2, ND2, YWHAE, SSR1, CCDC91, PRKAG2, ADPGK, CHFR, PRNP, CDYL, SPTLC1, CHMP1B, KBTBD2, MST4, CDC42EP3, UBXN4, PGGT1B, CCR2, ZNF426, SP1, MED18, FLI1, LUC7L2, CD46, CASKIN1, UGP2, ARNTL, PLEKHF2, ZNF117, ITGB1, MAP3K1, FBXW7, SRGAP2B, ZNF136, ARPC5, FBXL18, TMED2, YWHAZ, SNAP23, TMEM30A, CD46, INSIG1, SRSF2, API5, FLI1, SLC35E1, PAPOLA, MLLT10, SLC35B4, ARL2BP, CNOT8, SYPL1, BRWD3, RBBP4, GLCCI1, MBP, RAB8B, YTHDF3, TOR1AIP1, ATF1, TMEM230, LRCH3, ARID2, CNOT8, ZBTB20, PSMD10, RHOP, ATF71P, LOC100131541, STYX, CN1H4, EMC1, MACF1, NOP14-AS1, HHEX, DHX36, DAPP1, WTAP, PSEN1, MAP3K7, PPP2R5E, FAM108B1, TAB2, FAR1, METTL21A, FYTTD1, TMED2, TROVE2, LNPEP, CAB39, RC3H2, SLBP, SNAP23, VWA9, MGAT2, OCIAD1, SH2D1B, PEX7, CD4, BZW1, RNF125, GNL3L, TRMT10B, RHEB, TMF1, STAG3L1, WSB1, PDE4B, ARID2, ATXN3, CUL4B, PRMT2, CTSS, ANAPC2, GLUD1, SGPP1, FAM178A, 2-Sep, KCTD5, ZEB1, RAC1, UVSSA, RBM4, ALKBH7, 214405_PM_at_EST1, SIVA1, 214482_PM_at_EST2, CHD2, POLR2C, 1556865_PM_at_EST3, GTF2H4, RNF25, DICER1, C9orf86, C5orf24, KIDINS220, ADPGK, HNRNPA0, 236237_PM_at_EST4, BAX, MBNL1, RAB5A, POLR2G, CELF2, 1561909_PM_at_EST5, FNBP1, FOXO3 /// FOXO3B, 233303_PM_at_EST6, 244219_PM_at_EST7, R3HCC1, DLST, CALM3, U2AF1, ANTXR2, LILRA4, TLE4, SMARCC1, BET1L, VAMP2, MRPS18A, KLF7, 242726_PM_at_EST8, USP34, APPL2, 240991_PM_at_EST9, NCR3, TXN1P, SDHAF1, HECTD1, C6orf62, 243751_PM_at_EST10, ATAD2B, MLL3, ATF6, C1orf128, SERPINF1, PAFAH1B1, C2ORF7, FOXO3 /// FOXO3B, CHMP4A, ANXA11, TAF10, DLEU2, 15622_PM_at_EST11, SEPT9, RBM5, MGEA5, TRAF4, LOC100132707, OTUD4, KLHL12, MED1, 216112_PM_at_EST12, ACSL4, ATXN7L3b, DCTN3, MGEA4, MS4A6A, CCDC69, H2AFY, TMEM165, INO80D, PSEN1, C15orf17, RBM27, GZMM, ATP6, ZDHHC1, TLE4, SDHC, HNRNPUL1, SF3A2, 236545_PM_at_EST13, CDH23, LOC100506866, C4orf48, EMD, NEK1, HNRNPM, 241240_PM_at_EST15, LIMD2, THOC2, 243046_PM_at_EST16, BAT2L2, ZCCHC6, 228723_PM_at_EST17, 242695_PM_at_EST18, PLEC, U1MC1, LRRFIP1, 1556055_PM_at_EST19, AFFX-, M27830_5_at_EST20, GRB10, CD84, KLHDC3, BAX, NRD1, RASA2, 1559589_PM_a_at_EST21, MTPAP, ZFP36L2, AGPAT1, KIDINS220, ISOC2, KLF7, MED27, TLR4, ABHD14B, 244349_PM_at_EST22, 244418_PM_at_EST23, MLXIP, PPID, MRPL43, ND3 /// SH3KBP1, TNRC6B, KLHL28, SLC25A37, NELF, FARS2, ZCCHC6, TRIM25, TAF15, LTB, 221995_PM_s_at_EST24, IFNGR1, 228826_PM_at_EST25, C7orf16, NEDD9, NDUFA7, ZC3H11A, DNAJA4, ERICH1, RALB, MPZL1, EZR, RBKS, TMOD1 /// TSTD2, LOC729683, PTK2B, APBB11P, UBXN4, SETD5, 243032_PM_at_EST26, 216380_PM_x_at_EST27, TRAPPC4, CKB, CANX, 1558624_PM_at_EST28, SIVA1, 240652_PM_at_EST29, HOXA1, C11orf49, SLC11A1, C9orf86, IVNS1ABP, PDXP /// SH3BP1, CHTF8, FKBP5, FGFR1OP2, SECISBP2L, ARF1, B4GALT1, PHF19, C16orf5, C11orf59, PIP4K2A, GCLC, EMILIN2, NGLY1, ANKHD1 /// ANKHD1-EIF4EBP3, DLEU2, PBLS, RALGAPA2, 230733_PM_at_EST30, 1557804_PM_at_EST31, PKN2, and GGNBP2, wherein the trained algorithm is a three-way classifier capable of distinguishing between at least three conditions, and wherein one of the at least three conditions is acute rejection, wherein one of the at least three conditions is acute dysfunction with no rejection, and wherein the trained algorithm has a negative predictive value of greater than 70%; and
(d) administering a higher dosage of the immunosuppressive drug or administering a new immunosuppressive drug in order to treat the acute rejection detected or predicted in the transplant recipient in step (c).

31. The method of claim 30, wherein a frozen robust multichip average (fRMA) algorithm is used to produce normalized expression level data in (b).

* * * * *